(12) United States Patent
Stockwell et al.

(10) Patent No.: US 10,947,188 B2
(45) Date of Patent: Mar. 16, 2021

(54) SMALL MOLECULE FERROPTOSIS INDUCERS

(71) Applicant: THE TRUSTEES OF COLUMBIA UNIVERSITY IN THE CITY OF NEW YORK, New York, NY (US)

(72) Inventors: Brent R. Stockwell, New York, NY (US); Kenichi Shimada, Boston, MA (US); Rachid Skouta, Amherst, MA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 16/445,104

(22) Filed: Jun. 18, 2019

(65) Prior Publication Data

US 2019/0315681 A1    Oct. 17, 2019

Related U.S. Application Data

(63) Continuation-in-part of application No. PCT/US2017/066822, filed on Dec. 15, 2017.

(60) Provisional application No. 62/436,064, filed on Dec. 19, 2016.

(51) Int. Cl.
*C07C 311/15* (2006.01)
*C07D 401/12* (2006.01)
*C07D 407/12* (2006.01)

(52) U.S. Cl.
CPC .......... *C07C 311/15* (2013.01); *C07D 401/12* (2013.01); *C07D 407/12* (2013.01)

(58) Field of Classification Search
CPC .................................................. C07C 311/15
USPC ........................................................ 514/316
See application file for complete search history.

(56) References Cited

U.S. PATENT DOCUMENTS

2010/0137354 A1    6/2010  Cholody et al.

FOREIGN PATENT DOCUMENTS

WO    2008140792 A1    9/2008
WO    2010082912 A1    7/2010

OTHER PUBLICATIONS

Ward, J. H. "Hierarchical Grouping to Optimize an Objective Function," J. Am. Stat. Assoc. 1963, 58 (301), 236-244. https://doi.org/10.1080/01621459.1963.10500845.
Wolpaw, et al. "Modulatory profiling identifies mechanisms of small molecule-induced cell death," Proc. Natl. Acad. Sci. USA 108, E771-E780 (2011).
Yagoda, et al. "RAS-RAF-MEK-dependent oxidative cell death involving voltage-dependent anion channels," Nature 447, 864-868 (2007).
Yang, et al. "Peroxidation of Polyunsaturated Fatty Acids by Lipoxygenases Drives Ferroptosis," Proc. Natl. Acad. Sci. 2016, 113 (34), E4966-E4975. https://doi.org/10.1073/pnas.1603244113.
Shimada, et al. "Global Survey of Cell Death Mechanisms Reveals Metabolic Regulation of Ferroptosis," Nat Chem Biol. Jul. 2016;12(7):497-503.
Pubchem, Compound Summary for SID 173334080, National Center for Biotechnology Information. PubChem Database. REGID_for_CID_3097937, Source=Meiler Lab, Vanderbilt University, SID=173334080, https://pubchem.ncbi.nlm.nih.gov/substance7173334080 (accessed on Jan. 24, 2020).
International Search Report for PCT/US2017/066822 dated Apr. 13, 2018.
Alegre-Aguaron, E. et al. "Growth factor priming differentially modulates components of the extracellular matrix proteome in chondrocytes and synovium-derived stem cells." PLoS One 9, e88053 (2014).
Altschul, et al. "Basic Local Alignment Search Tool," J. Mol. Biol. 1990, 215 (3), 403-410. httpildoi.org/10.1016/S0022-2836(05)80360-2.
Aravind, et a. "The domains of death: evolution of the apoptosis machinery," Trends Biochem. Sci. 24, 47-53 (1999).
Backman, et al. "ChemMine tools: an online service for analyzing and clustering small molecules," Nucleic Acids Res. 39, W486-W491 (2011).
Berghe, et al. "Regulated necrosis: the expanding network of non-apoptotic cell death pathways," Nat. Rev. Mol. Cell Biol. 2014;15:135-147.
Yang, et al. "Synthetic lethal screening identities compounds activating iron-dependent, nonapoptotic cell death in oncogenic-RAS-harboring cancer cells," Chem. Biol. 15, 234-245 (2008).
Dhugh, et al. "Squalene epoxidase as hypocholesterolemic drug target revisited," Prog. Lipid Res. 42, 37-50 (2003).

(Continued)

*Primary Examiner* — Taofiq A Solola
(74) *Attorney, Agent, or Firm* — Bryan Cave Leighton Paisner LLP

(57) ABSTRACT

The present invention provides, inter alia, a compound according to formula (I):

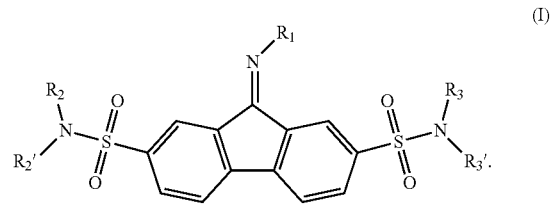

Also provided are compositions containing a pharmaceutically acceptable carrier and a compound according to the present invention. Further provided are methods for regulating GPX4 in a cell and methods for inducing ferroptosis in a cell.

19 Claims, 64 Drawing Sheets
(60 of 64 Drawing Sheet(s) Filed in Color)

(56) References Cited

OTHER PUBLICATIONS

Degterev, et al. "Chemical inhibitor of nonapoptotic cell death with therapeutic potential for ischemic brain injury," Nat. Chem. Biol. 1, 112-119 (2005).

Degterev, et al. "Identification of RIP1 kinase as a specific cellular target of necrostatins," Nat. Chem. Biol. 4, 313-321 (2008).

Dixon, et al. "Ferroptosis: An Iron-Dependent Form of Nonapoptotic Cell Death," Cell. 2012;149:1060-1072.

Dixon, et al. "Pharmacological inhibition of cystine-glutamate exchange induces endoplasmic reticulum stress and ferroptosis," eLife. 2014;3:e02523.

Dixon, et al. "Human haploid cell genetics reveals roles for lipid metabolism genes in nonapoptotic cell death," ACS Chem. Biol. 10, 1604-1609 (2015).

Fradejas, et al. "Mammalian Trit1 is a tRNA([Ser]Sec)-isopentenyl transferase required for full selenoprotein expression," Biochem. J. 450, 427-432 (2013).

Fuchs, et al. "Programmed cell death in animal development and disease," Cell 147, 742-758 (2011).

Gaulton, et al. "ChEMBL: A Large-Scale Bioactivity Database for Drug Discovery," Nucleic Acids Res. 2012, 40 (D1), D1100-D1107. http://doi.org/10.1093/nar/gkr777.

Gregori-Puigjane, et a. "Identifying Mechanism-of-Action Targets for Drugs and Probes," Proc. Natl. Acad. Sci. 2012, 109 (28), 11178-11183. https://doi.org/10.1073/pnas.1204524109.

Gueven, et al. "Border between natural product and drug: comparison of the related benzoquinones idebenone and coenzyme Q10," Redox Biol. 4, 289-295 (2015).

Hahn, et al. "Creation of human tumour cells with defined genetic elements," Nature 400, 464-468 (1999).

Hayano, et al. "Loss of cysteinyl-tRNA synthetase (CARS) induces the transsulfuration pathway and inhibits ferroptosis induced by cystine deprivation," Cell Death Differ 23, 270-278 (2016).

Henke, et al. "The Plasma Membrane Channel ORAl1 Mediates Detrimental Calcium Influx Caused by Endogenous Oxidative Stress," Cell Death Dis. 2013, 4 (1), e470. https://doi.org/10.1038/cddis.2012.216.

Hirsch, et al. "A transcriptional signature and common gene networks link cancer with lipid metabolism and diverse human diseases," Cancer Cell 17, 348-361 (2010).

Hitomi, et al. "Identification of a molecular signaling network that regulates a cellular necrotic cell death pathway," Cell 135, 1311-1323 (2008).

Hu, et al. "Promiscuity Progression of Bioactive Compounds over Time," F1000Research 2015 https://doi.org/10.12688/f1000research.6473.2.

Imai, et al. "Biological significance of phospholipid hydroperoxide glutathione peroxidase (PHGPx, GPx4) in mammalian cells," Free Radic. Biol. Med. 34, 145-169 (2003).

Kaczmarek, et al. "Necroptosis: the release of damage-associated molecular patterns and its physiological relevance," Immunity 38, 209-223 (2013).

Kamphorst, et al. "Liquid chromatography-high resolution mass spectrometry analysis of fatty acid metabolism," Anal. Chem. 83, 9114-9122 (2011).

Keiser, et al. "Relating Protein Pharmacology by Ligand Chemistry," Nat. Biotechnol. 2007, 25 (2), 197-206. https://doi.org/10.1038/nbt1284.

Keiser, et al. "Predicting New Molecular Targets for Known Drugs," Nature 2009, 462 (7270), 175-181.

Kono, et al. "How dying cells alert the immune system to danger," Nat. Rev. Immunol. 8, 279-289 (2008).

Linkermann, et al. "Synchronized renal tubular cell death involves ferroptosis," Proc. Natl. Acad. Sci. USA 111, 16836-16841 (2014).

Linkermann, et al. "Regulated cell death and inflammation: an auto-amplification loop causes organ failure," Nat. Rev. Immunol. 14, 759-767 (2014).

Liu, et al. "Structural insights into the catalytic mechanism of human squalene synthase," Acta Crystallogr. D Biol. Crystallogr. 70, 231-241 (2014).

Rogers, et al. "Extended-Connectivity Fingerprints," J. Chem. Inf. Model. 2010, 50 (5), 742-754. https://doi.org/10.1021/ci100050t.

Romanowska, et al. "Effects of selenium supplementation on expression of glutathione peroxidase isoforms in cultured human lung adenocarcinoma cell lines," Lung Cancer 55, 35-42 (2007).

Santos, et al. "Lipid metabolism in cancer," FEBS J. 279, 2610-2623 (2012).

Yang, et al. "Regulation of ferroptotic cancer cell death by GPX4," Cell 156, 317-331 (2014).

Shimada, et al. "Cell-line selectivity improves the predictive power of pharmacogenomic analyses and helps identify NADPH as biomarker for ferroptosis sensitivity," Cell Chem. Biol. 23, 225-235 (2016).

Shintoku et al. "Lipoxygenase-mediated Generation of Lipid Peroxides Enhances Ferroptosis Induced by Erastin and RSL3," Cancer Sci. 2017, 108 (11), 2187-2194. https://doi.org/10.1111/cas.13380.

Shoemaker, R.N. "The NCI60 human tumour cell line anticancer drug screen," Nat. Rev. Cancer 6, 813-823 (2006).

Skouta, et al. "Ferrostatins inhibit oxidative lipid damage and cell death in diverse disease models," J. Am. Chem. Soc. 136, 4551-4556 (2014).

Song, et al. "Deletion of Pim kinases elevates the cellular levels of reactive oxygen species and sensitizes to K-Ras-induced cell killing," Oncogene 34, 3728-3736 (2015).

Subramanian, et al. "Gene Set Enrichment Analysis: A Knowledge-Based Approach for Interpreting Genome-Wide Expression Profiles," Proc. Natl. Acad. Sci. U. S. A. 2005, 102 (43), 15545-15550. https://doi.org/10.1073/pnas.0506580102.

Takahashi, et al. "Necrostatin-1 analogues: critical issues on the specificity, activity and in vivo use in experimental lisease models," Cell Death Dis. 3, e437 (2012).

Tansey, et al. "Structure and regulation of mammalian squalene synthase," Biochim. Biophys. Acta 1529, 49-62 (2000).

Tobaben, et al. "Bid-Mediated Mitochondrial Damage Is a Key Mechanism in Glutamate-Induced Oxidative Stress and AIF-Dependent Cell Death in Immortalized HT-22 Hippocampal Neurons, " Cell Death Differ. 2011, 18 (2), 282-292. https://doi.org/10.1038/cdd.2010.92.

Vanden Berghe, et al. "Regulated necrosis: the expanding network of non-apoptotic cell death pathways," Nat. Rev. Mol. Cell Biol. 15, 135-147 (2014).

Viswanathan, et al. "Dependency of a Therapy-Resistant State of Cancer Cells on a Lipid Peroxidase Pathway," Nature 2017, 547 (7664), 453. https://doi.org/10.1038/nature23007.

(Wolpaw AJ, et al.)

GPX1 (red); actin (green)

GPX4 (green); actin (red)

GPX4 (down), GFP-GPX4(up)
(green), actin (red)

Se supplementation
GPX4 (green); actin (red)

left 4 lanes: MG132, right 4 lanes: CHX
GPX4 (green); actin (red)

siTRIT1 treatment
GPX4 (green); actin (red)

pull-down with
active vs inactive probes pull-down with competition
GPX4 (green); marker (red)

cerivastain/MVA treatment
GPX4(green); actin (red)

the mevalonate pathway modulator
treatments; GPX4 (green) actin (red)

SMALL MOLECULE FERROPTOSIS INDUCERS

CROSS-REFERENCE TO RELATED APPLICATIONS

The present application is a continuation in part of PCT international application No. PCT/US2017/066822, filed Dec. 15, 2017, which claims priority to U.S. Provisional Patent Application No. 62/436,064, filed on Dec. 19, 2016. The entire contents of the aforementioned applications are incorporated by reference as if recited in full herein.

GOVERNMENT FUNDING

This invention was made with government support under grant no. CA097061, awarded by the National Institutes of Health. The government has certain rights in the invention.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

Ferroptosis is a non-apoptotic form of regulated cell death. Its relevance to certain pathological conditions has been reported, such as periventricular leukomalacia, nephrotic tubular death, and Huntington's disease (Skouta et al. 2014, Linkermann et al. 2014). It is distinct from other regulated cell death phenotypes, such as apoptosis and necroptosis (Berghe et al. 2014, Dixon et al. 2014). Ferroptosis is characterized by extensive lipid peroxidation, which can be suppressed by iron chelators or lipophilic antioxidants. Mechanistically, ferroptosis inducers are divided into two classes: (1) inhibitors of cystine import via system $x_c^-$ (e.g., erastin) (Dixon et al. 2012, Dixon et al. 2014), which subsequently causes depletion of glutathione (GSH) (Hayano et al. 2015), and (2) covalent inhibitors (e.g., (1S, 3R)-RSL3) of glutathione peroxidase 4 (GPX4) (Yang et al. 2014). Since GPX4 reduces lipid hydroperoxides using GSH as a co-substrate (Imai et al. 2003), both compound classes ultimately result in loss of GPX4 activity, followed by elevated levels of lipid reactive oxygen species (ROS) and consequent cell death.

There is some crosstalk among distinct regulated cell death phenotypes (Berghe et al. 2014, Linkermann et al. 2014). Each proposed cell death phenotype has generally been studied using different models (Hitomi et al. 2008). However, a universal comparison of different cell death phenotypes would be highly beneficial to understand the mechanisms governing cell death.

In view of the foregoing, there exists an ongoing need to provide new and improved compounds for regulating GPX4 and inducing ferroptosis in cells. The present disclosure is directed towards solving this and other needs.

SUMMARY

One embodiment of the present invention is a compound according to formula (I):

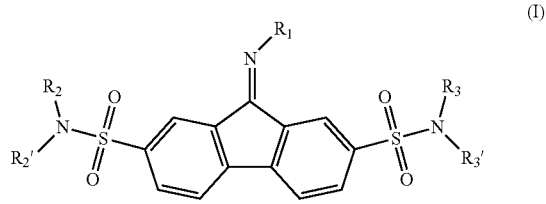

wherein:

$R_1$ is selected from the group consisting of H, OH, and —(OCH$_2$CH$_2$)$_x$OH;

X is an integer from 1 to 6; and $R_2$, $R_2'$, $R_3$, and $R_3'$ independently are selected from the group consisting of H, $C_{3-8}$cycloalkyl, and combinations thereof, or $R_2$ and $R_2'$ may be joined together to form a pyridinyl or pyranyl and $R_3$ and $R_3'$ may be joined together to form a pyridinyl or pyranyl;

or an N-oxide, crystalline form, hydrate, or pharmaceutically acceptable salt thereof; with the proviso that the compound is not

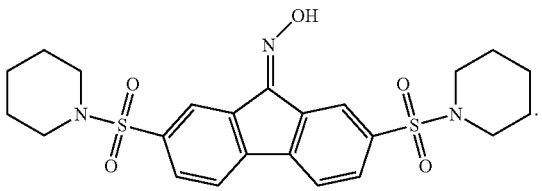 [SMILES: O=S(=O)(c1ccc2c(c1)C(=NO)c1cc(S(=O)(=O)N3CCCCC3)ccc1-2)N1CCCCC1]

Another embodiment of the present invention is a method for inducing ferroptosis in a cell. This method comprises contacting the cell with an effective amount of a compound having the structure of formula (I):

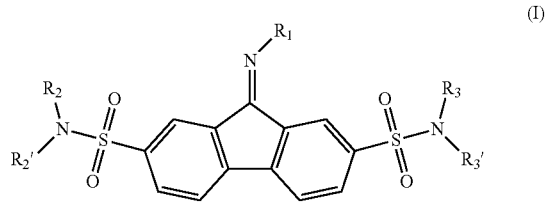

wherein:

$R_1$ is selected from the group consisting of H, OH, and —(OCH$_2$CH$_2$)$_x$OH;

X is an integer from 1 to 6; and $R_2$, $R_2'$, $R_3$, and $R_3'$ independently are selected from the group consisting of H, $C_{3-8}$cycloalkyl, and combinations thereof, or $R_2$ and $R_2'$ may be joined together to form a pyridinyl or pyranyl and $R_3$ and $R_3'$ may be joined together to form a pyridinyl or pyranyl;

or an N oxide, crystalline form, hydrate, or pharmaceutically acceptable salt thereof.

An additional embodiment of the present invention is a method for decreasing GPX4 in a cell. This method comprising contacting the cell with an effective amount of a compound having the structure of formula (I):

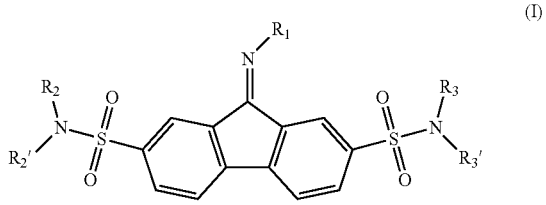

wherein:
  $R_1$ is selected from the group consisting of H, OH, and —$(OCH_2CH_2)_xOH$;
  X is an integer from 1 to 6; and
  $R_2$, $R_2'$, $R_3$, and $R_3'$ independently are selected from the group consisting of H, $C_{3-8}$cycloalkyl, and combinations thereof, or $R_2$ and $R_2'$ may be joined together to form a pyridinyl or pyranyl and $R_3$ and $R_3'$ may be joined together to form a pyridinyl or pyranyl;
or an N-oxide, crystalline form, hydrate, or pharmaceutically acceptable salt thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows the experimental scheme to identify regulated non-apoptotic cell death inducers with high modulatability. The numbers in red indicate the number of compounds satisfying each criterion.

FIG. 1B shows the hierarchical clustering of modulatory profiles of 10 CILs with high modulatability and 30 characterized lethal compounds from several classes of lethal mechanisms. Lethal compounds are listed on the right. Ten CILs are indicated by red shading. Forty-six modulators are listed along the bottom (28 death modulators in two cell lines, HT-1080 and BJeLR). Antioxidants (anti-ox) and iron chelators (Fe-chel) are indicated by brown shading. MoA, mechanism of action; Topo, topoisomerase.

FIG. 2A and FIG. 2E show the $HRAS^{G12V}$ selectivity. Viability of four engineered BJ cell lines treated with CIL56 (FIG. 2A) or FIN56 (FIG. 2E) for 48 h. mut, cells tumor-transformed as a result of $HRAS^{G12V}$ overexpression; wt, isogenic cells without $HRAS^{G12V}$.

FIG. 2B shows the lipid RoS generation. Flow cytometry analysis with BODIPY-581/591 $C_{11}$ staining in HT-1080 cells incubated with test compounds for 6 h. DFOM, 152 μM deferoxamine.

FIG. 2C and FIG. 2F show the effects of ferroptosis inhibitors on viability of HT-1080 cells cotreated with CIL56 (FIG. 2C) or FIN56 (FIG. 2F) for 48 h. αtoc, 100 μM α-tocopherol; U0126 was applied at 3.8 μM.

FIG. 2D shows the chemical structures of CIL56 and FIN56.

Experiments for FIGS. 2A-2F were performed in biological triplicate, and data are presented as mean±s.e.m. of technical triplicates.

FIGS. 3A-3F show that FIN56-induced ferroptosis decreases GPX4 expression.

Figure 3A:
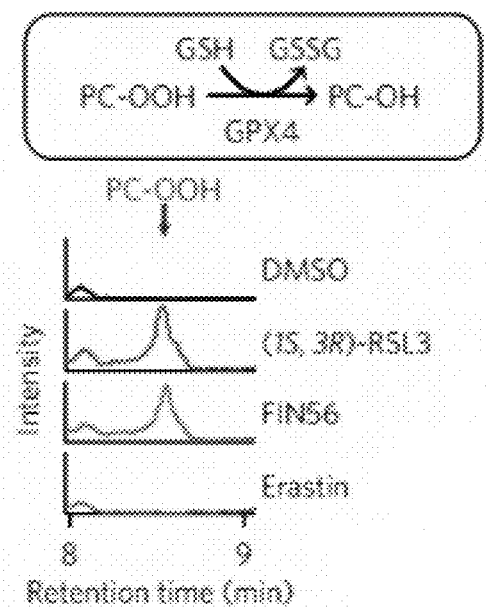

FIG. 3A shows the GPX4 enzymatic activity in BJeLR cells after ferroptosis-inducer treatment. GSSG, oxidized glutathione; PC, phosphatidylcholine.

Figure 3B:
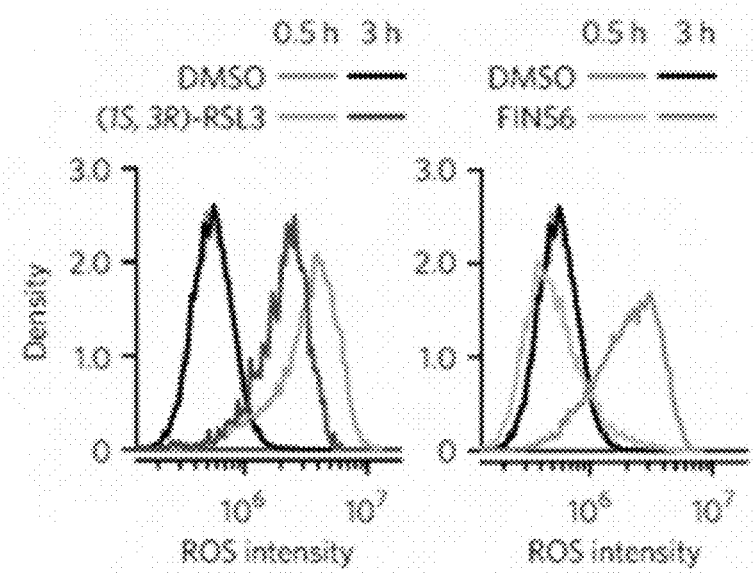

FIG. 3B shows the kinetics of ROS generation after treatment with 0.5 μM (1S, 3R)-RSL3 or 5 μM FIN56, detected with 25 μM $H_2$-DCFDA staining in BJeLR cells.

Figure 3C:
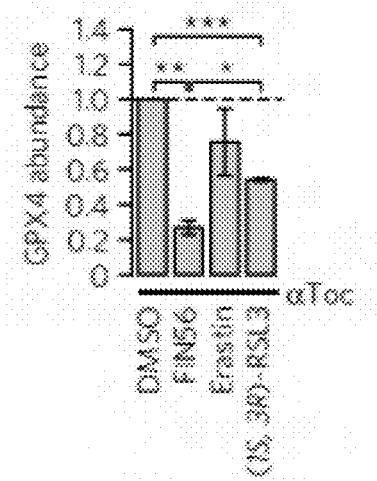

FIG. 3C shows the GPX4 protein abundance in BJeLR cells after cotreatment with 100 μM α-tocopherol and ferroptosis inducers for 10 h.

Figure 3D:
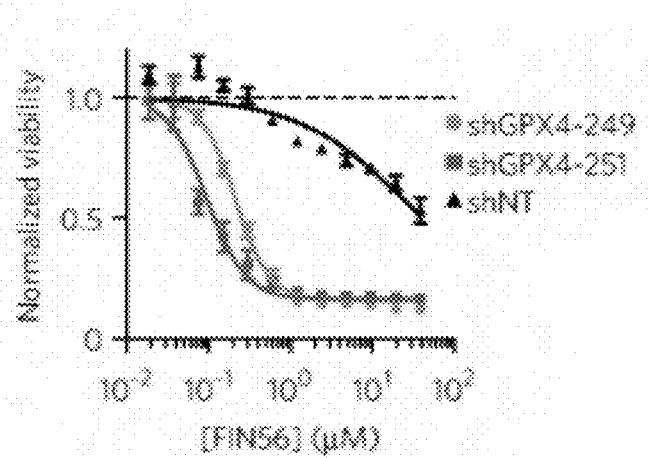

FIG. 3D shows the effect of shRNA targeting GPX4 (shGPX4) on FIN56-induced ferroptosis in BJeLR cells. shNT, nontargeting shRNA.

Figure 3E:
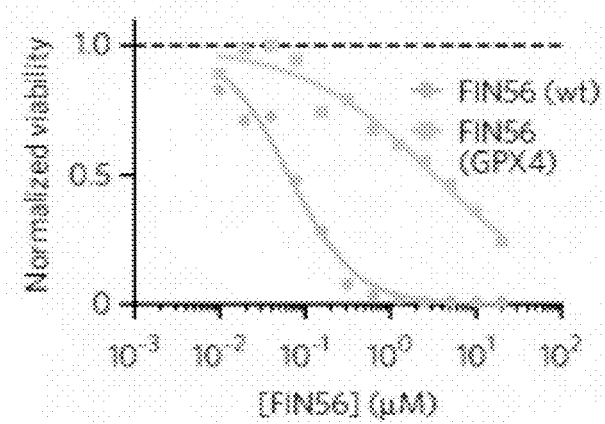

FIG. 3E shows the effects of GFP-GPX4 fusion-protein overexpression on sensitivity to FIN56 in BJeLR cells.

Figure 3F:
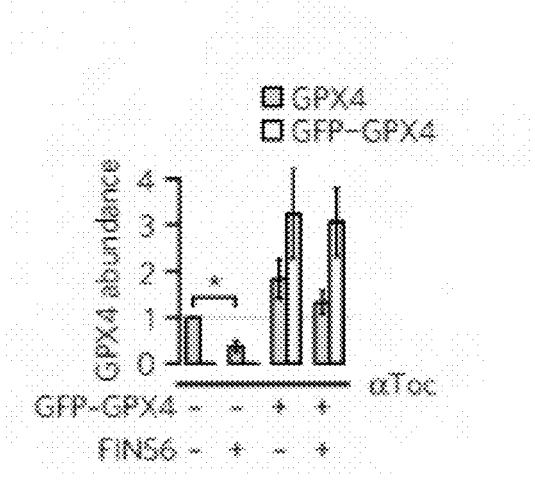

FIG. 3F shows the effects of GFP-GPX4 fusion-protein overexpression on endogenous and exogenous GPX4 protein abundance after FIN56 treatment.

Experiments in FIGS. 3A-3F were done in biological triplicate. Representative results are shown for FIG. 3A, FIG. 3B and FIG. 3E; data in FIG. 3C and FIG. 3F are the mean±s.e.m. of biological triplicates, in which *P<0.05, P<0.005, *P<0.0005 (paired two-tailed t-test); data in FIG. 3D are the mean±s.e.m. of technical triplicates.

FIGS. 4A-4D show the SQS encoded by FDFT1 as FIN56's target protein.

Figure 4A:
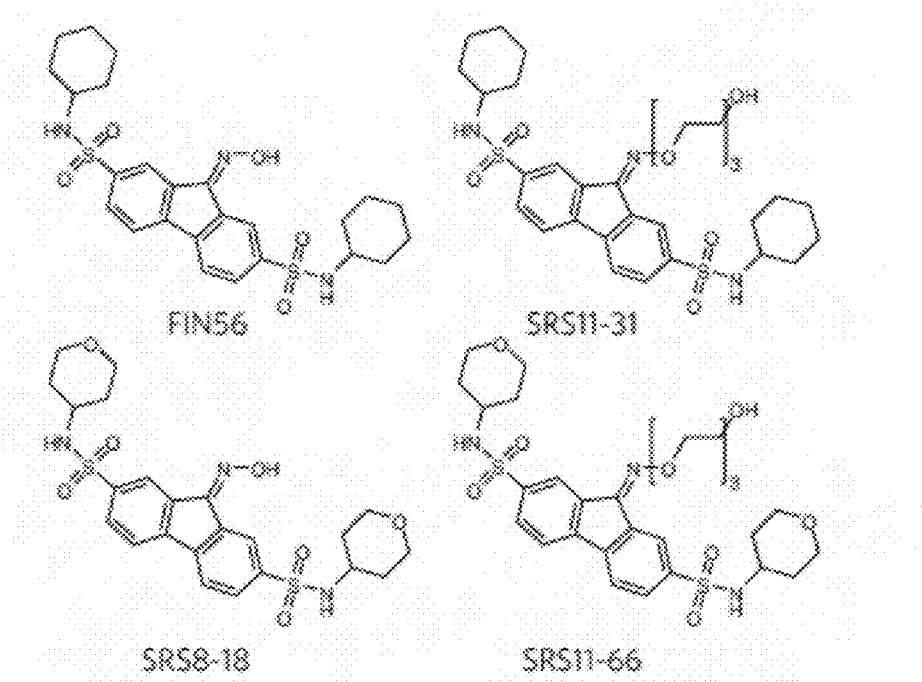

FIG. 4A shows the structures of active and inactive FIN56 analogs with PEG linkers.

Figure 4B:
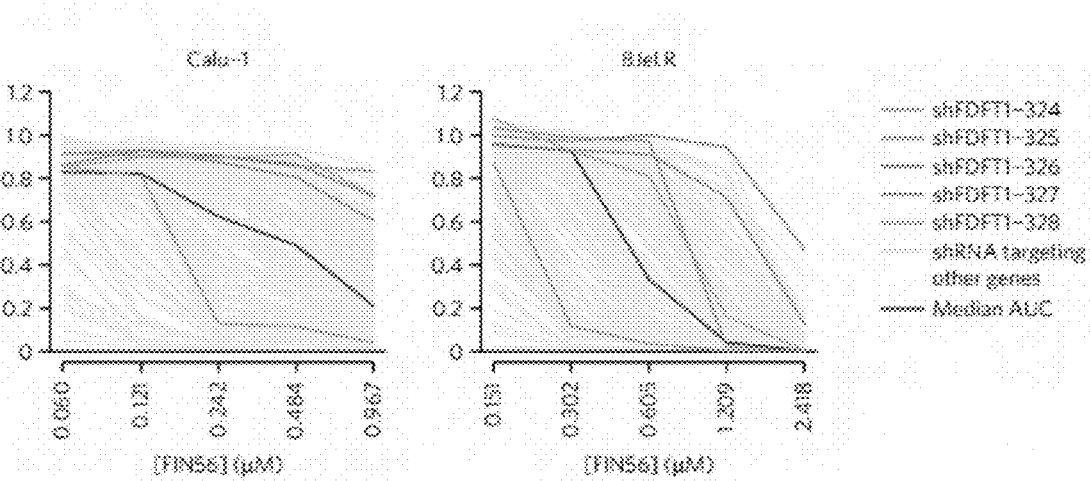

FIG. 4B shows the effects of five shRNAs against FDFT1 on FIN56. Results in two of the four cell lines are shown. The black line in each graph (median AUC among tested shRNAs) represents a shRNA that had no effect in each cell line.

Figure 4C:
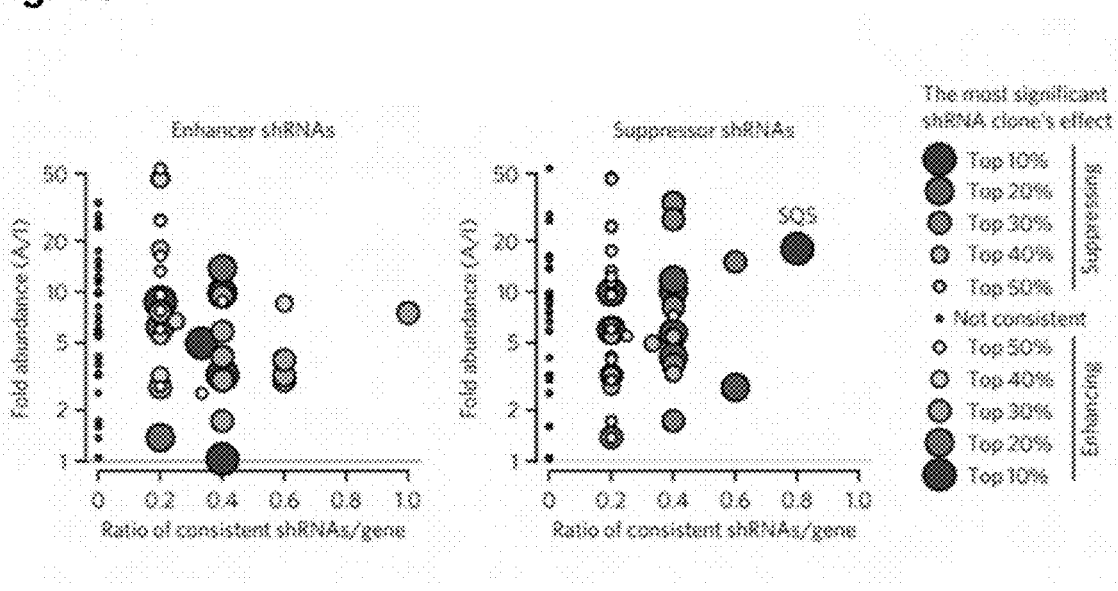

FIG. 4C shows the summary of proteomic target identification and effect of shRNA screening targeting 70 identified genes on FIN56. Each dot summarizes the result of multiple shRNAs targeting a gene. Each shRNA was considered 'consistent' when it exerted the indicated effect (enhancing or suppressing FIN56). X-axis represents the ratio of the number of consistent shRNAs inducing the indicated effect (i.e., enhancing or suppressing FIN56) to the total number of shRNAs targeting the gene. Y-axis shows fold enrichment of protein abundance on active versus inactive probe beads in a pulldown assay.

Figure 4D:
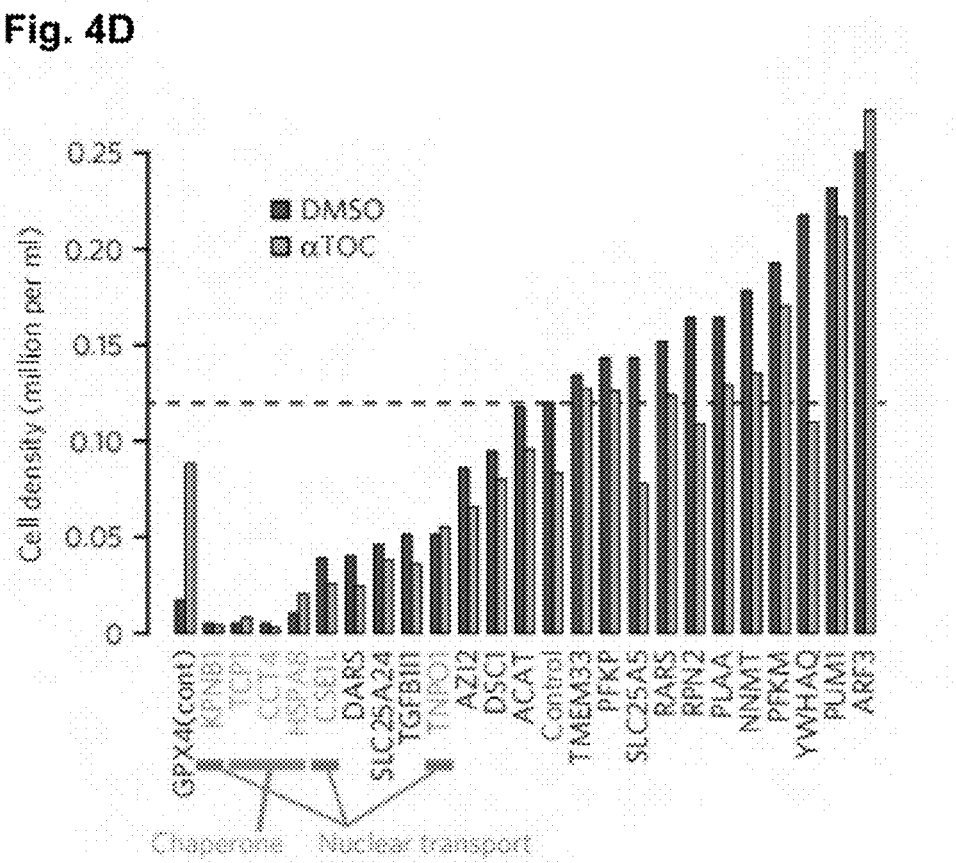

FIG. 4D shows the effect of siRNAs against loss-of-function candidates on BJeLR cell viability. Cells were grown in the presence of DMSO or α-tocopherol.

shRNA screens in FIG. 4B and FIG. 4C were performed once in four cell lines. The siRNA experiment in FIG. 4D was performed in BJeLR twice, and results indicate the mean of biological replicates.

FIGS. 5A-5H show the results of validating SQS as the functionally relevant target for FIN56's lethality.

Figure 5A:
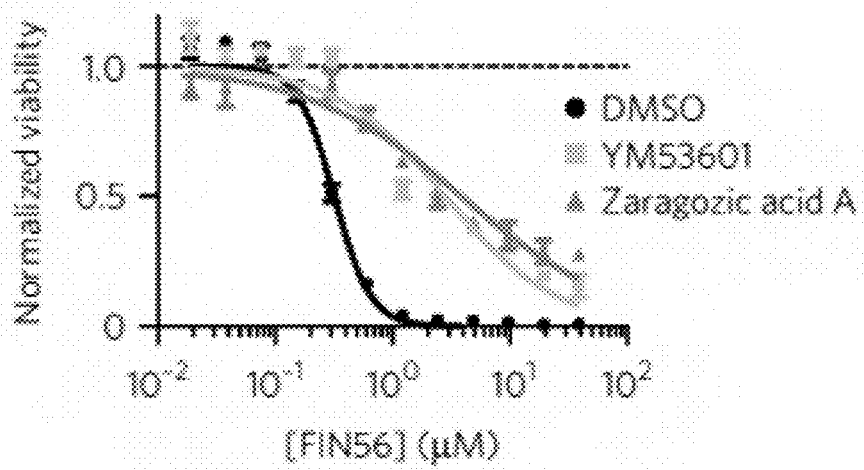

FIG. 5A shows the effects of chemical inhibitors of SQS on FIN56's lethality.

Figure 5B:
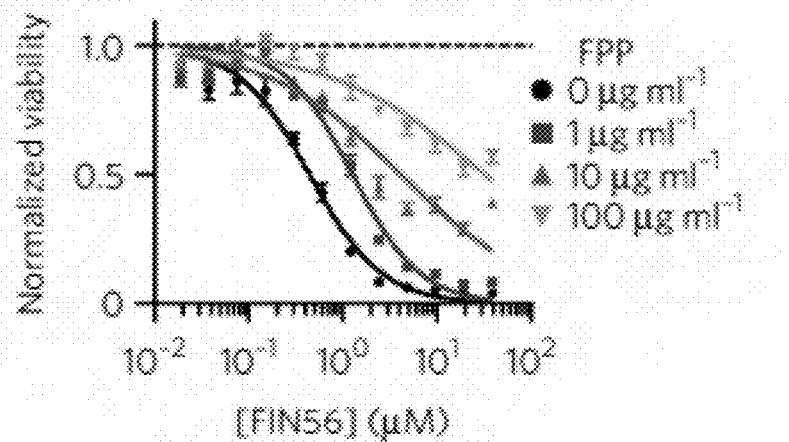

FIG. 5B shows the effects of FPP on FIN56's lethality.

Figure 5C:
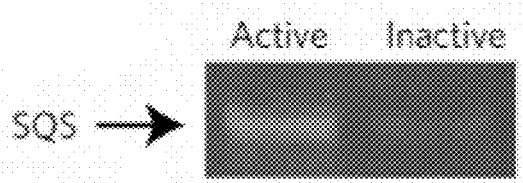

FIG. 5C shows the detection of SQS via pulldown assay from HT-1080 whole-cell lysate with active or inactive probes. Note that the probes are the same as those used for chemoproteomic target identification.

Figure 5D:
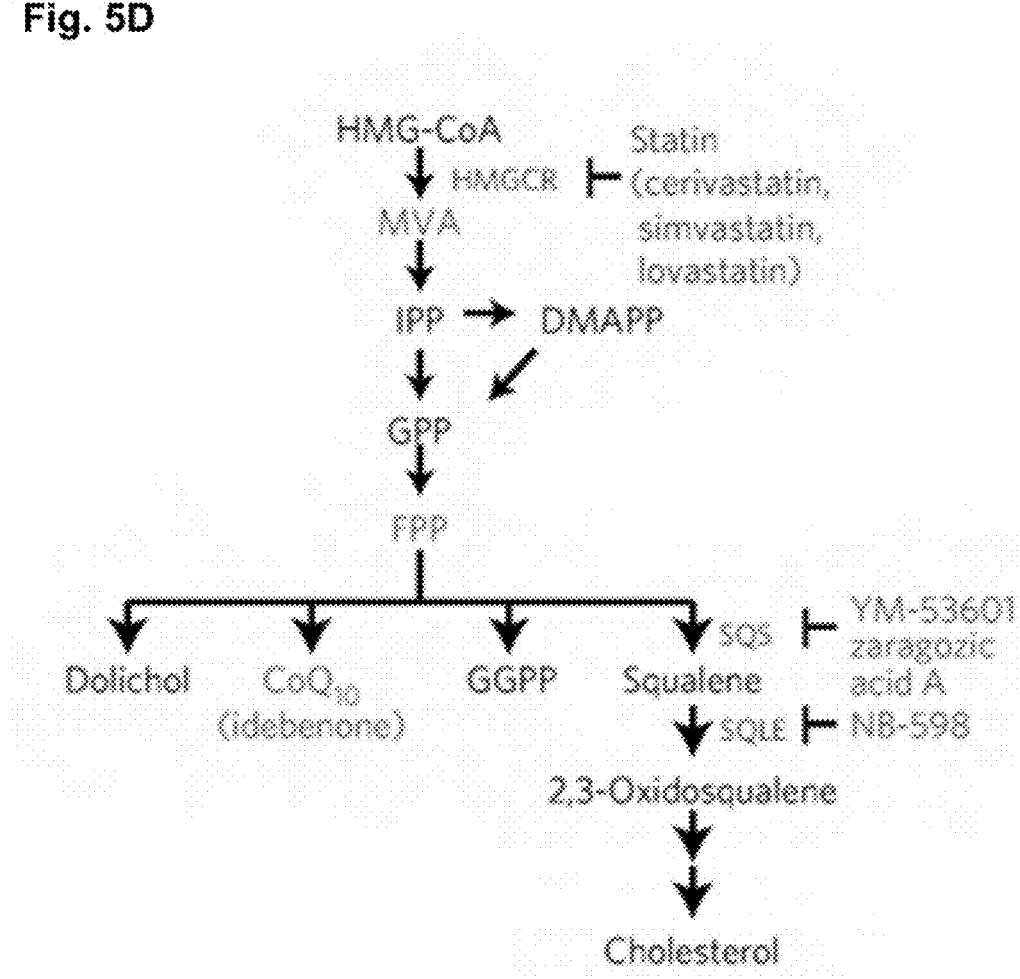

FIG. 5D shows the schematic of the mevalonate pathway. The larger font indicates metabolites, and the smaller font indicates enzymes responsible for the reactions or small molecules. Red or blue text indicates molecules (inhibitors or metabolites) that suppressed or enhanced FIN56's lethality, respectively. The detailed results are shown in FIG. 5E and FIG. 5F.

Figure 5E:
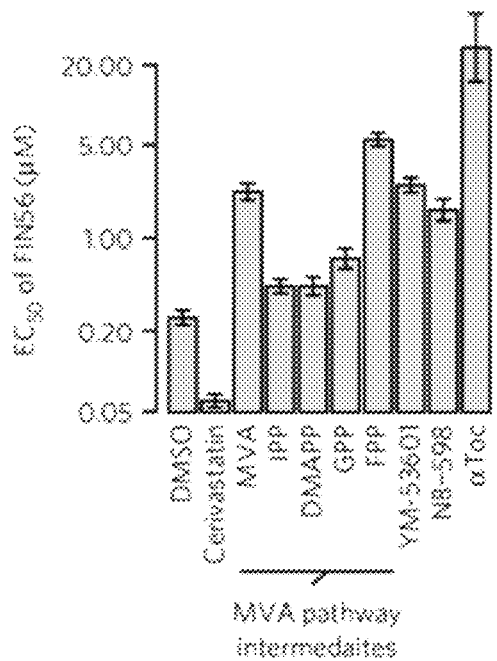

FIG. 5E shows the perturbation of the mevalonate pathway and effects on FIN56's lethality. Concentrations: cerivastatin, 1 µM; metabolites, 100 µM; YM-53601, 5 µM; NB-598, 25 µM; α-tocopherol, 100 µM.

Figure 5F:
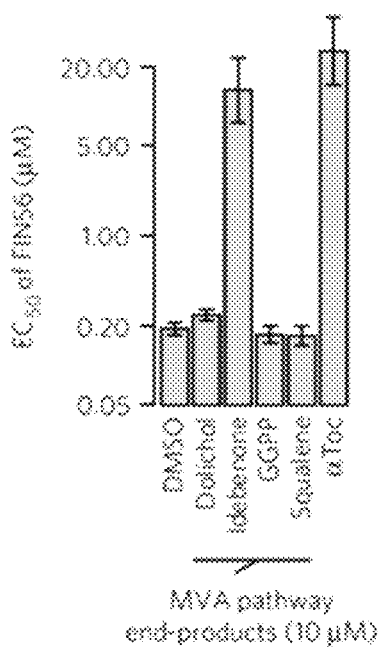

FIG. 5F shows the supplementation of 10 µM end-products of the MVA pathway and their effects on FIN56.

Figure 5G:
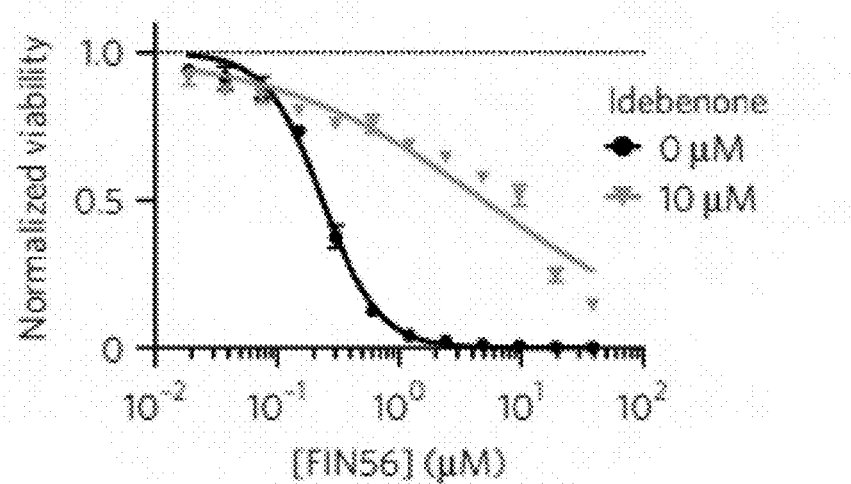

FIG. 5G shows the effect of 10 µM idebenone on FIN56 in HT-1080 cells.

Figure 5H:
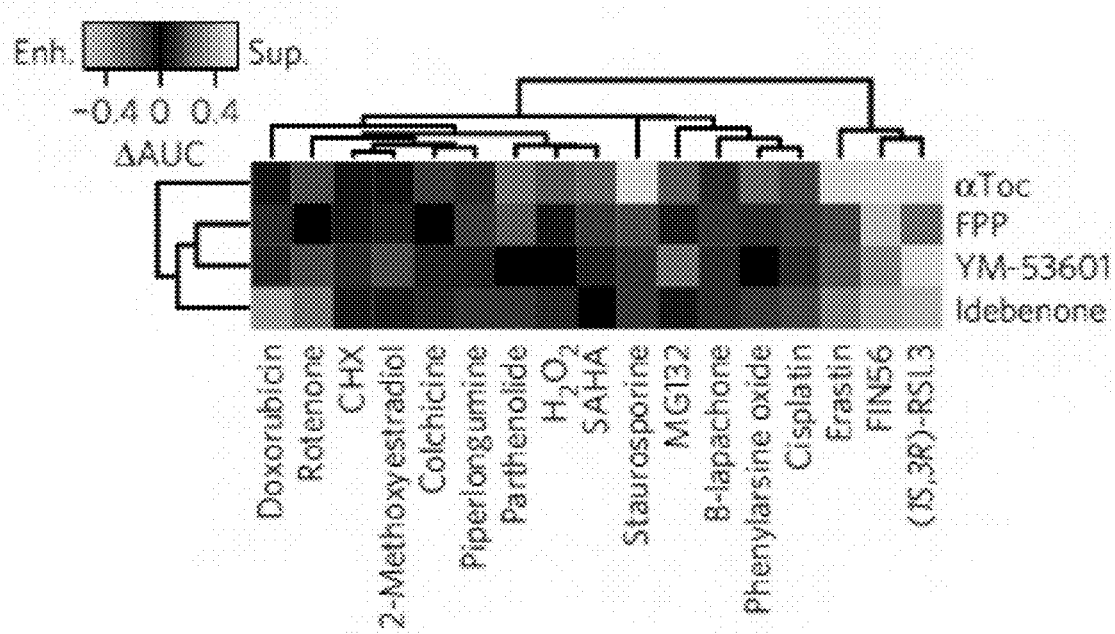

FIG. 5H shows the modulatory profiling between the modulators of the MVA pathway and various lethal compounds inducing oxidative stress. Enh, enhancement; sup., suppression; IPP, isopentenyl-pyrophosphate (PP); DMAPP, dimethylallyl-PP; GPP, geranyl-PP; FPP, farnesyl-PP; GGPP, geranylgeranyl-PP.

Experiments shown in FIG. 5A, FIG. 5B and FIG. 5G were performed in biological replicates, and data are presented as mean±s.e.m. of technical triplicates; experiments shown in FIG. 5E and FIG. 5F were performed in biological duplicates, and data are presented as mean±s.e. of $EC_{50}$ estimation from sigmoidal curve-fitting; experiment shown in FIG. 5H was performed in singlicate.

FIGS. 6A-6D show that ACC inhibitor prevents GPX4 protein degradation.

Figure 6A:
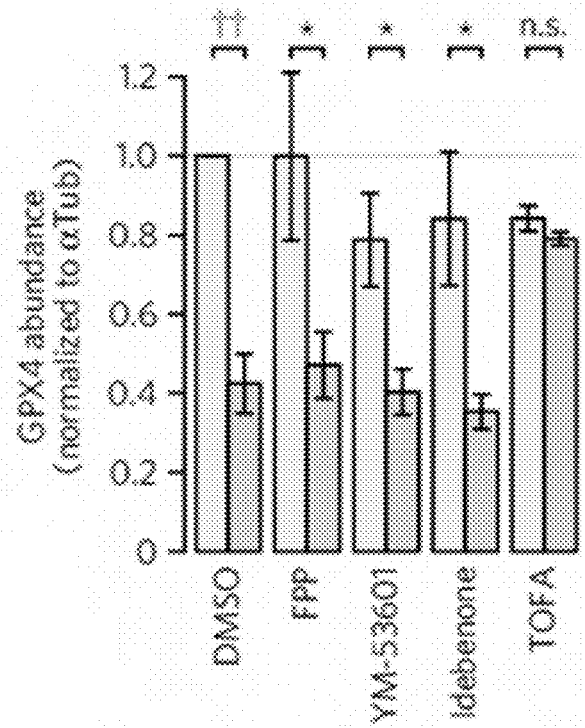

FIG. 6A shows the effects of mevalonate pathway modulators and ACC inhibitor on GPX4 abundance with 0.1% DMSO (green) or 5 µM FIN56 (yellow). αTub, α-tubulin. *P<0.05, †† P<0.001 (paired two-tailed t-test); n.s., not significant. Modulator concentrations: DMSO, 0.1%; FPP, 10 µM; YM-53601, 5 µM; idebenone, 10 µM; TOFA, 10 µM.

Figure 6B:
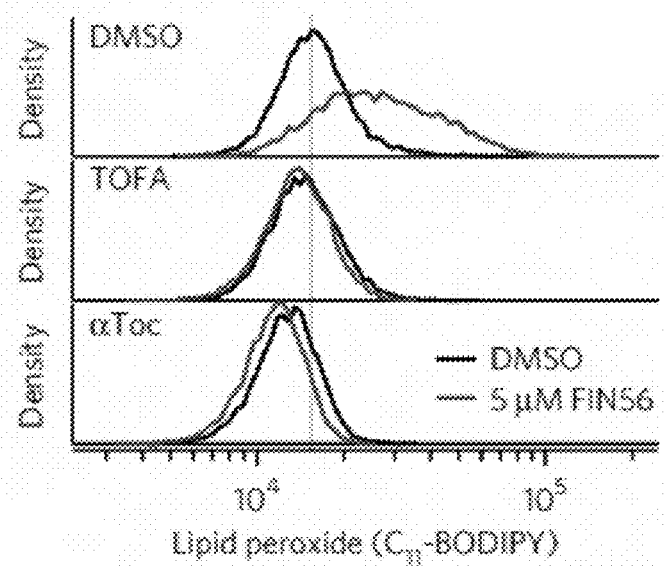

FIG. 6B shows the lipid peroxide levels after treatment with DMSO, TOFA or α-tocopherol.

Figure 6C:
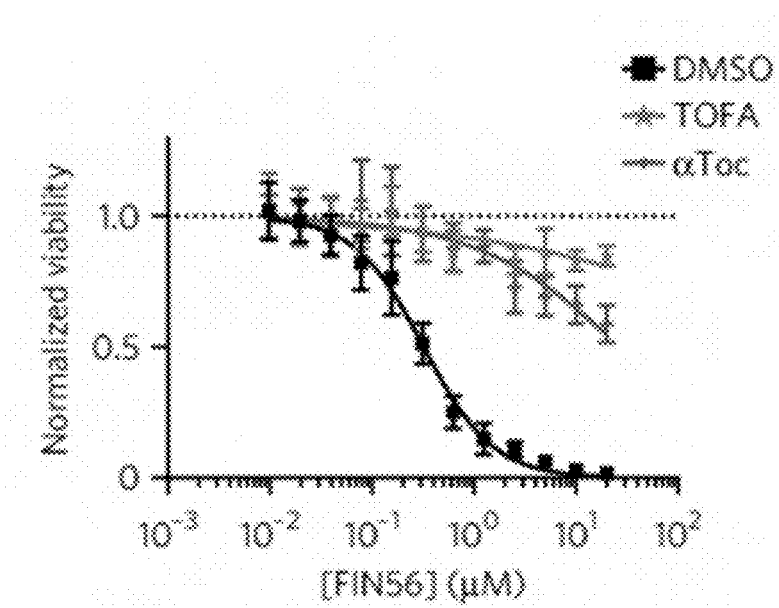

FIG. 6C shows the effects of TOFA and α-tocopherol on FIN56 lethality.

Figure 6D:
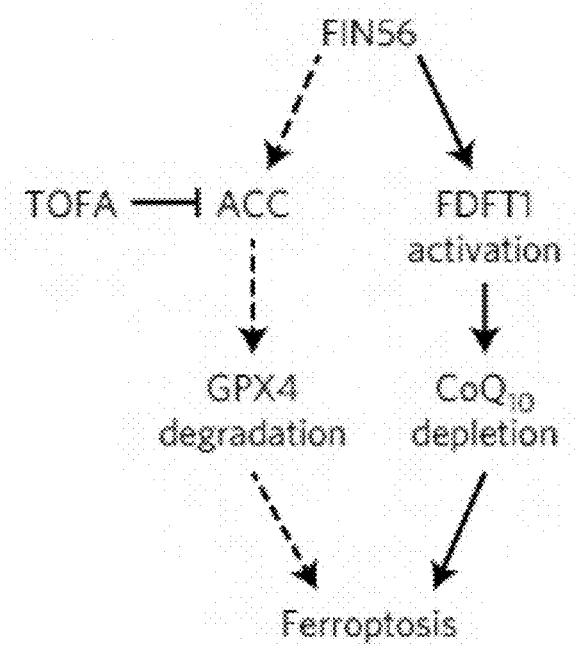

FIG. 6D shows the model of FIN56's mechanism of action. Dashed arrows indicate that the mechanistic details are still elusive.

Experiments for FIGS. 6A-6C were performed in biological triplicates. Data in FIG. 6A and FIG. 6C are presented as the mean±s.e.m. of triplicates; single representative results are shown in FIG. 6B.

FIGS. 7A-7D show the screening for caspase-3/7 independent lethal compounds (CIL).

Figure 7A:
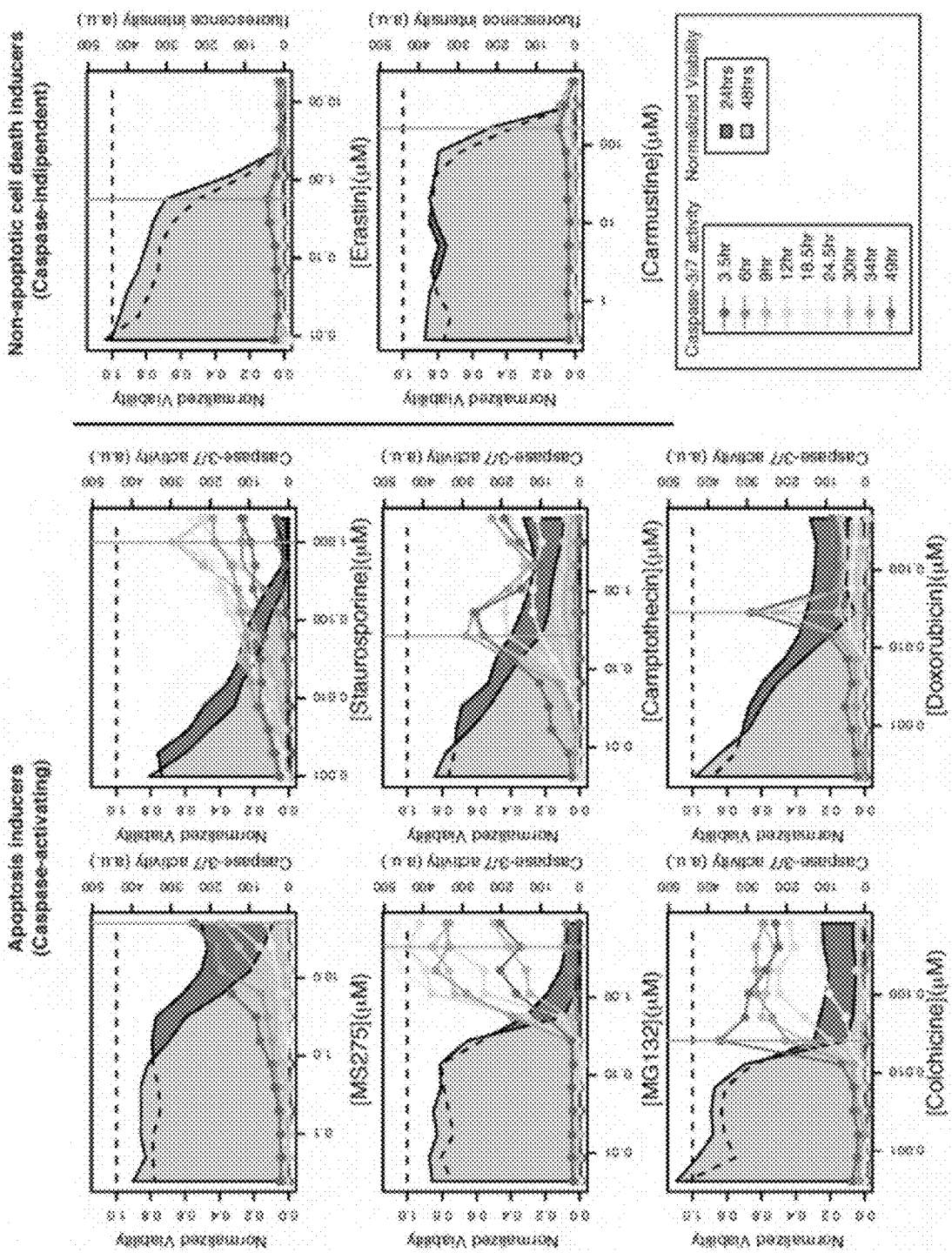

FIG. 7A shows the caspase-3/7 activation assay (Apo-ONE Homogeneous caspase-3/7Assay). Six apopotetic and two non-apoptotic inducers were tested to optimize the assay conditions for screening. Grey area represents normalized viability 24 or 48 hrs after lethal compound treatment, and the colored lines indicate Apo-ONE fluorescent signals after indicated time points. Vertical orange lines indicate concentrations shown in FIG. 7B.

Figure 7B:
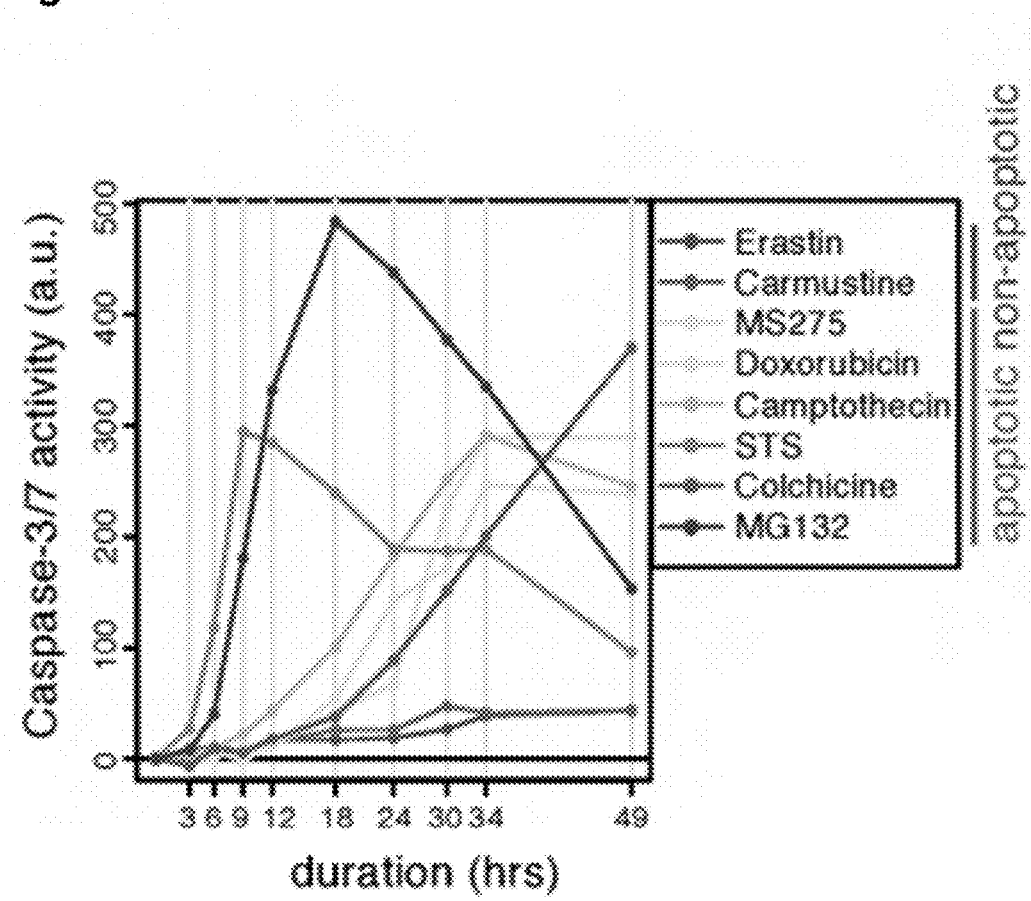

FIG. 7B shows the kinetics of Apo-ONE fluorescence intensity upon lethal compound treatment.

Figure 7C:
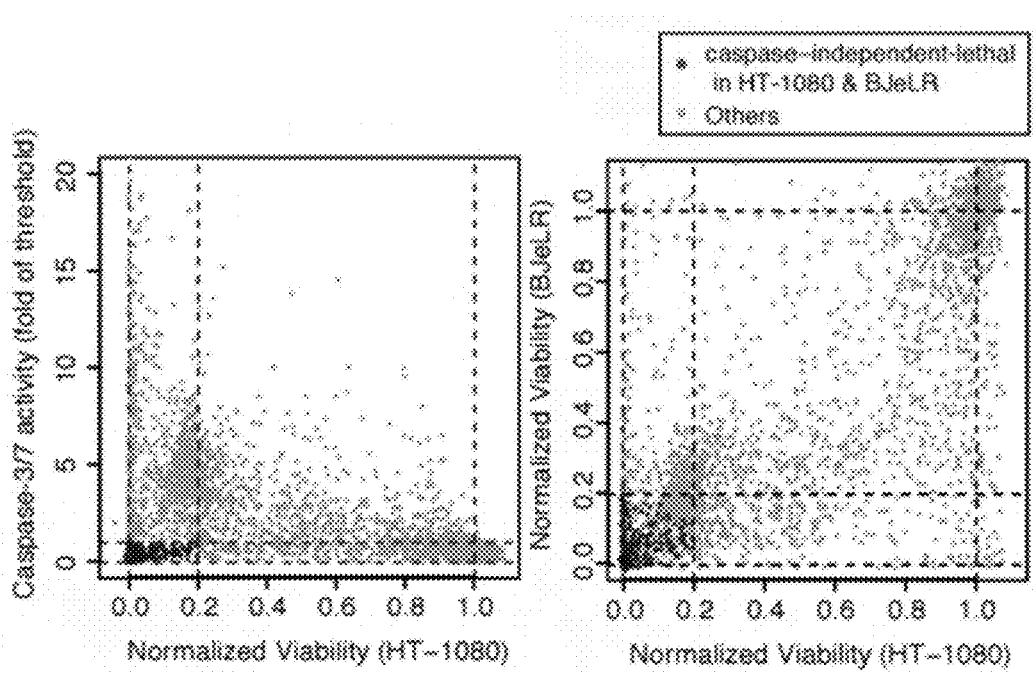

FIG. 7C shows the summary of chemical screening of 3,169 compounds for caspase-independent lethality in two cell lines, HT-1080 and BJeLR cells. Blue dots represent CILs.

Figure 7D:
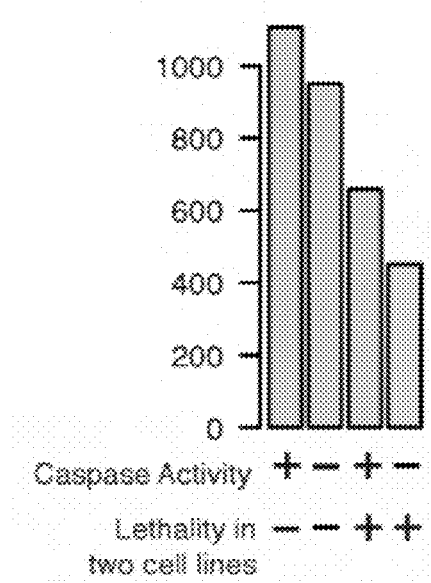

FIG. 7D shows the statistical summary of screening. The numbers of compounds lethal in both HT-1080 and BJeLR cells and/or activating caspase-3/7 are shown.

Viability and Caspase-activity in FIG. 7A were tested in duplicates; representative results were shown. Screening in FIG. 7C was performed once. Plots in FIG. 7B and FIG. 7D were generated from FIG. 7A and FIG. 7C, respectively.

FIGS. 8A-8E show the modulatory profiling scheme and modulatability.

Figure 8A:
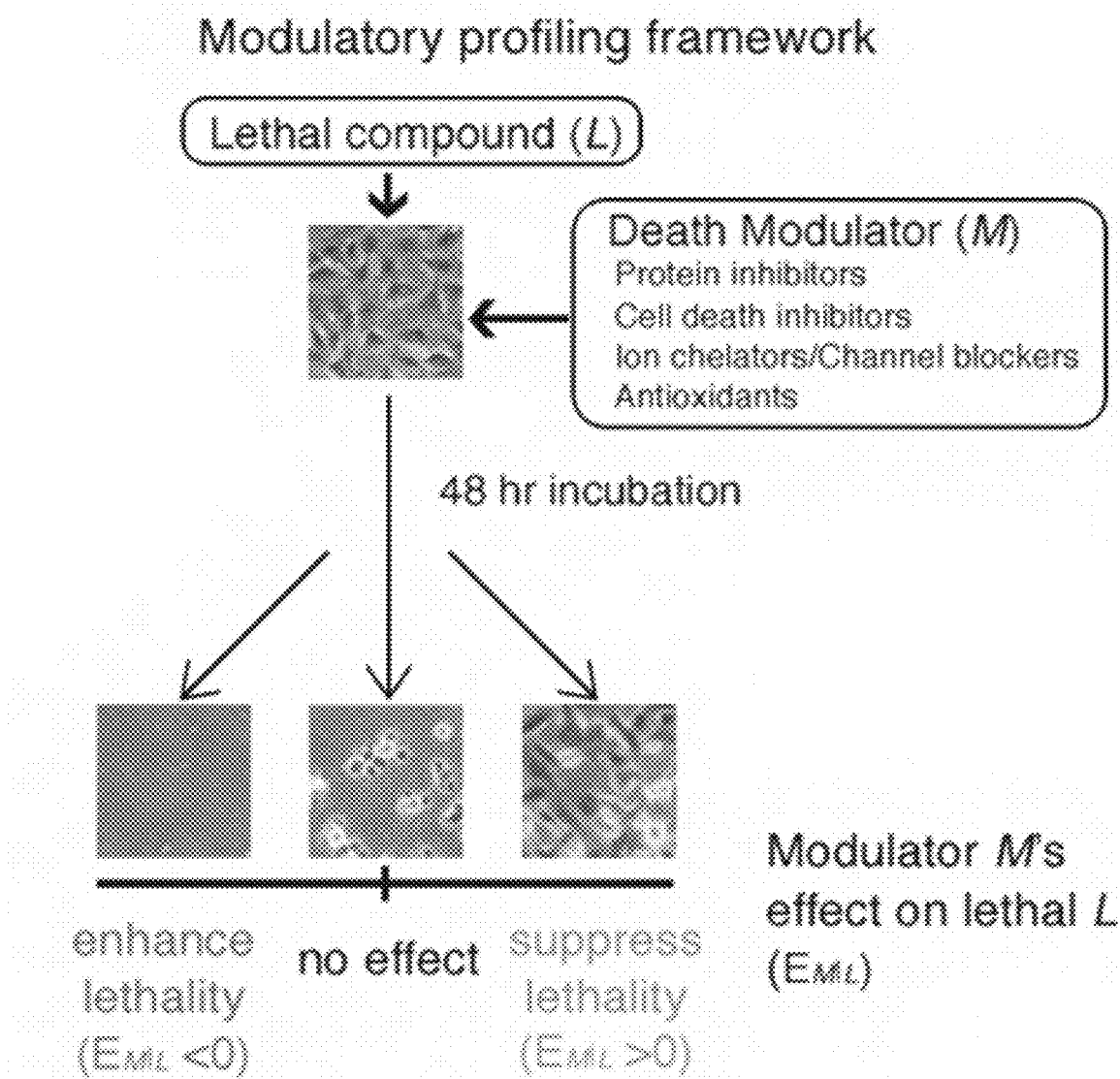

FIG. 8A shows the scheme of the modulatory profiling experiment. Two cell lines (HT-1080 and BJeLR) were co-treated with a lethal compound and a death modulator.

Figure 8B:
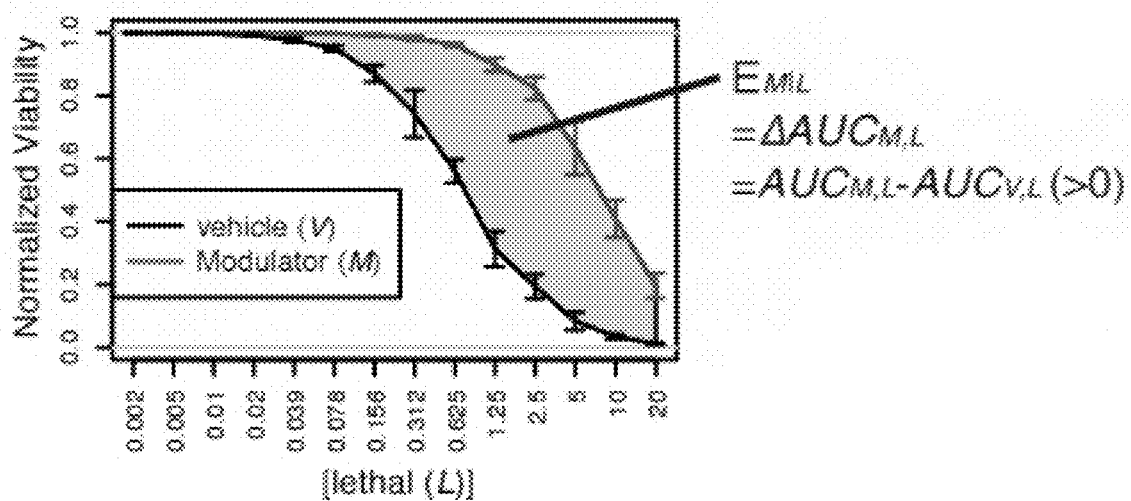

FIG. 8B shows that the modulator (M)'s effect (EMIL) on the lethal compound (L) was assessed by computing a difference of areas under two dose-response curves (EM|L=AUCmodulator−AUCvehicle).

Figure 8C:
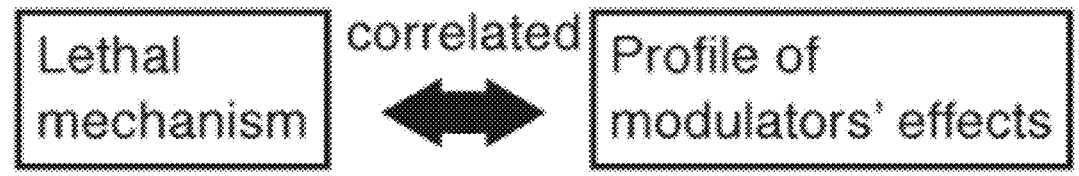

FIG. 8C shows relationship between modulatory profiles and mechanism of action. In Wolpaw et al. 2011, modulatory profiles of lethals were correlated with their mechanisms of actions.

Figure 8D:
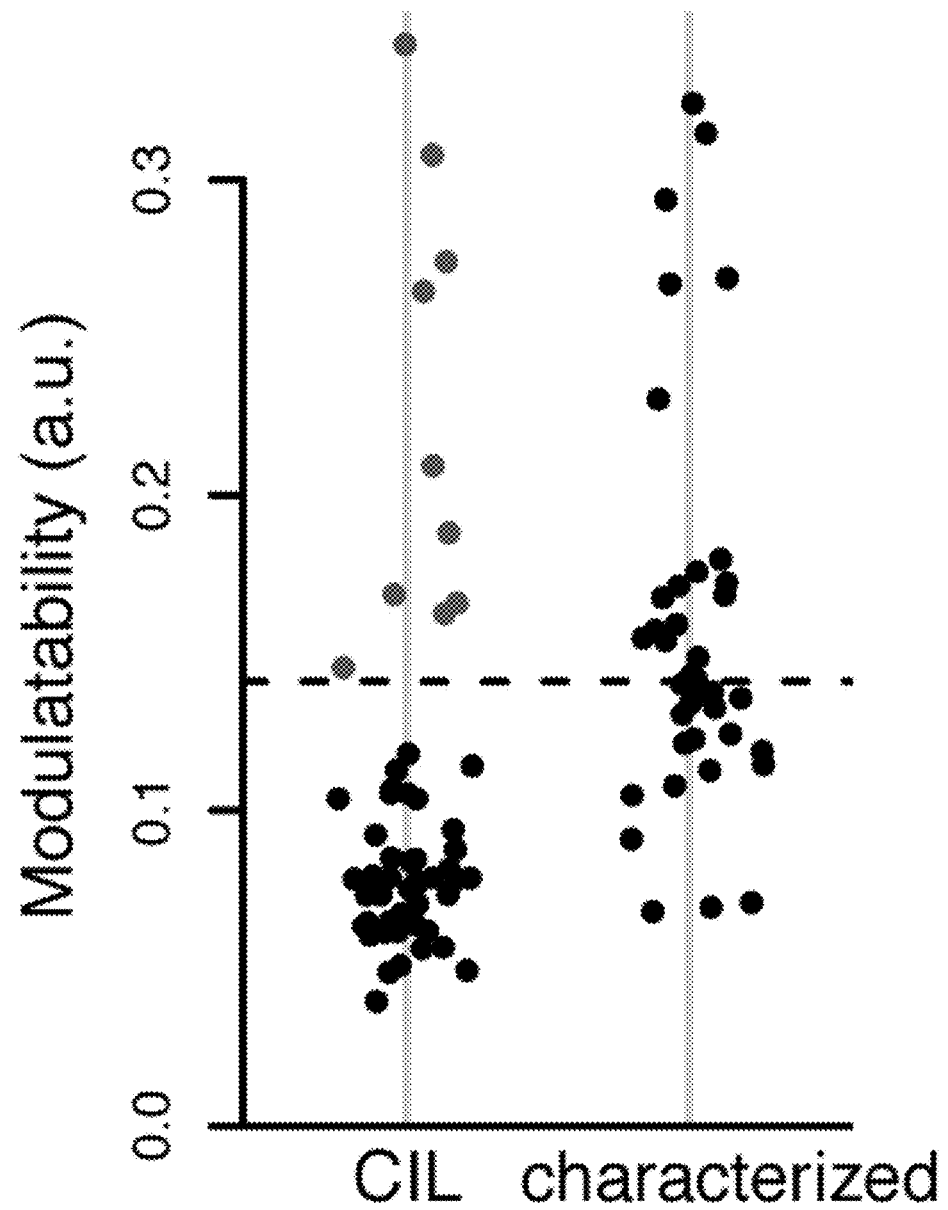

FIG. 8D shows the modulatability of 56 CILs and 30 characterized compounds. The dashed line represents the median value of the modulatability of characterized compounds. Ten CILs above the line (red dots) were defined as CILs with high modulatability, which were expected to activate specific pathway(s) to induce cell death.

Figure 8E:
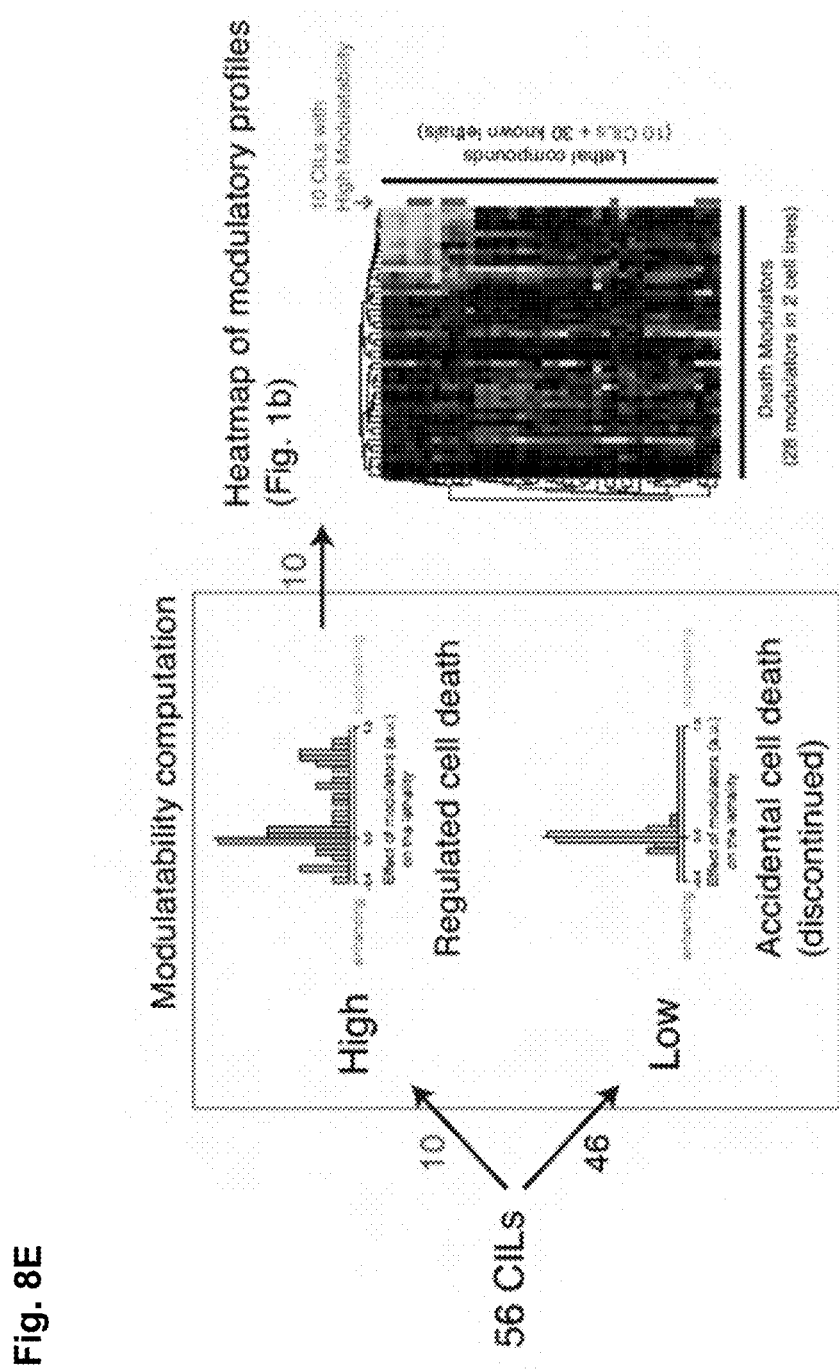

FIG. 8E shows the scheme describing how modulatability of lethal compounds is associated with specific regulated cell-death.

Plot in FIG. 8D was generated from the modulatory profiles (see FIG. 1B) and done once.

FIGS. 9A-9E show that CILs with high modulatability were functionally clustered into three classes.

Figure 9A:
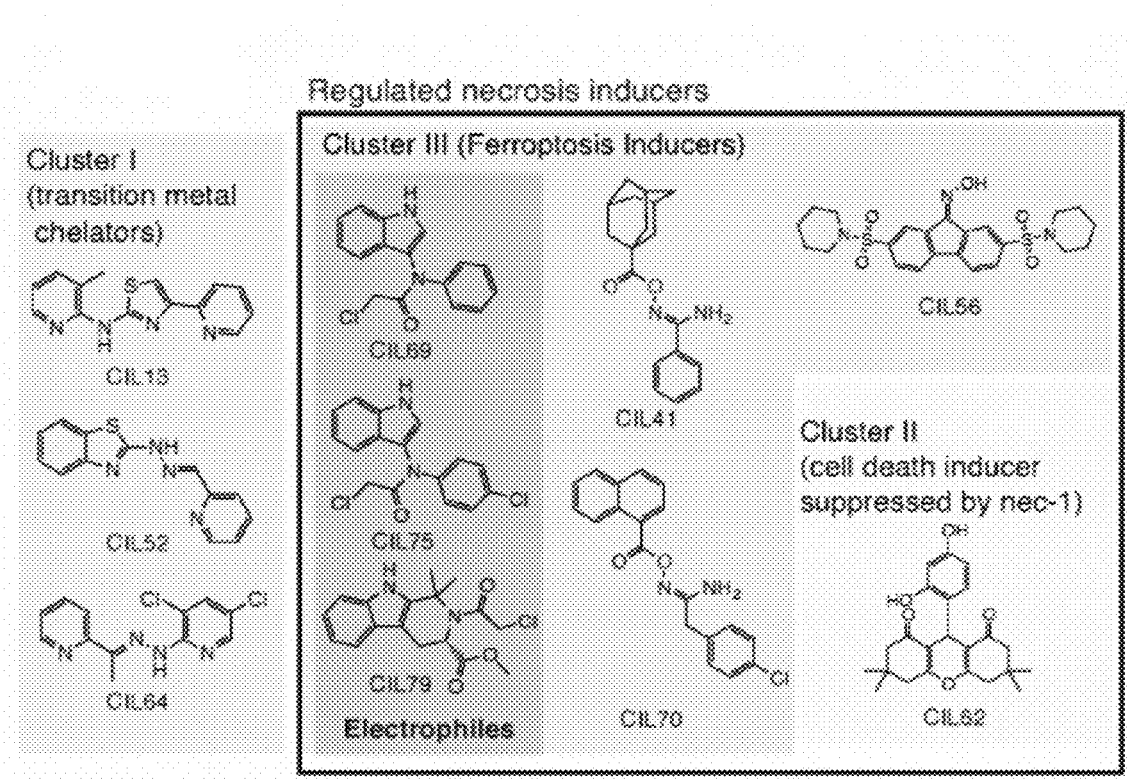

FIG. 9A shows the chemical structures of the ten CILs with high modulatability. The background colors of the compounds correspond to the clusters in FIG. 1B.

Figure 9B:
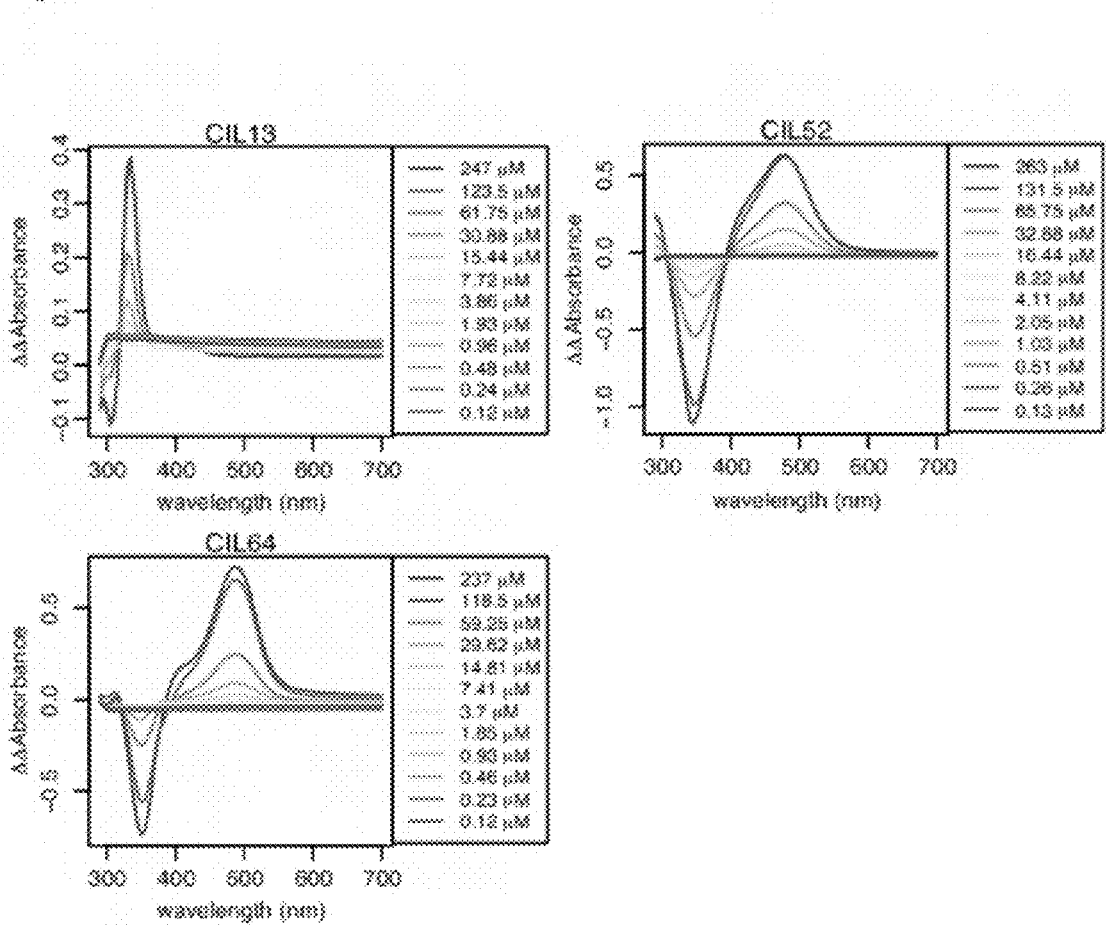

FIG. 9B shows the changes in absorbance spectrum of each compound upon cobalt (II) supplementation in vitro.

Figure 9C:
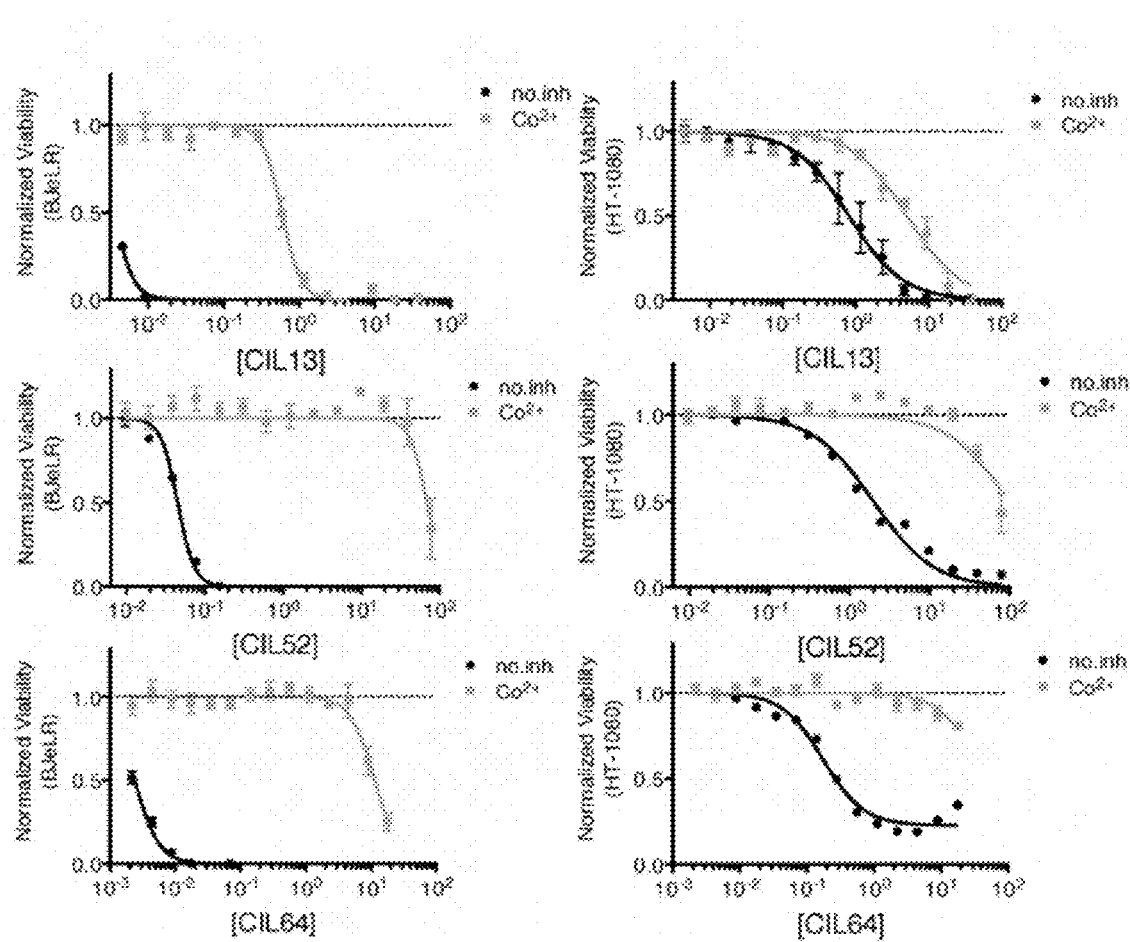

FIG. 9C shows the suppression of CIL13, 52 and 64 with the supplementation of $CoCl_2$.

Figure 9D:
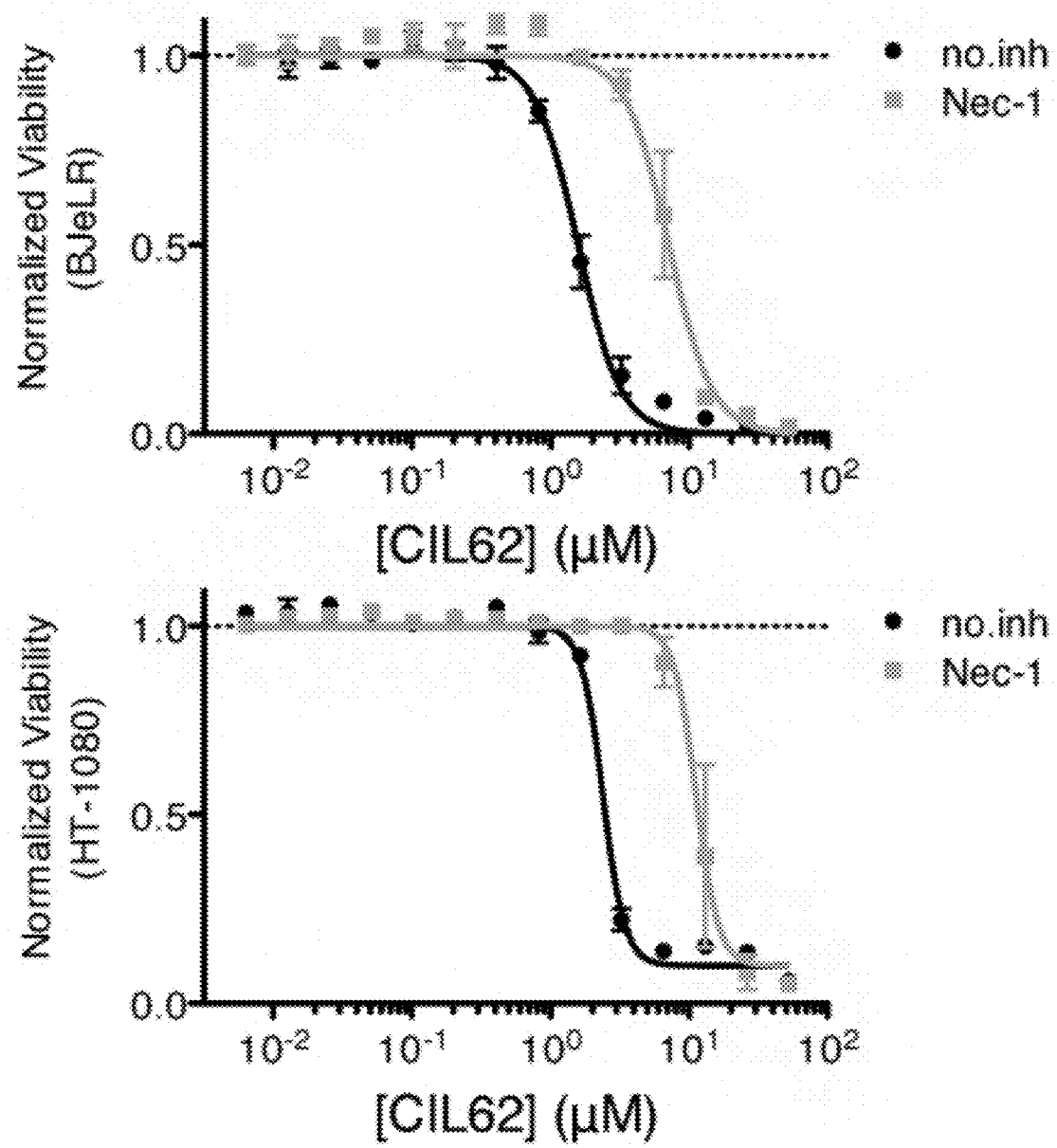

FIG. 9D shows that 19 µM (5 µg/mL) Necrostatin-1 (Nec-1) suppressed CIL62.

Figure 9E:
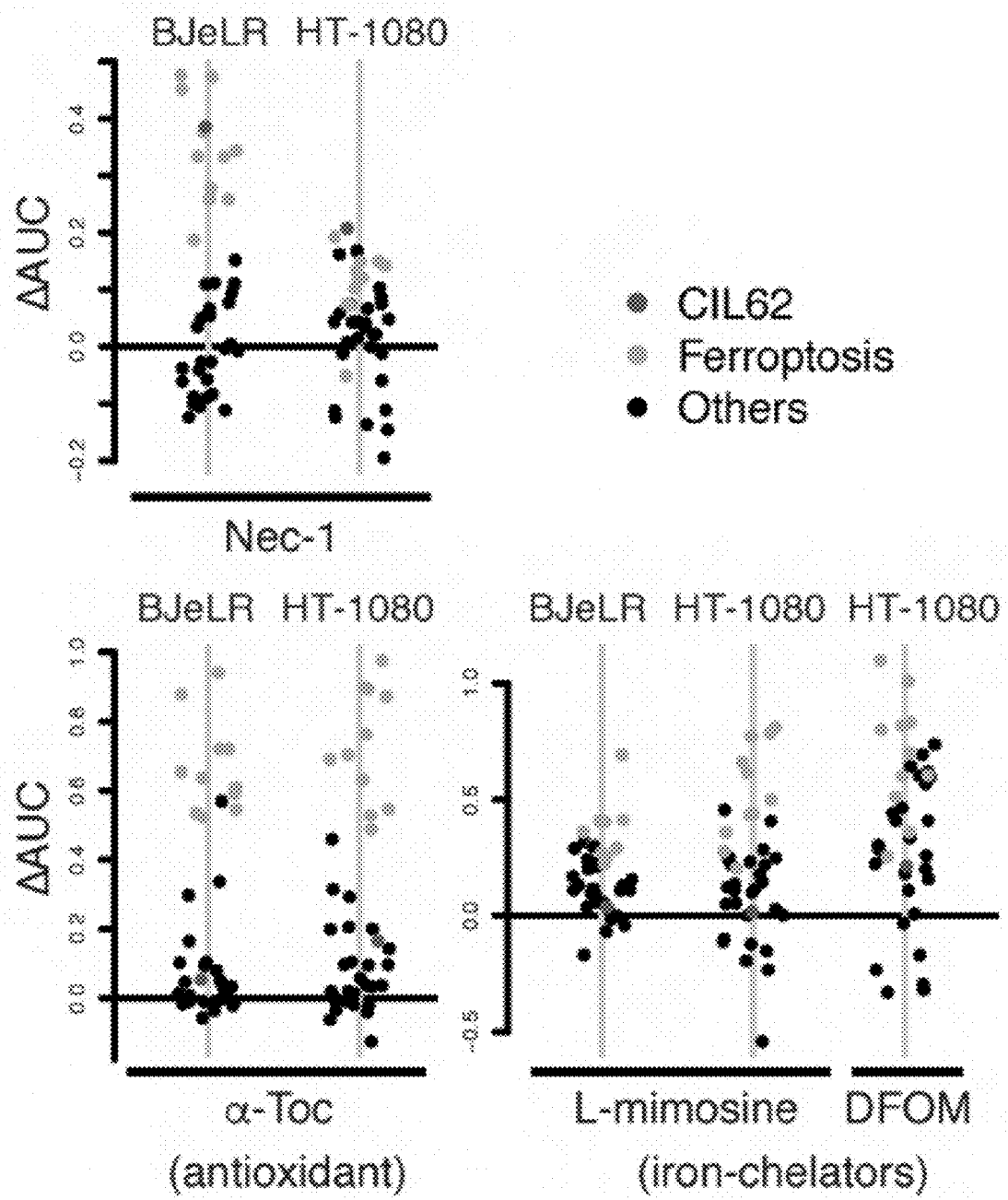

FIG. 9E shows that both CIL62 (red) and ferroptosis inducers (orange) were suppressed by 19 µM Nec-1, but CIL62 was not suppressed by the ferroptosis inducers (anti-oxidants or iron-chelators).

Figure 1A:
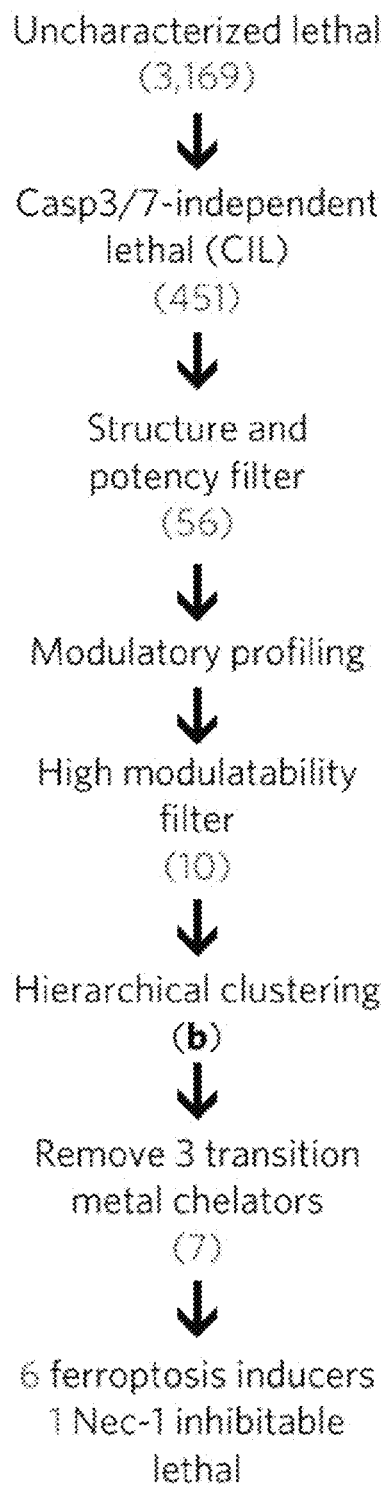
FIGS. 1A-1B show that modulatory profiling revealed three types of regulated non-apoptotic cell death.
Figure 1B:
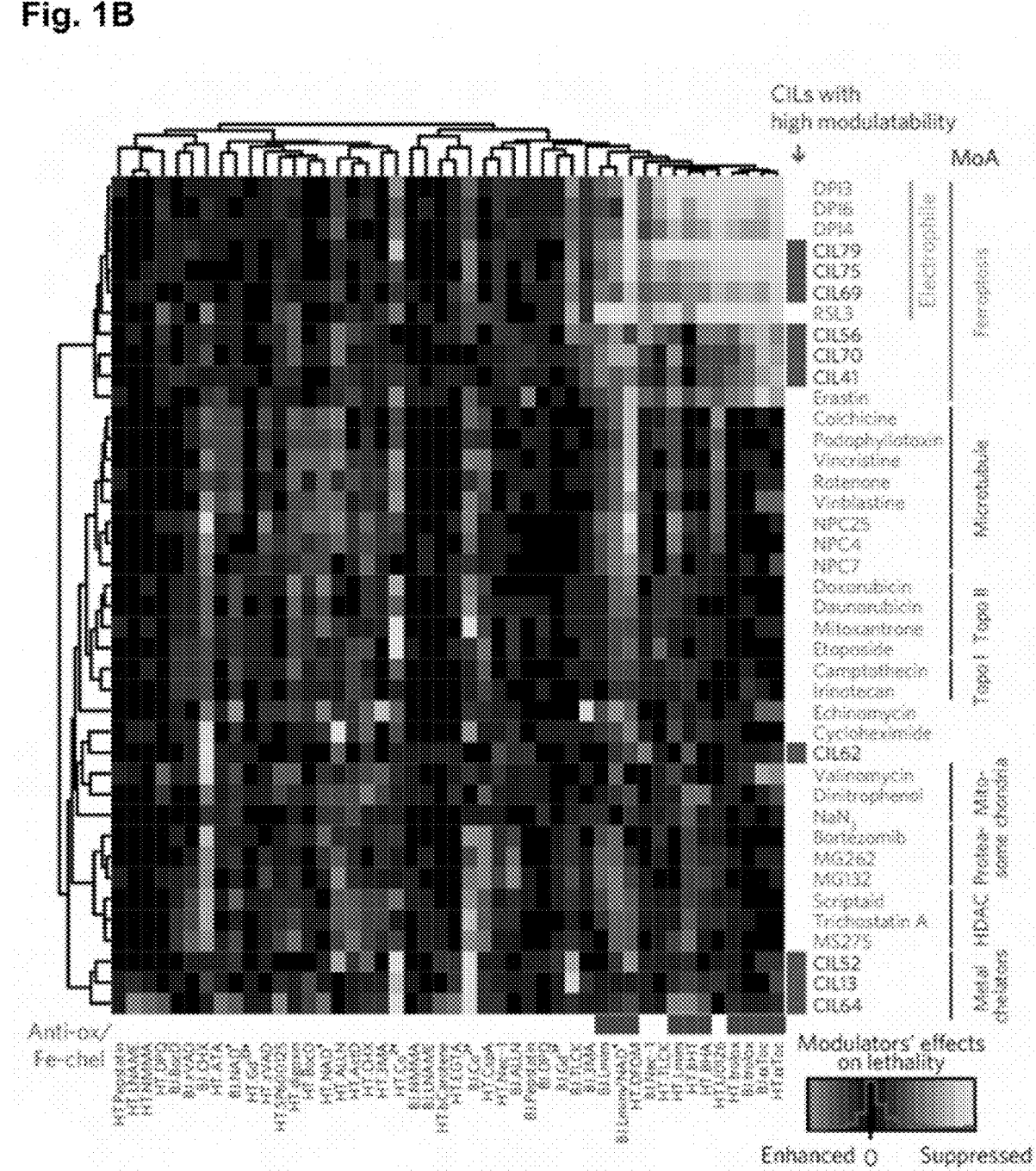

Measurements in FIG. 9B was done once; experiments in FIGS. 9C-9E were extracted from the modulatory profiles (see FIG. 1B). Error bars in FIG. 9C and FIG. 9D are s.e.m. of technical triplicates.

Figure 10A:
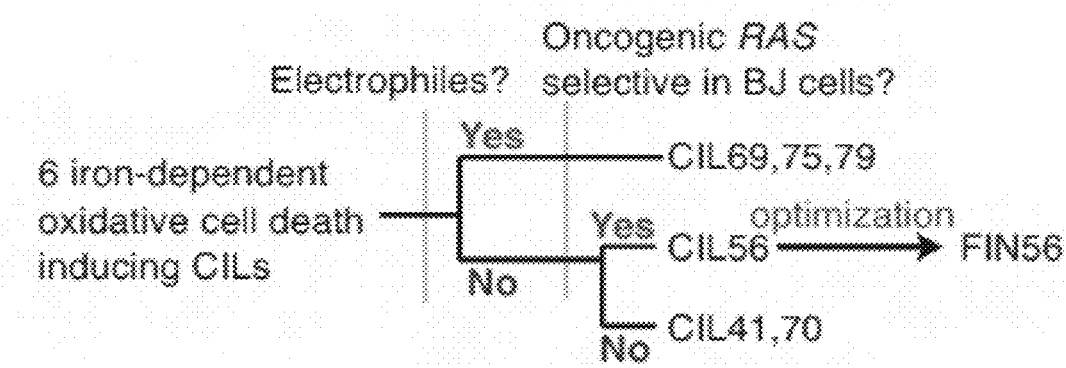

FIGS. 10A-10E show that CIL41/70 induce iron-dependent oxidative stress but not oncogenic-RAS selective in the BJ series. FIG. 10A shows the properties of 6 CILs (41, 56, 69, 70, 75, 79).

Figure 10B:
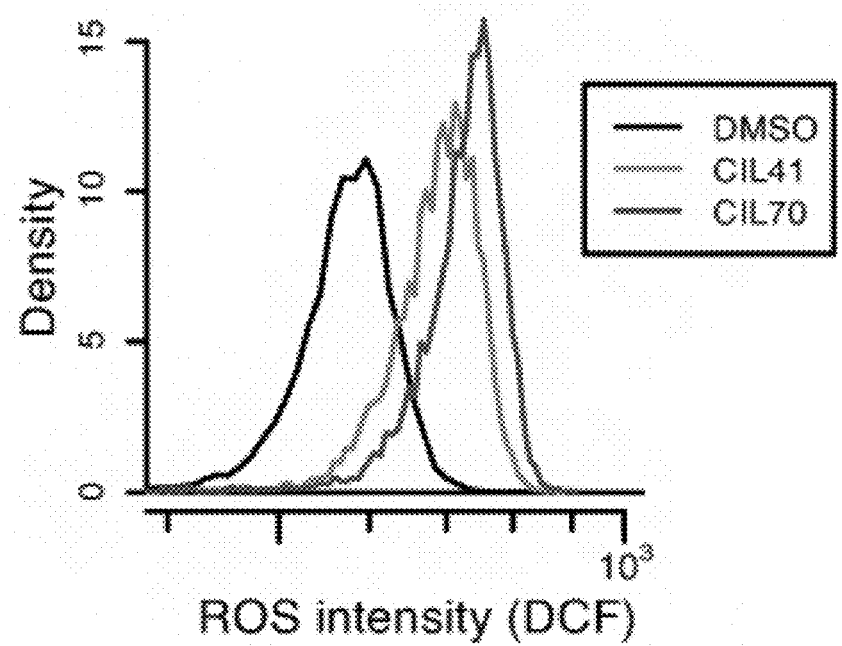

FIG. 10B shows that CIL41/70 treatment caused H2-DCFDA-detectable ROS generation.

Figure 10C:
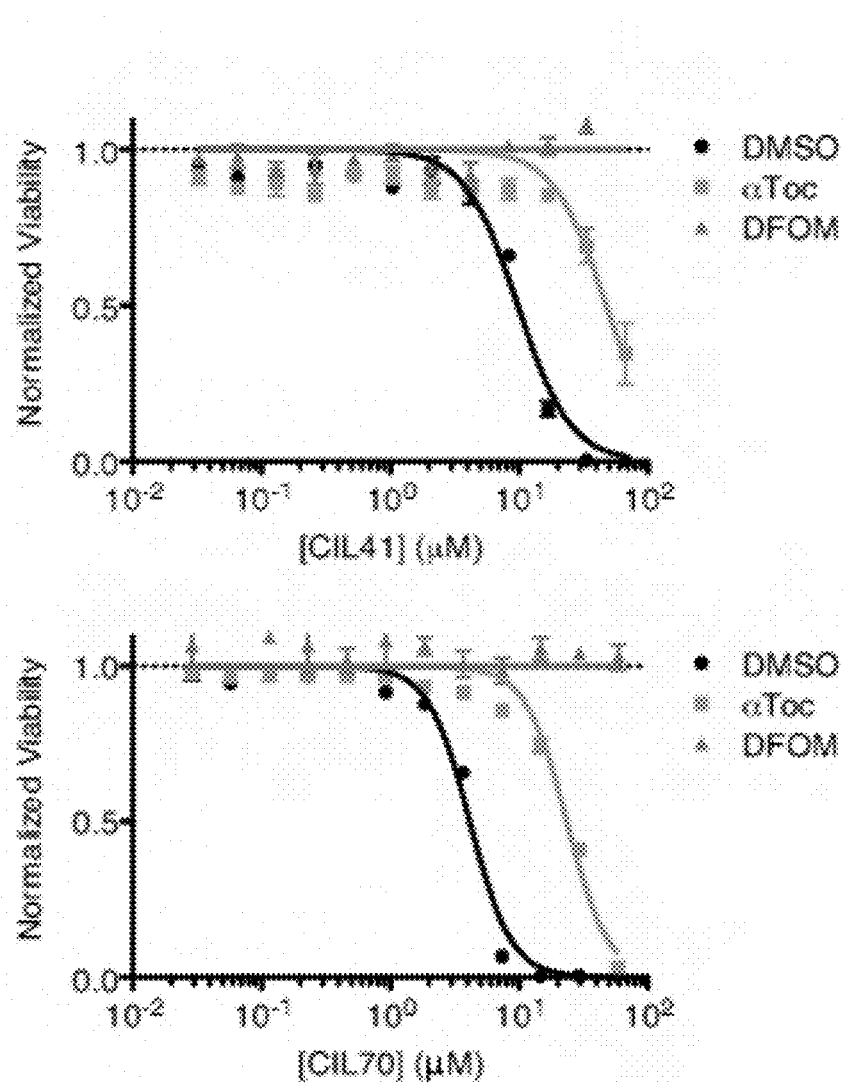

FIG. 10C shows the suppression of CIL41/70 lethality by ferroptosis inhibitors (the antioxidant α-tocopherol (αToc) and the iron-chelator deferoxamine (DFOM)).

Figure 10D:
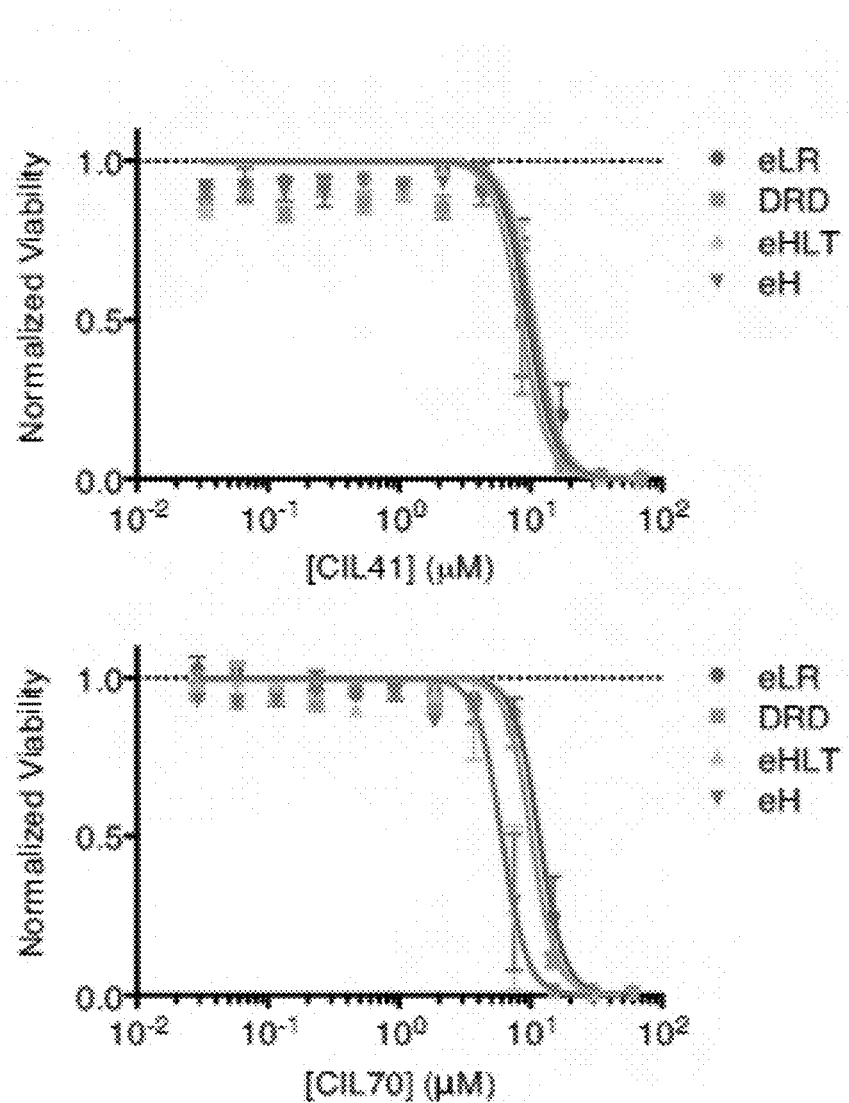

FIG. 10D shows that CIL41/70 do not induce selective lethality in the BJ cell line panel.

Figure 10E:
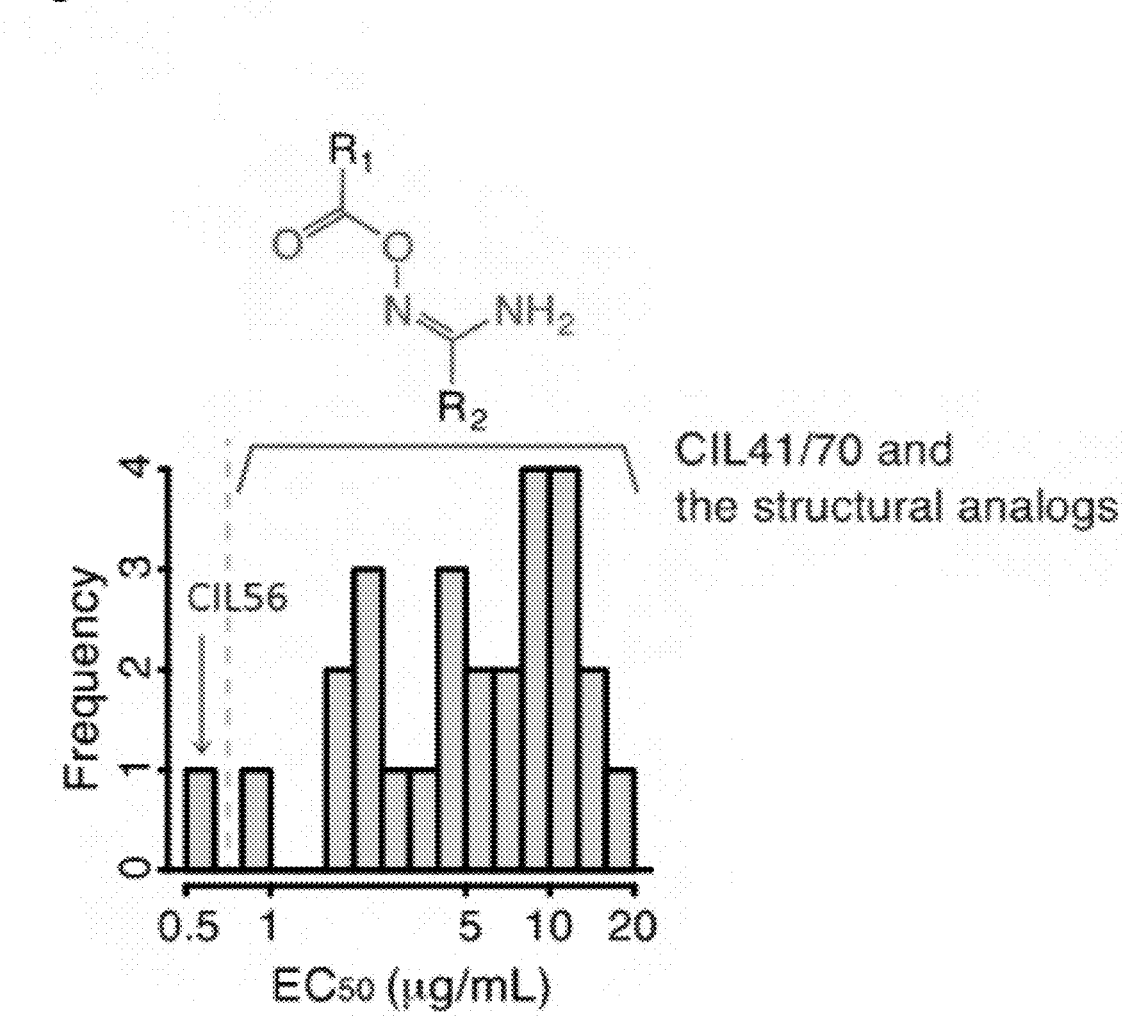

FIG. 10E shows the $EC_{50}$ of CIL56, CIL41/70 and the structural analogs of CIL41/70.

Experiments in FIG. 10B-10D were done in biological triplicates and single representative results are shown; error-bars indicate s.e.m. of technical triplicates; screening in FIG. 10E was done once.

Figure 11:
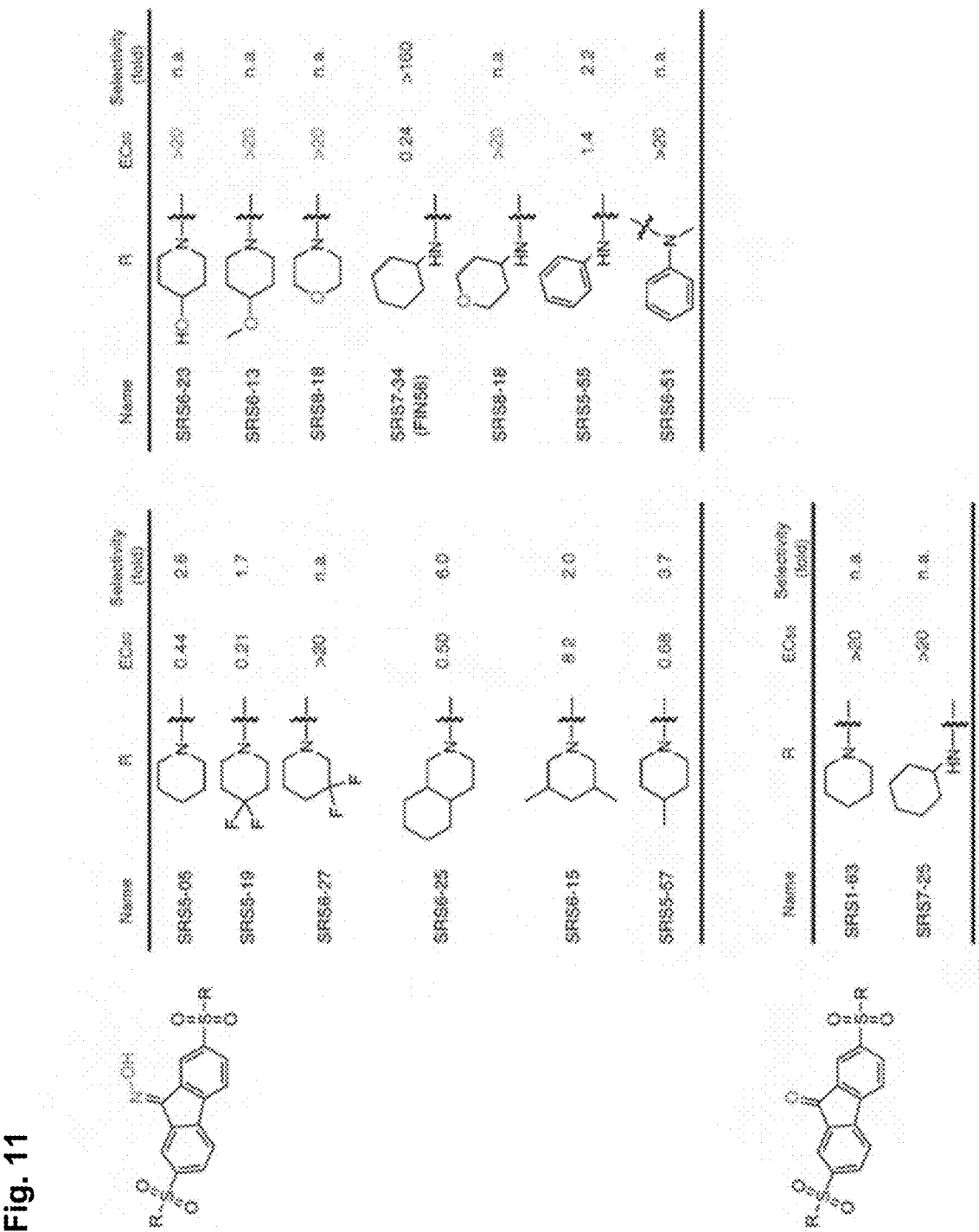

FIG. 11 shows the structure activity relationship study of CIL56 and selective induction of ferroptosis. It shows the structural analogs of CIL56 and their capability of inducing ferroptosis. Piperidine rings and oxime group in CIL56 were substituted by different moieties. $EC_{50}$ and selectivity (fold suppression by α-tocopherol) of the synthesized analogs were shown. $EC_{50}$ and selectivity measurements were done in two biological replicates, three technical replicates each.

Figure 12A:
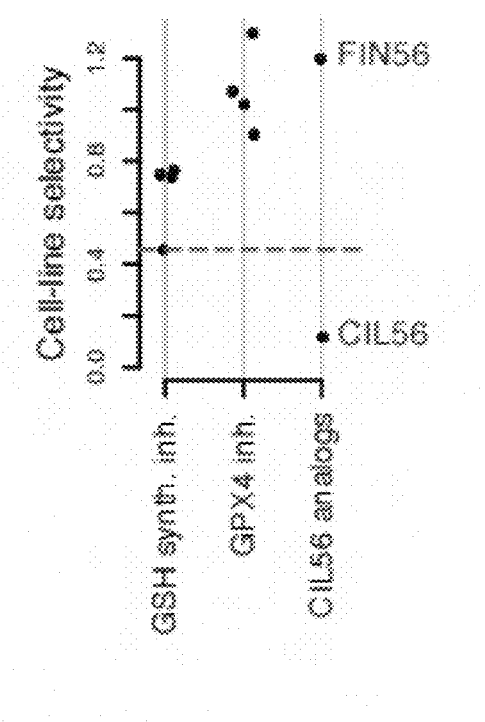
Figure 12B:
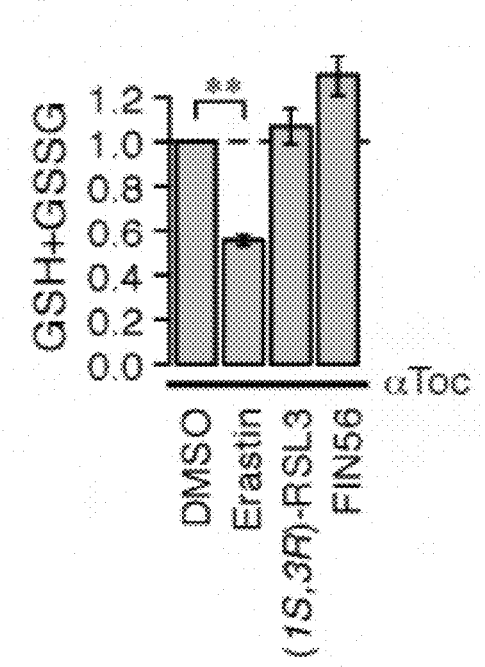
Figure 12C:
Figure 12D:
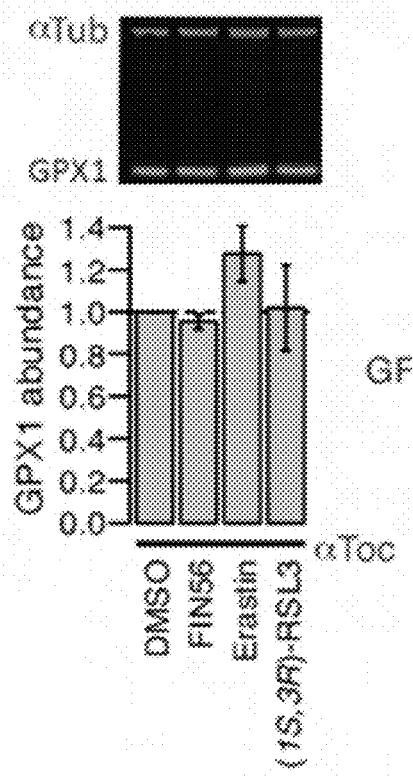
Figure 12E:
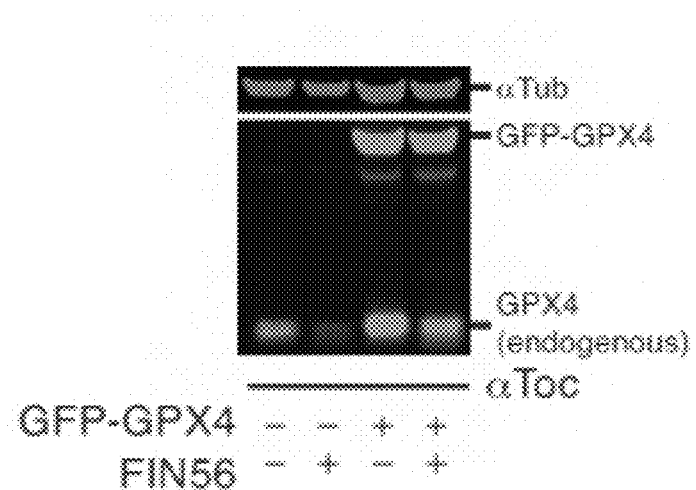
Figure 12F:
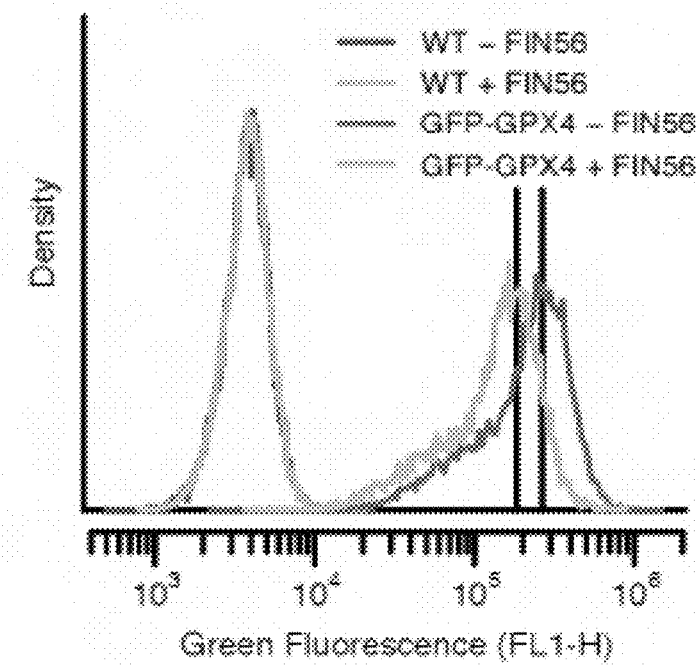
Figure 12G:
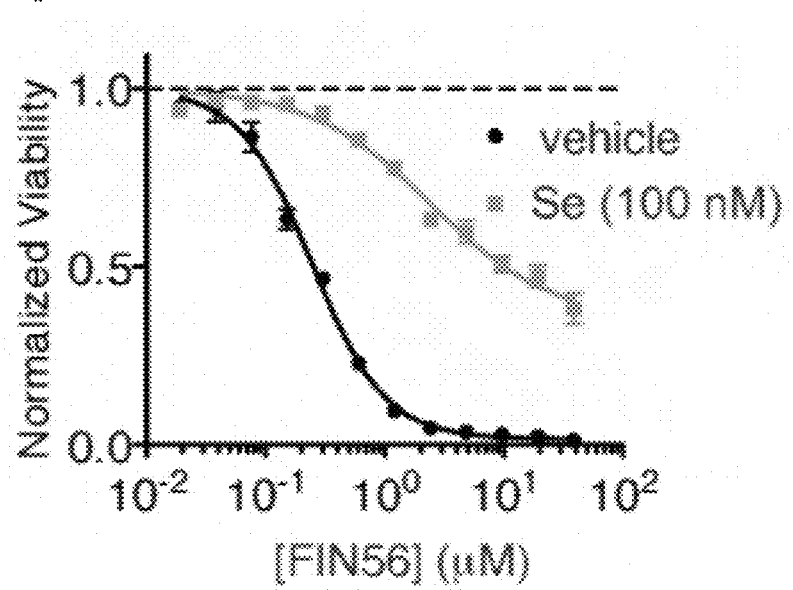
Figure 12H:
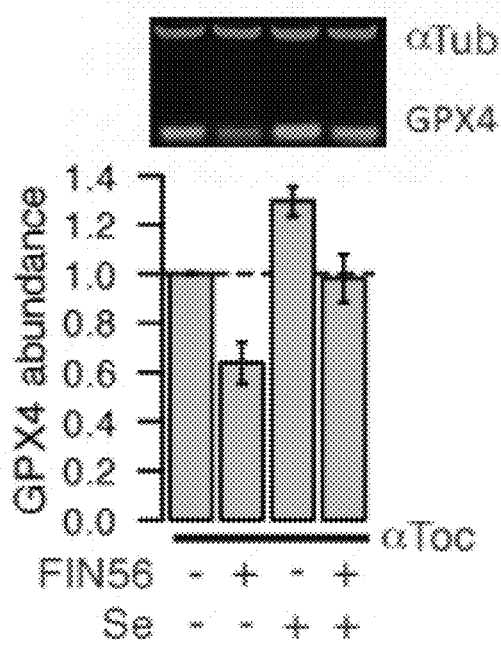
Figure 12I:
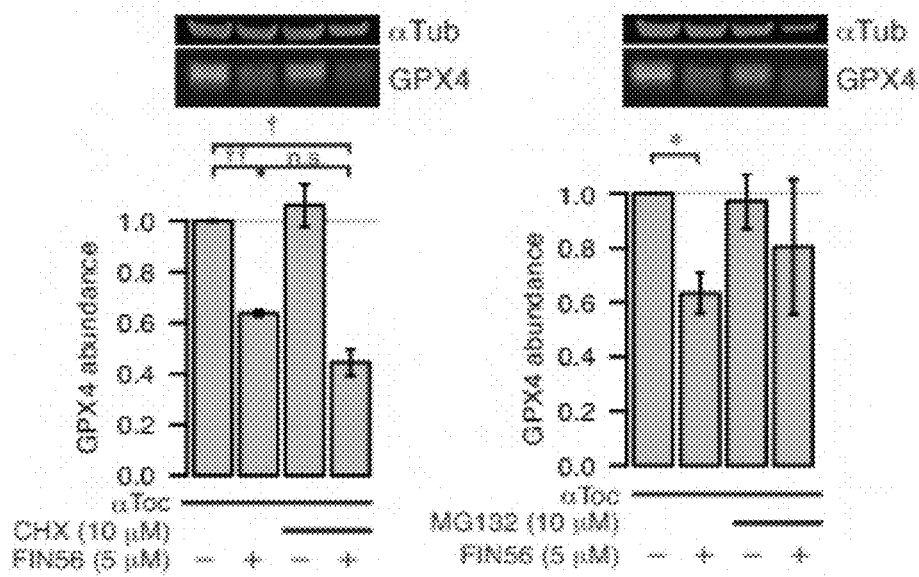
Figure 12J:
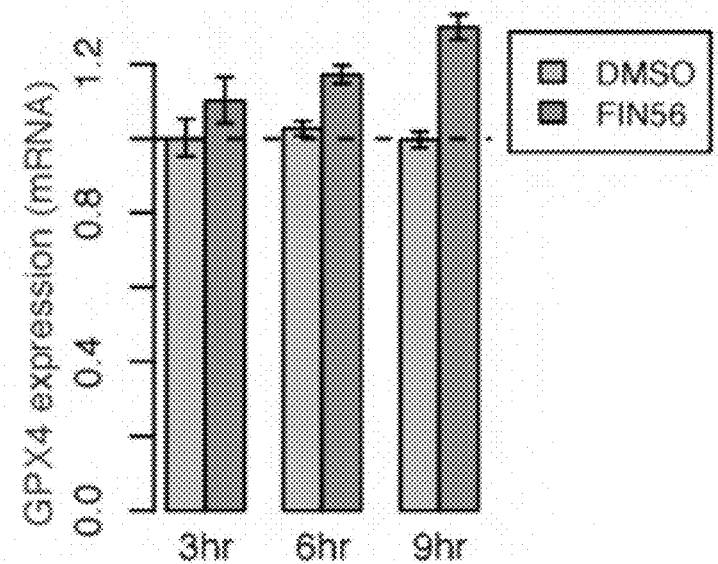
Figure 12K:
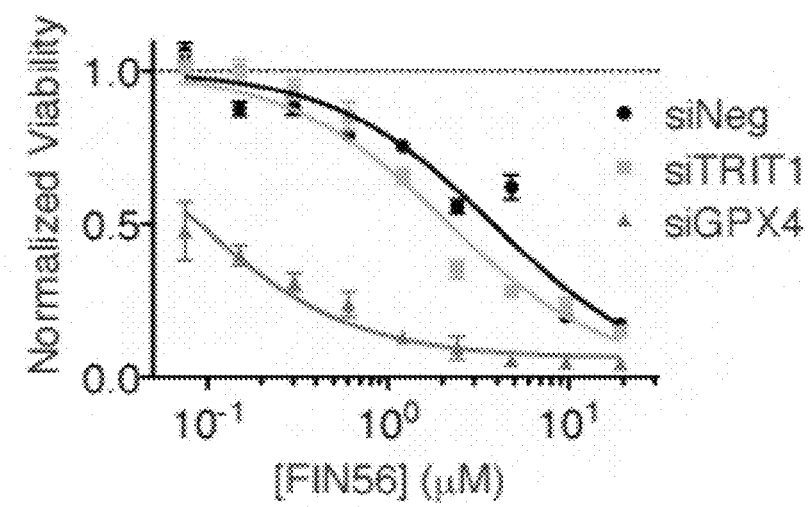
Figure 12L:
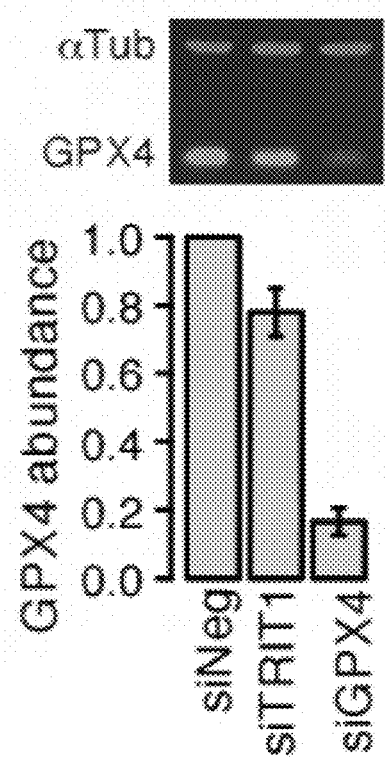
Figure 12M:
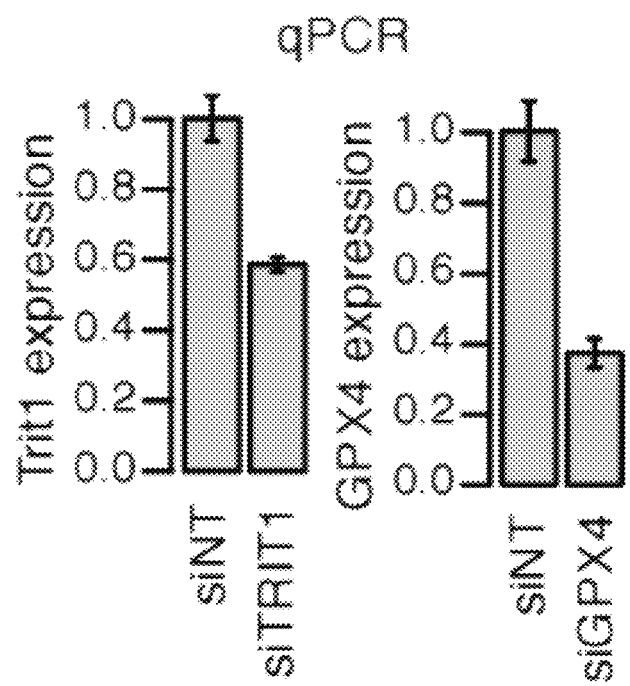
Figure 12N:
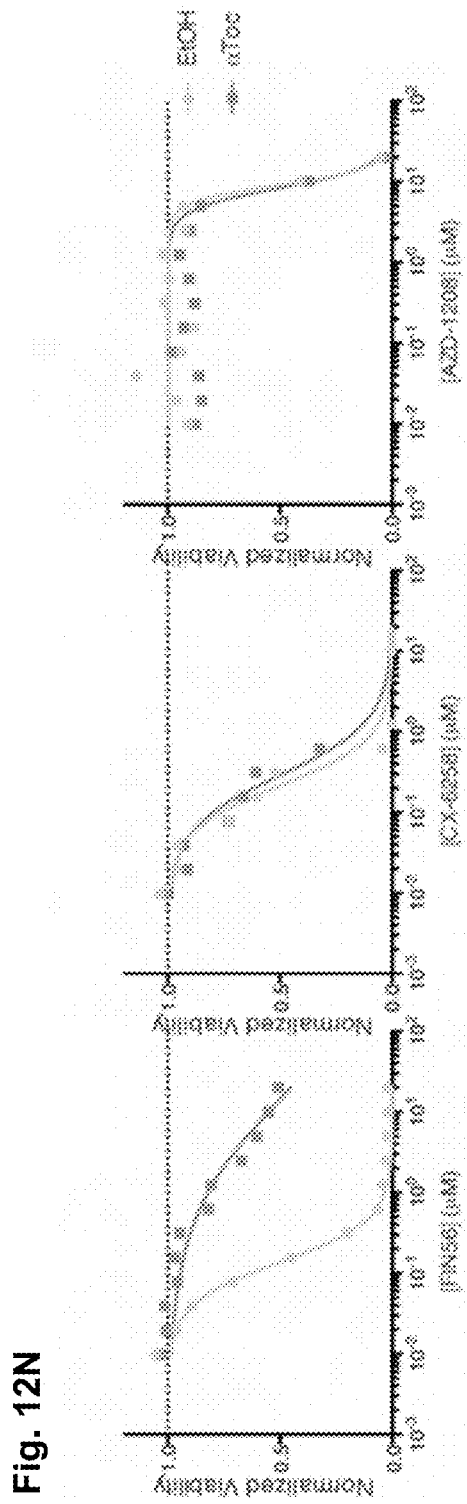

FIGS. 12A-12N show the mechanisms regulating GPX4 protein abundance.

FIG. 12A shows the cell-line-selectivity of GSH synthesis inhibitors, GPX4 inhibitors, and CIL56 analogs in the NCI60 cell line panel.

FIG. 12B shows the abundance of total glutathione (GSH and GSSG) in HT-1080 cells upon co-treatment with 100 μM αToc and ferroptosis inducers for ten hours. αToc: α-tocopherol.

FIG. 12C shows the GPX4 abundance in BJeLR cells upon 100 μM αToc and ferroptosis inducers. (Corresponding western to FIG. 3C)

FIG. 12D shows the results of GPX1 proteins in BJeLR cells upon co-treatment with 100 μM αToc and ferroptosis inducers for ten hours. GPX protein levels are normalized to α-tubulin protein levels within each sample.

FIG. 12E and FIG. 12F show the effects of GFP-GPX4 fusion protein overexpression on endogenous and exogenous GPX4 protein abundance with or without FIN56 treatment measured using (FIG. 12E) western (corresponding to FIG. 3F), and (FIG. 12F) FACS (green fluorescence).

FIG. 12G and FIG. 12H show the results of with or without pre-treatment of 100 nM selenium for 12 hrs and their effects on (FIG. 12G) FIN56 lethality in HT-1080 cells and (FIG. 12H) GPX4 abundance.

FIG. 12I shows the effects of translation inhibition (CHX) and proteosomal inhibition (MG132) on GPX4 abundance.

FIG. 12J shows the GPX4 transcripts level upon 5 μM FIN56.

FIG. 12K shows the effects of siRNA against GPX4 and TRIT1 on FIN56 lethality.

FIG. 12L shows the effects of GPX4 and TRIT1 knockdown on GPX4 protein level.

FIG. 12M shows the efficiency of knockdown assessed by RT-qPCR.

FIG. 12N shows that Pan-PIM inhibitors, CX-6258 and AZD-1208 were tested in 2-fold dilution series. Although they induce lethality in HT-1080 cells at higher concentrations, the lethality was not suppressed by αToc, indicating the death phenotype was not the same as ferroptosis.

In FIGS. 12C, 12D, 12E, 12H, and 12I, HT-1080 cells were co-treated with FIN56 and αToc. Experiments in FIGS. 12B-12N were done in biological triplicates; single representative results are shown and error-bars indicate s.e.m. of technical triplicates for FIGS. 12F, 12G, 12J, 12K, 12M and 12N; mean and s.e.m. of biological triplicates were shown for FIGS. 12B, 12C, 12D, 12E, 12H, 12I and 12L.

Figure 13:
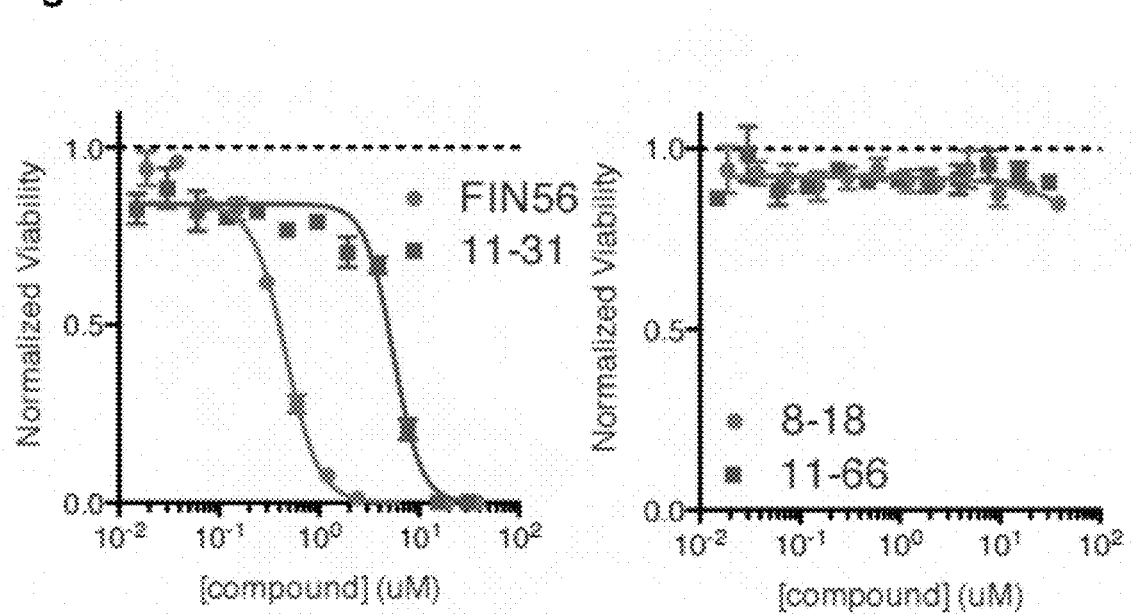

FIG. 13 shows the potency of CIL56 analogs in HT-1080. It shows the potency of CIL56 analogs (see FIG. 4A) in HT-1080 cells in 48 hrs. The experiment was done in biological triplicates. Error-bars indicate s.e.m. of technical triplicates.

FIGS. 14A-14D show the Interpretation of shRNA screen experiment targeting proteins identified in chemoproteomics.

Figure 14A:
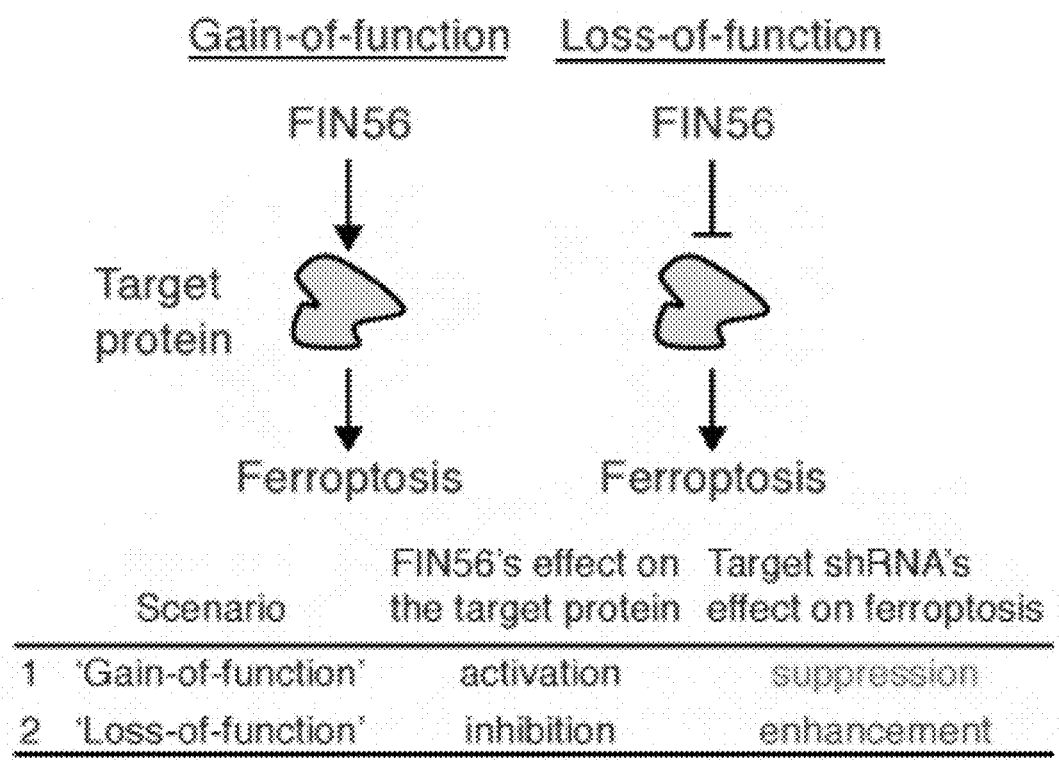

FIG. 14A shows two possible scenarios when FIN56 binds to its target protein. Depending on the scenarios, expected effect of shRNAs against genuine targets on FIN56's lethality is opposite.

Figure 14B:
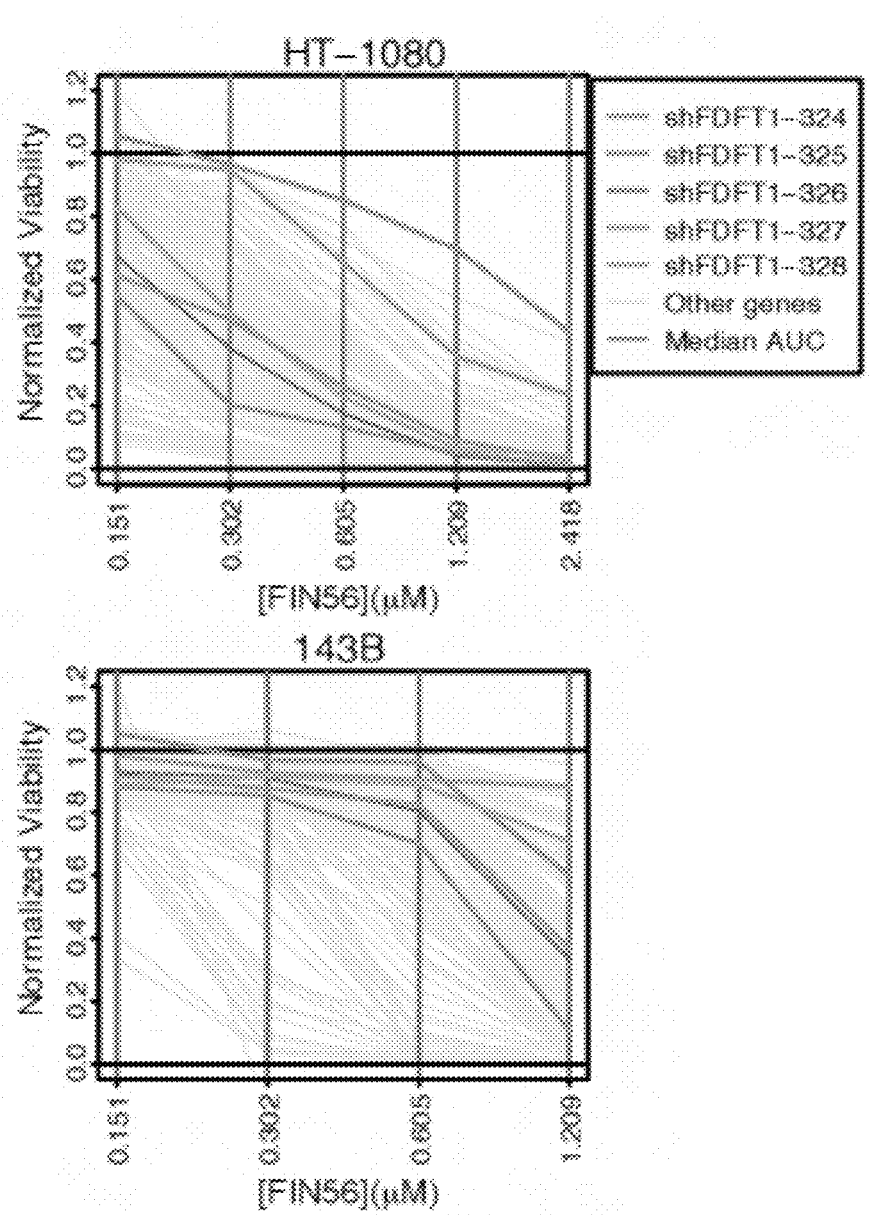

FIG. 14B shows the effects of shRNAs targeting 70 different proteins identified in chemoproteomics on FIN56. Two of the four cell lines are shown (See FIG. 4C for the other two). shFDFT1's were featured with polychromatic lines.

Figure 14C:
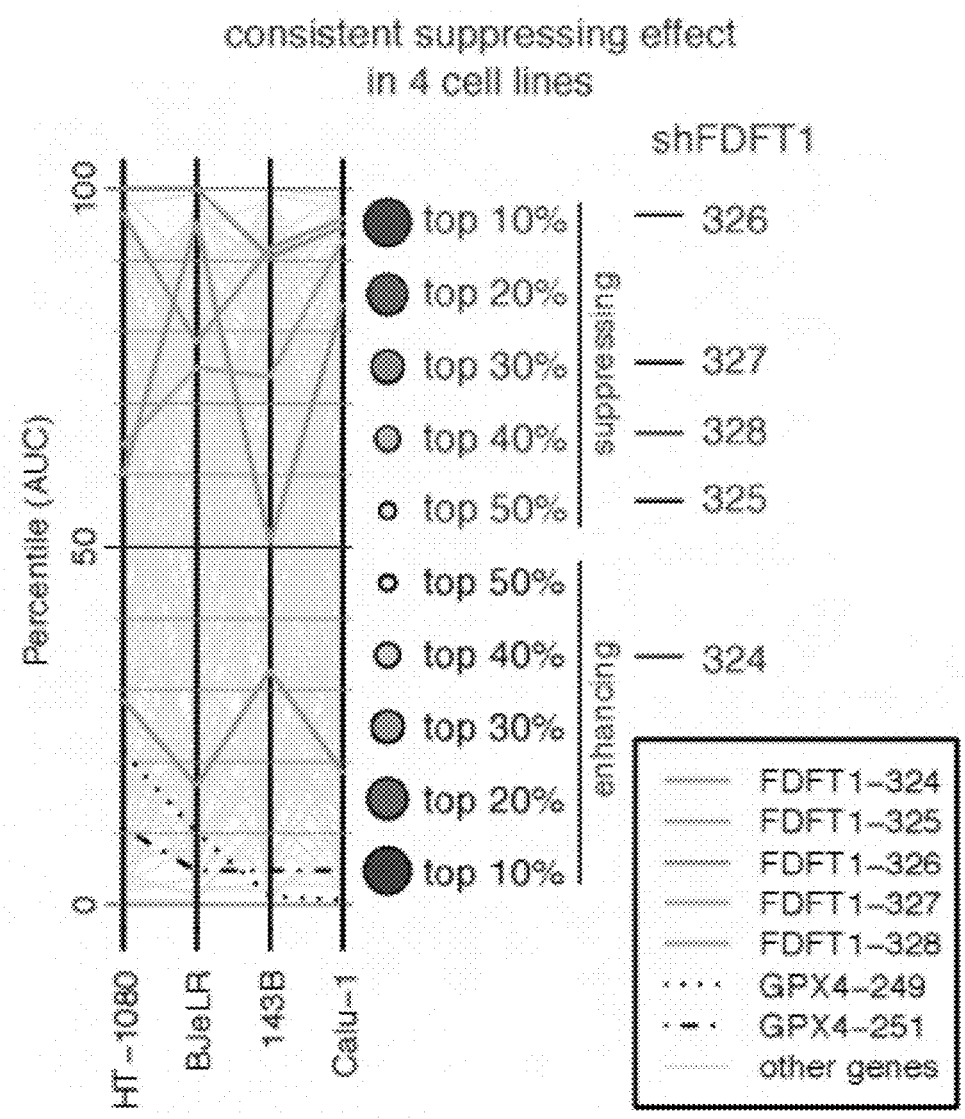

FIG. 14C shows the summary of the shRNA screens. Effects of shRNAs targeting the 70 proteins in the four cell lines. Each shRNA's effect in each cell line was represented by AUC, and ranked across the shRNAs in each cell line, The ranks were scaled between 0 and 100. Five shFDFT1 as well as two control shGPX4 are featured; shFDFT1 clones 326, 327, 328, and 325 are constantly within top 10, 20, 30, and 50 percentiles across the four cell lines.

Figure 14D:
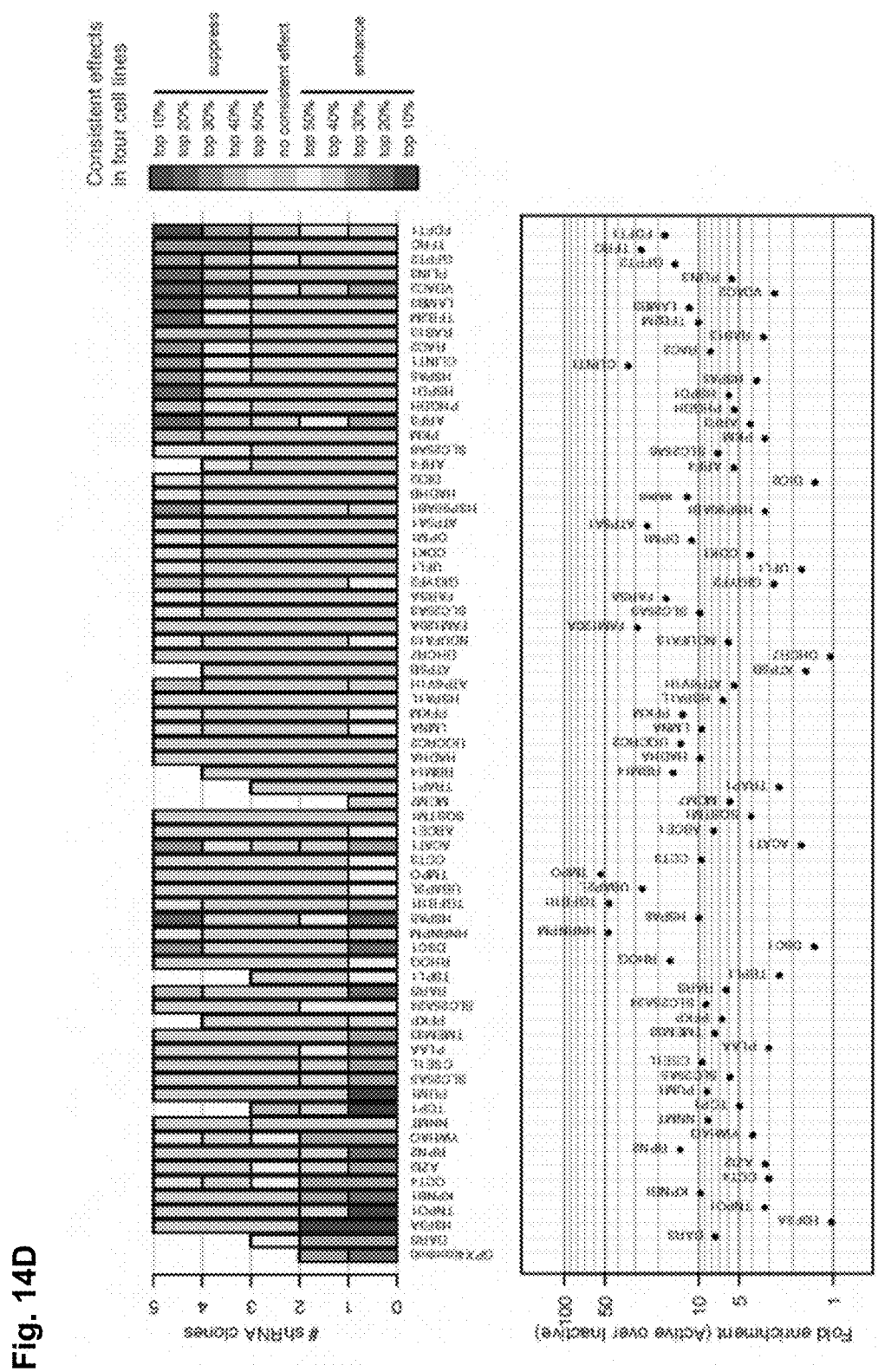

FIG. 14D shows the relationship between the shRNA screen and the protein fold enrichment from the proteomic analysis. Top panel: the shRNA screen (different representation of FIG. 14C). The height of the barplot corresponds to the number of shRNAs targeting the gene. Colors of the segments indicate each shRNA's consistent effect (red—suppression, blue—enhancement, grey—not consistent). Bottom panel: fold enrichment of protein pull-down with active probe vs inactive ones in chemoproteomic analysis. Two plots (see FIG. 4B) show the same result as FIG. 14C, emphasizing the ratio between '#consistent enhancer or suppressor shRNAs' vs '#shRNAs targeting each gene'. shRNA treatment and FIN56 treatment was done once in each cell line.

Figure 15:
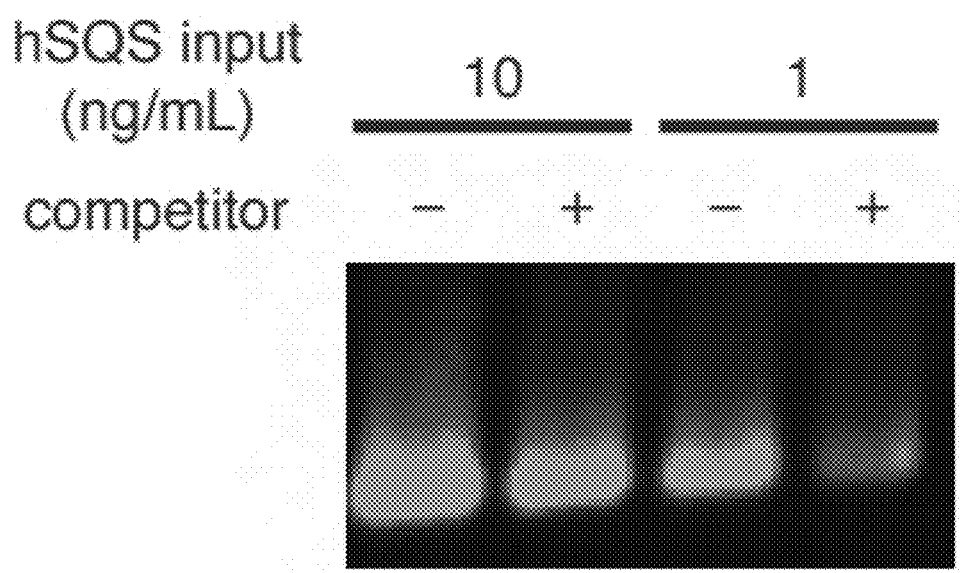

FIG. 15 shows the result of SQS pulldown and competition assay. SQS pull-down using purified truncated SQS, active probe and FIN56 as competitor. 190 μL of 10 ng/mL and 1 ng/mL purified truncated human SQS were preincubated with vehicle (DMSO) or 100 μM FIN56 for two hours, and further incubated with 5 μL of active probe for another two hours. Pull-down and western were done in biological triplicates and a representative result is shown.

FIGS. 16A-16D show the synergy between statins and FIN56.

Figure 16A:
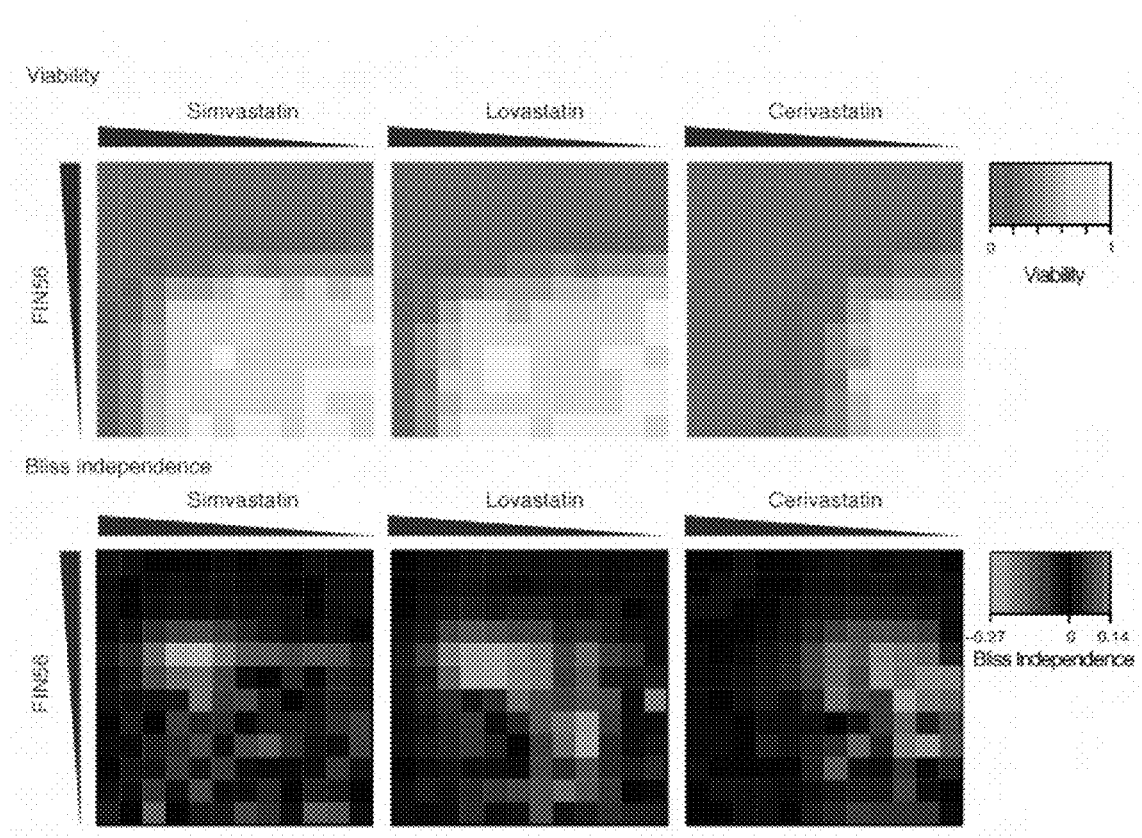

FIG. 16A shows the synergy between three statins and FIN56 was measured and computed using Bliss independence.

Figure 16B:
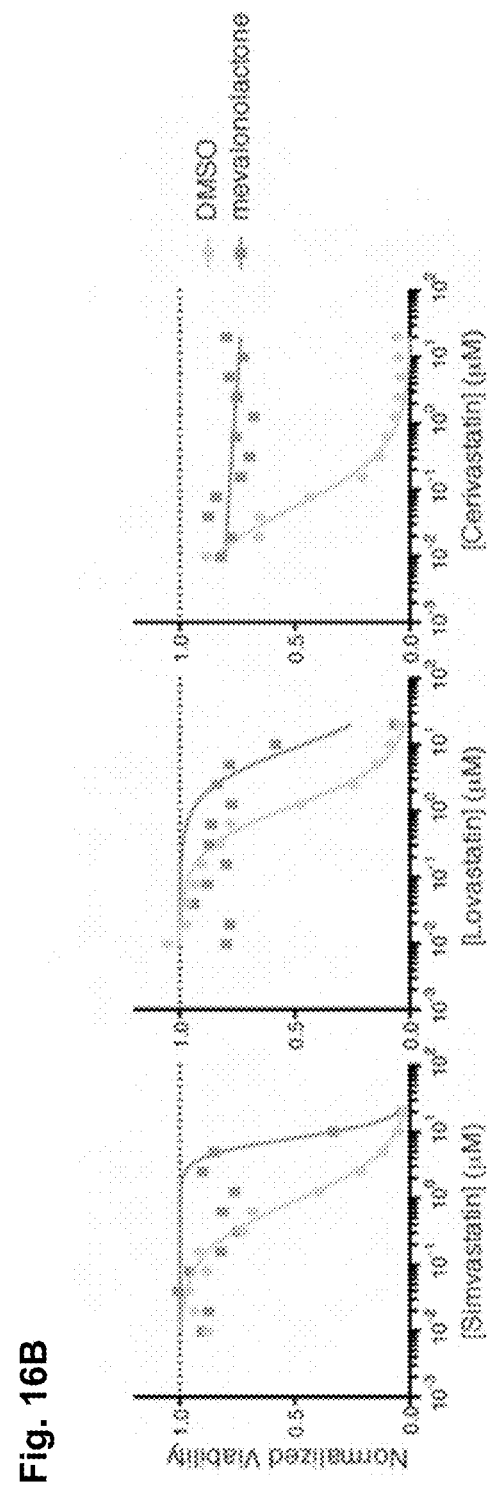

FIG. 16B shows statins' lethality and specificity. Three statins were tested in dilution series in HT-1080 cells with or without mevalonolactone. Lethality of Simvastatin and Lovastatin was not suppressed by mevalonolactone, indicating that they interact with off-targets at higher concentrations while cerivastatin more selectively targets HMG-CoA reductase.

Figure 16C:
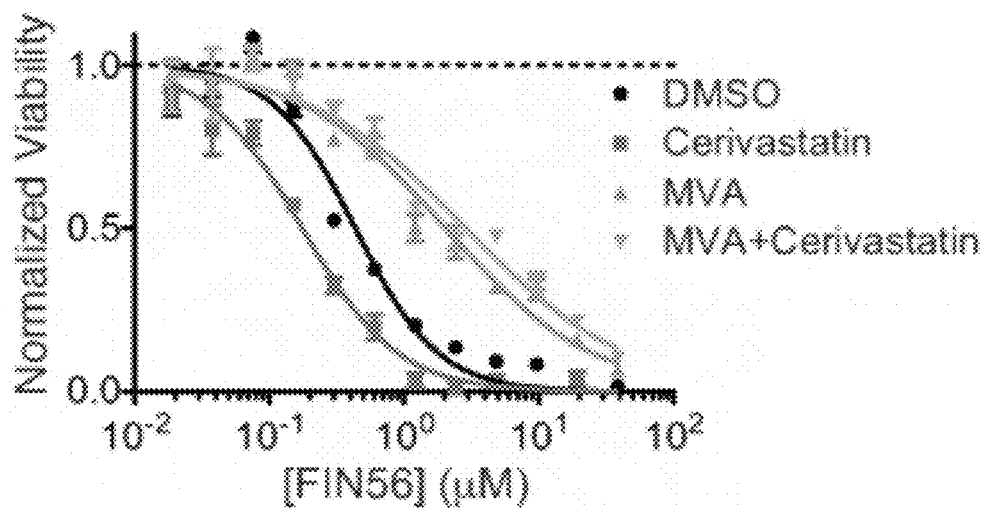

FIG. 16C shows the effects of 1 μM cerivastatin and/or 100 μM mevalonolactone (MVA) in HT-1080 cells.

Figure 16D:
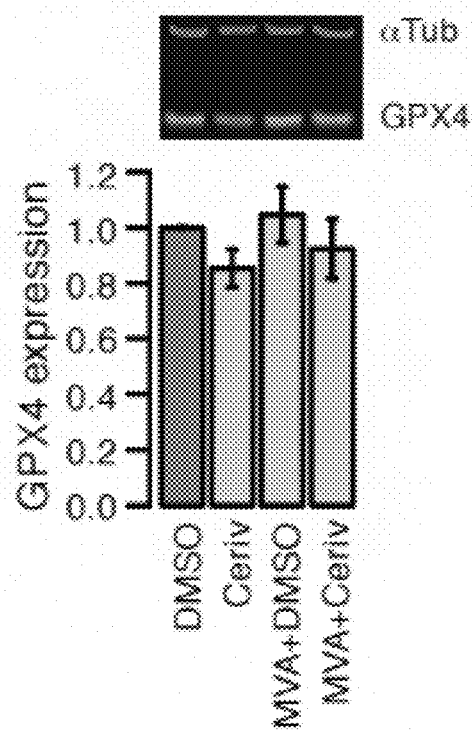

FIG. 16D shows the effects of supplementing the mevalonate pathway modulators for 24 hrs on GPX4 protein level in HT-1080 cells.

Experiments in FIGS. 16A, 16C and 16D were done in biological triplicates; experiment in FIG. 16B was done in biological duplicate; FIG. 16A and FIG. 16C show single representative results; mean of the technical triplicates were shown for viability and Bliss computation in FIG. 16B; error bars are s.e.m. in FIG. 16C; mean and s.e.m. of the biological replicates were shown in FIG. 16D.

Figure 17A:
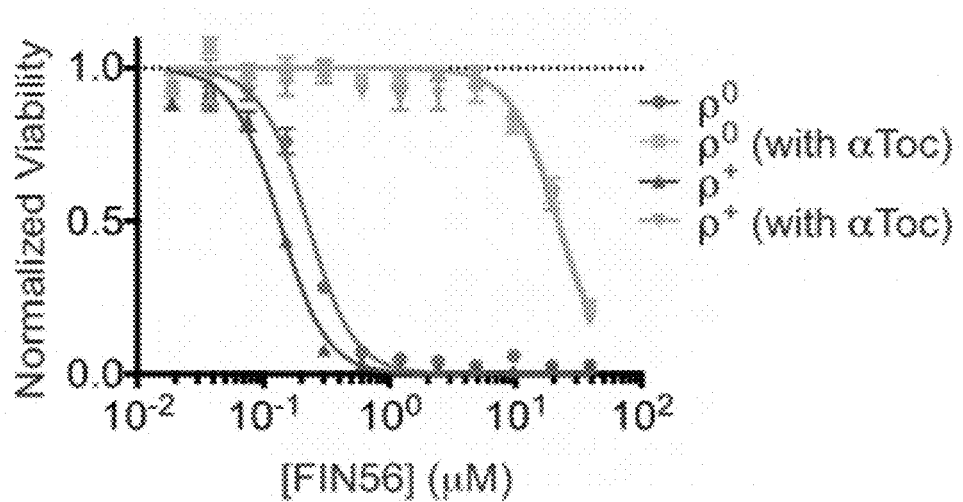
Figure 17B:
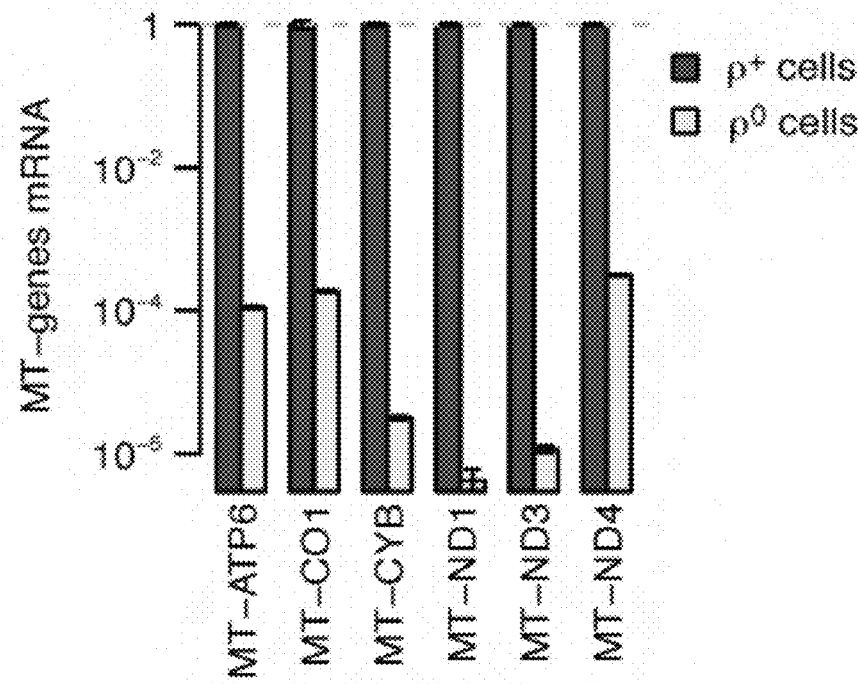
Figure 17C:
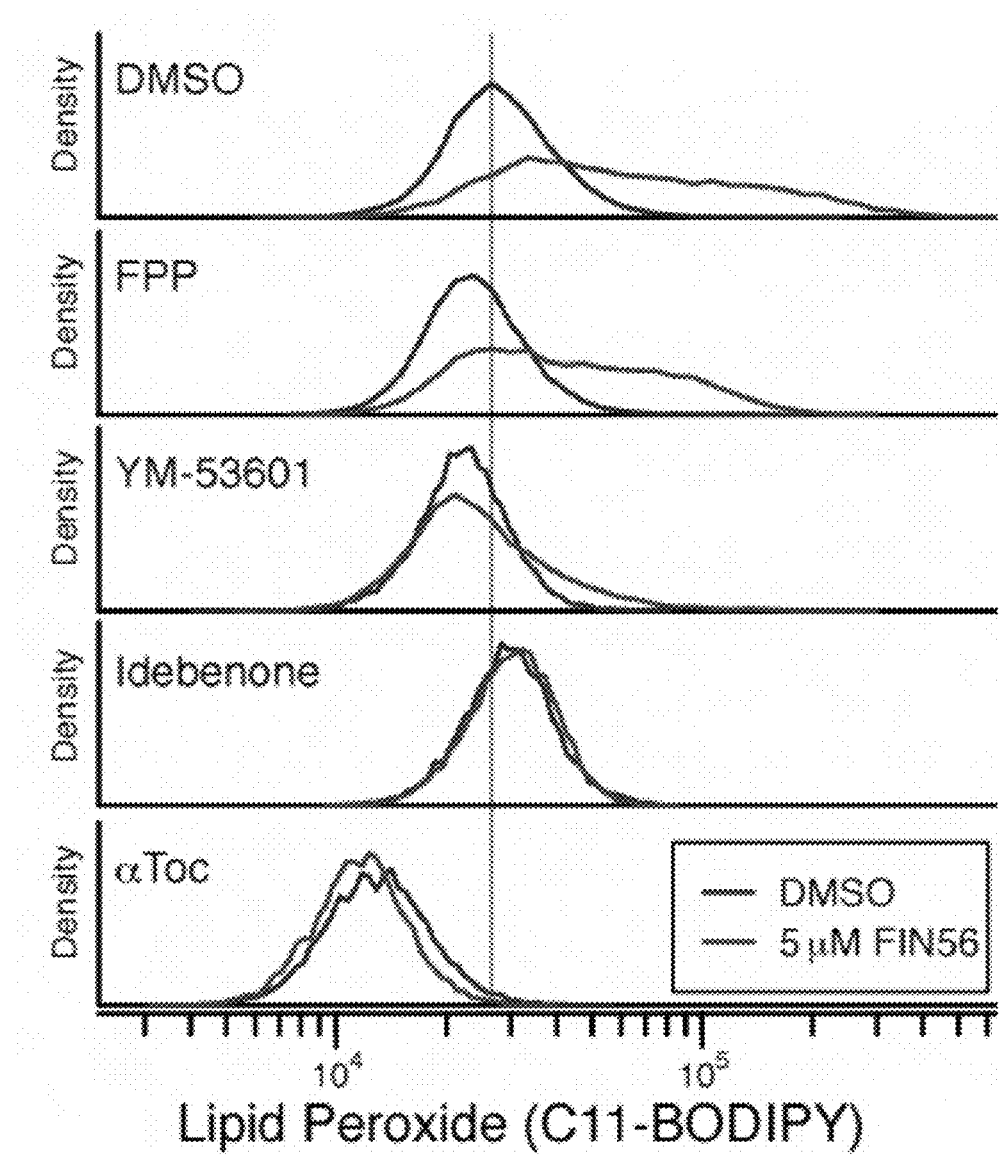

FIGS. 17A-17C show that modulators of the mevalonate pathway do not target respiration chain nor act as lipid antioxidant.

FIG. 17A shows 143B lung adenocarcinoma cells with or without mitochondrial DNA ($\rho^0$ and $\rho^+$ cells).

FIG. 17B shows the confirmation that mitochondrial DNA-encoded genes are not expressed.

FIG. 17C shows the lipid peroxide levels upon the mevalonate pathway modulator treatments and α-tocopherol.

Experiments in FIGS. 17A and 17B were done in biological singlicate and error bars are s.e.m. of three technical replicates; experiments in FIG. 17C was done in biological duplicate.

Figure 18:
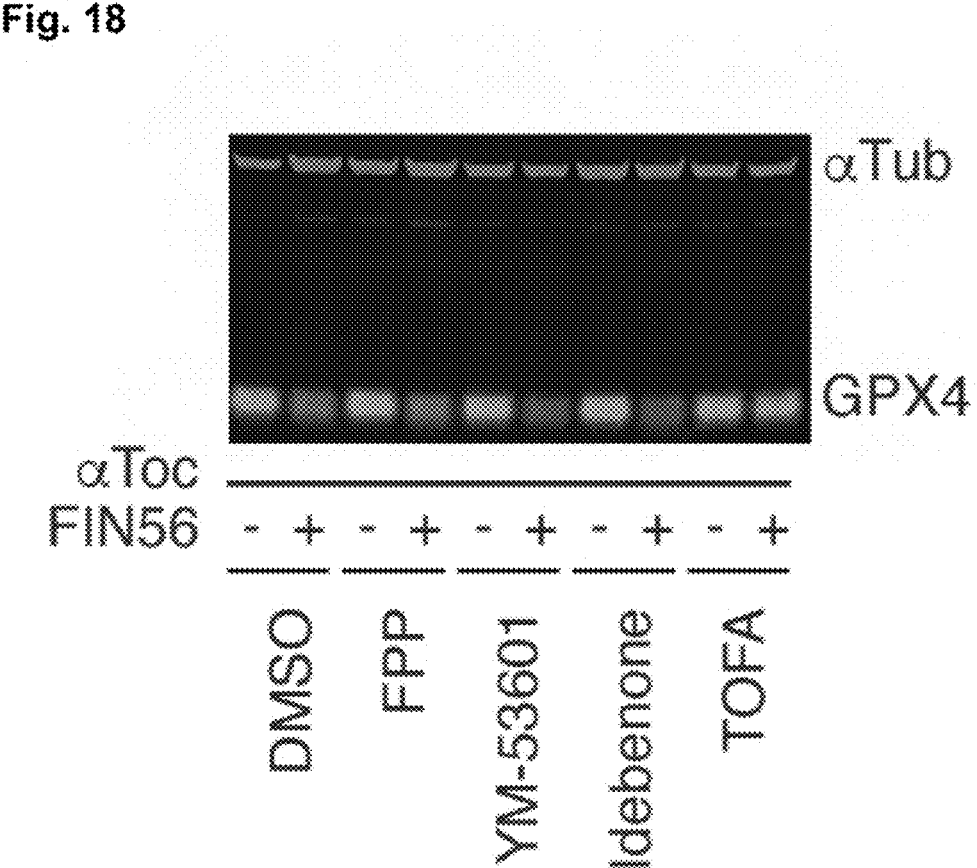

FIG. 18 shows the effects of the mevalonate pathway modulators and an ACC inhibitor on FIN56-induced GPX4 loss. It is a representative western blot of FIG. 6A. The western was done in three biological replicates.

Figure 19A:
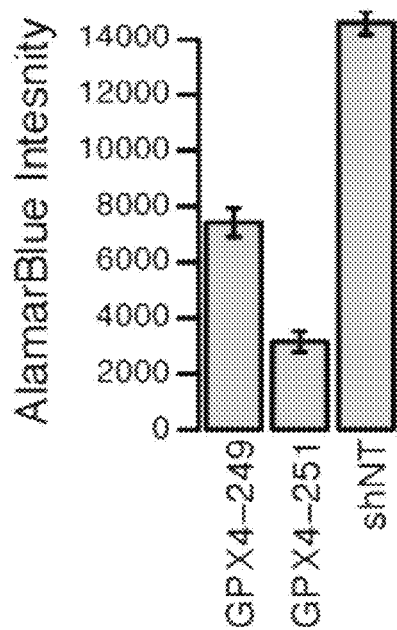
Figure 19B:
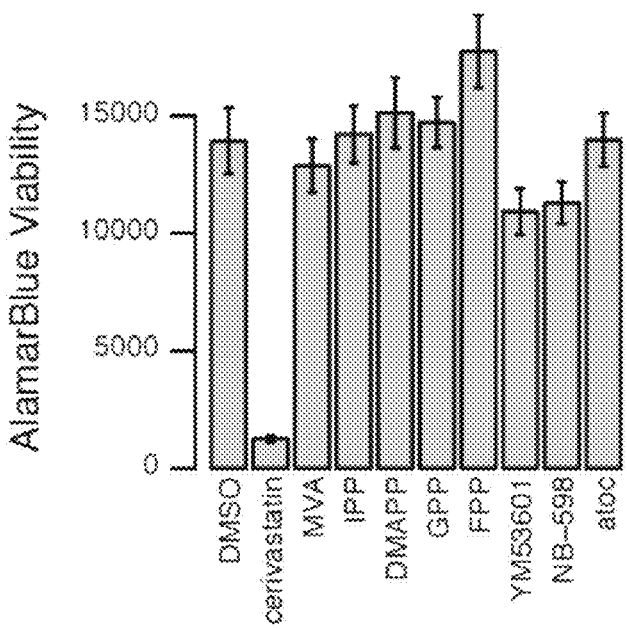
Figure 19C:
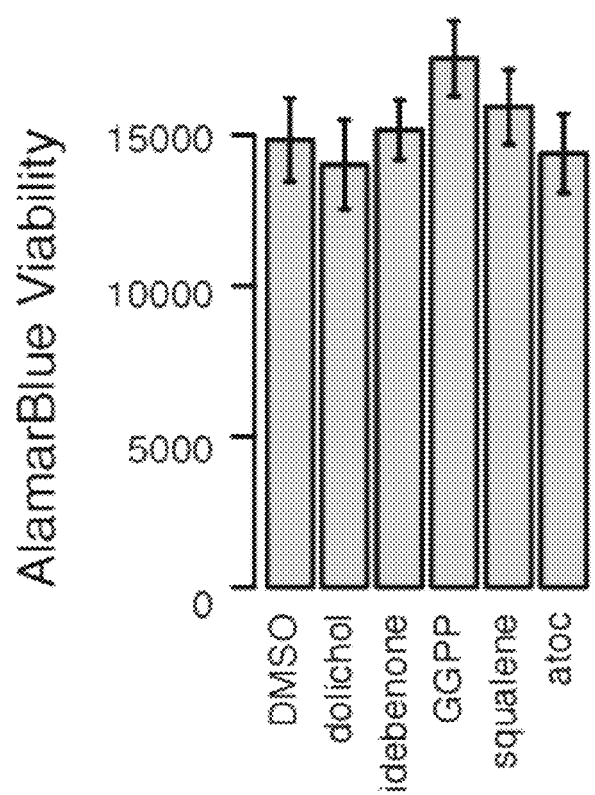
Figure 20A:
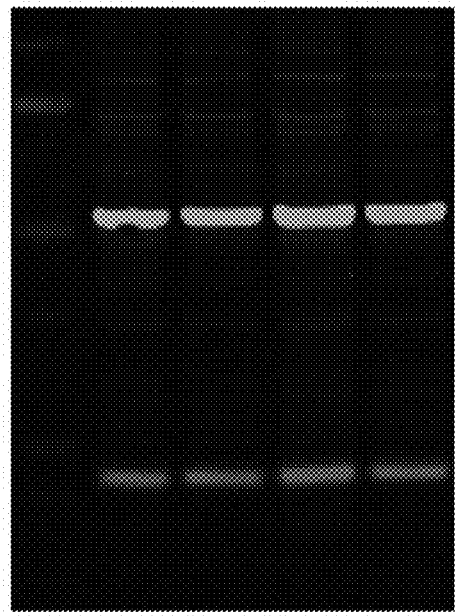
Figure 20B:
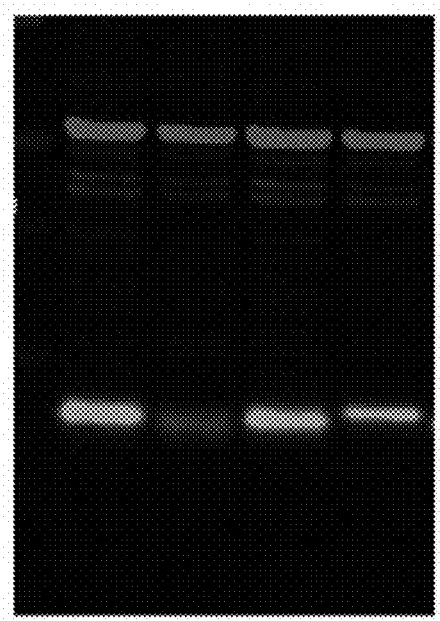
Figure 20C:
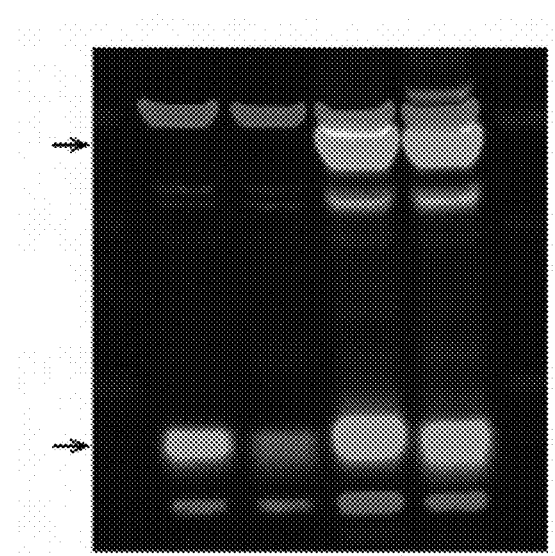
Figure 20D:
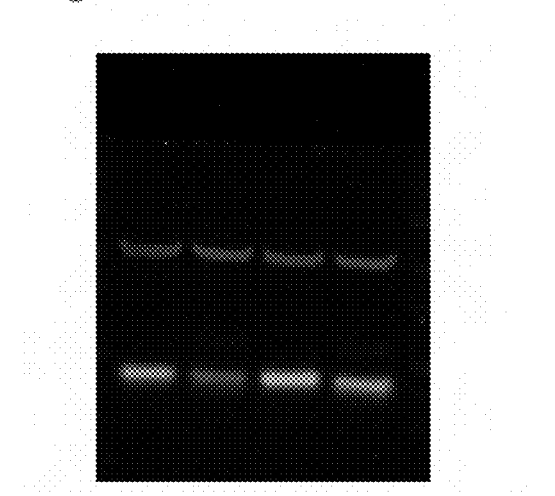
Figure 20E:
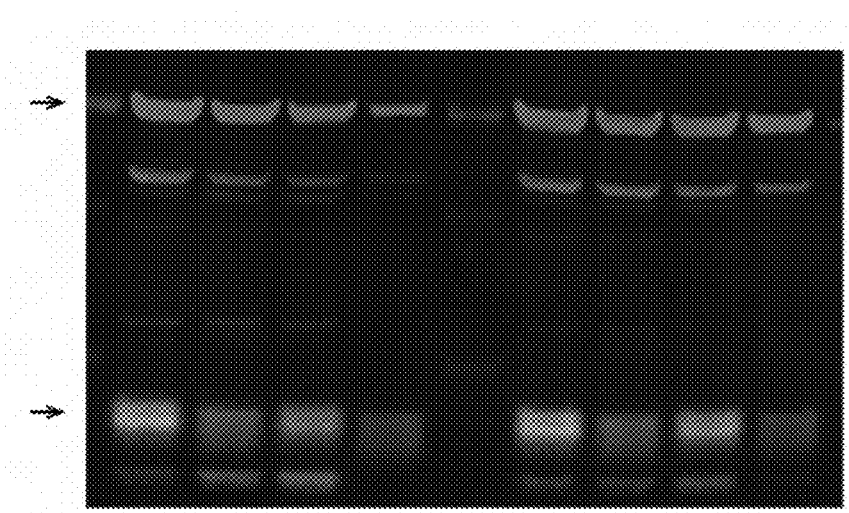
Figure 20F:
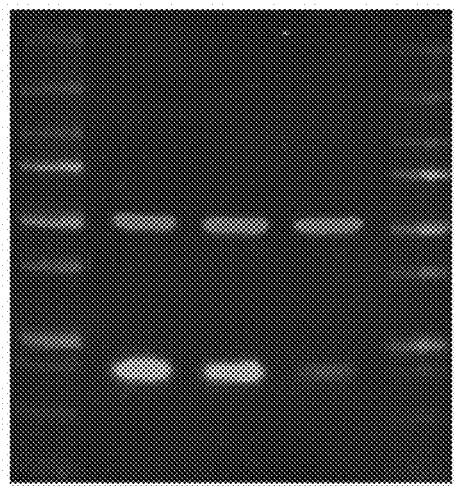
Figure 20G:
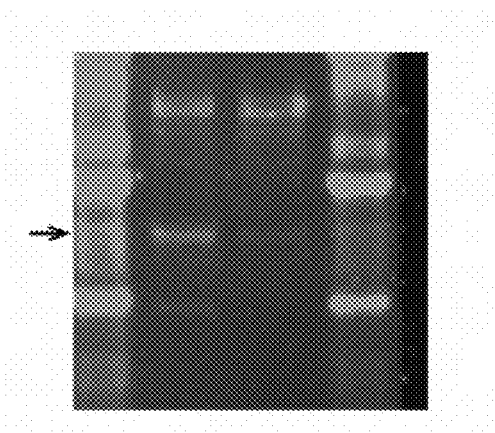
Figure 20H:
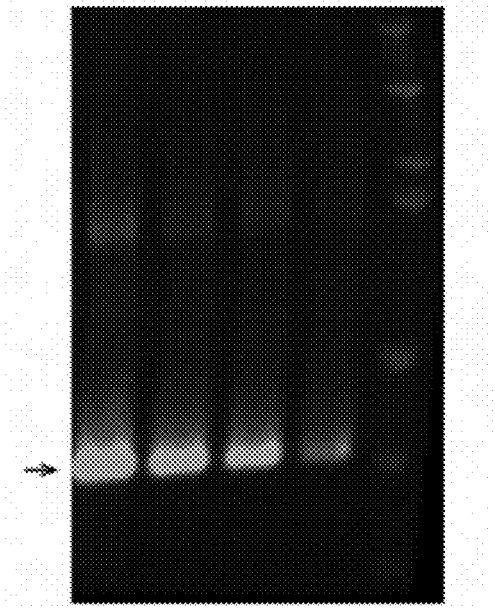
Figure 20I:
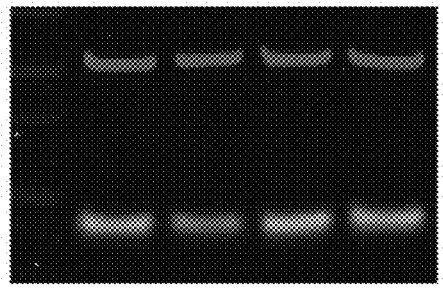
Figure 20J:
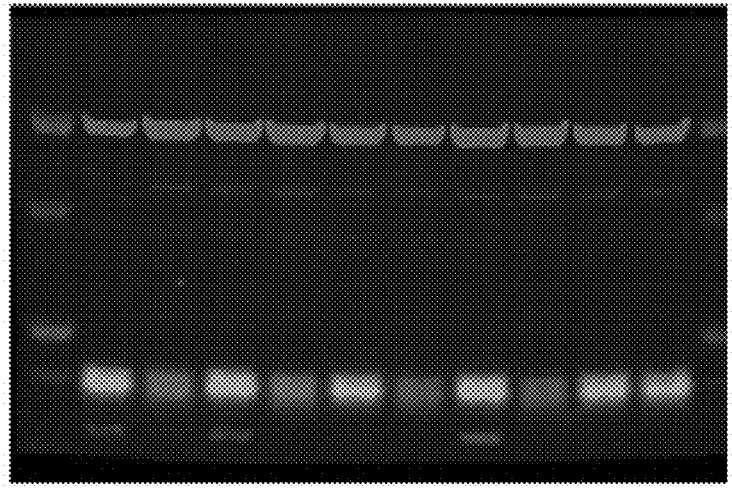

FIGS. 19A-19C show the modulators' effects on HT-1080 viability. FIG. 19A-19C respectively corresponds to: FIG. 3C; FIG. 5E; and FIG. 5F. Error bars are s.e.m. of technical triplicates.

FIGS. 20A-20J show the full gel images respectively corresponding to: FIG. 12C (left); FIG. 12C (right); FIG. 12D; FIG. 12G; FIG. 12H; FIG. 12K; FIG. 11C; FIG. 15; FIG. 16D; FIG. 18.

Figure 21:
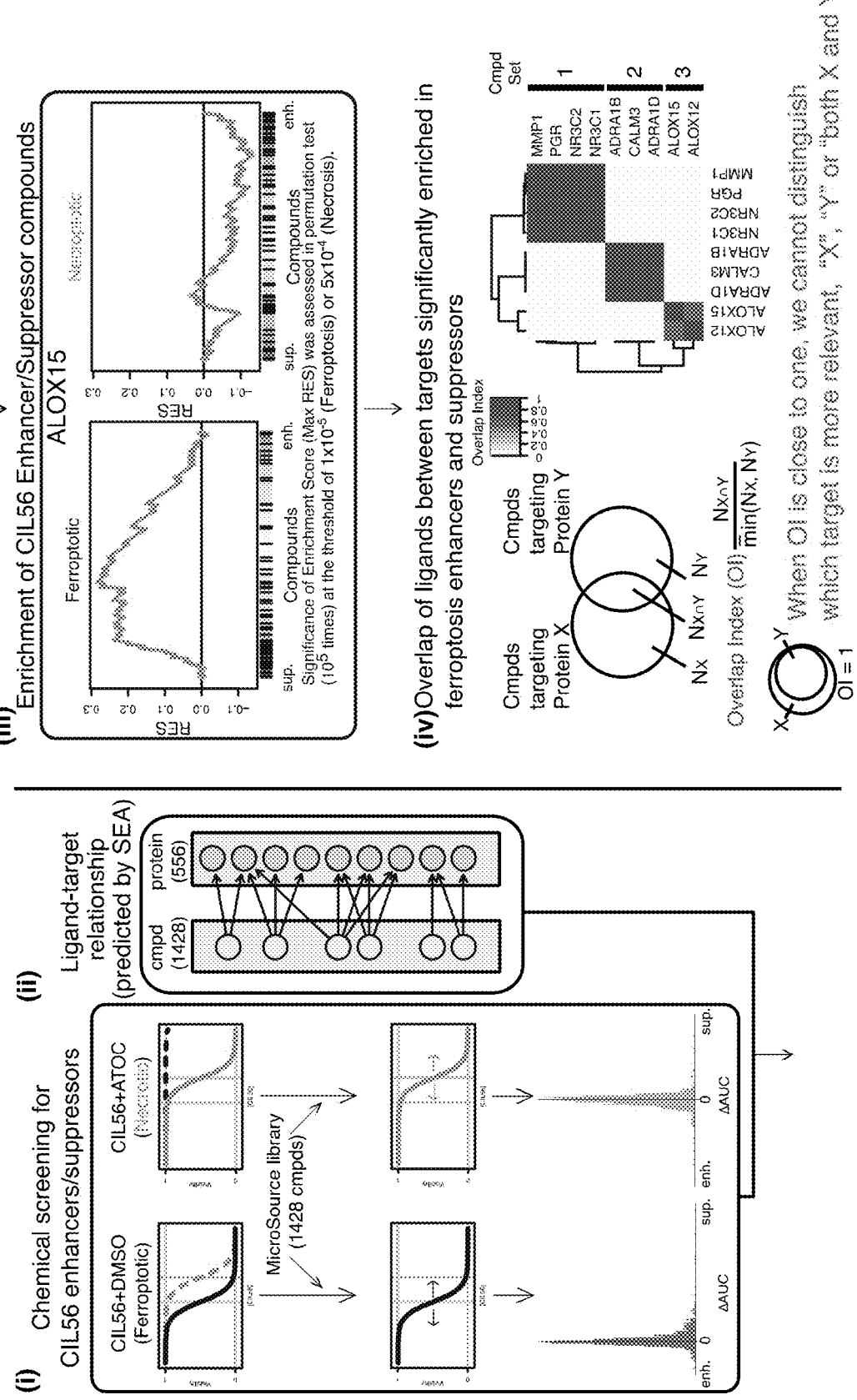

FIG. 21 shows the workflow of Target Enrichment Analysis (TEA).

Figure 22:
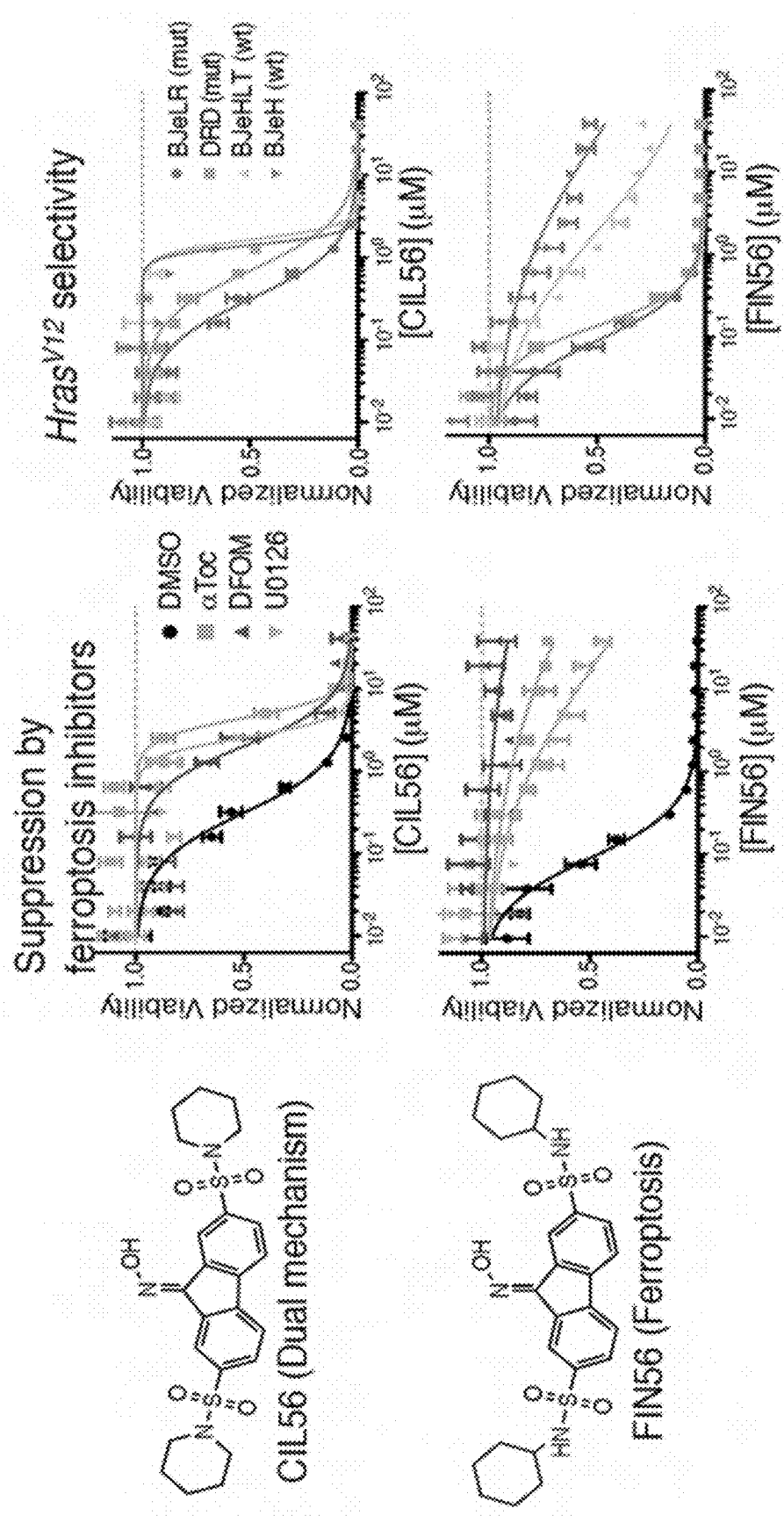

FIG. 22 shows the dual mechanism of CIL56 and ferroptosis induced by FIN56.

Figure 23A:
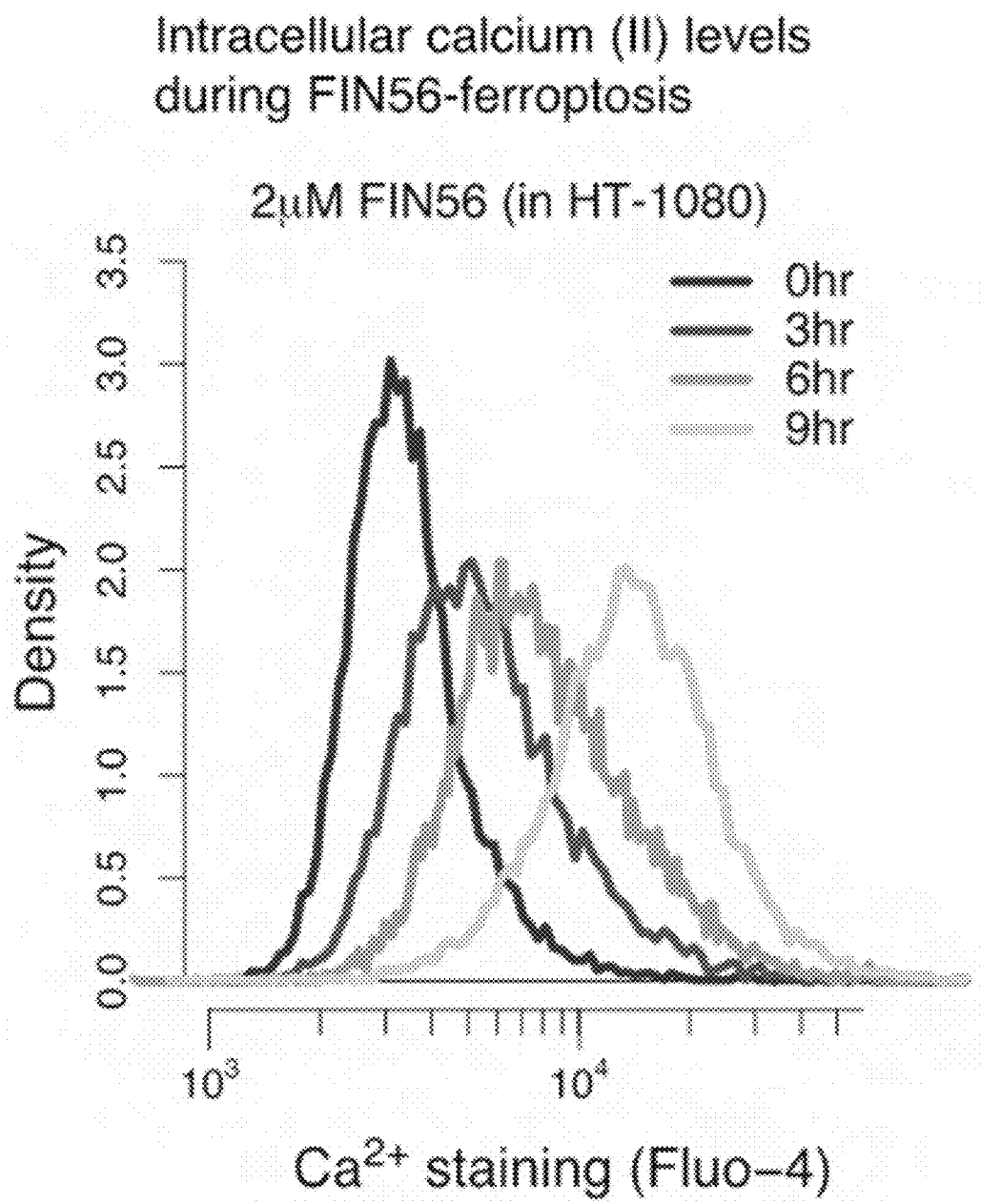
Figure 23B:
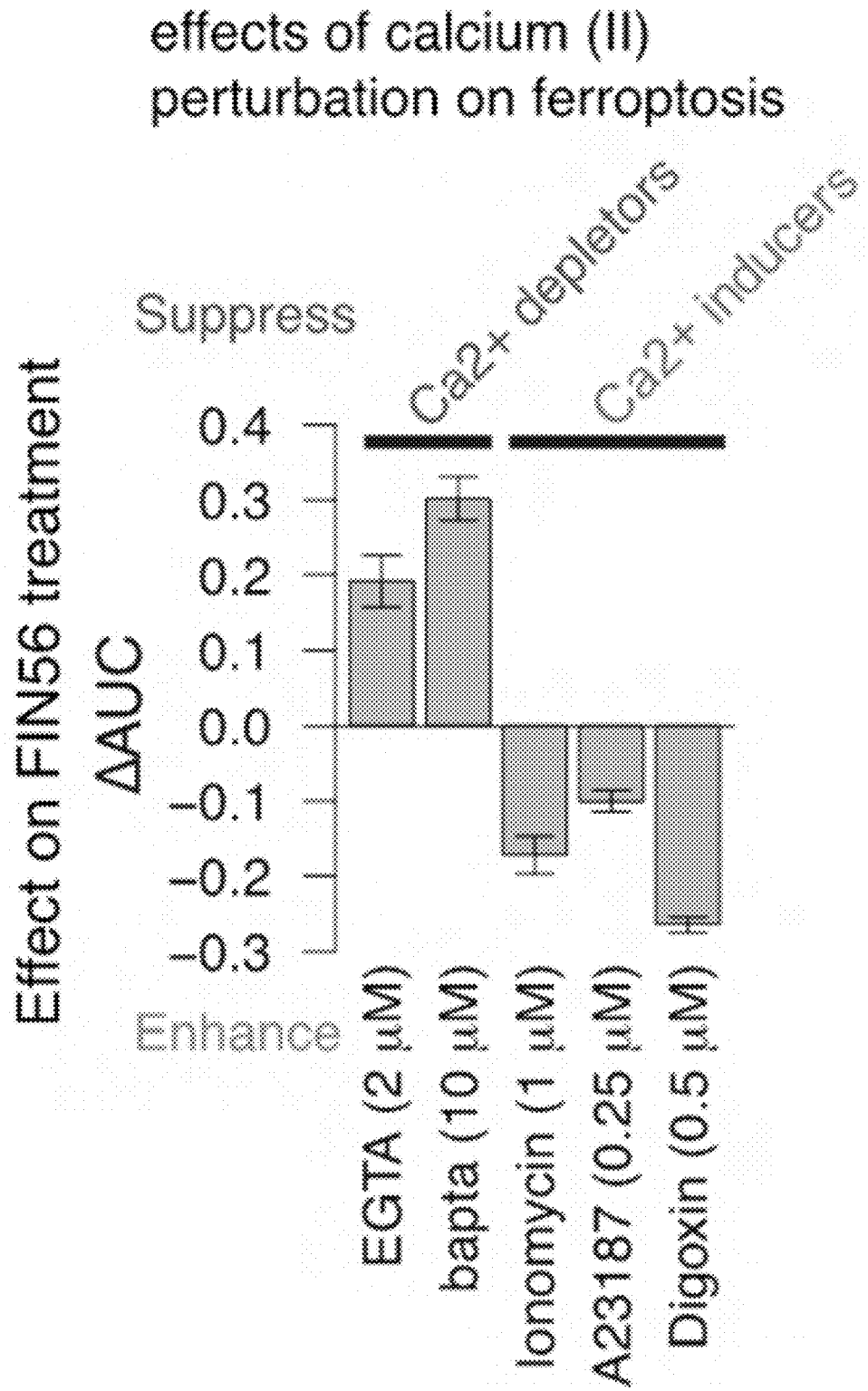

FIGS. 23A-23B show that FIN56-induced ferroptosis involves Ca(II) signaling.

FIG. 23A shows the flow cytometry to monitor intracellular Ca(II) levels in Fluo-4 stained HT-1080 cells.

FIG. 23B shows the effects of Ca(II) inducers and depleters on FIN56 lethality in HT-1080 cells.

DETAILED DESCRIPTION OF THE INVENTION

One embodiment of the present invention is a compound according to formula (I):

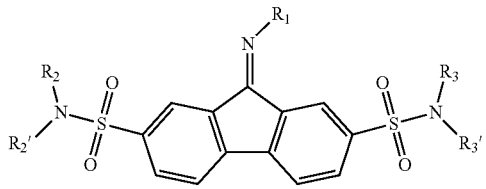

(I)

wherein:
$R_1$ is selected from the group consisting of H, OH, and —(OCH$_2$CH$_2$)$_x$OH;
X is an integer from 1 to 6; and
$R_2$, $R_2'$, $R_3$, and $R_3'$ independently are selected from the group consisting of H, C$_{3-8}$cycloalkyl, and combinations thereof, or $R_2$ and $R_2'$ may be joined together to form a pyridinyl or pyranyl and $R_3$ and $R_3'$ may be joined together to form a pyridinyl or pyranyl;
or an N-oxide, crystalline form, hydrate, or pharmaceutically acceptable salt thereof; with the proviso that the compound is not

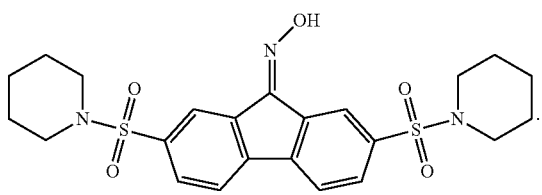 [SMILES: O=S(=O)(c1ccc2c(c1)C(=NO)c1cc(S(=O)(=O)N3CCCCC3)ccc1-2)N1CCCCC1]

In one aspect of this embodiment, the compound has the structure of formula (II):

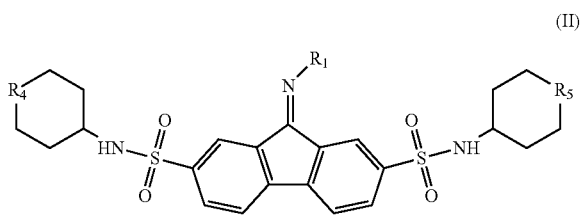

(II)

wherein:
$R_1$ is selected from the group consisting of OH and —(OCH$_2$CH$_2$)$_x$OH;
X is an integer from 1 to 6; and
$R_4$ and $R_5$ are independently selected from the group consisting of CH$_2$ and O;
or an N-oxide, crystalline form, hydrate, or pharmaceutically acceptable salt thereof.

Preferably, $R_1$ is OH. Also preferably, $R_4$ and $R_5$ are each CH$_2$.

In another aspect of this embodiment, the compound is selected from the group consisting of:

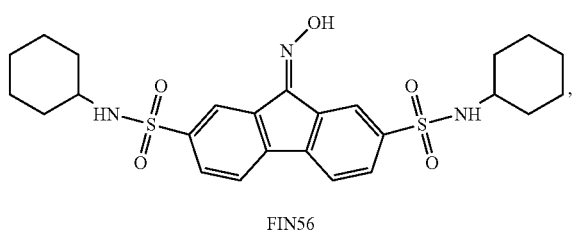

FIN56

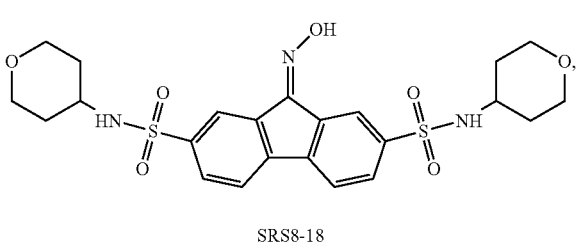

SRS8-18

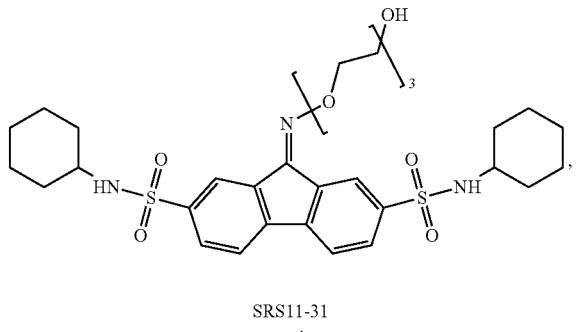

SRS11-31
and

-continued

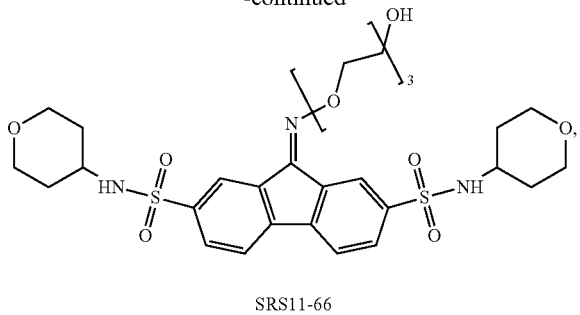

SRS11-66 and combinations thereof, or an N-oxide, crystalline form, hydrate, or pharmaceutically acceptable salt thereof.

Preferably, the compound is FIN56:

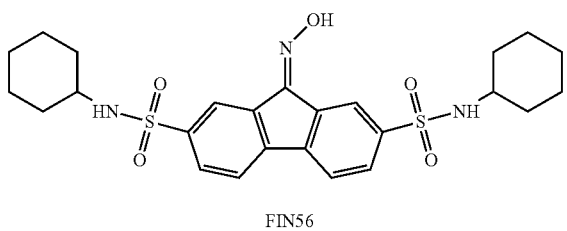 [SMILES: O=S(=O)(NC1CCCCC1)c1ccc2c(c1)C(=NO)c1cc(S(=O)(=O)NC3CCCCC3)ccc1-2 ; "FIN56"]

FIN56 or an N-oxide, crystalline form, hydrate, or pharmaceutically acceptable salt thereof.

Another embodiment of the present invention is a composition. This composition comprises a pharmaceutically acceptable carrier, adjuvant, or vehicle, and one or more compounds according to the present invention.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In certain embodiments, a straight chain or branched chain alkyl has 10 or fewer carbon atoms in its backbone (e.g., C1-C10 for straight chains, C3-C10 for branched chains). Likewise, certain cycloalkyls have from 3-8 carbon atoms in their ring structure, including 5, 6 or 7 carbons in the ring structure.

Moreover, unless otherwise indicated, the term "alkyl" (or "cycloalkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, an aromatic, or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like. Exemplary substituted alkyls are described below. Cycloalkyls can be further substituted with alkyls, alkenyls, alkoxys, alkylthios, aminoalkyls, carbonyl-substituted alkyls, —CF3, —CN, and the like.

The term "cycloalkyl" means a univalent group derived from cycloalkanes by removal of a hydrogen atom from a ring carbon atom.

The term "$C_{x-y}$" when used in conjunction with a chemical moiety, such as, alkyl and cycloalkyl, is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc.

The term "substituted" refers to moieties having substituents replacing a hydrogen on one or more carbons of the backbone. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinatean amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

As set forth previously, unless specifically stated as "unsubstituted," references to chemical moieties herein are understood to include substituted variants. For example, reference to an "aryl" group or moiety implicitly includes both substituted and unsubstituted variants.

As used herein, an "N-oxide" means a compound containing an N—O bond with three additional hydrogen and/or side chains attached to N, so that there is a positive charge on the nitrogen. The N-oxides of compounds of the present invention may be synthesized by simple oxidation procedures well known to those skilled in the art. For example, the oxidation procedure described by P. Brougham et al. (Synthesis, 1015-1017, 1987), allows the two nitrogen of a piperazine ring to be differentiated, enabling both the N-oxides and N,N'-dioxide to be obtained. Other oxidation procedures are disclosed in, e.g., U.S. Patent Publication No. 20070275977; S. L. Jain, J. K. Joseph, B. Sain, Synlett, 2006, 2661-2663; A. McKillop, D. Kemp, Tetrahedron, 1989, 45, 3299-3306; R. S. Varma, K. P. Naicker, Org. Lett., 1999, 1, 189-191; and N. K. Jana, J. G. Verkade, Org. Lett., 2003, 5, 3787-3790. Thus, the present invention includes these and other well-known procedures for making N-oxides, so long as the end product is sufficiently effective as set forth in more detail below.

The term "crystalline form", as used herein, refers to the crystal structure of a compound. A compound may exist in one or more crystalline forms, which may have different structural, physical, pharmacological, or chemical characteristics. Different crystalline forms may be obtained using variations in nucleation, growth kinetics, agglomeration, and breakage. Nucleation results when the phase-transition energy barrier is overcome, thereby allowing a particle to form from a supersaturated solution. Crystal growth is the enlargement of crystal particles caused by deposition of the chemical compound on an existing surface of the crystal. The relative rate of nucleation and growth determine the size distribution of the crystals that are formed. The thermodynamic driving force for both nucleation and growth is supersaturation, which is defined as the deviation from thermodynamic equilibrium. Agglomeration is the formation of larger particles through two or more particles (e.g., crystals) sticking together and forming a larger crystalline structure.

As used herein, a "hydrate" means a compound that contains water molecules in a definite ratio and in which water forms an integral part of the crystalline structure of the compound. Methods of making hydrates are known in the art. For example, some substances spontaneously absorb water from the air to form hydrates. Others may form hydrates upon contact with water. In most cases, however, hydrates are made by changes in temperature or pressure. Additionally, the compounds of the present invention as well as their salts may contain, e.g., when isolated in crystalline form, varying amounts of solvents, such as water. Included within the scope of the invention are, therefore, all hydrates of the compounds and all hydrates of salts of the compounds of the present invention, so long as such hydrates are sufficiently effective as set forth in more detail below.

As used herein, a "pharmaceutically acceptable salt" means a salt of the compounds of the present invention which are pharmaceutically acceptable, as defined herein, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

A composition of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a composition of the present invention may be administered in conjunction with other treatments. A composition of the present invention maybe encapsulated or otherwise protected against gastric or other secretions, if desired.

The compositions of the invention are pharmaceutically acceptable and may comprise one or more active ingredients in admixture with one or more pharmaceutically-acceptable carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21 st Edition, Lippincott Williams and Wilkins, Philadelphia, Pa.). More generally, "pharmaceutically acceptable" means that which is useful in preparing a composition that is generally safe, non-toxic, and neither biologically nor otherwise undesirable and includes that which is acceptable for veterinary use as well as human pharmaceutical use.

Pharmaceutically acceptable carriers are well known in the art (see, e.g., Remington, The Science and Practice of Pharmacy (21 st Edition, Lippincott Williams and Wilkins, Philadelphia, Pa.) and The National Formulary (American Pharmaceutical Association, Washington, D.C.)) and include sugars {e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

Another embodiment of the present invention is a method of inducing ferroptosis in a cell. This method comprises contacting the cell with an effective amount of a compound having the structure of formula (I):

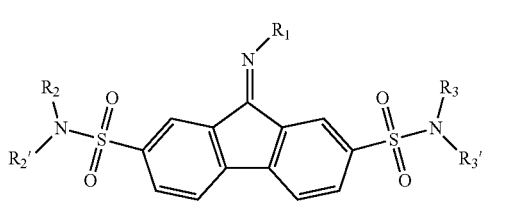

(I)

wherein:

R₁ is selected from the group consisting of H, OH, and —(OCH₂CH₂)ₓOH;

X is an integer from 1 to 6; and

R₂, R₂', R₃, and R₃' independently are selected from the group consisting of H, C₃₋₈cycloalkyl, and combinations thereof, or R₂ and R₂' may be joined together to form a pyridinyl or pyranyl and R₃ and R₃' may be joined together to form a pyridinyl or pyranyl;

or an N-oxide, crystalline form, hydrate, or pharmaceutically acceptable salt thereof.

As used herein, "ferroptosis" means regulated cell death that is iron-dependent. Ferroptosis is characterized by the overwhelming, iron-dependent accumulation of lethal lipid reactive oxygen species. Ferroptosis is distinct from apoptosis, necrosis, and autophagy. Assays for ferroptosis are as disclosed, for instance, in Dixon et al., 2012.

Preferred compounds that fall within the structure of formula I are as set forth above.

In one aspect of this embodiment, the cell is mammalian, preferably human. In other aspects of this embodiment, the cell is from a laboratory animal. In addition to humans, categories of mammals within the scope of the present invention include, for example, agricultural animals, veterinary animals, laboratory animals, etc. Some examples of agricultural animals include cows, pigs, horses, goats, etc. Some examples of veterinary animals include dogs, cats, etc. Some examples of laboratory animals include rats, mice, rabbits, guinea pigs, etc.

In one aspect of this embodiment, the method is carried out in vitro. In other aspects of this embodiment, the method is carried out in vivo or ex vivo.

As used herein, in vitro refers to a process performed in an artificial environment created outside a living multicellular organism (e.g., a test tube or culture plate) used in experimental research to study a disease or process. As used herein, in vitro includes processes performed in intact cells growing in culture.

As used herein, in vivo means that which takes place inside an organism and more specifically to a process performed in or on the living tissue of a whole, living multicellular organism (animal), such as a mammal, as opposed to a partial or dead one.

As used herein, ex vivo refers to a process performed in an artificial environment outside the organism on living cells or tissue which are removed from an organism and subsequently returned to an organism.

Another embodiment of the present invention is a method for decreasing GPX4 in a cell. This method comprises contacting the cell with an effective amount of a compound having the structure of formula (I):

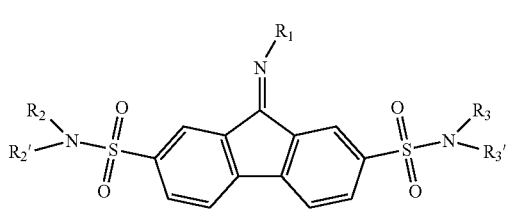

(I)

wherein:

R₁ is selected from the group consisting of H, OH, and —(OCH₂CH₂)ₓOH;

X is an integer from 1 to 6; and

R₂, R₂', R₃, and R₃' independently are selected from the group consisting of H, C₃₋₈cycloalkyl, and combinations thereof, or R₂ and R₂' may be joined together to form a pyridinyl or pyranyl and R₃ and R₃' may be joined together to form a pyridinyl or pyranyl;

or an N-oxide, crystalline form, hydrate, or pharmaceutically acceptable salt thereof.

Preferred compounds that fall within the structure of formula I are as set forth above.

In one aspect of this embodiment, the cell is mammalian, preferably human. In other aspects of this embodiment, the cell is from a laboratory animal. In addition to humans, categories of mammals within the scope of the present invention include, for example, agricultural animals, veterinary animals, laboratory animals, etc. Some examples of agricultural animals include cows, pigs, horses, goats, etc. Some examples of veterinary animals include dogs, cats, etc. Some examples of laboratory animals include rats, mice, rabbits, guinea pigs, etc.

In one aspect of this embodiment, the method is carried out in vitro. In other aspects of this embodiment, the method is carried out in vivo or ex vivo.

As used herein, "GPX4" refers to glutathione peroxidase 4, a glutathione metabolism enzyme.

The compositions of the invention may, optionally, contain additional ingredients and/or materials commonly used in such compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropyl methyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

Compositions suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

It is understood that the disclosure of a compound herein encompasses all stereoisomers of that compound. As used herein, the term "stereoisomer" refers to a compound made up of the same atoms bonded by the same bonds but having different three-dimensional structures which are not interchangeable. The three-dimensional structures are called configurations. Stereoisomers include enantiomers and diastereomers.

The terms "racemate" or "racemic mixture" refer to a mixture of equal parts of enantiomers. The term "chiral center" refers to a carbon atom to which four different groups are attached. The term "enantiomeric enrichment" as used herein refers to the increase in the amount of one enantiomer as compared to the other.

It is appreciated that to the extent compounds of the present invention have a chiral center, they may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The stereoisomers may also be separated by usual techniques known to those skilled in the art including fractional crystallization of the bases or their salts or chromatographic techniques such as LC or flash chromatography. The (+) enantiomer can be separated from the (−) enantiomer using techniques and procedures well known in the art, such as that described by J. Jacques, et al., Enantiomers, Racemates, and Resolutions", John Wiley and Sons, Inc., 1981. For example, chiral chromatography with a suitable organic solvent, such as ethanol/acetonitrile and Chiralpak AD packing, 20 micron can also be utilized to effect separation of the enantiomers.

The following examples are provided to further illustrate the methods of the present invention. These examples are illustrative only and are not intended to limit the scope of the invention in any way.

EXAMPLES

The invention is further illustrated by the following examples, which are offered for illustrative purposes, and are not intended to limit the invention in any manner. Those of skill in the art will readily recognize a variety of noncritical parameters, which can be changed or modified to yield essentially the same results.

Example 1

Materials and Methods

Chemicals.

3,169 uncharacterized lethal compounds, as well as structural analogs of CIL41/70, were purchased from Asinex, Chem Bridge, Chem Div, Enamine, InterBioScreen, May-Bridge, TimTec, Vitas M Labs, and Zelinsky. Chemical modulators (see Table 2) used in modulatory profiling were obtained as previously described (Wolpaw et al. 2011). U0126 was obtained from LC Laboratories. Deferoxamine mesylate, α-tocopherol, sodium selenite, zaragozic acid A, mevalonolactone and simvastatin were purchased from Sigma-Aldrich. Cerivastatin was obtained from Waterstone Technology. Lovastatin was obtained from Santa Cruz Biotechnology. YM-53601 and TOFA were purchased from Cayman Chemical. Isoprenoid pyrophosphate (isopentenyl-PP, dimethylallyl-PP, geranyl-PP, farnesyl-PP and geranylgeranyl-PP) ammonium salts were purchased from Isoprenoids. Idebenone was purchased from Tocris Bioscience. Pim kinase inhibitors (CX-6258 and AZD-1208) were purchased from Selleck Chemicals. Erastin and (1S,3R)-RSL3 were synthesized as described previously (Yang et al. 2014; Yagoda et al. 2007). NB-598 maleate was purchased from ChemScene. CIL56, FIN56, and their structural analogs were synthesized as described by Cholody et al. in the international patent application PCT/US2008/006015 (published as WO2008140792A1). Building blocks for these compounds were purchased from Matrix Scientific and Sigma-Aldrich. The purity of the purchased compounds was not assessed. Structures of 56 CILs and CIL41/70 analogs are presented in Tables 4 and 5. The total synthesis of CIL56 analogs and their 1H NMR data are described in Example 8.

Cell Lines and Media.

Four engineered BJ cell lines (BJeLR, DRD, BJeHLT, and BJeH) were obtained from Robert Weinberg (Whitehead Institute). 143B cells (osteosarcoma) were from Eric Schon (Columbia University). Calu-1 (lung adenocarcinoma) and HT-1080 (fibrosarcoma) cells were from American Type Culture Collection. The four BJ cell lines were grown in DMEM high-glucose media (Life Technologies), 20% Medium 199 (Sigma), and 15% heat-inactivated FBS (FBS). HT-1080 cells were grown in DMEM high-glucose media with 1% non-essential amino acids (Life Technologies) and 10% FBS. 143B cells were grown in DMEM high-glucose media with 1% glutamine and 10% FBS. Calu-1 cells were grown in McCoy's 5A media (Life Technologies) supplemented with 10% FBS. All the cell lines were grown at 37° C. under 5% $CO_2$. Cell lines were not tested for mycoplasma.

Cell Viability Assay.

1,000 cells per 36 µl were seeded in each well in 384-well plates. Lethal compounds were dissolved, and a twofold, 12-point dilution series was prepared in DMSO. Compound solutions were further diluted with media at 1:25, and 4 µl per well of the diluted solutions was added to cell cultures immediately after cells were seeded. When ferroptosis inhibitors (100 µM α-tocopherol, 152 µM deferoxamine, or 10 µM U0126) were used in cotreatments with lethal inducers, they were supplemented to cell culture when the lethal compounds were added, and the cells were then incubated for 24 h. When other cell-death-modulating compounds (100 nM sodium selenite, 1 µM cerivastatin, 100 µg/mL mevalonic acid) were used in cotreatments, they were supplemented to cell culture for 24 h before lethal compounds were added to cell culture, after which cells were further incubated for 24 h at 37° C. under 5% $CO_2$. On the day of the viability measurement, we added 10 µl per well of 50% Alamar Blue diluted in media (Life Technologies) and further incubated the cells at 37° C. for 6 h. Fluorescence intensity (excitation/emission: 530/590) was measured with a Victor 3 plate reader (PerkinElmer), and the normalized viability was calculated as $V_L=(I_L-I_0)/(I_V-I_0)$, where $V_L$, $I_0$, $I_V$, and $I_L$ are the normalized viability and the raw fluorescence intensities from the wells containing media, cells treated with a vehicle (negative control), and cells with the lethal compound (L), respectively. When the effect of a chemical modulator (M) on L was calculated, we instead used the equation $V_{L|M}=(I_{M,L}-I_0)/(I_{M,V}-I_0)$, where $V_{L|M}$, $I_{M,L}$ and $I_{M,V}$ are the normalized viability, and fluorescence intensity from cells treated with M and V, and from cells with M and L, respectively. The viability was typically measured in biological triplicate unless otherwise specified. A representative dose-response curve, the mean and standard error of normalized viability from one replicate were plotted. HT-1080 viability after modulator treatments corresponding to FIG. 3C and FIGS. 5E-5F is available in FIGS. 19A-19C.

Caspase-3/7 Activation Assay.

The Apo-ONE Homogeneous Caspase-3/7 Assay (Promega) was used according to the manufacturer's protocol, with a minor modification. First, we optimized the assay (FIG. 7A-7B). HT-1080 cells were seeded at 1,000 cells per 40 µl in each well of a 384-well plate, incubated for 1 h, and treated with test compounds for different durations (from 3.5 to 48 h). 15 µl of culture media was aspirated from each well, and 5 µl of a mixture of lysis buffer and caspase-3/7 fluorogenic substrate from the kit was added. Plates were kept in the dark at room temperature for 16 h, and the fluorescence (excitation/emission: 490/535) of each well was measured using a Victor 3 plate reader. In the optimization, the fluorescence of apoptosis-inducer-treated cells started increasing after 6-12 h, and lethal compounds that induced strong positive signals in the end (i.e., apoptosis inducers) were distinguished from non-apoptotic inducers as early as after 18 h. We therefore treated cells with lethal compounds for 18 h in further analyses. In the screening mode, we incubated HT-1080 cells with screening molecules for 18 h, processed cells, and measured the fluorescence. Compounds inducing fluorescence with similar intensity as vehicle (DMSO) treatments were defined as caspase-independent lethals.

Discovery of Novel Ferroptosis Inducers Using Modulatory Profiling.

Collection of CILs. First, collected uncharacterized synthetic compounds from various vendors for different screening purposes. Of those, we found 3,169 compounds to be lethal in BJeLR cells. We first sought compounds that induced non-apoptotic cell death in two ferroptosis-susceptible cell lines, HT-1080 and BJeLR. We tested the 3,169 compounds at 5.3 µg/mL in those two cell lines, and 451 compounds showed (i) an $EC_{80}<2.8$ µg/mL in both cell lines and (ii) no activation of caspase-3/7 at 5.3 µg/mL. Cell viability and caspase-3/7 activity assays were performed as described above. The 95th percentile of Apo-ONE fluorescence from 0.13% DMSO-treated cells was set as the threshold of caspase-independent lethality, and the raw fluorescent value of each well was divided by the threshold for normalization; lethal compounds were considered caspase-3/7-independent when the normalized fluorescent values were less than one. These compounds were defined as CILs. Next, we computed the structural similarity among the 451 compounds based on Pubchem's fingerprint (Backman et al. 2011) and removed structurally similar compounds (cutoff: Tanimoto coefficient of 0.9). We also removed compounds that did not satisfy Lipinski's rule of five with a minor modification (no more than five hydrogen bond donors, no more than ten hydrogen bond acceptors, molecular weight ranging from 250 to 500, a partition coefficient log P not greater than five) and compounds whose biological activities were known. Finally, we retested the selected compounds in twofold dilution series in the two cell lines and closely examined 56 compounds with low $EC_{50}$ in modulatory profiling.

Modulatory profiling of CILs. Examined 56 CILs using modulatory profiling (Wolpaw et al. 2011) (FIG. 8). HT-1080 and BJeLR cells were seeded at 1,000 cells per 40 μl in each well of a 384-well plate. They were cotreated with a lethal compound (L) and a death modulator (M) in technical triplicates. We added 56 CILs to cells in a twofold, 14-point dilution series. Death modulators were reagents known to perturb cell death signaling pathways and were treated at a single concentration, as described previously (Wolpaw et al. 2011). Cells were incubated with lethal compounds and modulators for 48 h, and the normalized viability was measured as described above. For each combination of L and M, the area under the dose-response curve (AUC) was computed. An effect of M on L ($E_{M|L}$) was represented by the difference in AUCs between the modulator ($AUC_{M,L}$) and the modulator ($AUC_{V,L}$), or $E_{M|L}=AUC_{M,L}-AUC_{V,L}$ (see FIG. 8B). When M suppresses or enhances the effect of L, $E_{M|L}>0$ or $E_{M|L}<0$, respectively.

The modulatability of each L (mL) was an average of the absolute value of the effect of all M's on L, or $m_L=\Sigma_M|E_{M|L}|/n_M$, where $n_M$ is the number of modulators, 46. Large $m_L$ indicates that L induces a selective cell death phenotype (Wolpaw et al. 2011). Computed $m_L$ for each CIL and each known lethal compound from different classes of mechanism of action (i.e., HDAC inhibitors, proteosomal inhibitors, mitochondrial uncouplers, topoisomerase I and II inhibitors, microtubule destabilizers, and ferroptosis inducers). $m_L$ of CILs larger than the median value of known lethal compounds' $m_L$ were considered 'high'; we identified high-modulatability CILs. For generating hierarchical clustering of the modulatory profiles, the distance between modulatory profiles (P) of two compounds $P_i$ and $P_j$ was defined by $d_{ij}=1-Corr_{Pearson}(P_i,P_j)$, and hierarchical clustering with an average-linkage method was used to generate dendrograms.

Cobalt (II) Binding Assay In Vitro.

For each cluster I compound (CIL13, −52, and −64), prepared two-fold dilution series with DMSO. We added 30 μL per well of either water or 10 μM cobalt (II) chloride solution to each well of a 384-well plate. Dilution series of each compound in DMSO were added by 10 μL per well. After solutions had been mixed by shaking of the plate using a Victor 3 plate reader (PerkinElmer), absorbance was scanned between 300 and 700 nm for each compound. Finally the following Absorbance value for each compound was plotted (see FIG. 9B):

$$\Delta\Delta\Delta Absorbance = \Delta Abs_{CIL,Co2+} - \Delta Abs_{CIL,water}$$
$$= (Abs_{CIL,Co2+} - Abs_{DMSO,Co2+}) -$$
$$(Abs_{CIL,water} - Abs_{DMSO,water})$$

where Abs is the absorbance at each wavelength.

Search of Commercially Available Structural Analogs of CIL41/70.

Structural analogs possessing the core scaffold of CIL41/70 (SMILES: C(=O)([*])O/N=C([*])/N) were searched for in eMolecules (see, e.g., http://www.emolecules.com) and purchased from the vendors listed above. Their lethality was tested once in HT-1080 cells in technical triplicates.

Analysis of ROS Generation.

Grew 200,000 HT-1080 or BJeLR cells in six-well plates at 37° C. for 16 h. Cells were treated with test compounds, trypsinized, pelleted, and washed once with PBS. For lipophilic or aqueous ROS detection, cells were re-suspended in Hanks' Balanced Salt Solution (HBSS; Life Technologies) containing test compounds as well as $C_{11}$-BODIPY(581/591) (2 μM) or $H_2$-DCFDA (25 μM), respectively (Life Technologies), and incubated for 10 min at 37° C. Cells were then pelleted, re-suspended in 500 μL HBSS, strained through a 40-μm cell strainer (BD Falcon), and analyzed using a BD Accuri C6 flow cytometer (BD Biosciences). Both dyes were measured in the FL1 channel. Experiments were done in biological triplicates.

Glutathione-Quantification Assay.

Seeded 500,000 HT-1080 cells in a 10-cm dish. Cells were grown at 37° C. for 16 h. On the day of the analysis, cells were cotreated with 100 μM α-tocopherol and either vehicle (DMSO) or a ferroptosis inducer (10 μM erastin, 0.5 μM (1S,3R)-RSL3, or 5 μM FIN56) and incubated for 10 h. Cells were then trypsinized, pelleted, washed once with 400 μL of ice-cold PBS containing 1 mM EDTA, and sonicated. After the cell debris had been pelleted and removed, both oxidized and reduced glutathione in 120 μL of sample was quantified in technical triplicates using the QuantiChrome glutathione assay kit (BioAssay Systems). The glutathione quantity was normalized to the protein concentration measured via Bradford assay (Bio-Rad).

GPX4 Enzymatic Activity Assay.

Seeded 17 million BJeLR cells in 225-$cm^2$ tissue culture flasks (Corning). We then added vehicle (0.1% DMSO for 11 h) or test compound (10 μM erastin for 11 h, 0.5 μM (1S,3R)-RSL3 for 2 h, or 5 μM FIN56 for 10 h). The GPX4 enzymatic activity assay was performed as described previously (Yang et al. 2014). Briefly, 10 million cells were resuspended in cell lysis buffer. Cells were sonicated to make cell lysates that were then cleared by centrifugation at 14,000 r.p.m. for 10 min. The protein concentration of the cleared cell lysates was determined via Bradford protein assay. Mixed 200 μg of cellular protein with phosphatidyl choline hydroperoxide, a GPX4-specific substrate, and reduced glutathione, a GPX4 cofactor. The mixture was incubated at 37° C. for 30 min and then subjected to lipid extraction using chloroform:methanol (2:1) solution. The lipid extract was evaporated using a Rotavap and re-dissolved in 100% ethanol before being injected into the LC-MS instrument for 2-linoleoyl1-palmitoyl-sn-glycero-3-phosphocholine (PLPC) quantitation.

Reverse-Transcription Quantitative PCR.

Trypsinized 0.2 to 1 million cells grown in six-well dishes, pelleted them, resuspended them in Buffer RLT (Qiagen), and homogenized them with QIAshredder (Qiagen). RNA was further extracted using the RNeasy Mini Kit (Qiagen). We converted 2 μg of extracted RNA from each sample into cDNA using TaqMan reverse-transcription reagents (Life Technologies). qPCR primers were designed to detect all splicing variants using Primer Express 2.0 (Applied Biosystems). The designed primers were confirmed to amplify only the designated gene transcripts using in silico PCR (see, e.g., http://genome.ucsc.edu/cgi-bin/ hgPcr). For qPCR reactions, primers, cDNA, and Power SYBR Green PCR Master Mix (Applied Biosystems) were mixed, and quantitation was performed using a StepOnePlus real-time PCR system (Applied Biosystems). Experiments were done in biological triplicates.

Western Blotting.

Seeded 300,000 cells (HT-1080 or BJeLR) per well in six-well plates. For cotreatment, ferroptosis inducers (10 µM erastin for 11 h, 0.5 µM (1S, 3R)-RSL3 for 2 h, or 5 µM FIN56) and 100 µM α-tocopherol were added to cell culture at the same time, and cells were then incubated for 10 h (FIG. 2E). When other death-modulating compounds (100 nM sodium selenite, 1 µM cerivastatin, 100 µg/mL mevalonic acid, 30 µM C75, or 2 µM cerulenin) were used in cotreatments, cells were pre-incubated with the modulators for 24 h before being treated with ferroptosis inducers for 6 h. Cell lysis, SDS-PAGE and protein transfer to PVDF membrane were performed as previously described (Dixon et al. 2012). We used the following antibodies: anti-human α-tubulin (Santa Cruz Biotechnology, sc-32293, 1:10,000 dilution), anti-human GPX4 (Abcam, ab41787, 1:2,000 dilution), anti-human GPX1 (R&D Systems, AF3798, 1:1,000 dilution), and anti-human SQS (Abcam, ab109723 for full-length, ab195046 for truncated, both at 1:1,000 dilution). Secondary antibodies were from LI-COR (1:3,000 dilution). The PVDF membranes labeled with primary and secondary antibodies were scanned using an Odyssey Imaging System (LI-COR). Experiments were performed in biological triplicates, and the mean±s.e. of intensity was plotted. Full gel images are shown in FIGS. 20A-20J.

Gene-Knockdown Experiment.

shRNAs designed by the RNAi Consortium were used, and gene knockdown was performed as described previously (9). For siRNA-mediated gene-knockdown experiments, HT-1080 cells were reverse-transfected with 5 nM siRNA. siRNA targeting GPX4 (Dharmacon, #L-011676-00) or TRIT1 (Dharmacon, #L-018831-02) or nontargeting siRNA (Qiagen) was mixed with 2 µL Lipofectamine RNAiMAX (Invitrogen) in a well of a 12-well plate. After incubation for 30 min at room temperature, 30,000 cells were added to each well, and knockdown was allowed to proceed for 48 h. Cells were then harvested and re-seeded for RT-qPCR, viability assay, and western blotting. For RT-qPCR, cells were re-seeded into 12 well plates and harvested the following day as described above. For viability assay, 1,000 cells per well were reseeded into 384-well plates for 24 h and were then incubated with compounds for another 24 h before the addition of Alamar Blue. Compounds were added in a 12-point twofold dilution series, with the highest concentrations of compound being 36.5 µM (erastin), 10 µM ((1S,3R)-RSL3), and 38.7 µM (FIN56). For western blotting, cells were harvested 48 h after knockdown (no re-seeding).

FIN56 Target Identification.

Conjugation of active and inactive probes with Profinity epoxide resin. Incubated 6 µmol of active (SRS11-31) or inactive (SRS11-66) probes dissolved in 500 µL DMSO and 300 mg of Profinity epoxide resin (Bio-Rad) in saturated sodium bicarbonate at 45° C. for 3 d. The conjugation reaction was ended by adding 120 µL of 1 M ethanolamine to the reaction mixture. The conjugated probe beads were used for further protein pulldown assay.

Affinity chromatography with active and inactive probe beads. Seeded 8 million HT-1080 cells in two 15-cm polystyrene tissue culture dishes and allowed the cells to grow overnight. Culture media was removed from dishes, and cells were washed five times with cold PBS. After the PBS had been completely removed, the cells were treated with 2 mL of lysis buffer (25 mM MOPS (pH 7.2), 15 mM EGTA, 15 mM MgCl$_2$, 2 mM DTT, 1 mM sodium orthovanadate, 1 mM sodium fluoride, 0.5% NP-40, 60 mM β-glycerophosphate, protease inhibitor cocktail (Sigma-Aldrich P8340)) per plate, scraped, and collected. Cells were then agitated at 4° C. for 15 min, after which insoluble components were precipitated at 14,000 g at 4° C. for 10 min, the supernatant was removed, and the protein concentration was measured via Bradford assay.

Incubated 250 µg of protein (up to 400 µL of the whole-cell lysate) with active and inactive probe beads, added 20 mL of bead buffer (50 mM Tris-HCl (pH 7.4), 250 mM NaCl, 5 mM EDTA, 5 mM EGTA, 5 mM NaF, 0.1% NP-40), and incubated the mixture at 4° C. for 12 h. Beads were then collected using Poly-prep chromatography columns (Bio-Rad). Beads were then washed with 8 mL of bead buffer three times and transferred to Eppendorf tubes.

Bacterial expression and purification of truncated human SQS for competition assay. The plasmid encoding the truncated human squalene synthase (SQS 31-370) in pET28a expression vector, kindly provided by Chia-I Liu and Andrew H. J. Wang (Academia Sinica, Taiwan), was confirmed by DNA sequencing (Gene Wiz, Inc.) and then used to transform Escherichia coli BL21-Gold (DE3) competent cells (Agilent Technologies). The cells with the construct were grown in LB media supplemented with 100 µg/mL ampicillin at 37° C. until the OD$_{600}$ reached 1. Protein expression was induced with 0.5 mM isopropyl β-D-thiogalactoside at 17° C. overnight (12-13 h). Cells were pelleted (4,000 g, 20 min, 4° C.) and lysed by sonication in SQS buffer (50 mM Tris, pH 7.4, 250 mM NaCl, 5 mM imidazole, 5 mM MgCl$_2$, 1 mM TCEP). Cell lysate was then centrifuged at 15,000 g for 45 min at 4° C. The supernatant was loaded onto a chromatography column containing Ni Sepharose 6 Fast Flow beads (GE Life Sciences) equilibrated with SQS buffer. After two washes and one nonspecific wash of the beads, the bound SQS was eluted with 250 mM imidazole in the same buffer. The purity of eluted fractions was verified by SDS-PAGE as more than 90% pure. The fractions containing SQS were concentrated, flash-frozen, and stored at −80° C. Protein concentration was determined using absorbance at 280 nm with a molar extinction coefficient (ε) of 42,860 M$^{-1}$ cm$^{-1}$ (for reduced SQS with an N-terminal His$_{12}$ tag as calculated from the amino acid sequence by ExPASy ProtParam).

SQS competition assay with purified truncated SQS, FIN56, and active probe. Purified truncated SQS was prepared as described above. The protein solution was diluted with bead buffer (50 mM Tris-HCl, pH 7.4, 250 mM NaCl, 5 mM EDTA, 5 mM EGTA, 5 mM NaF, 0.1% NP-40, 1 mM TCEP). We mixed 190 µL of 1 or 10 ng/mL SQS solution with 10 µL of DMSO or competitor solution (2 mM FIN56 solution in DMSO), with DMSO and FIN56 at final concentrations of 5% and 100 µM, respectively. This mixture was rotated and incubated at 4° C. for 2 h. We added 15 µL of active probe-bead solution (33% slurry) to the solution and incubated it for another 2 h. The beads were spun down (500 r.p.m., 4° C., 1 min), and supernatant was removed and washed with 500 µL of bead buffer three times. After the third wash, 20 µL of 3×SDS sample loading buffer was added, and the mixture was boiled at 95° C. for 5 min. Samples were spun for 1 min at 13,000 r.p.m. in a table-top centrifuge, and 10 µL of each sample was loaded on gels for SDS-PAGE. SQS was confirmed by immunoblotting.

Proteomic analysis for target identification. At Quantitative Proteomics Center at Columbia University, the proteins in pulldown samples with active (SRS11-31) and inactive (SRS11-66) beads were eluted at 80° C. in 50 mM ammonium bicarbonate with 0.1% Rapigest detergent with protease inhibitor cocktail P8340 (Sigma-Aldrich). Biological triplicate culture and affinity pulldowns for bound active and inactive compound were prepared. Cysteines in the protein samples were reduced with dithiothreitol and alkylated with iodoacetamide, and proteins were digested with trypsin (6 ng/µL, Promega Corp, #V511A, in 50 mM ammonium bicarbonate). A digest of yeast alcohol dehydrogenase (50 fmol) was added as an internal detection control.

Three chromatograms were recorded for each of six biological replicates (three active, three inactive), yielding 12 chromatograms. Analytical separation was done on a NanoAcquity UPLC (Waters), with a 120-min chromatogram on a 75-µm inner diameter×25-cm HSS T3 1.8-µm-particle-diameter reverse-phase C18 column at a flow rate of 300 nL/min with an acetonitrile/formic acid gradient at 45° C. Identification and quantitation of proteins bound to the beads was done by label-free proteomic profiling on a Synapt G2 HDMS (quadrupole-time-of-flight) mass spectrometer (Waters) using data-independent scanning ($MS^E$) as described previously (Yang et al. 2014), except that spectra were recorded in positive-ion sensitivity mode without ion mobility. Spectra were searched against a human UniProt complete proteome with ProteinLynx Global Server version 2.5 RC9 (Waters) and post-processed with Elucidator software version 3.3.0.1.SP3_CRE52.21 (Ceiba Solutions, Inc.) as described previously (Alegre-Aguarón et al. 2014).

Target validation using custom shRNA library. Custom lentiviral shRNA libraries were generated using plasmids encoding the first generation of the RNAi Consortium shRNAs targeting 70 genes identified by chemoproteomics according to the RNAi Consortium's instructions. These lentiviral shRNAs were laid out in an arrayed format using 384-well plates and were infected in four cell lines (HT-1080, BJeLR, Calu-1, and 143B). Our rationale for the screening design was that if shRNAs target the bona fide FIN56 targets, those shRNAs should show 'consistent' FIN56-enhancing or -suppressing effects in all four cell lines, depending on how FIN56 acts on the target protein (FIG. 14A). If the shRNAs act on off-targets to change sensitivity to FIN56, their effects should be less consistent. Gene knockdown was performed as described above; 400 cells per well in 384-well plates were seeded and incubated for a day, lentivirus-containing shRNAs were infected in them on the next day, and puromycin was added 2 d after infection. Cells were treated with twofold eight-point dilution series of FIN56 after 24 h and incubated for another 48 h before Alamar Blue was added, after which the cells were incubated for 6 h.

Data analysis for discovering functionally relevant targets. Alamar Blue fluorescence intensity data were normalized as described above. For each cell line, dose-response curves for FIN56 for each shRNA treatment were plotted and overlaid on a single plot first. From among eight tested concentrations of FIN56, extreme (low or high) concentrations that did not kill or completely kill cells treated with any shRNAs were removed; eventually four or five more informative concentrations were used for further analysis, as in FIG. 4B and FIG. 14B. For each shRNA treatment, the AUC after FIN56 treatment in dilution series was computed and rank-ordered across all tested shRNAs in each cell line. Based on their 'consistency' across four cell lines and the magnitude of effects, shRNAs were classified into 11 categories (5 consistently suppressing groups (top 10%, top 20%, etc.), 5 consistently enhancing groups (top 10%, etc.), and nonconsistent). Note that 'nonconsistent' indicates that the shRNA induced FIN56-enhancing effects in some cell lines and FIN56-suppressing effects in others. A gene was ranked according to the consistent effects of shRNAs targeting it. When at least one of the shRNAs targeting a gene showed consistent FIN56-enhancing or -suppressing effects, the gene was considered a potentially functionally relevant target of FIN56, through loss-of-function or gain-of-function scenarios, respectively.

Validation of loss-of-function targets using pooled siRNAs. Candidate loss-of-function targets of FIN56 were further targeted by pooled siRNAs. Previously, pooled siRNA against GPX4, a target of RSL3, was shown to phenocopy RSL3; siGPX4 induced ferroptosis that was suppressed by α-tocopherol as well as oncogenic Ras selectivity across BJ series. Expecting that siRNAs against bona fide loss-of-function targets would induce ferroptosis, we treated siRNAs against the candidates as well as GPX4 as a positive control. siRNAs were transfected into BJeLR cells. We incubated 1 mL of Opti-MEM (Life Technologies) mixed with 20 µmol of pooled siRNA and 5 µL of RNAiMAX (Life Technologies) to form a complex for 15 min, and we then aliquoted 500 µL per well into six-well dishes. Next, 120,000 BJeLR cells per 1.5 mL in each well were seeded and grown for 2 d. Cells were then trypsinized and seeded again at 120,000 per well and grown with or without supplementation of α-tocopherol. After 2 d, cells were trypsinized and cell density was measured using an automated cell counter (Vicell, Beckman Coulter).

Statistical Analysis and Data Visualization.

Dose-response curve plotting and $EC_{50}$ computation were done with Prism 5.0c. P values for the differences in $EC_{50}$ values were computed on the basis of model comparison with Akaike's information criterion. The rest of the statistics and plotting were done using R language and the following R packages and functions: ChemmineR package for Pubchem's fingerprint and Tanimoto coefficient computation, heatmap.2 function in the gplots package for plotting heat maps, and flowCore and flowViz packages modified for plotting .fcs files in flow cytometry. The statistical significance of protein expression (on western blots) was calculated using paired two-tailed t-tests.

TABLE 1

Small molecule screening data.

| Category | Parameter | Description |
| --- | --- | --- |
| Assay | Type of assay | Cell-based assay |
|  | Target | Casepase-independent lethality in HT-1080 and BJeLR. |
|  | Primary measurement | i) Lethality: Alamar Blue (Life Technologies) Viability in both HT-1080 and BJeLR cells. ii) Apo-ONE Homogeneous Caspase-3/7 Assay (Promega) |

TABLE 1-continued

Small molecule screening data.

| Category | Parameter | Description |
|---|---|---|
| | Key reagents | Alamar Blue (Life Technologies); Apo-ONE Homogeneous Caspase-3/7 Assay reagents (Promega) |
| | Assay protocol | Grow cells treated with lethal compounds. Lysed cells and measured Apo-ONE Caspase-3/7 fluorescence after 16 hours. Separately, HT-1080 and BJeLR were incubated with compounds for 48 hours and added Alamar Blue, incubated for another 6 hours. |
| | Additional comments | |
| Library | Library size | 3,169 compounds |
| | Library composition | Uncharacterized compounds pre-selected for lethality in BJ-eLR cell line. |
| | Source | Diversity-oriented library was purchased from the following companies: TimTec, InterBioScreen, ChemBridge. |
| | Additional comments | |
| Screen | Format | 384 well plate |
| | Concentration(s) tested | 5.3 ug/mL |
| | Plate controls | DMSO (0.4%) as non-lethal control. No lethal control |
| | Reagent/compound dispensing system | Beckman Coulter Biomek FX Workstation |
| | Detection instrument and software | Perkin Elmer Victor3 |
| | Assay validation/QC | |
| | Correction factors | None |
| | Normalization | i) Viability: median of 28 wells with DMSO treated cells in each 384-well plate was set as one. All the wells were scaled proportionally, ii) Caspase-3/7 activity: 95 percentile of HMSO treated cells were set as one. All the wells were scaled proportionally. |
| | Additional comments | |
| Post-HTS analysis | Hit criteria | Compounds that induces i) Viability < 0.2 in both HT-1080 and BJeLR cell lines, and ii) Caspase-3/7 activity < 1 were considered caspase-independent lethal, |
| | Hit rate | 451/3,169 = 14.2% |
| | Additional assay(s) | Of 451 hits, 56 structurally diverse and potent compounds were selected, purchased and tested for Modulatory Profiling. |
| | Confirmation of bit purity and structure | The selected 56 compounds were further reordered from another vendors, tested for caspase independent lethality in 12-point 2-fold dilution series. |
| | Additional comments | All 56 compounds were confirmed positive. |

TABLE 2

Death modulators used in modulatory profiling.

| Chemical or Genetic Modulator | Abbreviation | Mechanism | HT1080 | BJeLR | conc (µM) | Ferroptosis suppressor |
|---|---|---|---|---|---|---|
| α-tocophenol | Atoc | Antioxidant | x | x | 100 | x |
| Butylated hydroxyanisole | BHA | Antioxidant | x | | 140 | x |
| Butylated hydroxytoluene | BHT | Antioxidant | x | | 115 | x |
| (+)-6-Hydroxy-2,5,7,8-tetramethylchromane-2-carboxylic acid | Trolox | Antioxidant | x | x | 150 | x |
| Cobalt (II) | Co2 | Calcium channels blocker | x | x | 1200 | |
| Gadolinium (III) | Gd3 | Calcium channels blocker (via sodium leak channel, stretch activated channel) | x | x | 30 | |

TABLE 2-continued

Death modulators used in modulatory profiling.

| Chemical or Genetic Modulator | Abbreviation | Mechanism | HT1080 | BJeLR | conc (μM) | Ferroptosis suppressor |
|---|---|---|---|---|---|---|
| Ethyleneglycol-O,O'-bis(2-amino ethyl)-N,N,N',N'-tetraacetic acid | EGTA | Calcium ion chelator | x | | 2000 | |
| Digoxin | Dig | Inhibitor of Na$^-$/K$^-$ ATPase (increase calcium ion influx) | x | | 0.13 | |
| Deteroxamine | dtom | iron ion chelator | x | | 150 | x |
| L-mimosine | Lmim | iron ion chelator, inhibitor of cell cycle at G1-S | x | 1* | 175 | x |
| Cycloheximide | CHX | Inhibitor of protein synthesis | x | x | 1.5 | |
| Actinomycin D | ActD | Inhibitor of RNA synthesis (RNAPII) | x | | 0.0012 | |
| Calpain Inhibitor I | ALLN | Inhibitor of calpain I/II and cathepsins B/L | x | x | 25 | |
| Na-tosyl-lys-chloromethylketone | TLCK | Inhibitor of trypsin-like serine proteasus | x | x | 135 | |
| Pepstatin | Pepstatin | Inhibitor of cathepsin D | x | x | 1 | |
| NG-Monomethyl-D-arginine | NMMA | Inhibitor of nitric oxide synthase | x | x | 7 | |
| NG-Nitro-L-arginine-methyl ester | LNAME | Inhibitor of nitric oxide synthase | x | x | 300 | |
| 1,4-diamino-2,3-dicyano-1,4-bis[2-aminophenylthio]butadiene | U0126 | Inhibitor of Mitogen-activated protein kinase kinase (MEK) 1/2 | x | | 11 | |
| Anthra(1,9-cd)pyrazol-6(2H)-one 1,9-Pyrazoloanthrone | SP600125 | Inhibitor of c-Jun N-terminal kinase 1/2/3 | x | | 10 | |
| Obz-val-ala-asp(OMe)-fluormethylketone | zVAO | Inhibitor of pan-caspases (apoptosis) | x | x | 45 | |
| t-butoxycarbonyl-asp-fluormethylketone | BocD | Inhibitor of pan-caspases (apoptosis) | x | x | 50 | |
| 3,4-dihydro-5-[4-(1-pipendinyl)butoxyl]-1(2H)-isoquinolinone | DPQ | Inhibitor of poly-ADP ribose polymerase 1(PARP1; PARP1-dependent cell death) | x | x | 10 | |
| 3-methyladenine | 3MA | Inhibitor of autophagosome formation (macroautophagy) | x | x | 5000 | |
| Necrostatin-1 | Nec1 | Inhibitor of receptor interactin protein kinase 1 (RIPK1) (necroptosis) and idoleamine 2,3-dioxygenase (IDO) | x | x | 20 | |
| Aunntricarboxylic Acid | ATA | Inhibitor of ribonuclease | x | | 40 | |
| Nicotinamide adenine dinucleotide, oxidized | NAD | Activities sirtuins, endogenious electrons carrier | x | 1* | 2000 | |
| β-Carolene | Bcarotene | Vitamin A precursor | x | | 0.2 | |
| Cyclosporin A | CspA | Binds cyclophilin D | x | | 5 | |

1*: used both individually and as a combination (NAD+ and Lmim)

TABLE 3

EC$_{50}$s of CILs classified with other ferroptosis inducers and the effects of ferroptosis suppressors on the CILs.

|  |  | CIL41 | CIL56 | CIL69 |
|---|---|---|---|---|
| HT-1080 |  | 5.67 (4.13 to 7.78) | 0.443 (0.287 to 0.683) | 0.551 (0.337 to 0.902) |
|  | DMSO |  |  |  |
| iron-chelators | Deferoxamine | 124 (96.3 to 159) | 1.36 (0.946 to 1.94) | 9.29 (6.23 to 13.9) |
|  | Lmim | 69.8 (65.9 to 73.8) | 1.53 (1.22 to 1.94) | 4.79 (3.52 to 6.52) |
| antioxidants | Atoc | 50 (44 to 56.8) | 2.49 (2.22 to 2.8) | 6.13 (4.79 to 7.86) |
|  | Trolox | 23.4 (20 to 27.3) | 1.31 (1.08 to 1.58) | 4.26 (3.45 to 5.26) |
|  | BHA | 26 (18.3 to 36.9) | 2.65 (2.02 to 3.47) | 4.79 (3.39 to 6.76) |
|  | BHT | 12.6 (9.47 to 16.7) | 1.69 (1.09 to 2.61) | 3.28 (2.32 to 4.62) |
| MEK inh | U0126 | 20.9 (16.6 to 26.4) | 2.81 (2.2 to 3.58) | 5.75 (4.01 to 8.24) |
| BJeLR | DMSO | 3.17 (2.58 to 3.88) | 0.213 (0.164 to 0.276) | 0.193 (0.126 to 0.294) |
| iron-chelators | Lmim | 22.4 (14.7 to 34.1) | 0.925 (0.646 to 1.32) | 0.976 (0.652 to 1.46) |
|  | Lmim_NAD | 22.6 (14.7 to 34.6) | 1.3 (0.884 to 1.91) | 0.889 (0.696 to 1.13) |
| antioxidants | Trolox | 23.2 (16 to 33.5) | 2.03 (1.5 to 2.73) | 2.05 (1.6 to 2.63) |
|  | atoc | 36.6 (27.2 to 49.3) | 2.49 (1.9 to 3.26) | 1.78 (1.45 to 2.2) |
|  |  | CIL70 | CIL75 | CIL79 |
| HT-1080 | DMSO | 4.44 (2.98 to 6.62) | 0.144 (0.101 to 0.205) | 0.271 (0.198 to 0.371) |
| iron-chelators | Deferoxamine | 157 (114 to 216) | 4.82 (3.75 to 6.2) | 32.4 (23.7 to 44.2) |
|  | Lmim | 47.8 (34.6 to 66) | 2.47 (1.67 to 3.64) | 12 (9.01 to 15.9) |
| antioxidants | Atoc | 32.2 (21.8 to 47.5) | 2.94 (2.23 to 3.89) | 11.7 (9.82 to 13.9) |
|  | Trolox | 11.1 (10.2 to 12.2) | 2.56 (2.22 to 2.95) | 10.2 (7.42 to 14.1) |
|  | BHA | 13.3 (10 to 17.7) | 2.75 (1.97 to 3.85) | 10.1 (7.02 to 14.4) |
|  | BHT | 6.5 (4.63 to 9.12) | 1.72 (1.27 to 2.34) | 6.3 (4.62 to 8.58) |
| MEK inh | U0126 | 10.3 (8.06 to 13.2) | 2.53 (1.72 to 3.7) | 14.3 (10.7 to 19.1) |
| BJeLR | DMSO | 1.76 (1.29 to 2.4) | 0.0598 (0.0411 to 0.0868) | 0.157 (0.121 to 0.204) |
| iron-chelators | Lmim | 13.1 (9.02 to 18.9) | 0.341 (0.198 to 0.589) | 0.667 (0.385 to 1.16) |
|  | Lmim_NAD | 14.8 (11.7 to 18.7) | 0.314 (0.209 to 0.472) | 0.566 (0.469 to 0.684) |
| antioxidants | Trolox | 7.1 (5.19 to 9.71) | 1.1 (0.824 to 1.48) | 8.32 (6.41 to 10.8) |
|  | atoc | 18.6 (15.5 to 22.3) | 1.04 (0.857 to 1.26) | 7.93 (6.09 to 10.3) |

* unit is µM; values indicate 'mean (range within 1 s.d.)'

The data in Table 3 are pulled out from the modulatory profiling. Values are point estimates as well as 95% confidential intervals in parentheses computed using sigmoidal curve-fitting in Prism are shown from co-treatment of modulaotrs (rows) and lethal compounds (columns) in two cell lines (HT-1080 and BJeLR).

TABLE 4

Structures of 56 CILs.

| Compound | Pubchem CID | Structure |
|---|---|---|
| CIL01 | 5771107 | 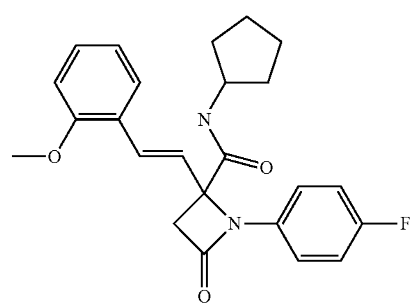 [SMILES: COc1ccccc1/C=C/C1(C(=O)NC2CCCC2)CC(=O)N1c1ccc(F)cc1] |
| CIL02 | 698314 | 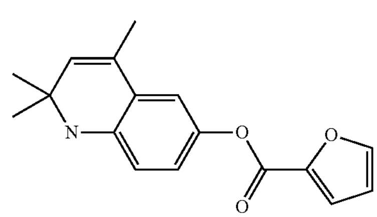 [SMILES: CC1=CC(C)(C)Nc2ccc(OC(=O)c3ccco3)cc21] |

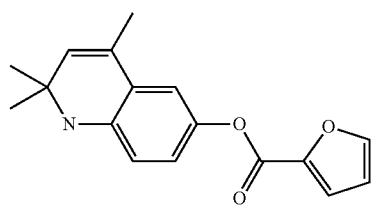

TABLE 4-continued
Structures of 56 CILs.
| Compound | Pubchem CID | Structure |
|---|---|---|
| CIL04 | 2927276 | 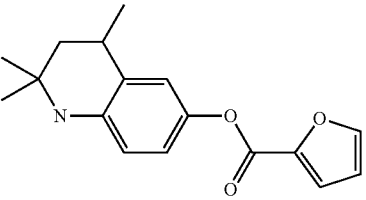 [SMILES: CC1CC(C)(C)Nc2ccc(OC(=O)c3ccco3)cc21] |
| CIL05 | 2802124 | 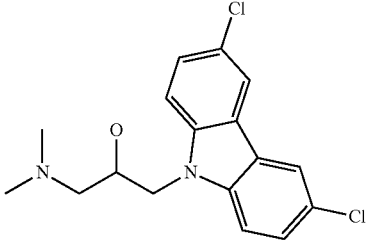 [SMILES: CN(C)CC(O)Cn1c2ccc(Cl)cc2c2cc(Cl)ccc21] |
| CIL06 | 776372 | 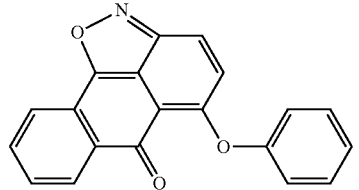 [SMILES: O=C1c2ccccc2-c2onc3ccc(Oc4ccccc4)c1c23] |
| CIL07 | 3113288 | 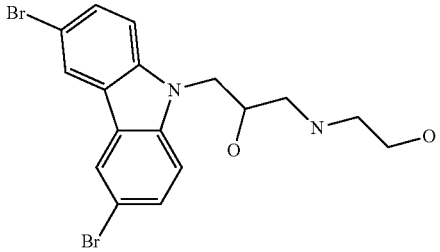 [SMILES: OCCNCC(O)Cn1c2ccc(Br)cc2c2cc(Br)ccc21] |
| CIL09 | 791069 | 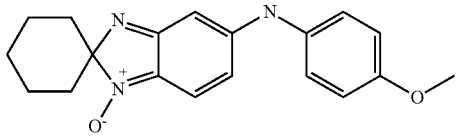 |
| CIL10 | 3221079 | 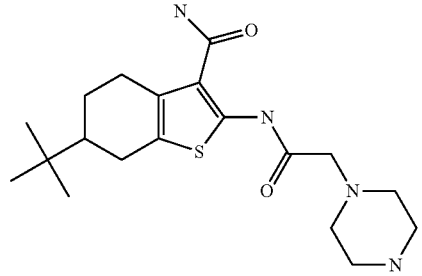 [SMILES: CC(C)(C)C1CCc2c(sc(NC(=O)CN3CCNCC3)c2C(N)=O)C1] |
| CIL11 | 96149 | 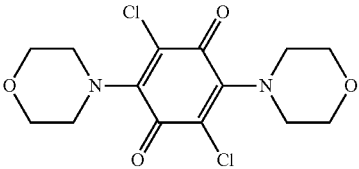 [SMILES: O=C1C(Cl)=C(N2CCOCC2)C(=O)C(Cl)=C1N1CCOCC1] |

TABLE 4-continued
Structures of 56 CILs.
| Compound | Pubchem CID | Structure |
|---|---|---|
| CIL13 | 972880 | 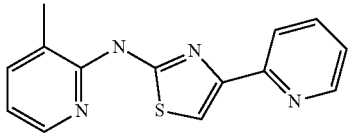 [SMILES: Cc1cccnc1Nc1nc(-c2ccccn2)cs1] |
| CIL15 | 2215161 | 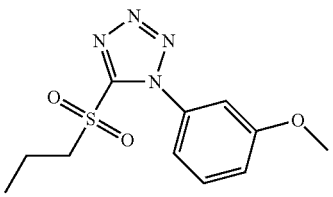 [SMILES: CCCS(=O)(=O)c1nnnn1-c1cccc(OC)c1] |
| CIL16 | 2221997 | 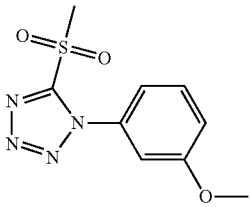 [SMILES: COc1cccc(-n2nnnc2S(C)(=O)=O)c1] |
| CIL17 | 1316704 | 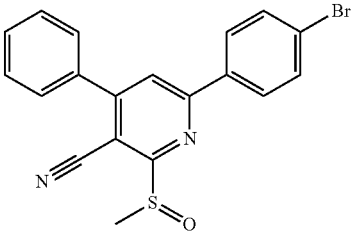 [SMILES: CS(=O)c1nc(-c2ccc(Br)cc2)cc(-c2ccccc2)c1C#N] |
| CIL18 | 659917 | 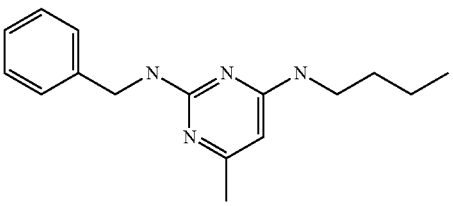 [SMILES: CCCCNc1cc(C)nc(NCc2ccccc2)n1] |
| CIL20 | 609767 | 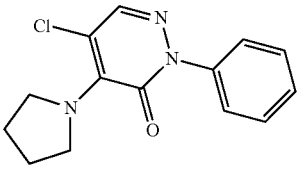 [SMILES: O=c1c(N2CCCC2)c(Cl)cnn1-c1ccccc1] |
| CIL22 | 779573 | 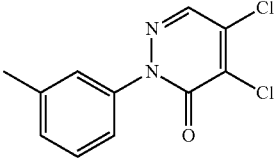 [SMILES: Cc1cccc(-n2ncc(Cl)c(Cl)c2=O)c1] |

TABLE 4-continued

Structures of 56 CILs.

| Compound | Pubchem CID | Structure |
|---|---|---|
| CIL23 | 779863 | 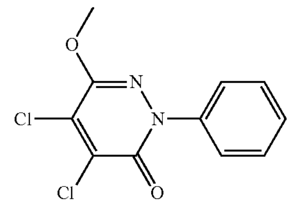 [SMILES: COc1nn(-c2ccccc2)c(=O)c(Cl)c1Cl] |
| CIL25 | 796505 | 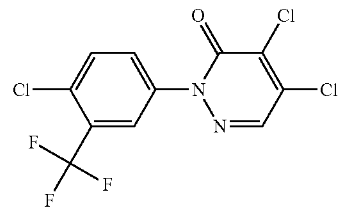 [SMILES: O=c1c(Cl)c(Cl)cnn1-c1ccc(Cl)c(C(F)(F)F)c1] |
| CIL26 | 3732278 | 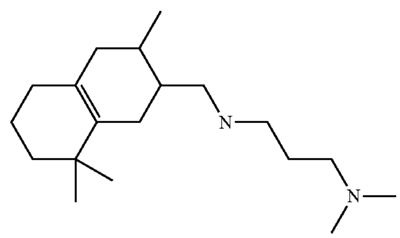 [SMILES: CC1CC2=C(CC1CNCCCN(C)C)C(C)(C)CCC2] |
| CIL27 | 1717988 | 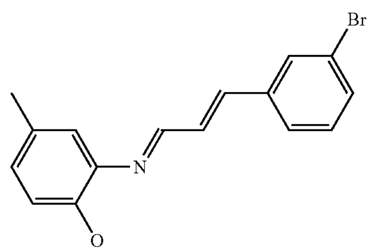 [SMILES: Cc1ccc(O)c(/N=C/C=C/c2cccc(Br)c2)c1] |
| CIL28 | 2855628 | 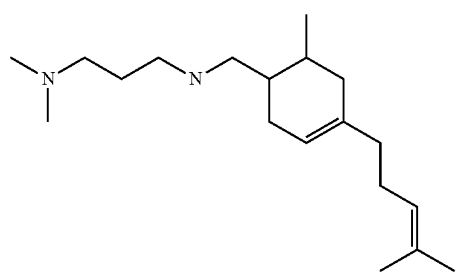 [SMILES: CC(C)=CCCC1=CCC(CNCCCN(C)C)C(C)C1] |
| CIL33 | 5333738 | 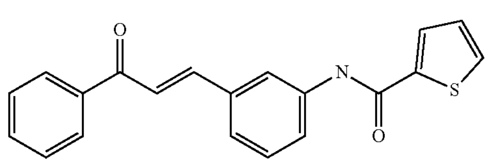 [SMILES: O=C(/C=C/c1cccc(NC(=O)c2cccs2)c1)c1ccccc1] |
| CIL34 | 781106 | 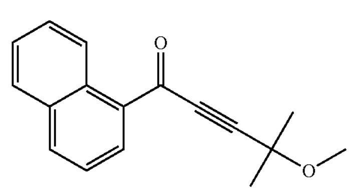 [SMILES: COC(C)(C)C#CC(=O)c1cccc2ccccc12] |

TABLE 4-continued

Structures of 56 CILs.

| Compound | Pubchem CID | Structure |
| --- | --- | --- |
| CIL36 | 2057920 | 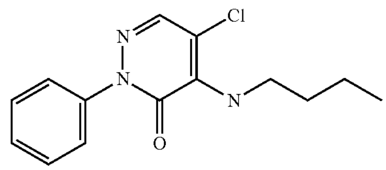 [SMILES: CCCCNc1c(Cl)cnn(-c2ccccc2)c1=O] |
| CIL40 | 2837694 | 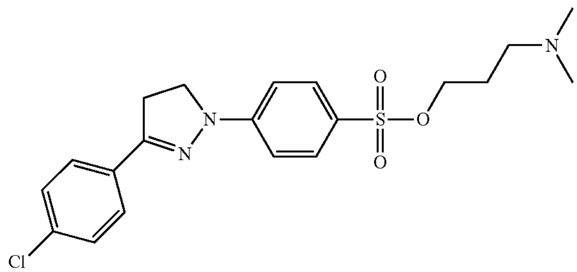 [SMILES: CN(C)CCCOS(=O)(=O)c1ccc(N2CCC(c3ccc(Cl)cc3)=N2)cc1] |
| CIL41 | 2841722 | 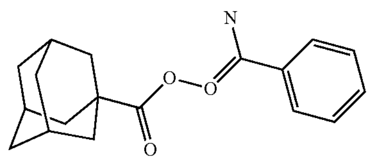 |
| CIL44 | 2259838 | 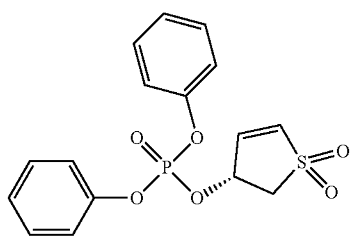 [SMILES: O=P(Oc1ccccc1)(Oc1ccccc1)O[C@@H]1C=CS(=O)(=O)C1] |
| CIL46 | 5728915 | 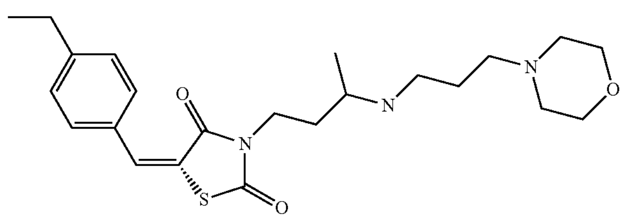 |
| CIL47 | 2904443 | 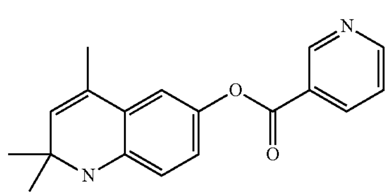 [SMILES: CC1=CC(C)(C)Nc2ccc(OC(=O)c3cccnc3)cc21] |
| CIL48 | 1263400 | 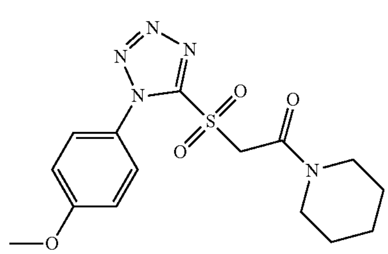 [SMILES: COc1ccc(-n2nnnc2S(=O)(=O)CC(=O)N2CCCCC2)cc1] |

TABLE 4-continued

Structures of 56 CILs.

| Compound | Pubchem CID | Structure |
| --- | --- | --- |
| CIL49 | 5286934 | 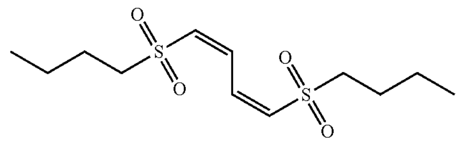 [SMILES: CCCCS(=O)(=O)/C=C\C=C/S(=O)(=O)CCCC] |
| CIL50 | 5308990 | 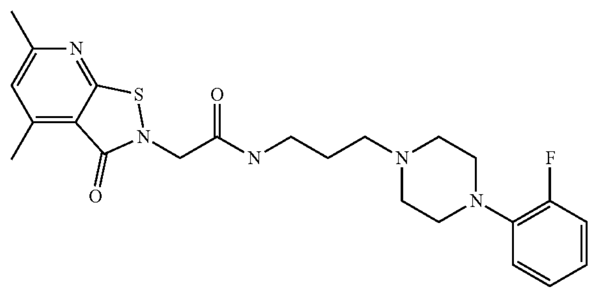 [SMILES: Cc1cc(C)c2c(=O)n(CC(=O)NCCCN3CCN(c4ccccc4F)CC3)sc2n1] |
| CIL51 | 2946035 | 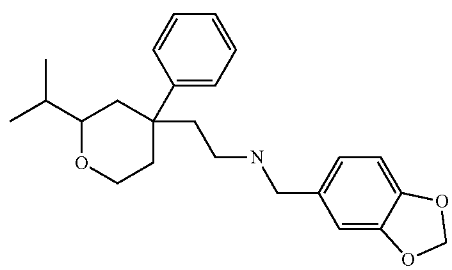 [SMILES: CC(C)C1CC(CCNCc2ccc3c(c2)OCO3)(c2ccccc2)CCO1] |
| CIL52 | 2857031 | 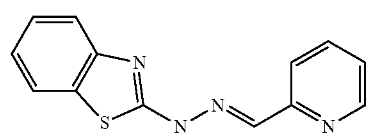 [SMILES: C(=N\Nc1nc2ccccc2s1)/c1ccccn1] |
| CIL55 | 6623618 | 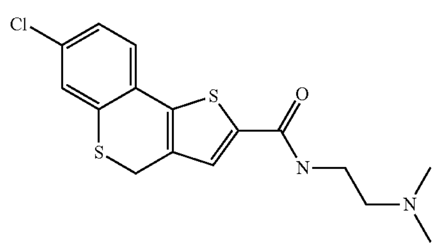 [SMILES: CN(C)CCNC(=O)c1cc2c(s1)-c1ccc(Cl)cc1SC2] |
| CIL56 | 654092 | 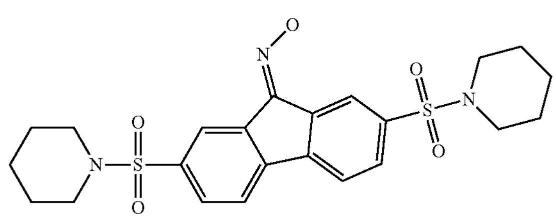 [SMILES: O=S(=O)(c1ccc2c(c1)C(=NO)c1cc(S(=O)(=O)N3CCCCC3)ccc1-2)N1CCCCC1] |
| CIL58 | 699693 | 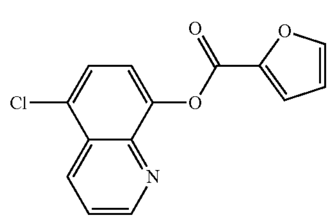 [SMILES: O=C(Oc1ccc(Cl)c2cccnc12)c1ccco1] |

TABLE 4-continued
Structures of 56 CILs.
| Compound | Pubchem CID | Structure |
|---|---|---|
| CIL60 | 779647 | 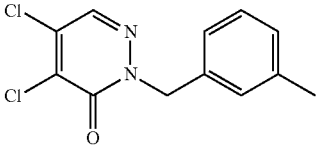 [SMILES: Cc1cccc(Cn2ncc(Cl)c(Cl)c2=O)c1] |
| CIL62 | 991372 | 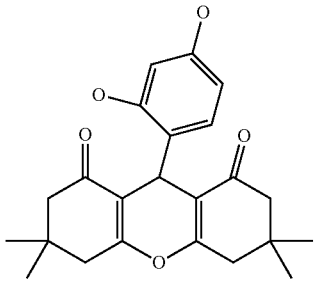 |
| CIL63 | 779402 | 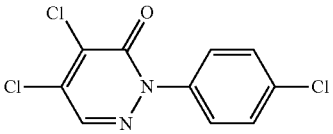 [SMILES: O=c1c(Cl)c(Cl)cnn1-c1ccc(Cl)cc1] |
| CIL67 | 3351416 | 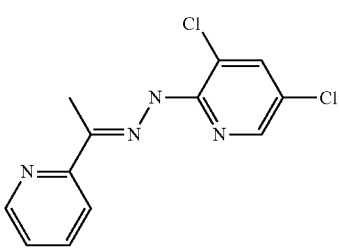 [SMILES: C/C(=N\Nc1ncc(Cl)cc1Cl)c1ccccn1] |
| CIL66 | 657546 | 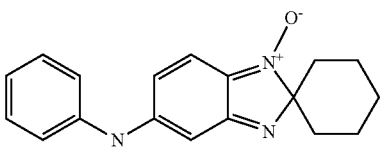 [SMILES: [O-][N+]1=c2ccc(Nc3ccccc3)cc2=NC12CCCCC2] |
| CIL67 | 6659101 | 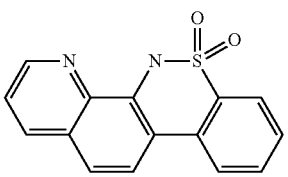 [SMILES: O=S1(=O)Nc2c(ccc3cccnc23)-c2ccccc21] |
| CIL69 | 818740 | 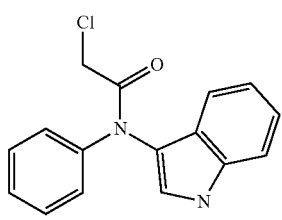 [SMILES: O=C(CCl)N(c1ccccc1)c1c[nH]c2ccccc12] |

TABLE 4-continued

Structures of 56 CILs.

| Compound | Pubchem CID | Structure |
|---|---|---|
| CIL70 | 9551837 | 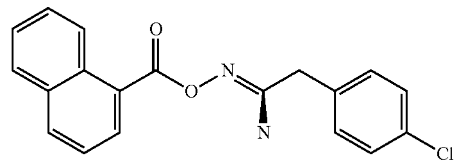 |
| CIL71 | 658723 | 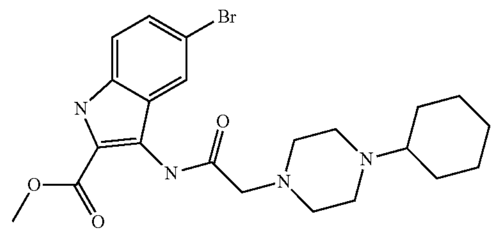 [SMILES: COC(=O)c1[nH]c2ccc(Br)cc2c1NC(=O)CN1CCN(C2CCCCC2)CC1] |
| CIL72 | 658341 | 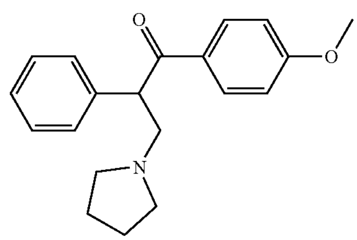 [SMILES: COc1ccc(C(=O)C(CN2CCCC2)c2ccccc2)cc1] |
| CIL74 | 4406635 | 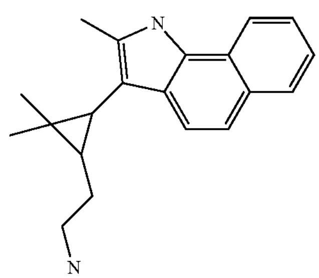 [SMILES: Cc1[nH]c2c(ccc3ccccc32)c1C1C(CCN)C1(C)C] |
| CIL75 | 818737 | 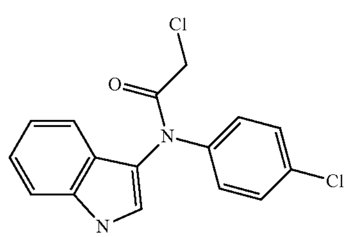 [SMILES: O=C(CCl)N(c1ccc(Cl)cc1)c1c[nH]c2ccccc12] |
| CIL76 | 3774616 | 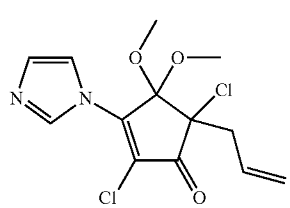 [SMILES: C=CCC1(Cl)C(=O)C(Cl)=C(n2ccnc2)C1(OC)OC] |

TABLE 4-continued

Structures of 56 CILs.

| Compound | Pubchem CID | Structure |
|---|---|---|
| CIL77 | 6298513 | 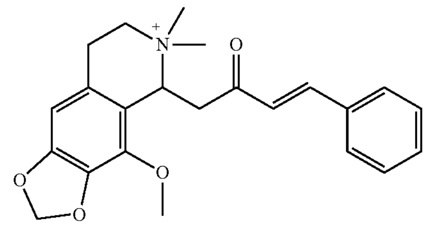 |
| CIL79 | 6545175 | 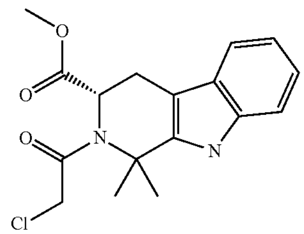 [SMILES: COC(=O)[C@@H]1Cc2c([nH]c3ccccc23)C(C)(C)N1C(=O)CCl] |
| CIL80 | 1187467 | 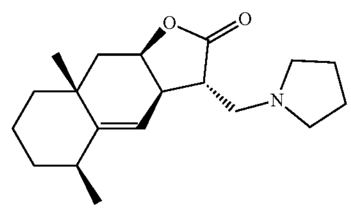 [SMILES: C[C@H]1CCC[C@]2(C)C[C@H]3OC(=O)[C@H](CN4CCCC4)[C@H]3C=C12] |
| CIL87 | NA | 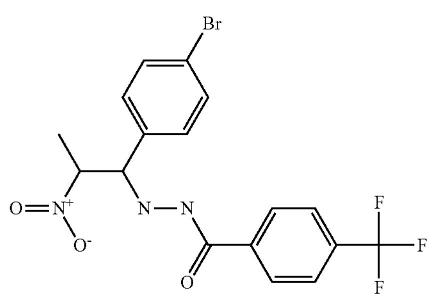 [SMILES: CC(C(NNC(=O)c1ccc(C(F)(F)F)cc1)c1ccc(Br)cc1)[N+](=O)[O-]] |
| CIL88 | NA | 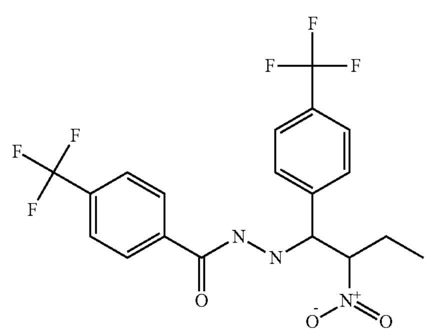 |
| CIL89 | NA | 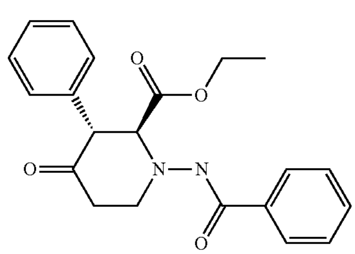 [SMILES: CCOC(=O)[C@@H]1[C@@H](c2ccccc2)C(=O)CCN1NC(=O)c1ccccc1] |

TABLE 5

CIL41/70 structural analogs.

| Compound | Structure |
|---|---|
| CB122 (0.98 ug/mL) | 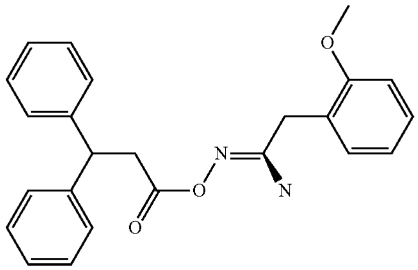 |
| CB70 (1.59 ug/mL) | 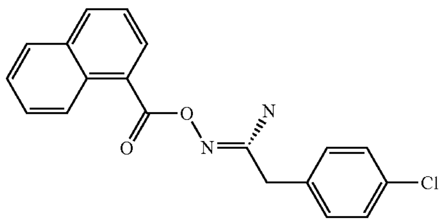 |
| VM1 (2 ug/mL) | 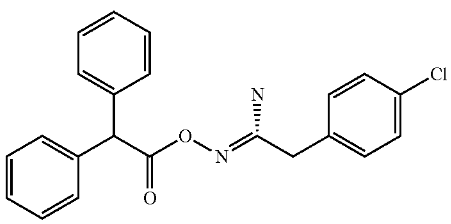 |
| CB69 (2.09 ug/mL) | 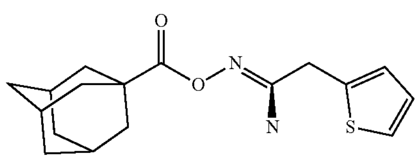 |
| CB115 (2.42 ug/mL) | 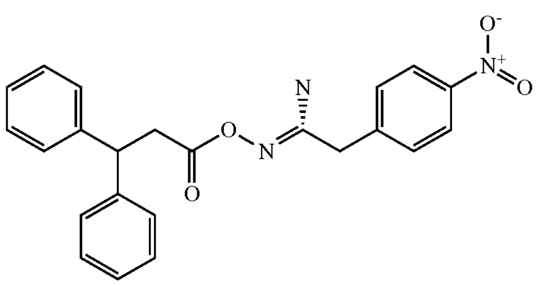 |
| MB14 (2.6 ug/mL) | 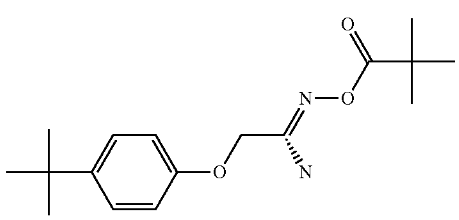 |
| CIL41 (2.8 ug/mL) | 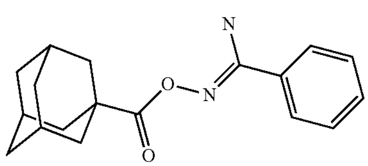 [SMILES: N/C(=N\OC(=O)C12CC3CC(CC(C3)C1)C2)c1ccccc1] |

TABLE 5-continued
CIL41/70 structural analogs.
| Compound | Structure |
|---|---|
| B02 (3.3 ug/mL) | 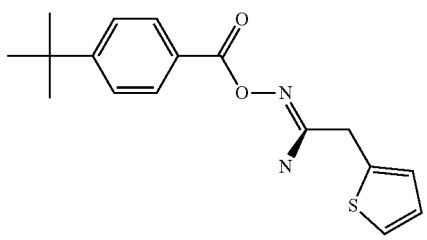 |
| CB56 (4.05 ug/mL) | 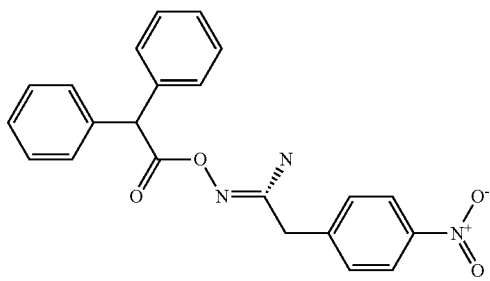 |
| CB98 (4.46 ug/mL) | 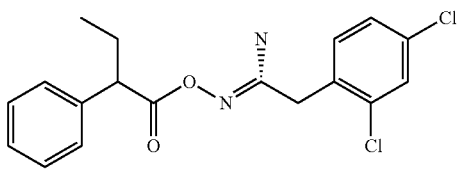 |
| CB147 (4.88 ug/mL) | 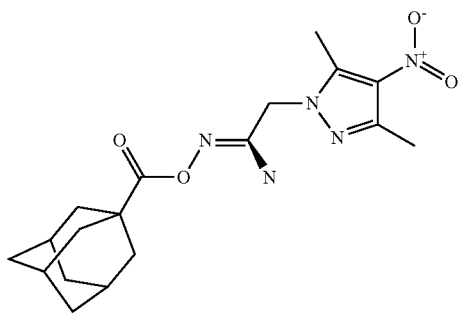 |
| A05 (5.04 ug/mL) | 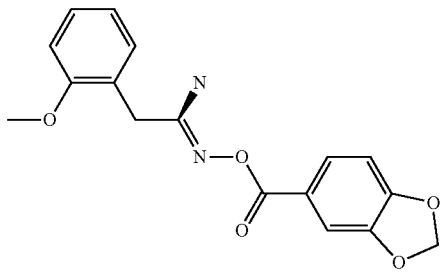 |
| CB116 (5.49 ug/mL) | 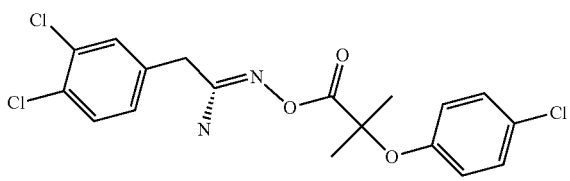 |

TABLE 5-continued
CIL41/70 structural analogs.
| Compound | Structure |
| --- | --- |
| MB6 (6.48 ug/mL) | 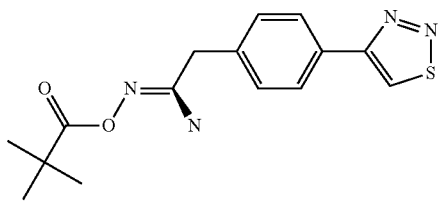 |
| CB49 (7.23 ug/mL) | 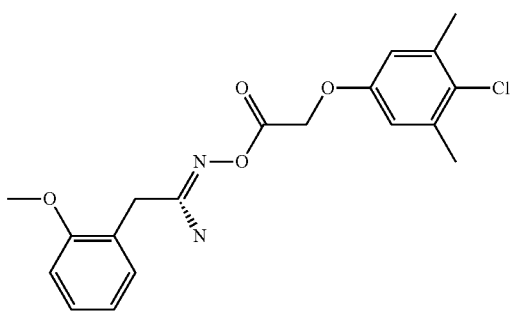 |
| CB140 (8.56 ug/mL) | 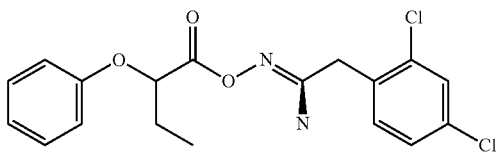 |
| VM3 (8.51 ug/mL) | 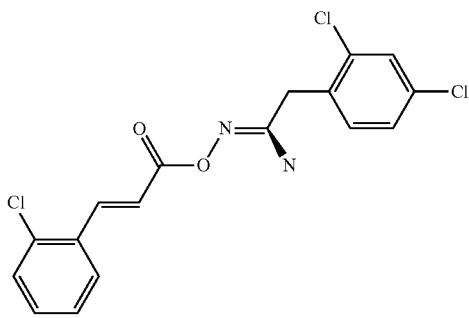 |
| CB62 (8.63 ug/mL) | 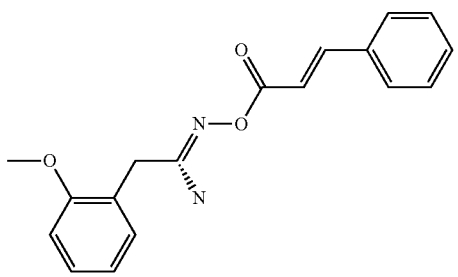 |

TABLE 5-continued
CIL41/70 structural analogs.
| Compound | Structure |
| --- | --- |
| CB126 (9.3 ug/mL) | 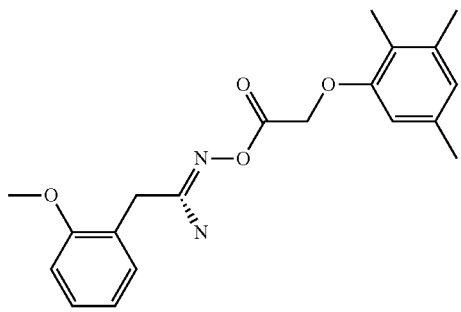 |
| CB18 (10.21 ug/mL) | 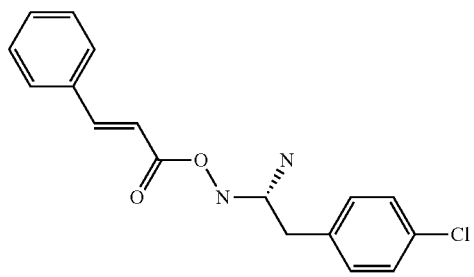 [SMILES: N[C@H](Cc1ccc(Cl)cc1)NOC(=O)/C=C/c1ccccc1] |
| EN2 (10.51 ug/mL) | 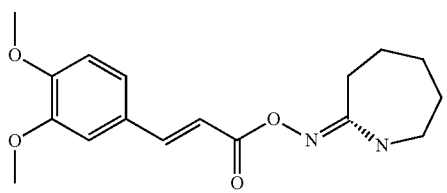 |
| CB111 (10.71 ug/mL) | 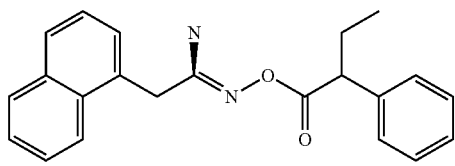 |
| AS2 (12.26 ug/mL) | 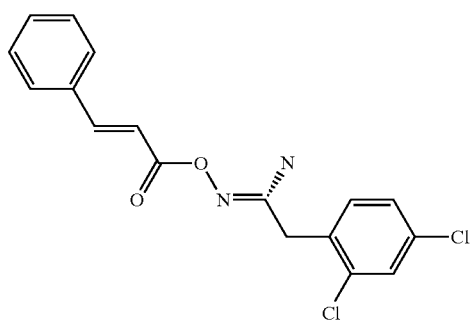 |
| CB14 (13.98 ug/mL) | 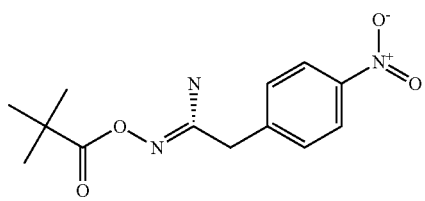 |

TABLE 5-continued
CIL41/70 structural analogs.
| Compound | Structure |
|---|---|
| ZE2 (15.63 ug/mL) | 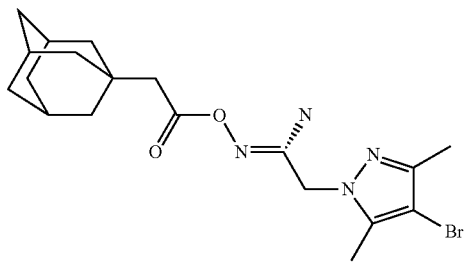 |
| CB58 (17.61 ug/mL) | 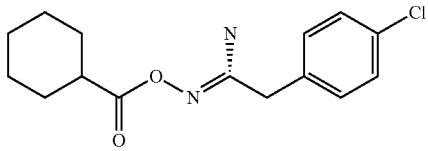 |
| AS1 (>20 ug/mL) | 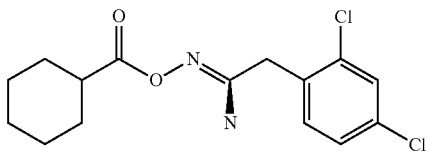 |
| CB1 (>20 ug/mL) | 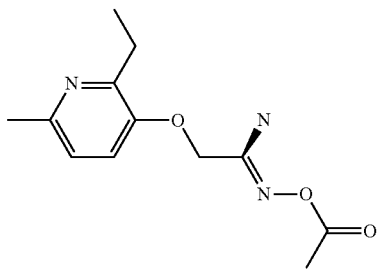 |
| CB2 (>20 ug/mL) | 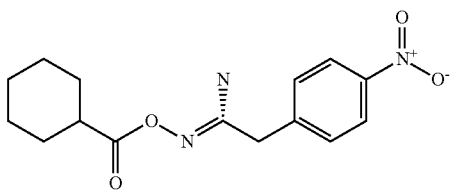 |
| CB3 (>20 ug/mL) | 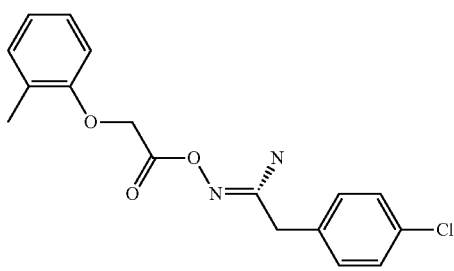 |

TABLE 5-continued
CIL41/70 structural analogs.
| Compound | Structure |
|---|---|
| CB4 (>20 ug/mL) | 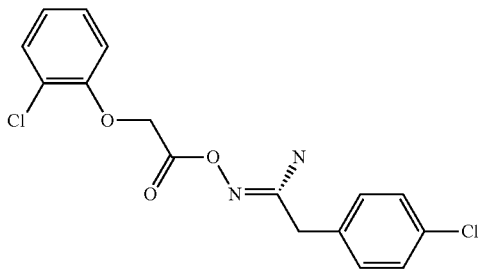 |
| CB5 (>20 ug/mL) | 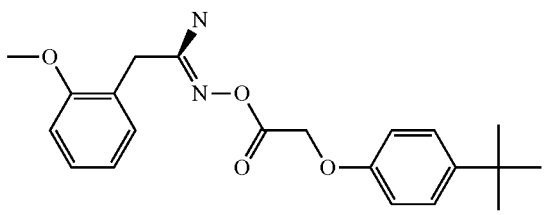 |
| CB6 (>20 ug/mL) | 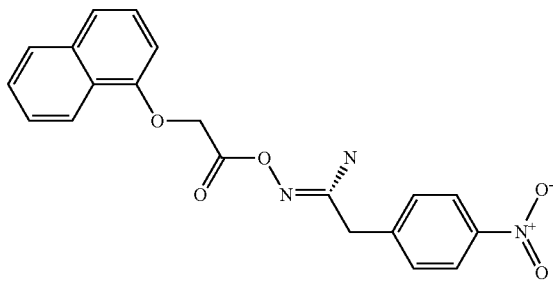 |
| CB7 (>20 ug/mL) | 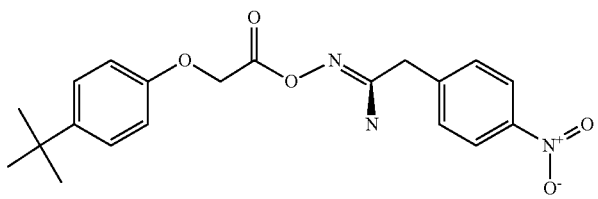 |
| CB8 (>20 ug/mL) | 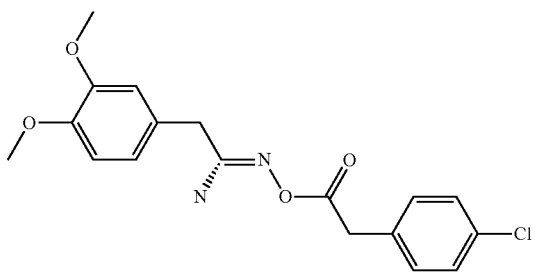 |
| CB9 (>20 ug/mL) | 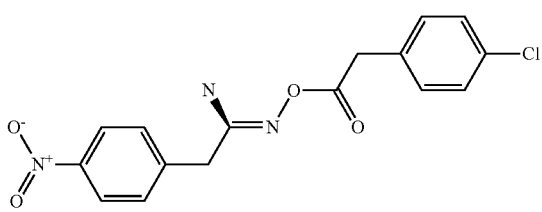 |

TABLE 5-continued
CIL41/70 structural analogs.
| Compound | Structure |
|---|---|
| CB10 (>20 ug/mL) | 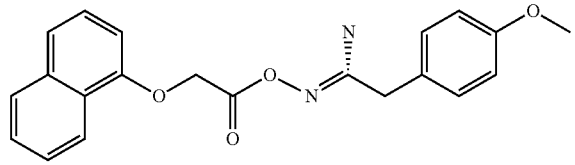 |
| CB11 (>20 ug/mL) | 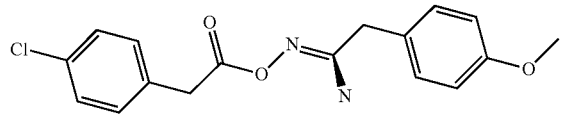 |
| CB12 (>20 ug/mL) | 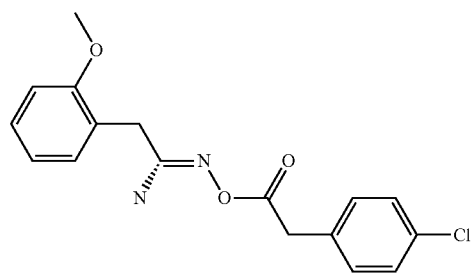 |
| CB13 (>20 ug/mL) | 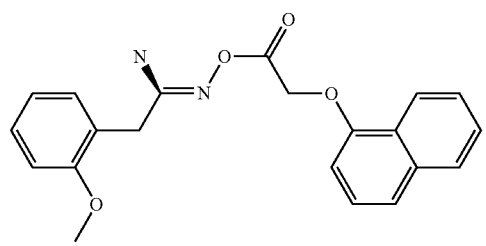 |
| CB15 (>20 ug/mL) | 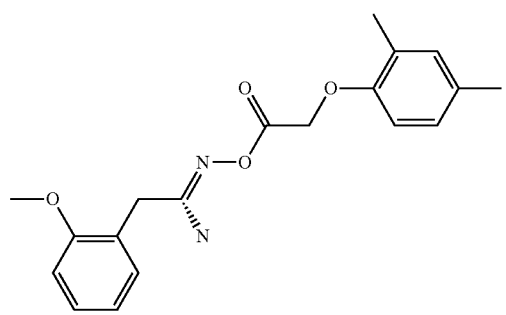 |
| CB16 (>20 ug/mL) | 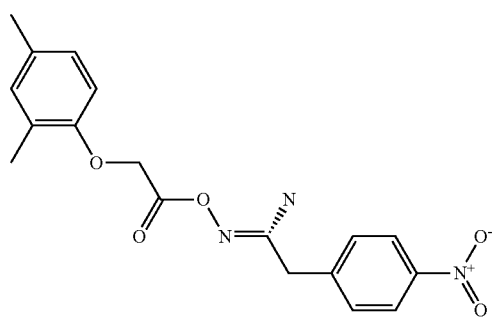 |

TABLE 5-continued
CIL41/70 structural analogs.
| Compound | Structure |
|---|---|
| CB17 (>20 ug/mL) | 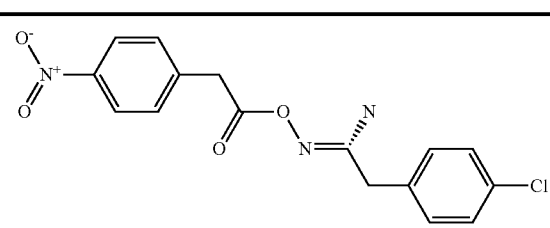 |
| CB19 (>20 ug/mL) | 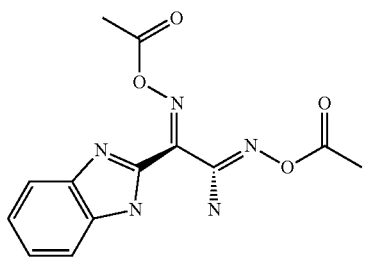 |
| CB20 (>20 ug/mL) | 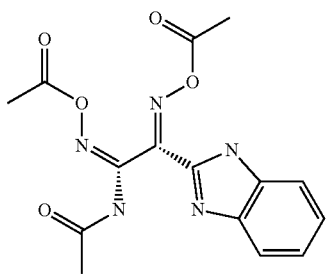 |
| CB21 (>20 ug/mL) | 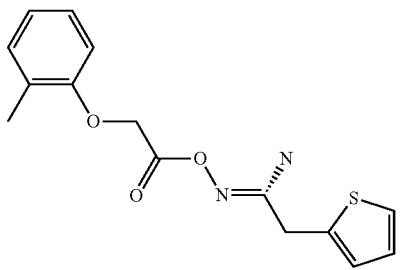 |
| CB22 (>20 ug/mL) | 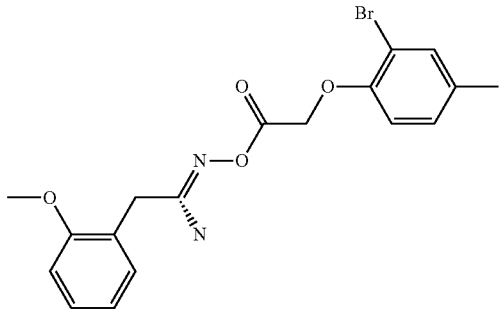 |
| CB23 (>20 ug/mL) | 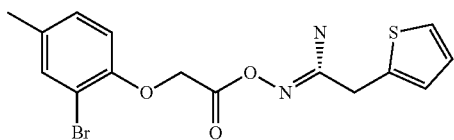 |

TABLE 5-continued
CIL41/70 structural analogs.
| Compound | Structure |
|---|---|
| CB24 (>20 ug/mL) | 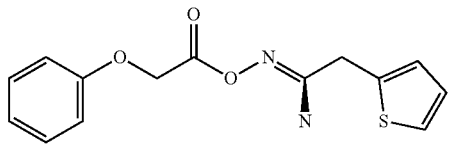 |
| CB25 (>20 ug/mL) | 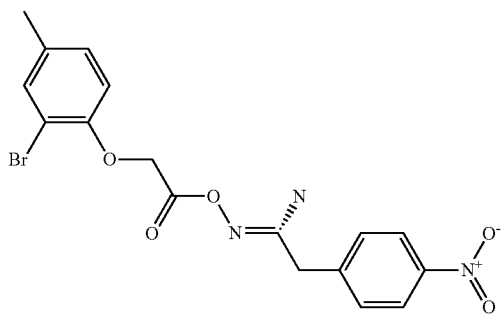 |
| CB26 (>20 ug/mL) | 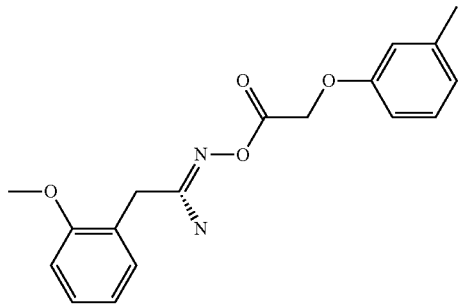 |
| CB27 (>20 ug/mL) | 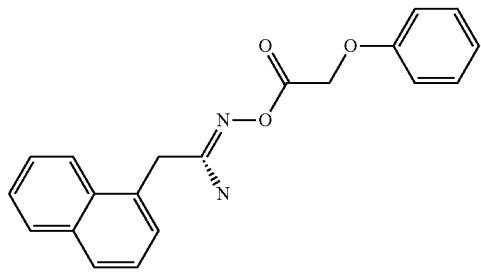 |
| CB28 (>20 ug/mL) | 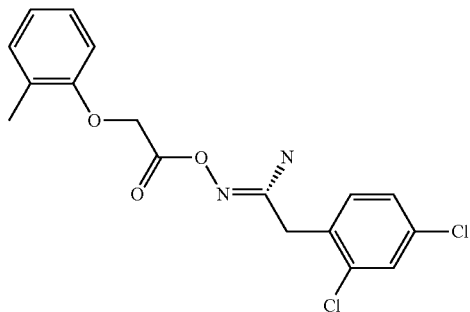 |

TABLE 5-continued
CIL41/70 structural analogs.
| Compound | Structure |
|---|---|
| CB29 (>20 ug/mL) | 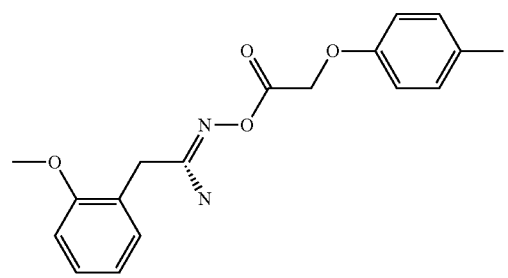 |
| CB30 (>20 ug/mL) | 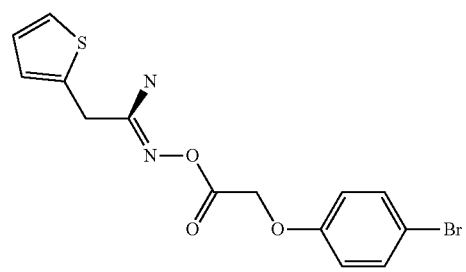 |
| CB31 (>20 ug/mL) | 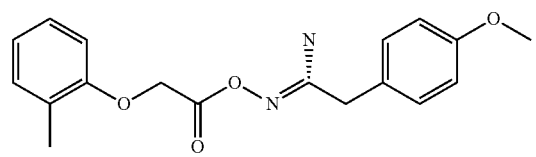 |
| CB32 (>20 ug/mL) | 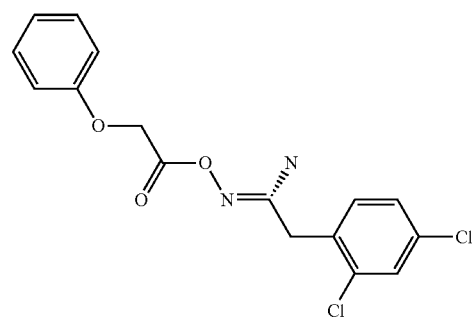 |
| CB33 (>20 ug/mL) | 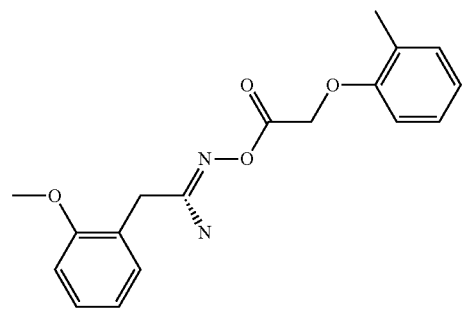 |

TABLE 5-continued
CIL41/70 structural analogs.
| Compound | Structure |
| --- | --- |
| CB34 (>20 ug/mL) | 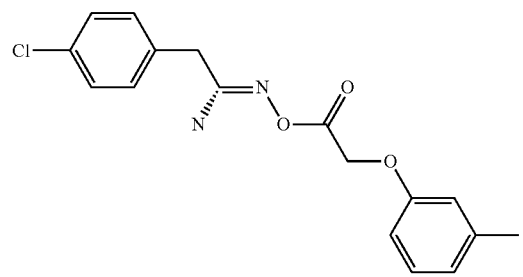 |
| CB35 (>20 ug/mL) | 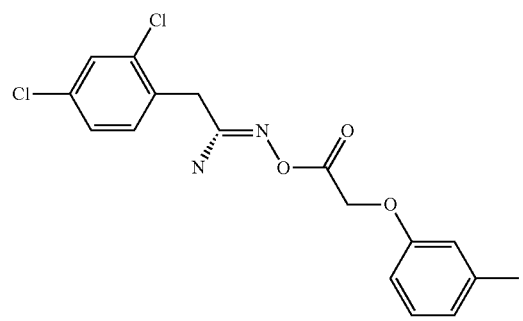 |
| CB36 (>20 ug/mL) | 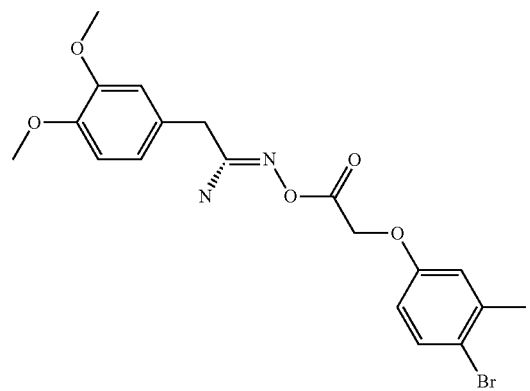 |
| CB37 (>20 ug/mL) | 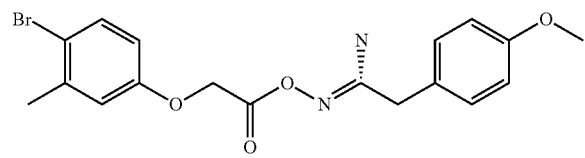 |
| CB38 (>20 ug/mL) | 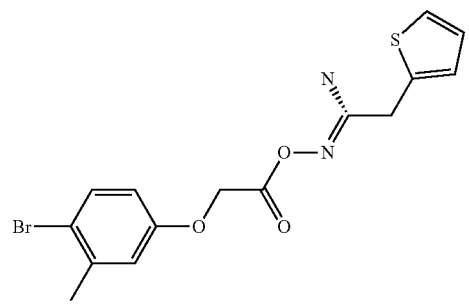 |

TABLE 5-continued

CIL41/70 structural analogs.

| Compound | Structure |
| --- | --- |
| CB39 (>20 ug/mL) | 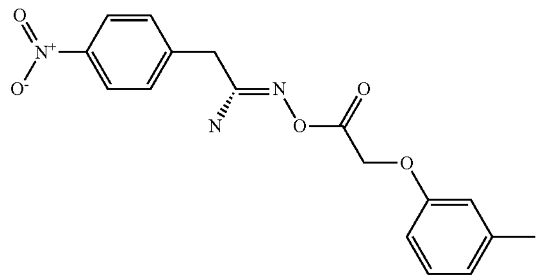 |
| CB40 (>20 ug/mL) | 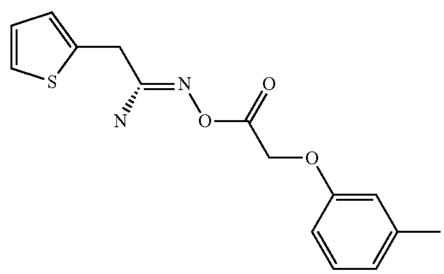 |
| CB41 (>20 ug/mL) | 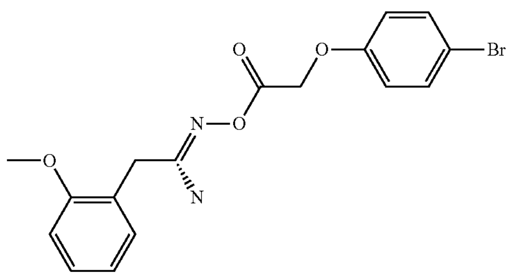 |
| CB42 (>20 ug/mL) | 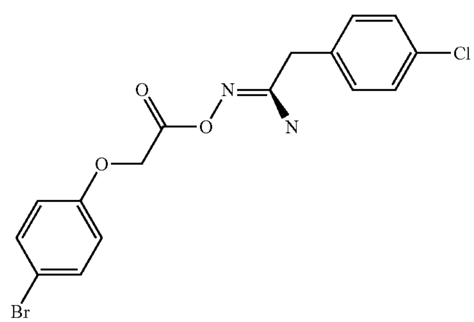 |
| CB43 (>20 ug/mL) | 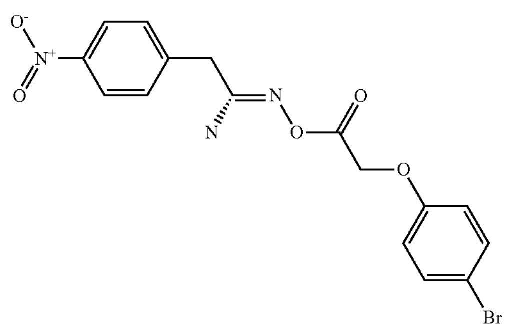 |

TABLE 5-continued
CIL41/70 structural analogs.
| Compound | Structure |
|---|---|
| CB44 (>20 ug/mL) | 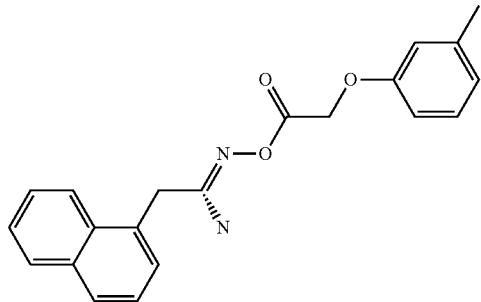 |
| CB45 (>20 ug/mL) | 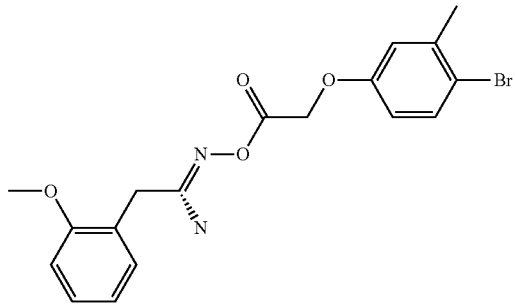 |
| CB46 (>20 ug/mL) | 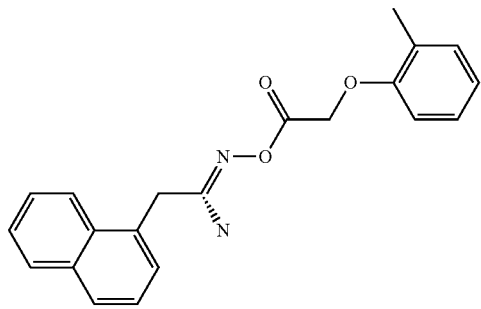 |
| CB47 (>20 ug/mL) | 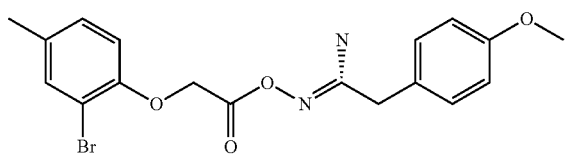 |
| CB48 (>20 ug/mL) | 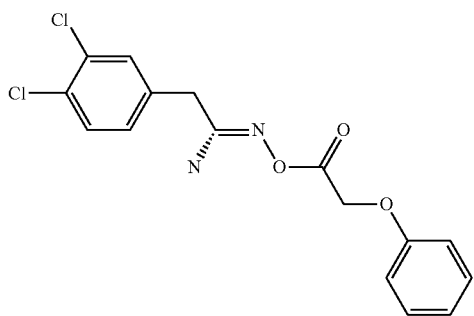 |

TABLE 5-continued
CIL41/70 structural analogs.
| Compound | Structure |
|---|---|
| CB50 (>20 ug/mL) | 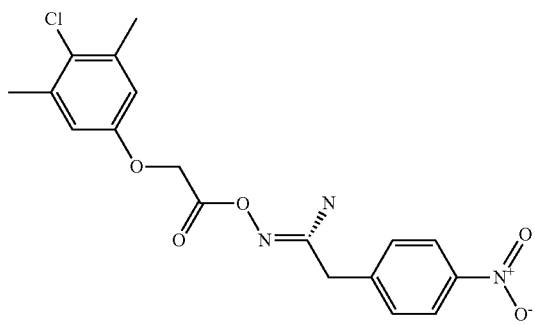 |
| CB51 (>20 ug/mL) | 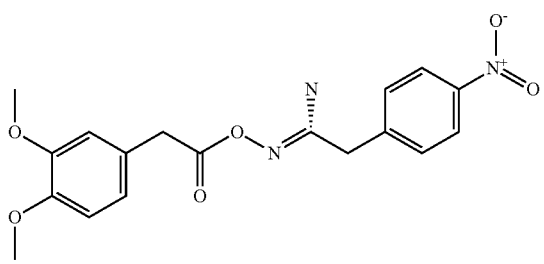 |
| CB52 (>20 ug/mL) | 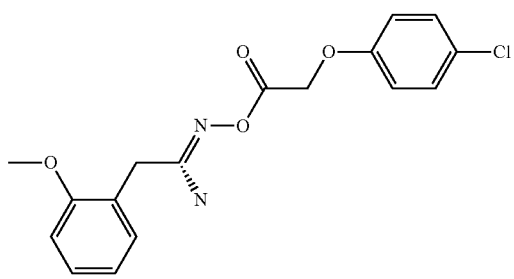 |
| CB53 (>20 ug/mL) | 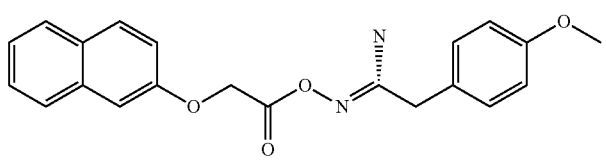 |
| CB54 (>20 ug/mL) | 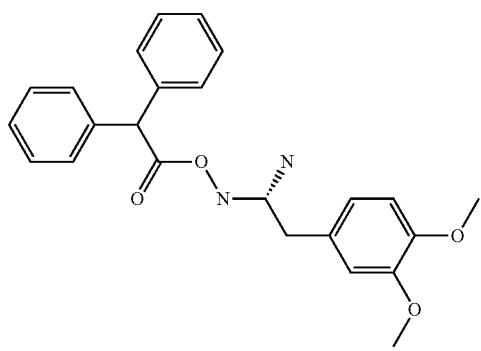 [SMILES: COc1ccc(C[C@@H](N)NOC(=O)C(c2ccccc2)c2ccccc2)cc1OC] |

TABLE 5-continued

CIL41/70 structural analogs.

| Compound | Structure |
| --- | --- |
| CB55 (>20 ug/mL) | 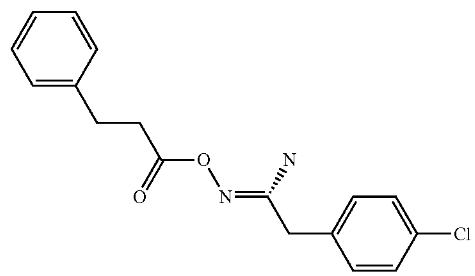 |
| CB57 (>20 ug/mL) | 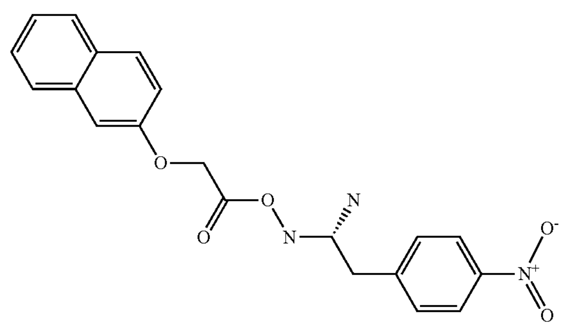 [SMILES: N[C@H](Cc1ccc([N+](=O)[O-])cc1)NOC(=O)COc1ccc2ccccc2c1] |
| CB59 (>20 ug/mL) | 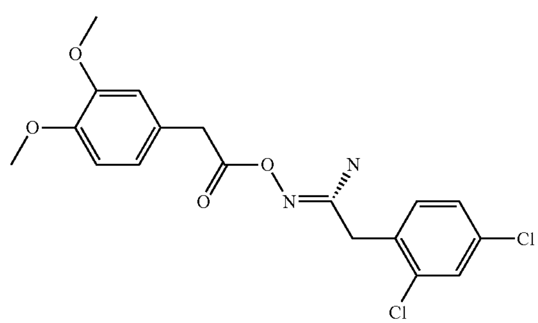 |
| CB60 (>20 ug/mL) | 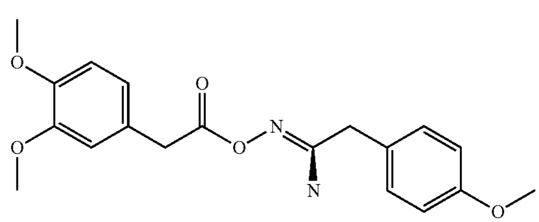 |
| CB61 (>20 ug/mL) | 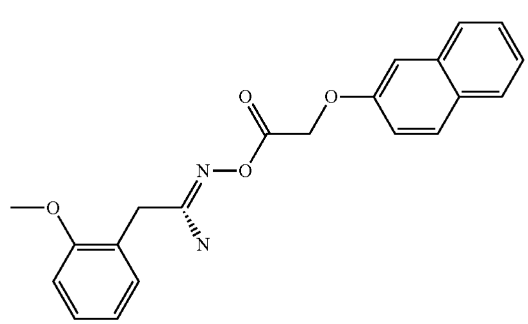 |

TABLE 5-continued

CIL41/70 structural analogs.

| Compound | Structure |
| --- | --- |
| CB63 (>20 ug/mL) | 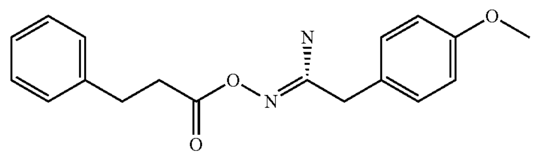 |
| CB64 (>20 ug/mL) | 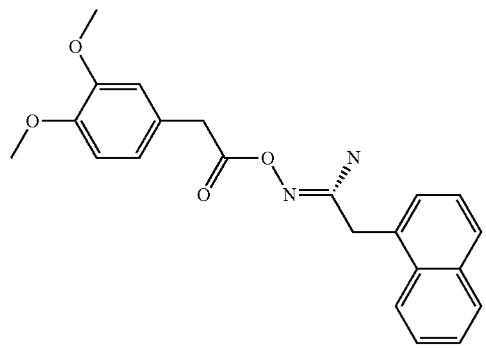 |
| CB65 (>20 ug/mL) | 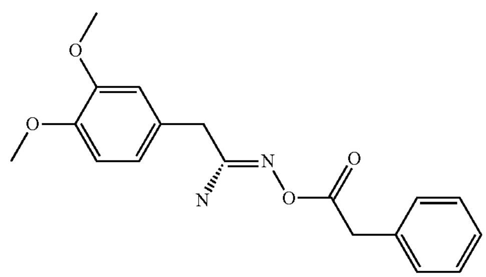 |
| CB66 (>20 ug/mL) | 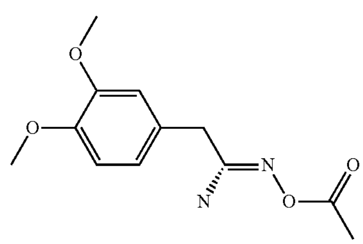 |
| CB67 (>20 ug/mL) | 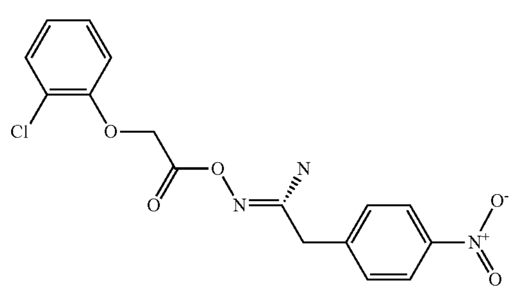 |

TABLE 5-continued
CIL41/70 structural analogs.
| Compound | Structure |
|---|---|
| CB68 (>20 ug/mL) | 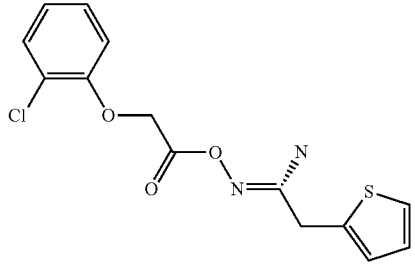 |
| CB70 (>20 ug/mL) | 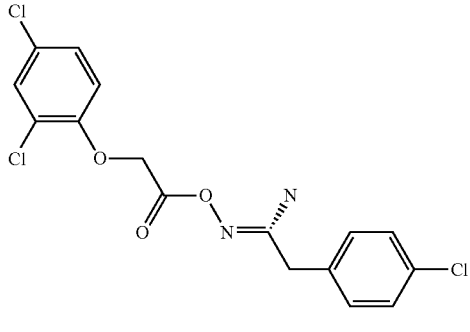 |
| CB71 (>20 ug/mL) | 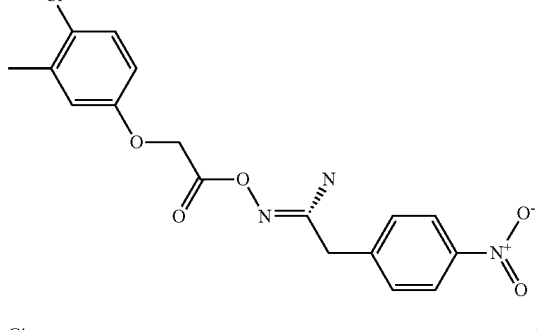 |
| CB72 (>20 ug/mL) | 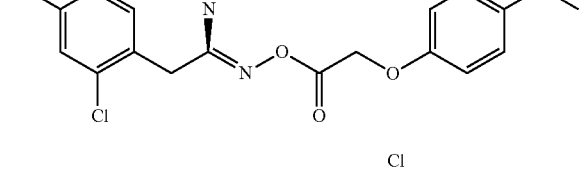 |
| CB73 (>20 ug/mL) | 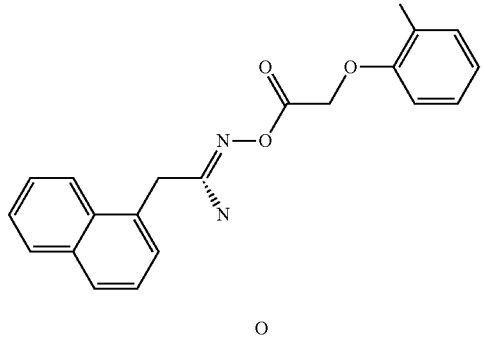 |
| CB74 (>20 ug/mL) | 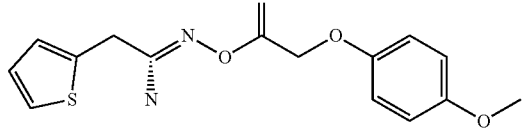 |

TABLE 5-continued

CIL41/70 structural analogs.

| Compound | Structure |
|---|---|
| CB75 (>20 ug/mL) | 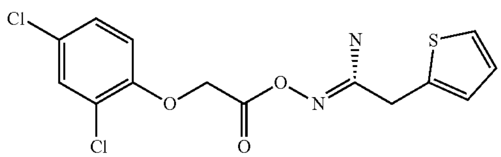 |
| CB76 (>20 ug/mL) | 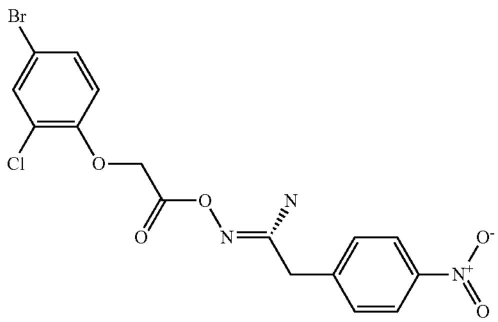 |
| CB77 (>20 ug/mL) | 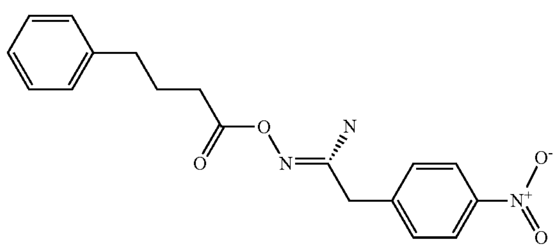 |
| CB78 (>20 ug/mL) | 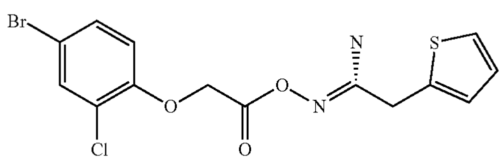 |
| CB79 (>20 ug/mL) | 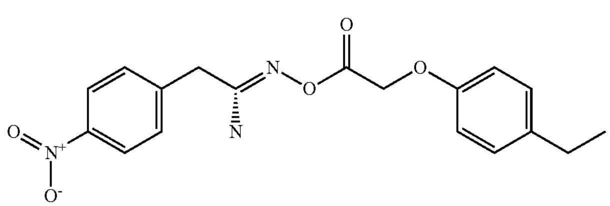 |
| CB80 (>20 ug/mL) | 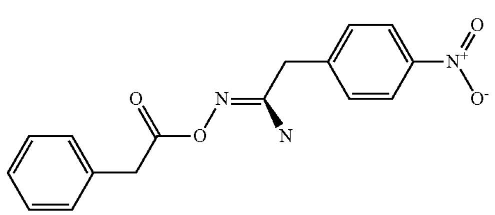 |
| CB81 (>20 ug/mL) | 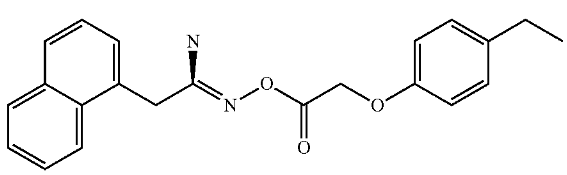 |

TABLE 5-continued

CIL41/70 structural analogs.

| Compound | Structure |
| --- | --- |
| CB82 (>20 ug/mL) | 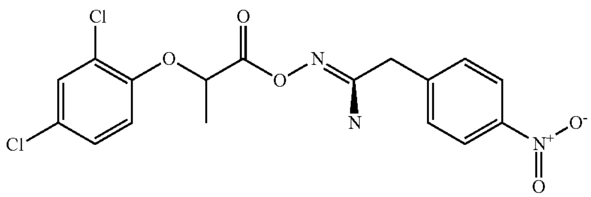 |
| CB83 (>20 ug/mL) | 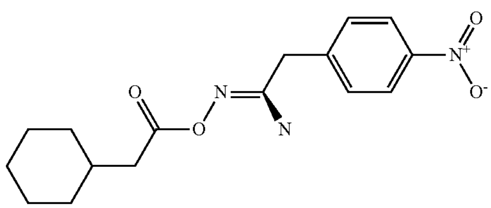 |
| CB84 (>20 ug/mL) | 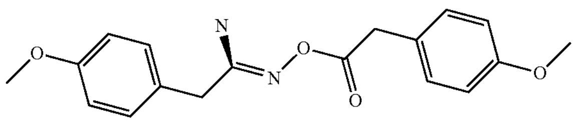 |
| CB85 (>20 ug/mL) | 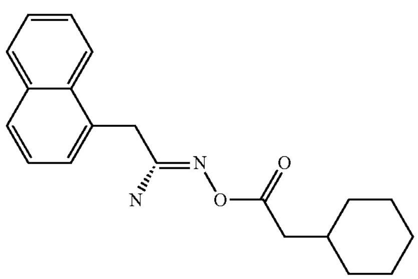 |
| CB86 (>20 ug/mL) | 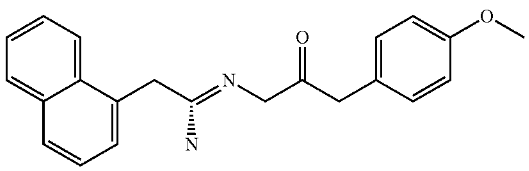 |
| CB87 (>20 ug/mL) | 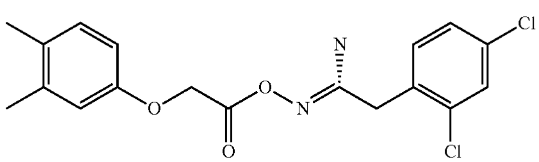 |
| CB88 (>20 ug/mL) | 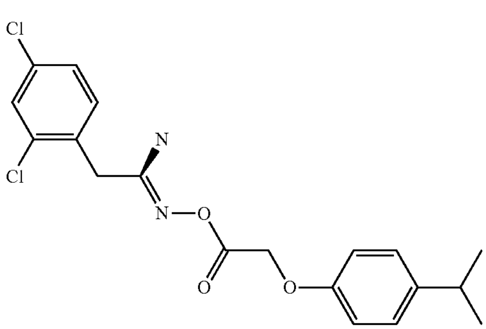 |

TABLE 5-continued

CIL41/70 structural analogs.

| Compound | Structure |
|---|---|
| CB89 (>20 ug/mL) | 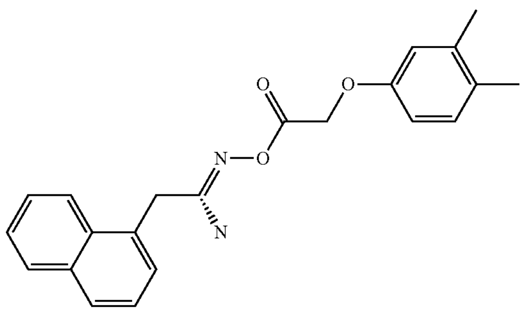 |
| CB90 (>20 ug/mL) | 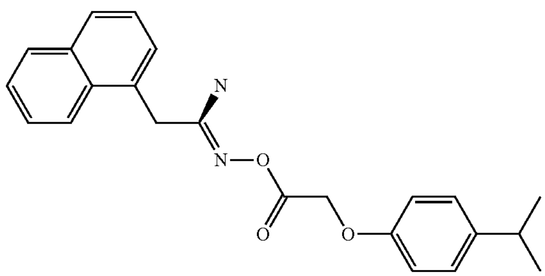 |
| CB91 (>20 ug/mL) | 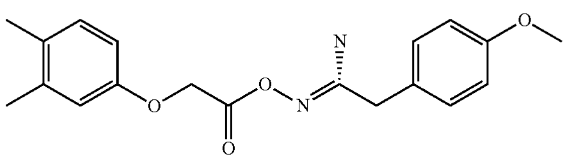 |
| CB92 (>20 ug/mL) | 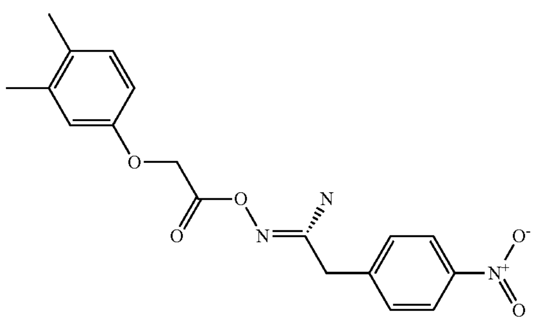 |
| CB93 (>20 ug/mL) | 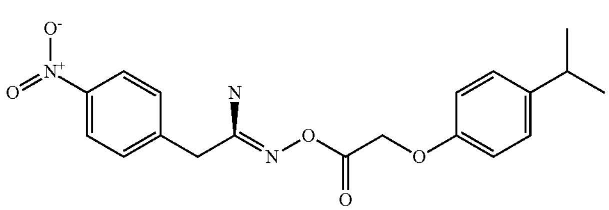 |

TABLE 5-continued

CIL41/70 structural analogs.

| Compound | Structure |
|---|---|
| CB94 (>20 ug/mL) | 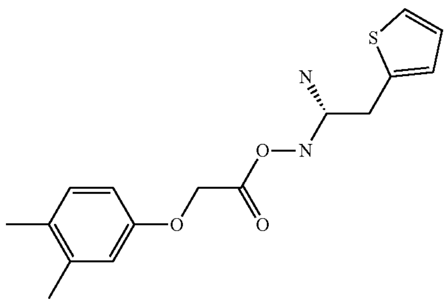 [SMILES: Cc1ccc(OCC(=O)ON[C@H](N)Cc2cccs2)cc1C] |
| CB95 (>20 ug/mL) | 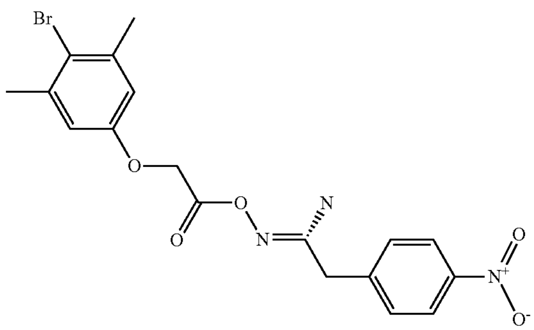 |
| CB96 (>20 ug/mL) | 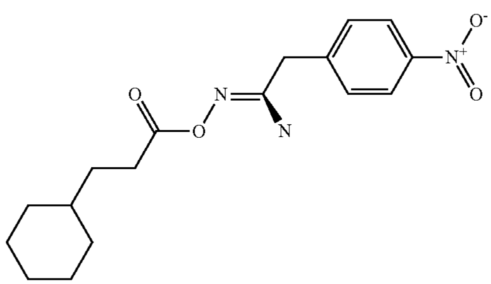 |
| CB97 (>20 ug/mL) | 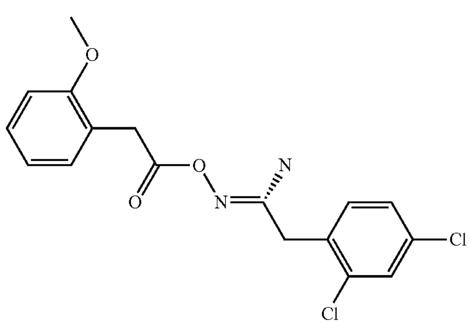 |
| CB99 (>20 ug/mL) | 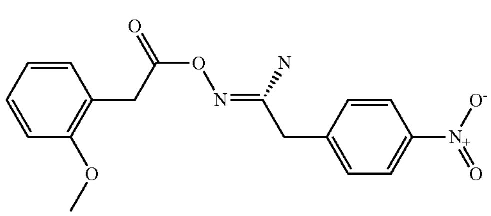 |

TABLE 5-continued
CIL41/70 structural analogs.
| Compound | Structure |
|---|---|
| CB100 (>20 ug/mL) | 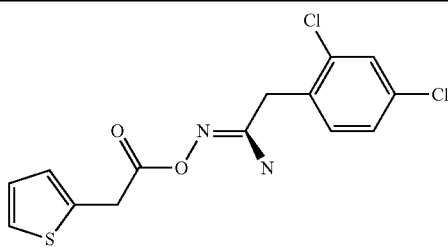 |
| CB101 (>20 ug/mL) | 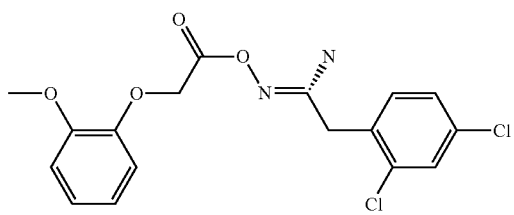 |
| CB102 (>20 ug/mL) | 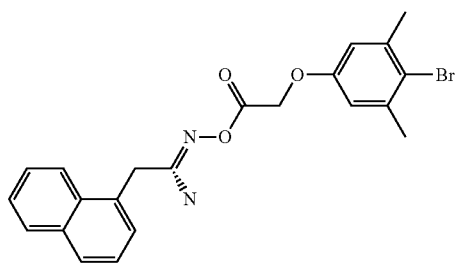 |
| CB103 (>20 ug/mL) | 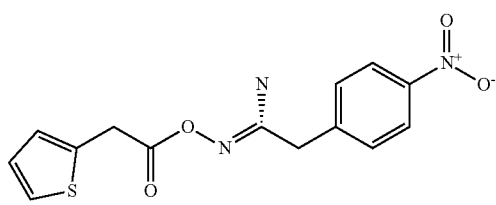 |
| CB104 (>20 ug/mL) | 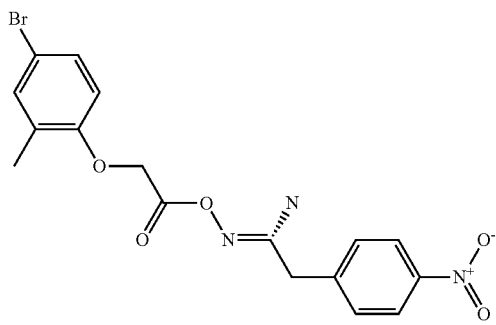 |
| CB105 (>20 ug/mL) | 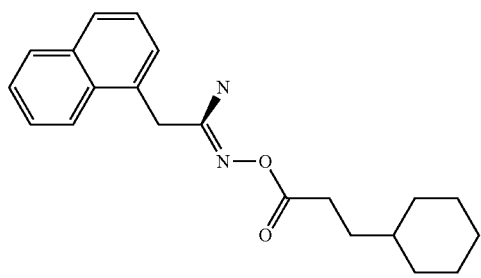 |

TABLE 5-continued

CIL41/70 structural analogs.

| Compound | Structure |
|---|---|
| CB106 (>20 ug/mL) | 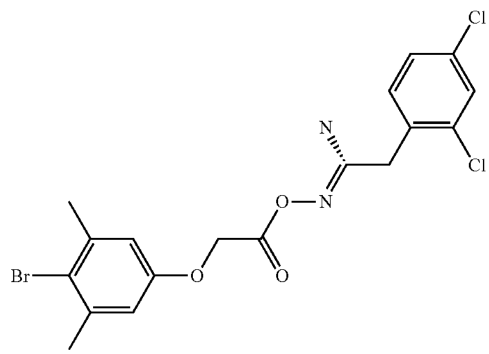 |
| CB107 (>20 ug/mL) | 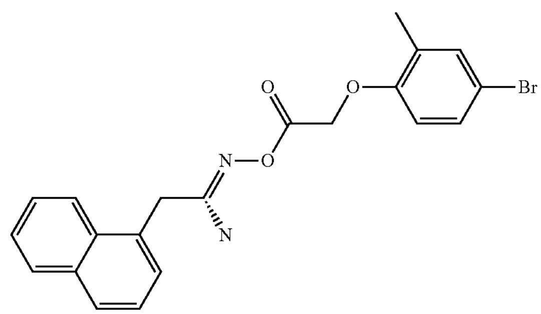 |
| CB108 (>20 ug/mL) | 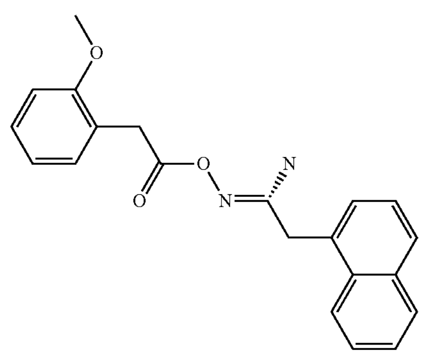 |
| CB109 (>20 ug/mL) | 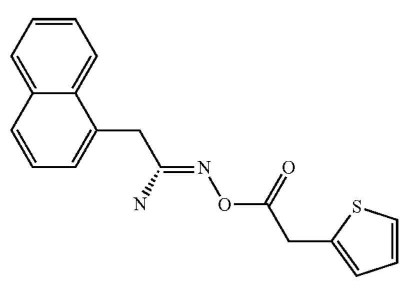 |
| CB110 (>20 ug/mL) | 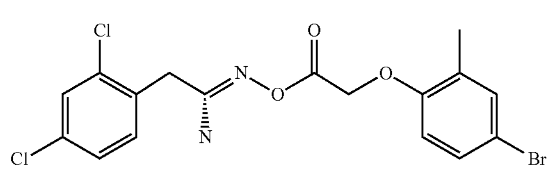 |

TABLE 5-continued
CIL41/70 structural analogs.
| Compound | Structure |
|---|---|
| CB112 (>20 ug/mL) | 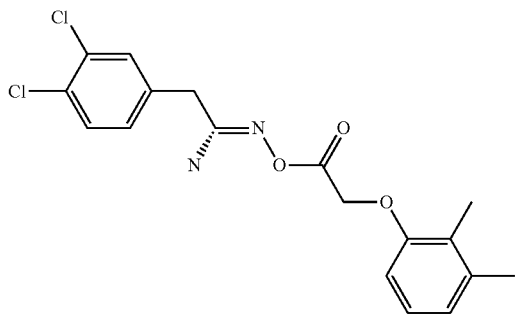 |
| CB113 (>20 ug/mL) | 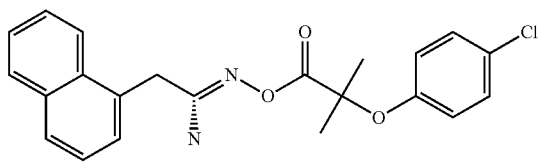 |
| CB114 (>20 ug/mL) | 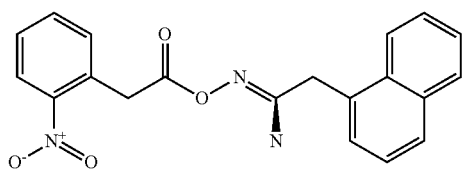 |
| CB117 (>20 ug/mL) | 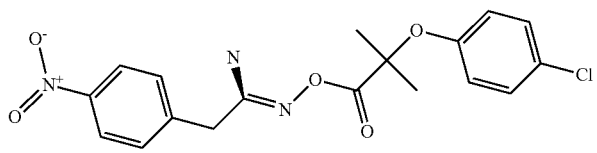 |
| CB118 (>20 ug/mL) | 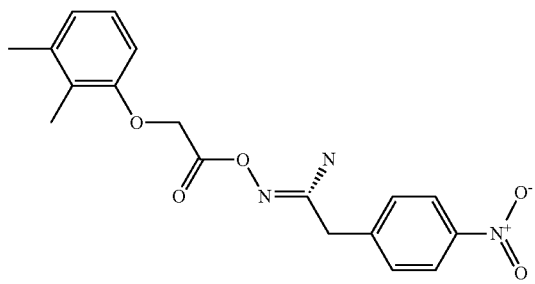 |
| CB119 (>20 ug/mL) | 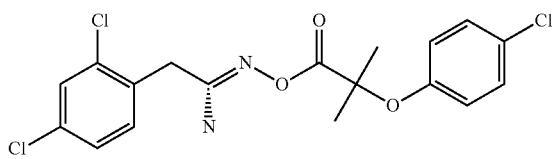 |

TABLE 5-continued

CIL41/70 structural analogs.

| Compound | Structure |
| --- | --- |
| CB120 (>20 ug/mL) | 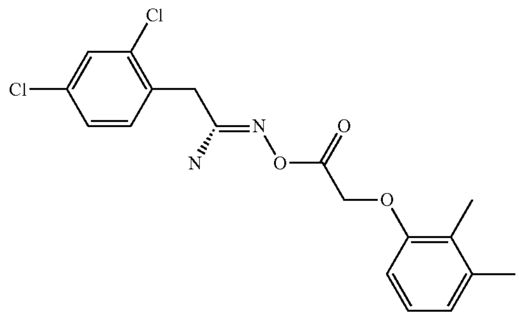 |
| CB121 (>20 ug/mL) | 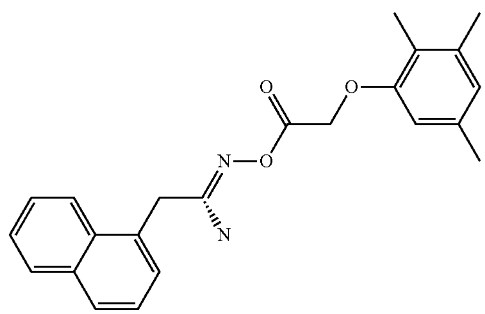 |
| CB123 (>20 ug/mL) | 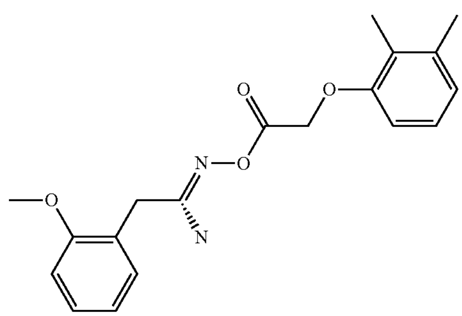 |
| CB124 (>20 ug/mL) | 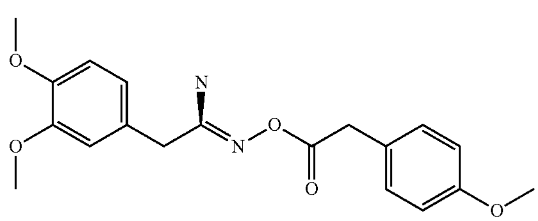 |
| CB125 (>20 ug/mL) | 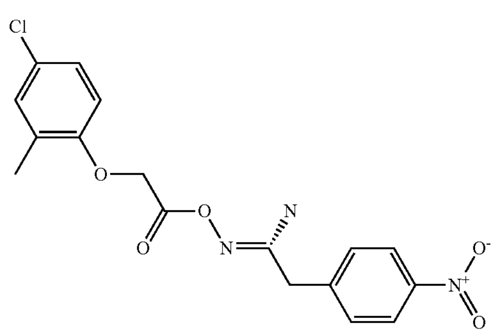 |

TABLE 5-continued
CIL41/70 structural analogs.
| Compound | Structure |
|---|---|
| CB127 (>20 ug/mL) | 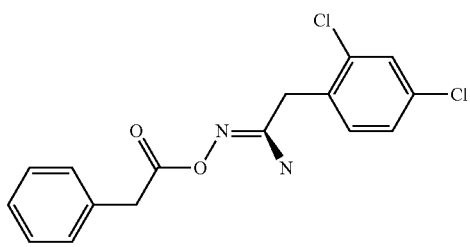 |
| CB128 (>20 ug/mL) | 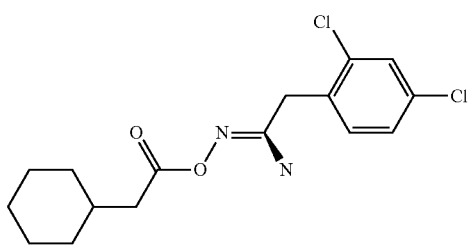 |
| CB129 (>20 ug/mL) | 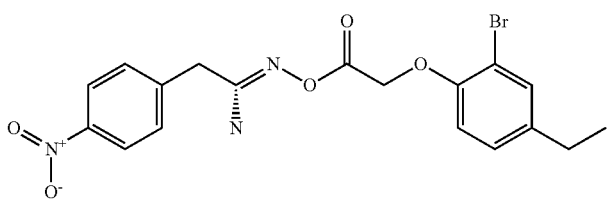 |
| CB130 (>20 ug/mL) | 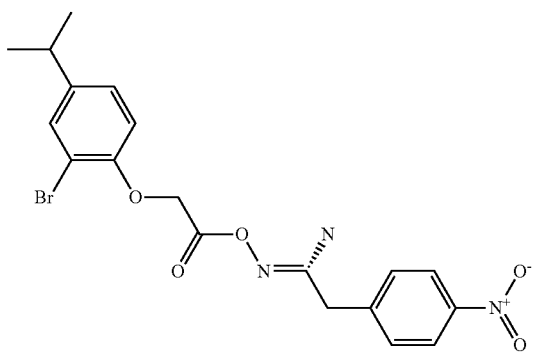 |
| CB131 (>20 ug/mL) | 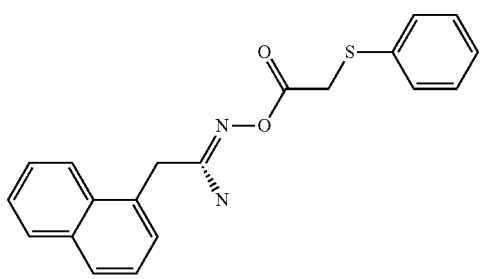 |

TABLE 5-continued
CIL41/70 structural analogs.
| Compound | Structure |
|---|---|
| CB132 (>20 ug/mL) | 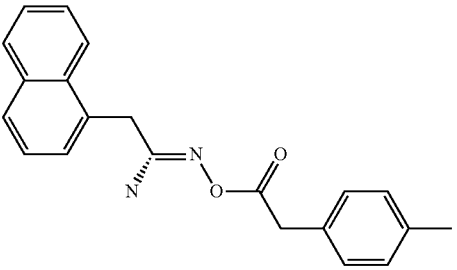 |
| CB133 (>20 ug/mL) | 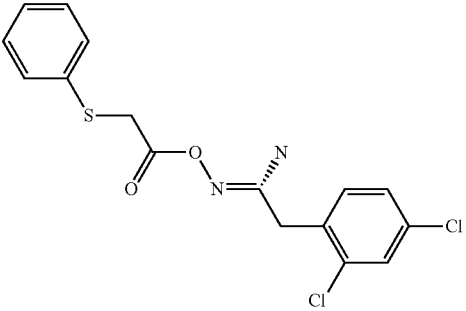 |
| CB134 (>20 ug/mL) | 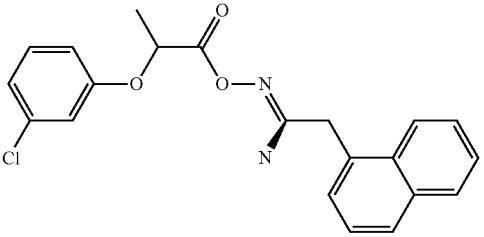 |
| CB135 (>20 ug/mL) | 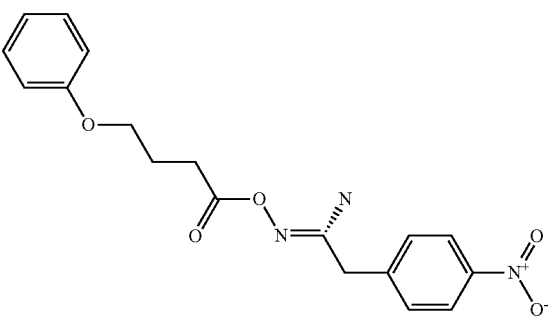 |
| CB136 (>20 ug/mL) | 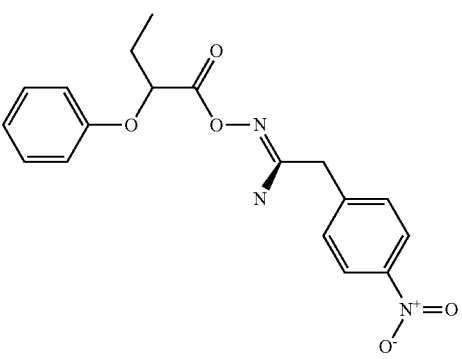 |

TABLE 5-continued

CIL41/70 structural analogs.

| Compound | Structure |
|---|---|
| CB137 (>20 ug/mL) | 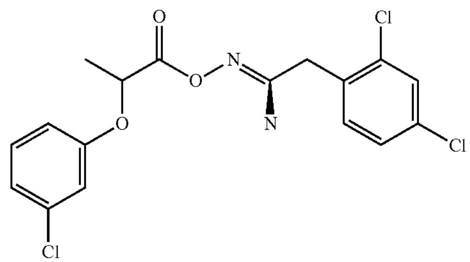 |
| CB138 (>20 ug/mL) | 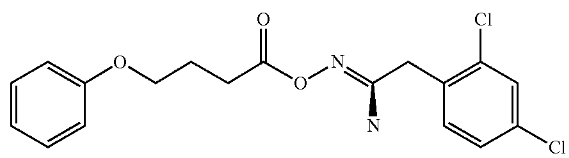 |
| CB139 (>20 ug/mL) | 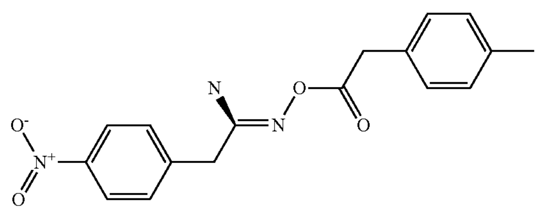 |
| CB141 (>20 ug/mL) | 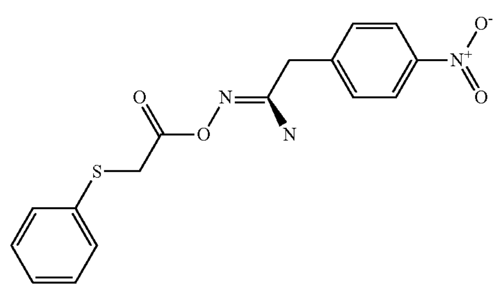 |
| CB142 (>20 ug/mL) | 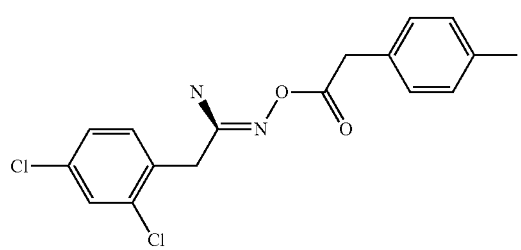 |
| CB143 (>20 ug/mL) | 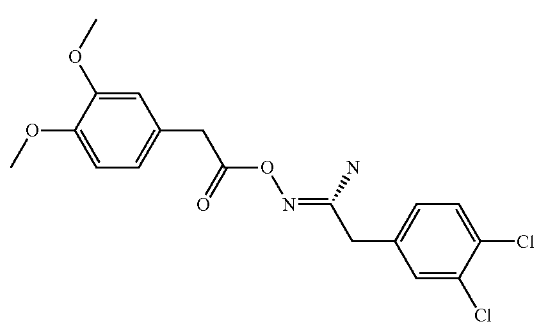 |

TABLE 5-continued
CIL41/70 structural analogs.
| Compound | Structure |
|---|---|
| CB144 (>20 ug/mL) | 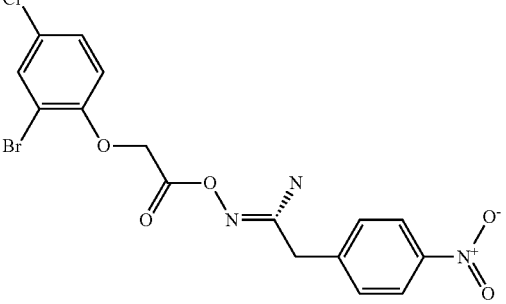 |
| CB145 (>20 ug/mL) | 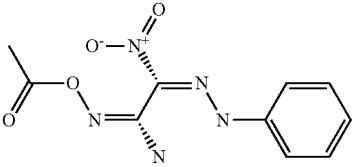 |
| CB146 (>20 ug/mL) | 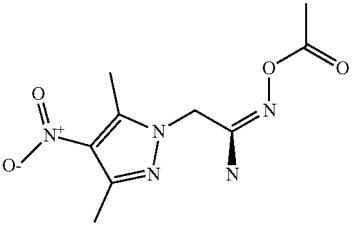 |
| CB148 (>20 ug/mL) | 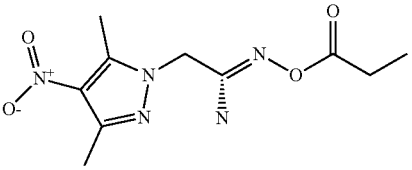 |
| CD1 (>20 ug/mL) | 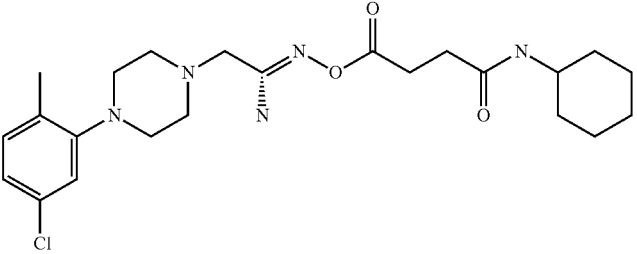 |
| EN1 (>20 ug/mL) | 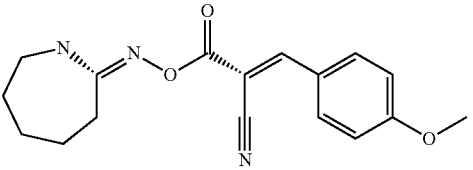 |
| EN3 (>20 ug/mL) | 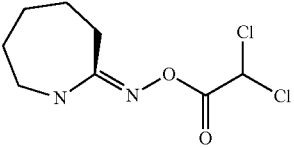 |

TABLE 5-continued
CIL41/70 structural analogs.
| Compound | Structure |
|---|---|
| EN4 (>20 ug/mL) | 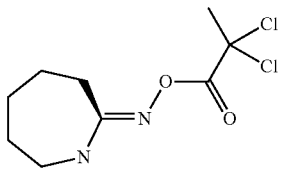 |
| EN5 (>20 ug/mL) | 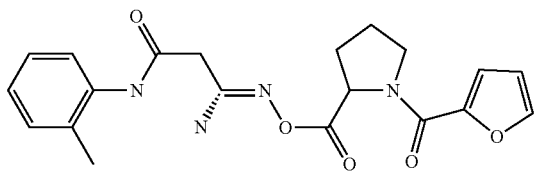 |
| EN6 (>20 ug/mL) | 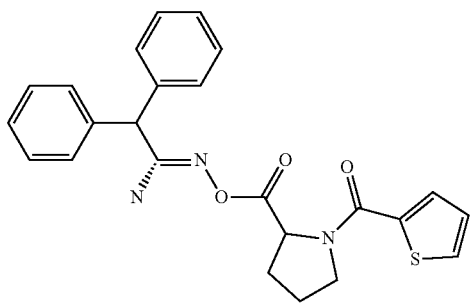 |
| EN7 (>20 ug/mL) | 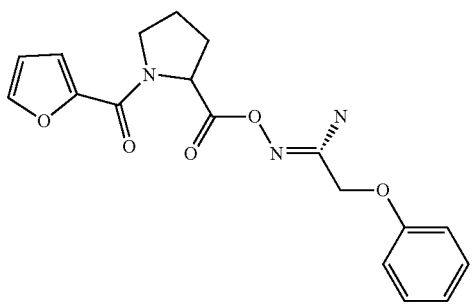 |
| EN8 (>20 ug/mL) | 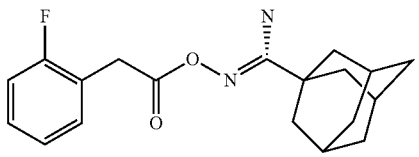 |
| EN9 (>20 ug/mL) | 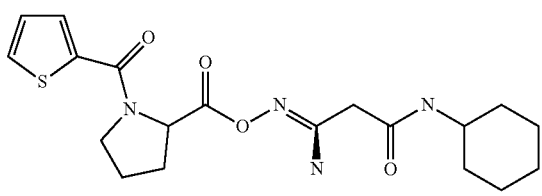 |
| EN10 (>20 ug/mL) | 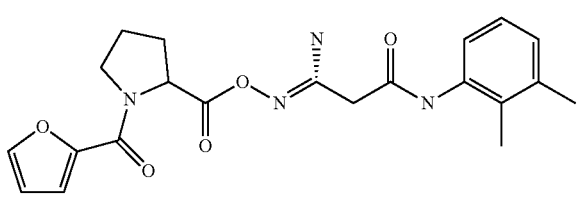 |

TABLE 5-continued

CIL41/70 structural analogs.

| Compound | Structure |
|---|---|
| EN11 (>20 ug/mL) | 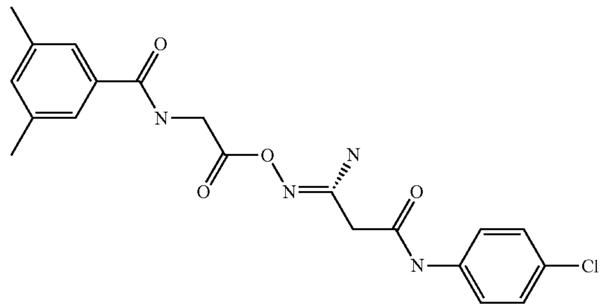 |
| MB1 (>20 ug/mL) | 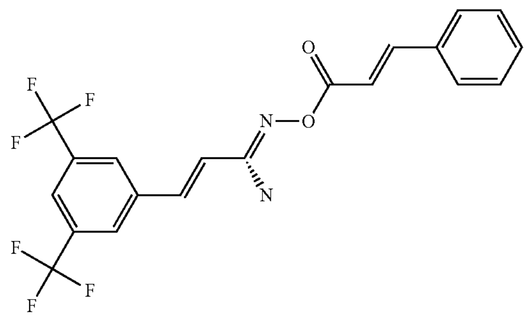 |
| MB2 (>20 ug/mL) | 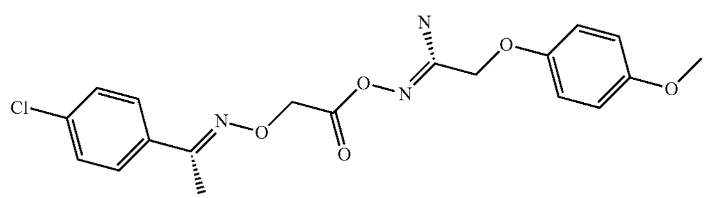 |
| MB3 (>20 ug/mL) | 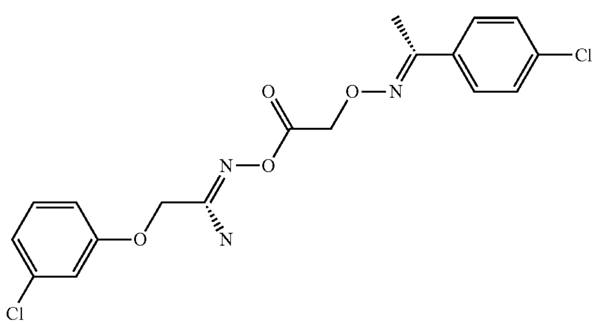 |
| MB4 (>20 ug/mL) | 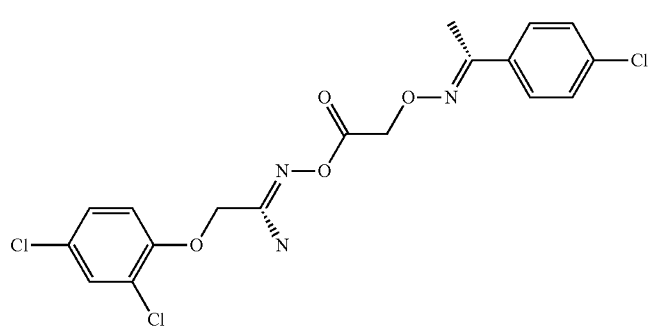 |

TABLE 5-continued
CIL41/70 structural analogs.
| Compound | Structure |
|---|---|
| MB5 (>20 ug/mL) | 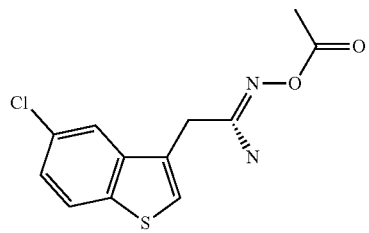 |
| MB7 (>20 ug/mL) | 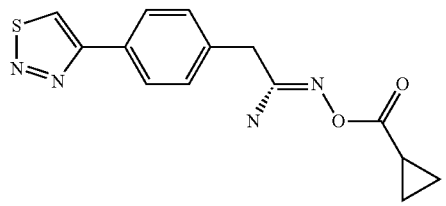 |
| MB8 (>20 ug/mL) | 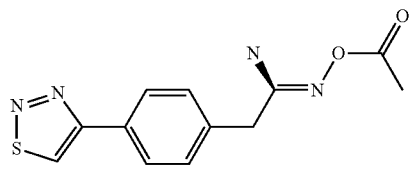 |
| MB9 (>20 ug/mL) | 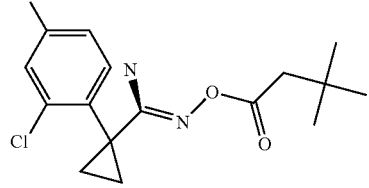 |
| MB10 (>20 ug/mL) | 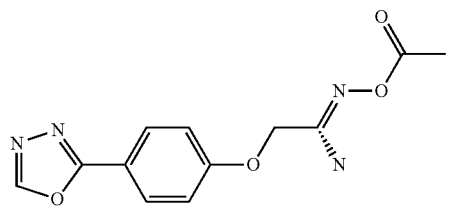 |
| MB11 (>20 ug/mL) | 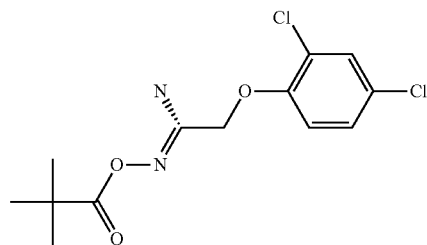 |
| MB12 (>20 ug/mL) | 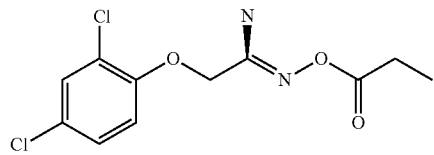 |

TABLE 5-continued
CIL41/70 structural analogs.
| Compound | Structure |
|---|---|
| MB13 (>20 ug/mL) | 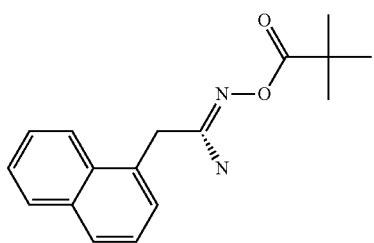 |
| MB15 (>20 ug/mL) | 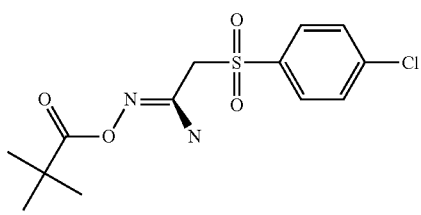 |
| MB16 (>20 ug/mL) | 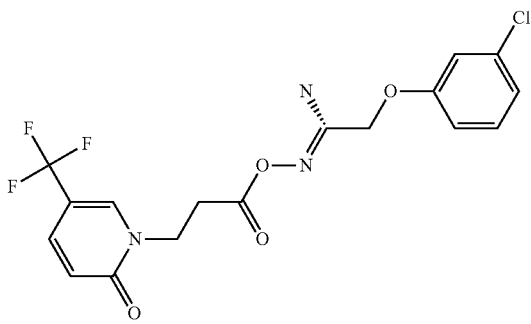 |
| MB17 (>20 ug/mL) | 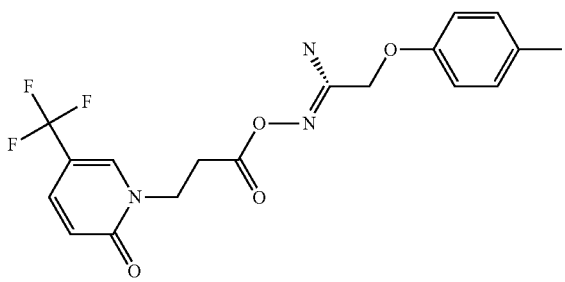 |
| VM2 (>20 ug/mL) | 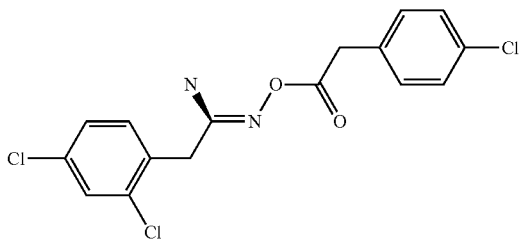 |

TABLE 5-continued
CIL41/70 structural analogs.
| Compound | Structure |
|---|---|
| VM4 (>20 ug/mL) | 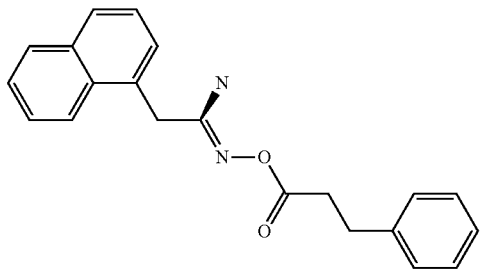 |
| VM5 (>20 ug/mL) | 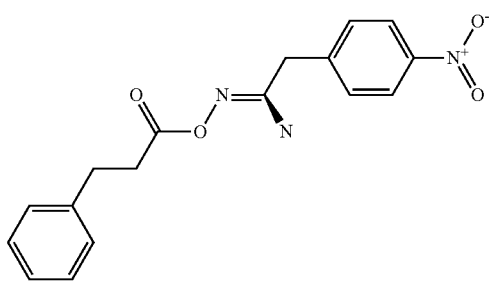 |
| ZE1 (>20 ug/mL) | 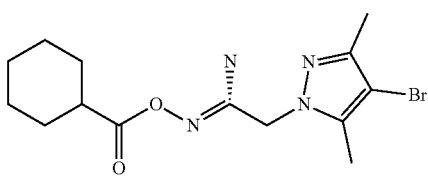 |
| ZE3 (>20 ug/mL) | 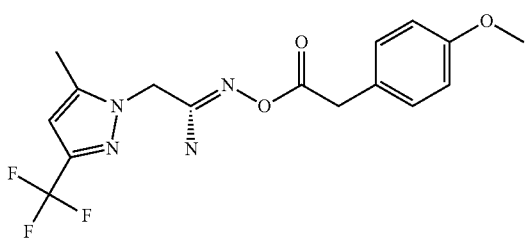 |
| ZE4 (>20 ug/mL) | 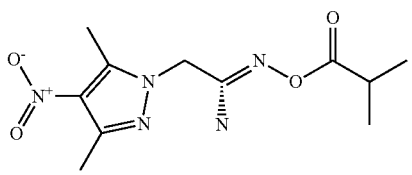 |
| ZE5 (>20 ug/mL) | 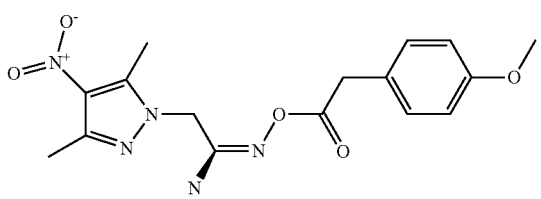 |
| ZE6 (>20 ug/mL) | 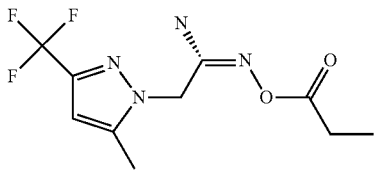 |

TABLE 5-continued
CIL41/70 structural analogs.
| Compound | Structure |
|---|---|
| ZE7 (>20 ug/mL) | 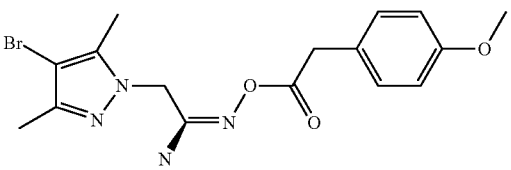 |
| ZE8 (>20 ug/mL) | 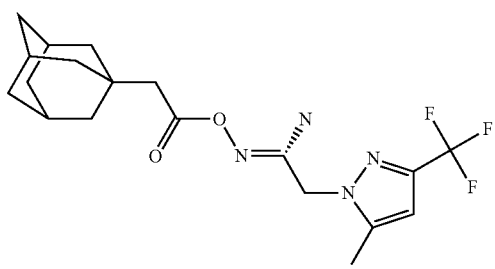 |
| ZE9 (>20 ug/mL) | 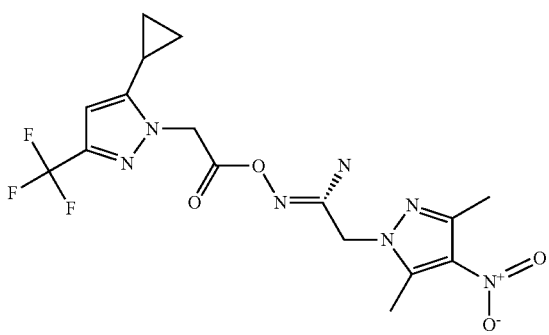 |
| ZE10 (>20 ug/mL) | 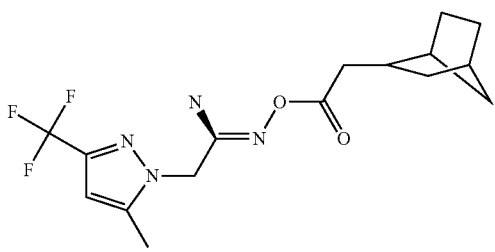 |
| ZE11 (>20 ug/mL) | 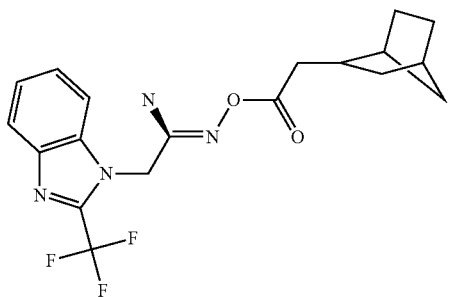 |

… 121 … 122
TABLE 5-continued
CIL41/70 structural analogs.
| Compound | Structure |
|---|---|
| ZE12 (>20 ug/mL) | 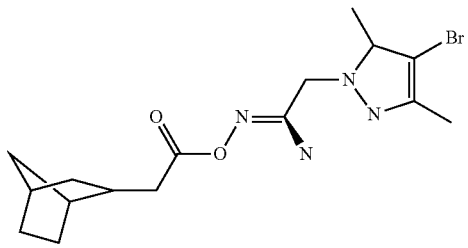 |
| ZE13 (>20 ug/mL) | 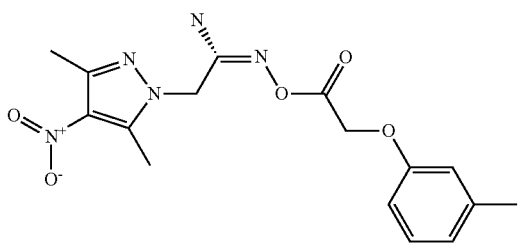 |
| ZE14 (>20 ug/mL) | 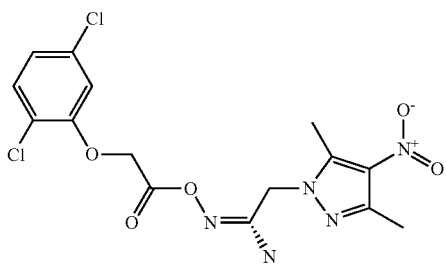 |
| ZE15 (>20 ug/mL) | 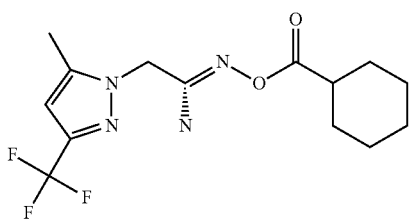 |
| ZE16 (>20 ug/mL) | 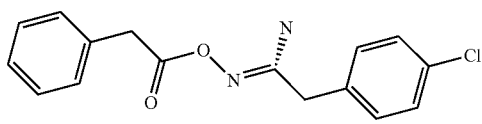 |
| ZE17 (>20 ug/mL) | 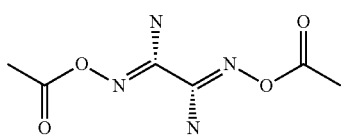 |

Example 2

Modulatory Profiling Revealed Three Kinds of Cell Death

To map the landscape of cell death, small-molecule inducers of regulated, non-apoptotic cell death were searched (FIG. 1A). Total of 3,169 lethal compounds were tested for induction of caspase-independent cell death in HT-1080 fibrosarcoma cells and BJeLR engineered transformed fibroblasts, cell lines used previously for modulatory profiling experiments (Hahn et al. 1999) (see Table 1). It was found that 451 compounds (14%) triggered cell death without activation of caspases 3 and 7, detected using a fluorogenic substrate. These compounds were defined as 'caspase-3/7-independent lethals' (CILs) (FIG. 7, and Tables 4 and 5). Thus, although most lethal compounds activate caspase activity (irrespective of whether caspase activity is required for their lethality), it was found that a considerable number of compounds were lethal without activating cleavage of the fluorogenic caspase-activity probe.

Fifty-six structurally diverse and potent ($EC_{80} < 2.8$ µg ml$^{-1}$) CILs were further examined using a modulatory profiling strategy. Previously, the clustering of modulatory profiles, or changes in the potency and efficacy of a lethal compound induced by cotreatment with chemical and genetic death modulators (Table 2), revealed that compounds with the same mechanism of action share similar modulatory profiles (Wolpaw et al. 2011). For evaluation of diverse regulated cell death programs, modulatory profiling should facilitate the grouping of pharmacological agents by their induction of specific regulated cell death programs. It was observed that ten compounds induced three types of regulated non-apoptotic cell death. A specific ferroptosis inducer was further identified through lead optimization and its mechanism of action was uncovered. In this analysis, 10 of the 56 CIL compounds exhibited 'high modulatability', meaning their lethality was considerably suppressed or enhanced by specific pharmacological or genetic agents (Wolpaw et al. 2011) (FIG. 8 and Tables 6-9); high modulatability correlates with activity through a specific lethal pathway. When analyzed along with other well-characterized lethal compounds, these CILs fell into three classes (FIG. 1B and FIG. 9A). The first class (CIL13, CIL52, and CIL64) acted via metal chelation, as these compounds were inhibited by cobalt (II) and bound to cobalt (II) in vitro (FIGS. 9B-9C). The second class (CIL62) induced cell death that was suppressed by necrostatin-1 (Degterev et al. 2005) (FIGS. 9D-9E; note that this does not necessarily imply necroptosis, as necrostatin-1 has necroptosis-independent effects (Takahashi et al. 2012)), and the third class (CIL41, CIL56 (1), CIL69, CIL70, CIL75, and CIL79) comprised ferroptosis inducers, as suggested by their suppression by canonical ferroptosis inhibitors (iron chelators and lipophilic antioxidants; Table 3) and clustering with known ferroptosis inducers. Six CIL compounds that clustered with ferroptosis inducers were selected for further studies.

Of the six ferroptotic CILs, three (CIL69, CIL75, and CIL79) are putative electrophiles and clustered most closely with known electrophilic ferroptosis inducers, such as (1S, 3R)-RSL3 (FIG. 10A). The remaining CILs consisted of two novel scaffolds: CIL41/70 and CIL56. CIL41/70 induced ROS accumulation, detected using $H_2$-DCFDA (FIG. 10B), and cell death that was strongly suppressed by ferroptosis inhibitors (i.e., the lipophilic antioxidant α-tocopherol and the iron chelator deferoxamine) (FIG. 10C).

All known ferroptosis inducers induce selective lethality in a BJ engineered cell line series, namely, BJeH, BJeHLT, DRD, and BJeLR cells. These cells were initially created to demonstrate that normal human fibroblasts can be transformed into tumor cells by the introduction of defined genetic elements (human telomerase, SV40 small and large T antigens, and oncogenic $HRAS^{G12V}$) (Hahn et al. 1999). BjeLR cells and DRD cells, which overexpress oncogenic RAS, were found to be more sensitive to ferroptosis inducers than BJeHLT cells and BJeH cells, which do not express oncogenic RAS. CIL41/70, unlike all other ferroptosis-inducing compounds reported to date, did not exhibit oncogenic RAS selectivity in the BJ engineered cell line series (Yang et al. 2008) (FIG. 10D). Moreover, 203 commercially available structural analogs of CIL41/70 were tested and they were less potent than CIL56 itself (Tables 4-5 and FIG. 10E). Given that CIL56 was the most potent compound, and that it retained some degree of selectivity toward oncogenic-RAS-expressing cells in the BJ series (FIG. 2A), CIL56 was believed to be more likely than CIL41/70 to yield a potent and selective probe of ferroptosis. Thus, CIL56 was selected for more detailed characterization.

TABLE 6

List of lethal compounds.

| name | known mechanism of action |
| --- | --- |
| MS275 | HDAC inhibitor |
| Scriptaid | HDAC inhibitor |
| TrichostatinA | HDAC inhibitor |
| Echinomycin | HIF1a inhibitor |
| Colchicine | microtubule inhibitor |
| NPC25 | microtubule inhibitor |
| NPC4 | microtubule inhibitor |
| NPC7 | microtubule inhibitor |
| Podophyllotoxin | microtubule inhibitor |
| Rotenone | microtubule inhibitor |
| Vinblastine | microtubule inhibitor |
| Vincristine | microtubule inhibitor |
| DPI3 | ferroptosis (electrophile) |
| DPI4 | ferroptosis (electrophile) |
| DPI6 | ferroptosis (electrophile) |
| RSL3 | ferroptosis (electrophile) |
| Bortezomib | Proteasome inhibitor |
| MG132 | Proteasome inhibitor |
| MG262 | Proteasome inhibitor |
| Erastin | ferroptosis |
| Camptothecin | TopoI inhibitor |
| Irinotecan | TopoI inhibitor |
| Daunorubicin | TopoII inhibitor |
| Doxorubicin | TopoII inhibitor |
| Etoposide | TopoII inhibitor |
| Mitoxantrone | TopoII inhibitor |
| Cycloheximide | Translational inhibitor |
| Dinitrophenol | mitochondrial uncoupler |
| NaN3 | mitochondrial uncoupler |
| Valinomycin | mitochondrial uncoupler |
| CIL1 | NA |
| CIL2 | NA |
| CIL4 | NA |
| CIL5 | NA |
| CIL6 | NA |
| CIL7 | NA |
| CIL9 | NA |

TABLE 6-continued

List of lethal compounds.

| name | known mechanism of action |
|---|---|
| CIL10 | NA |
| CIL11 | NA |
| CIL13 | Transition metal chelator |
| CIL15 | NA |
| CIL16 | NA |
| CIL17 | NA |
| CIL18 | NA |
| CIL20 | NA |
| CIL22 | NA |
| CIL23 | NA |
| CIL25 | NA |
| CIL26 | NA |
| CIL27 | NA |
| CIL28 | NA |
| CIL33 | NA |
| CIL34 | NA |
| CIL36 | NA |
| CIL40 | NA |
| CIL41 | ferroptosis |
| CIL44 | NA |
| CIL46 | NA |
| CIL47 | NA |
| CIL48 | NA |
| CIL49 | NA |
| CIL50 | NA |
| CIL51 | NA |
| CIL52 | Transition metal chelator |
| CIL55 | NA |
| CIL56 | ferroptosis |
| CIL58 | NA |
| CIL60 | NA |
| CIL62 | Nec-1 dependent cell death |
| CIL63 | NA |
| CIL64 | Transition metal chelator |
| CIL66 | NA |
| CIL67 | NA |
| CIL69 | ferroptosis (electrophile) |
| CIL70 | ferroptosis |
| CIL71 | NA |
| CIL72 | NA |
| CIL74 | NA |
| CIL75 | ferroptosis (electrophile) |
| CIL76 | NA |
| CIL77 | NA |
| CIL79 | ferroptosis (electrophile) |
| CIL80 | NA |
| CIL87 | NA |
| CIL88 | NA |
| CIL89 | NA |

TABLE 7

List of chemical death modulators.

| chemicals | full name | known biological function | tested conc ($\mu$M) |
|---|---|---|---|
| atoc | α-tocopherol | Antioxidant | 100 |
| bCarotene | β-carotene | Antioxidant | 0.19 |
| BHA | Butylated hydroxyanisole | Antioxidant | 139 |
| BHT | Butylated hydroxytoluene | Antioxidant | 113 |
| trolox | (±)-6-Hydroxy-2,5,7,8-tetramethylchromane-2-carboxylic acid | Antioxidant | 150 |
| CspA | Cyclosporin A | Binds cyclophilin | 5 |
| Co2+ | Cobalt (II) | calcium channel blocker | 656 |
| Gd3+ | Gadolinium (III) | calcium channel blocker | 20 |
| EGTA | Ethyleneglycol-O,O'-bis(2-amino ethyl)-N,N,N',N'-tetraacetic acid | calcium(II) chelator | 2000 |
| Pepstatin | Pepstatin | cathepsin D inhibitor | 1 |
| Lmim | L-mimosine | G1-S cell-cycle inhibitor, iron chelator | 175 |
| 3MA | 3-methyladenine | Inhibitor of autophagosome formation | 5000 |
| ALLN | Calpain Inhibitor 1 | Inhibitor of calpain I and II, cathepsins B,I | 6.3 |
| Nec-1 | Necrostatin-1 | Inhibitor of necroptosis | 19 |
| deferox | Deferoxamine | iron chelator | 152 |
| SP600125 | Anthra(1,9-cd)pyrazol-6(2H)-one1,9-Pyrazoloanthrone | JNK inhibitor | 10 |
| U0126 | 1,4-diamino-2,3-dicyano-1,4-bis[2-aminophenylthio)]butadiene | MEK1/2 inhibitor | 13.1 |
| digoxin | Digoxin | $Na^+/K^+$ ATPase inhibitor | 0.13 |
| LNAME | NG-Nitro-L-arginine-methyl ester | Nitric oxide synthase inhibitor | 300 |
| NMMA | NG-Monomethyl-D-arginine | Nitric oxide synthase inhibitor | 20 |
| ATA | Aurintricarboxylic Acid | Nuclease Inhibitor | 38 |
| BocD | t-butoxycarbonyl-Asp-fluomethylketone | pan-caspase inhibitor | 50 |
| zVAD | Cbz-Val-Ala-Asp(OMe)-fluormethylketone | pan-caspase inhibitor | 45 |
| DPQ | 3,4-dihydro-5-[4-(1-piperidinyl)butoxy]-1(2H)-isoquinolinone | PARP1 inhibitor | 10 |
| CHX | Cycloheximide | protein synthesis inhibitor | 1.5 |
| ActD | Actinomycin D | RNA polymerase inhibitor | 0.002 |
| TLCK | $N_\alpha$-tosyl-L-Lys-chloro methyl ketone | serine protease inhibitor | 135 |
| NAD+ | Nicotinamide Adenine Dinucleotide | Sirtuin activator, prevents ATP depletion | 2000 |
| L/mim/NAD+ | L-mimosine and $NAD^+$ co-treatment | | 175/2000 |

TABLE 8

List of cell lines.

| cells | full name | description |
|---|---|---|
| BJ | BJeLR | BJ fibroblast overexpressing hTert/SV40LT/SV40ST/Hras$^{G12V}$ |
| HT | HT-1080 | fibrosarcoma harboring Nras$^{Q61K}$ |

TABLE 9

Modulatory profiles of characterized and uncharacterized lethal compounds.

| | BJ.3MA | BJ.ALLN | BJ.Boc D | BJ.CHX | BJ.Co2+ |
|---|---|---|---|---|---|
| MS275 | −0.026059742 | −0.039317112 | 0.089435721 | 0.226620516 | 0.232568502 |
| Scriptaid | −0.020600458 | −0.078560038 | 0.031670618 | 0.268137819 | 0.240617478 |
| TrichostatinA | −0.004309497 | −0.087739323 | 0.096123823 | 0.258751821 | 0.309126126 |
| Echinomycin | 0.345698628 | 0.02426368 | 0.049246386 | 0.201520598 | 0.093210997 |
| Colchicine | 0.003025932 | −0.033558465 | −0.000908197 | 0.160992151 | 0.168765369 |
| NPC25 | −0.025141082 | −0.011859418 | 0.0284768 | 0.338638606 | 0.205559338 |
| NPC4 | −0.044629775 | −0.022535714 | −0.009005742 | 0.231995694 | 0.151230708 |
| NPC7 | −0.023899287 | −0.018930504 | −0.00265144 | 0.211134268 | 0.080494659 |
| Podophyllotoxin | −0.01267149 | −0.003672686 | 0.003541897 | 0.122809732 | 0.094971921 |
| Rotenone | −0.026596072 | −0.034348313 | −0.016740744 | 0.106622385 | 0.083795618 |
| Vinbiastine | 0.013104608 | −0.072276828 | 0.001717399 | 0.232808367 | 0.187592903 |
| Vincristine | −0.03566309 | −0.031708431 | −0.005015919 | 0.195548157 | 0.180588109 |
| DPI3 | 0.095722195 | −0.072359809 | −0.00375885 | −0.044207783 | 0.155678052 |
| DPI4 | 0.081304775 | −0.075963448 | −0.020600089 | −0.044823823 | 0.115974336 |
| DPI6 | 0.061477039 | −0.054000329 | −0.018112304 | −0.069274018 | 0.10520246 |
| RSL3 | 0.091035174 | 0.012662457 | 0.038324402 | 0.184102513 | 0.109106536 |
| Bortezomib | 0.001927724 | −0.103124775 | 0.030321225 | 0.298426073 | 0.237919799 |
| MG132 | −0.043463292 | −0.270072286 | 0.042157364 | 0.247614973 | 0.184937083 |
| MG262 | −0.036195527 | −0.198870912 | 0.017555267 | 0.243797991 | 0.110875339 |
| Erastin | 0.093482003 | −0.057509042 | −0.000616511 | 0.090809688 | −0.170369309 |
| Camptothecin | −0.020270594 | 0.033675205 | 0.079833441 | 0.123280564 | 0.028994781 |
| Irinotecan | −0.046340941 | 0.015018658 | 0.070216151 | 0.124862147 | 0.028550947 |
| Daunorubicin | 0.037934083 | 0.028460875 | 0.033216728 | 0.149732833 | 0.212207875 |
| Doxorubicin | 0.031127831 | 0.015547275 | 0.049656193 | 0.14122675 | 0.197065807 |
| Etoposide | −0.061955521 | 0.060991381 | 0.061201223 | 0.125509938 | 0.095103567 |
| Mitoxantrone | 0.033515749 | 0.062035607 | 0.037464053 | 0.143696892 | 0.453843256 |
| Cycloheximide | 0.038465272 | 0.094614356 | 0.02242339 | 0.361284466 | 0.237543606 |
| Dinitrophenol | −0.008182185 | −0.038382592 | −0.01714167 | 0.189038538 | −0.008315819 |
| NaN3 | −0.095593638 | −0.003819896 | −0.007272953 | 0.072620828 | −0.021225548 |
| Vatinomycin | 0.033259329 | 0.020633509 | 0.020464639 | 0.357294884 | 0.095951635 |
| CIL1 | 0.094702761 | −0.033187356 | −0.046498523 | −0.08681018 | 0.095722858 |
| CIL2 | 0.064313223 | −0.039784978 | −0.03807957 | 0.03999122 | −0.136186971 |
| CIL4 | 0.083161827 | −0.003082963 | −0.018283858 | −0.009993254 | −0.17469724 |
| CIL5 | 0.085235042 | −0.116283699 | −0.07609025 | −0.032403457 | 0.047047513 |
| CIL6 | 0.119061436 | −0.049603536 | −0.052467687 | 0.135265612 | 0.069605114 |
| CIL7 | 0.091880431 | −0.028761721 | −0.049458392 | −0.010559719 | 0.09998614 |
| CIL9 | 0.046502556 | −0.120198756 | −0.061705214 | 0.03696055 | −0.009162007 |
| CIL10 | 0.134017231 | −0.017134117 | −0.052123672 | −0.018050509 | 0.114193588 |
| CIL11 | 0.090044215 | 0.015376964 | −0.043226998 | 0.123905521 | 0.077708109 |
| CIL13 | 0.090834135 | −0.039328117 | −0.029889688 | −0.126427664 | 0.528659723 |
| CIL15 | 0.027611875 | −0.06757043 | −0.053211843 | 0.12872254 | 0.096097693 |
| CIL16 | 0.05063654 | −0.034913398 | −0.046915645 | 0.012206749 | 0.072067228 |
| CIL17 | 0.079269682 | −0.074781483 | −0.031155382 | −0.046204279 | −0.047640395 |
| CIL18 | 0.06540499 | −0.045068104 | −0.018410753 | −0.015819111 | 0.089434829 |
| CIL20 | 0.055003817 | −0.090980632 | −0.063733658 | −0.009676654 | 0.047634171 |
| CIL22 | −0.043294993 | −0.032323012 | −0.040599287 | 0.113573387 | 0.076154164 |
| CIL23 | −0.016130596 | −0.045611913 | −0.01959298 | −0.023034675 | −0.015941685 |
| CIL25 | 0.023740381 | −0.07208946 | −0.009758131 | −0.02730202 | −0.003244445 |
| CIL26 | 0.05123851 | −0.058398468 | −0.05573532 | −0.001732868 | 0.048705995 |
| CIL27 | 0.040295075 | −0.066042535 | −0.080491998 | 0.139881194 | 0.059305657 |
| CIL28 | 0.043299829 | −0.020647414 | −0.025487472 | −0.011194165 | 0.034165753 |
| CIL33 | 0.0619933 | −0.112365796 | −0.032294484 | 0.102623158 | 0.043114331 |
| CIL34 | 0.077008824 | −0.043739268 | −0.024624589 | 0.121487032 | 0.07311128 |
| CIL36 | 0.062946001 | −0.032362618 | −0.047302904 | −0.030872077 | −0.036468619 |
| CIL40 | 0.113089292 | −0.025923038 | −0.056067715 | −0.1422925 | 0.033483801 |
| CIL41 | 0.116955468 | −0.082112839 | −0.063738367 | −0.057101897 | −0.023784749 |
| CIL44 | 0.05755856 | −0.058803806 | −0.039629515 | 0.155313574 | 0.023867911 |
| CIL46 | 0.188432008 | −0.013738553 | −0.005903073 | 0.15984289 | −0.138932367 |
| CIL47 | 0.150522382 | −0.026277586 | 0.053970843 | −0.02690468 | −0.137946997 |
| CIL48 | 0.097888892 | −0.100752292 | −0.022253324 | 0.161924385 | 0.053915436 |
| CIL49 | 0.045036307 | −0.058638439 | −0.025704178 | 0.169190352 | 0.009716111 |
| CIL50 | −0.00161299 | −0.008923829 | 0.031127244 | 0.141459593 | −0.017803771 |
| CIL51 | 0.059081237 | −0.203188928 | −0.000882839 | 0.169570765 | 0.063992863 |

TABLE 9-continued

Modulatory profiles of characterized and uncharacterized lethal compounds.

| | | | | | |
|---|---|---|---|---|---|
| CIL52 | 0.011896568 | 0.010918623 | 0.018402924 | 0.037243011 | 0.7977955 |
| CIL55 | 0.063543912 | −0.046846172 | −0.014987852 | 0.037300771 | 0.03522058 |
| CIL56 | 0.145895802 | 0.058308053 | −0.010427691 | −0.072214121 | 0.126264931 |
| CIL58 | 0.034027705 | 0.018458023 | −0.007995419 | −0.049112036 | 0.238560717 |
| CIL60 | 0.067356791 | −0.004196565 | 0.026257063 | 0.180280969 | 0.038358824 |
| CIL62 | 0.009761947 | −0.062646512 | −0.008657967 | 0.516222526 | 0.015737354 |
| CIL63 | 0.040754174 | 0.05440433 | −0.010529835 | 0.095083008 | 0.021772384 |
| CIL64 | 0.02464908 | 0.014202785 | 0.011077585 | 0.047118757 | 0.940237984 |
| CIL66 | 0.041676948 | 0.087467313 | −0.03145846 | 0.083694083 | −0.031407325 |
| CIL67 | 0.023124894 | 0.021494083 | 0.005780137 | 0.308266858 | 0.037082001 |
| CIL69 | 0.077127838 | −0.000522215 | −0.003227696 | −0.03495043 | 0.172373945 |
| CIL70 | 0.101356041 | −0.07035852 | 0.00241214 | 0.130415593 | −0.000492503 |
| CIL71 | 0.011512823 | −0.055893307 | 0.015201388 | −0.063520521 | 0.026760788 |
| CIL72 | 0.017140014 | 0.004589548 | 0.026716057 | 0.25849909 | 0.117570684 |
| CIL74 | 0.036151004 | −0.025360323 | 0.043242954 | 0.014664752 | 0.213514501 |
| CIL75 | 0.046533481 | 0.013011291 | 0.03091594 | −0.009102995 | 0.204879929 |
| CIL76 | −0.036682826 | −0.053597155 | 0.032366316 | 0.260846556 | 0.167625358 |
| CIL77 | −0.057281353 | 0.018263122 | 0.056223402 | 0.25480136 | 0.186570503 |
| CIL79 | 0.07979903 | 0.027169014 | 0.029379264 | −0.046505369 | 0.176254231 |
| CIL80 | 0.006540475 | −0.004769237 | 0.008783432 | 0.135118471 | 0.095062234 |
| CIL87 | −0.002763545 | −0.08720998 | −0.013398191 | 0.295017043 | 0.141646385 |
| CIL88 | 0.030934243 | −0.142376485 | −0.01445462 | 0.235378859 | 0.053789327 |
| CIL89 | −0.01648407 | −0.120355803 | 0.03243382 | 0.19676153 | 0.017205043 |
| | BJ.DPQ | BJ.Gd3+ | BJ.LNAME | BJ.Lmin | BJ.Lmin/NAD+ |
| MS275 | −0.0096557 | 0.02299609 | 0.02320658 | −0.0011826 | 0.156946048 |
| Scriptaid | 0.00489165 | 0.0289045 | 0.03611375 | 0.11129574 | 0.211416066 |
| TrichostatinA | −0.0095226 | −0.0088019 | −0.0420318 | 0.08422628 | 0.159662164 |
| Echinomycin | −0.0043253 | 0.00204084 | 0.01198552 | 0.12050248 | 0.235093929 |
| Colchicine | −0.0305343 | −0.010606 | −0.0085479 | 0.05808173 | 0.140911627 |
| NPC25 | −0.0020323 | 0.00764977 | 0.01842301 | 0.15871171 | 0.181745644 |
| NPC4 | −0.0121288 | 0.01108163 | 0.03470683 | 0.12282908 | 0.189076249 |
| NPC7 | −0.0111977 | 0.00040178 | 0.02663201 | 0.10580065 | 0.20079283 |
| Podophyllotoxin | −0.0389641 | 0.01784317 | 0.00586807 | 0.05456671 | 0.101224933 |
| Rotenone | −0.022785 | 0.01421305 | −0.011312 | 0.06491961 | 0.143857129 |
| Vinbiastine | −0.0311986 | 0.00835127 | −0.0006349 | 0.0658354 | 0.171479031 |
| Vincristine | −0.030439 | 0.00794382 | −0.0071703 | 0.06034138 | 0.172069929 |
| DPI3 | 0.05023093 | 0.05621465 | 0.0011647 | 0.15320194 | 0.19306387 |
| DPI4 | 0.02148024 | 0.06864379 | 0.00316962 | 0.14433436 | 0.14432113 |
| DPI6 | 0.03271803 | 0.03553869 | 0.02698599 | 0.12687654 | 0.086661743 |
| RSL3 | 0.03115236 | 0.02447626 | 0.02931886 | 0.34623405 | 0.385813695 |
| Bortezomib | −0.0073919 | −0.03227 | −0.0086492 | 0.09993315 | 0.149126821 |
| MG132 | −0.0132706 | 0.03162845 | 0.01788625 | 0.14869399 | 0.206416573 |
| MG262 | 0.00506418 | 0.02134418 | 0.02271737 | 0.14366619 | 0.152015466 |
| Erastin | −0.0050575 | −0.0387997 | −0.0397056 | 0.11149699 | 0.153795532 |
| Camptothecin | −0.0111881 | −0.007898 | 0.00320584 | 0.0294683 | 0.116436878 |
| Irinotecan | 0.04602433 | −0.0076941 | 0.01821737 | 0.018475 | 0.080917834 |
| Daunorubicin | −0.0352683 | −0.0052472 | 0.00552589 | 0.05475302 | 0.143361824 |
| Doxorubicin | 0.00446182 | −0.0110536 | 0.01381765 | 0.05475337 | 0.147679846 |
| Etoposide | −0.0468961 | 0.01316612 | 0.00451468 | 0.04682368 | 0.101123735 |
| Mitoxantrone | −0.0581416 | 0.0106939 | 0.00757779 | 0.0436762 | 0.116200284 |
| Cycloheximide | 0.02122104 | 0.02359332 | 0.00769629 | 0.07750166 | 0.105686189 |
| Dinitrophenol | −0.0325051 | −0.0141327 | −0.0202006 | −0.0204979 | 0.076205151 |
| NaN3 | −0.0694736 | 0.01113264 | −0.0183243 | −0.0841719 | −0.007837039 |
| Vatinomycin | −0.0220075 | −0.0004394 | −0.0132299 | −0.0078469 | 0.152525695 |
| CIL1 | −0.01655 | −0.0015775 | −0.0210343 | −0.0142017 | −0.019472966 |
| CIL2 | 0.0039287 | 0.01321642 | −0.004423 | 0.0083184 | −0.019443953 |
| CIL4 | −0.0039688 | 0.05533373 | −0.0128845 | −0.0028673 | 0.086739015 |
| CIL5 | 0.00287621 | 0.01145922 | −0.0097869 | −0.036977 | −0.017375505 |
| CIL6 | 0.01365177 | 0.00684778 | −0.0263723 | −0.0387383 | −0.063801914 |
| CIL7 | 0.06720757 | −0.0189741 | −0.0318209 | 0.01256103 | 0.017714492 |
| CIL9 | −0.0122469 | −0.0103755 | 0.01335948 | −0.0396671 | 0.014992517 |
| CIL10 | −0.0269473 | 0.00792172 | 0.01363382 | −0.0234054 | −0.013959025 |
| CIL11 | −0.0156617 | 0.02904746 | −0.0003217 | −0.0403399 | 0.013439329 |
| CIL13 | 0.00739191 | 0.04262745 | 0.0154421 | −0.0341183 | −0.054563077 |
| CIL15 | −0.0123768 | 0.02534821 | −0.0245318 | −0.0004619 | −0.01163706 |
| CIL16 | −0.0173163 | −0.0250626 | −0.0127813 | −0.0223794 | −0.05229458 |
| CIL17 | 0.00467941 | −0.0400009 | −0.0080537 | −0.02464 | −0.032086352 |
| CIL18 | −0.0131845 | −0.0165879 | −0.0162754 | −0.0550532 | −0.050203511 |
| CIL20 | −0.0269595 | 0.04265912 | −0.0017472 | −0.0260292 | −0.03733821 |
| CIL22 | 0.00575155 | 0.00589901 | 0.01229865 | 0.002645 | 0.072783496 |
| CIL23 | 0.0043789 | 0.03265453 | −0.0212857 | −0.0161655 | 0.004125464 |
| CIL25 | 0.00185155 | 0.04216016 | −0.0044279 | 0.0162808 | 0.09245744 |
| CIL26 | 0.01829107 | 0.00454073 | −0.033216 | −0.013902 | 0.091113219 |
| CIL27 | 0.01710026 | −0.0240573 | −0.0438093 | 0.0147174 | 0.023647992 |
| CIL28 | 0.00923459 | −0.0774082 | −0.0485835 | −0.052998 | −0.025777883 |
| CIL33 | 0.02548824 | −0.0653931 | −0.0315674 | 0.01529408 | −0.012603667 |

TABLE 9-continued

Modulatory profiles of characterized and uncharacterized lethal compounds.

| | | | | | |
|---|---|---|---|---|---|
| CIL34 | 0.03951199 | −0.0319954 | −0.016312 | −0.0234022 | 0.042574773 |
| CIL36 | 0.13933756 | 0.01469476 | 0.0008728 | 0.02335875 | −0.094025018 |
| CIL40 | 0.01886595 | −0.0047375 | 0.00219723 | −0.0527296 | −0.06069381 |
| CIL41 | 0.02160659 | −0.0067674 | 0.00306986 | 0.20320555 | 0.150431554 |
| CIL44 | 0.05603523 | 0.00555618 | 0.00898119 | 0.03065188 | −0.049754257 |
| CIL46 | 0.03979168 | −0.0560629 | −0.0218477 | 0.25833718 | 0.18247054 |
| CIL47 | 0.06122321 | −0.0287511 | −0.024789 | −0.0169586 | −0.014373272 |
| CIL48 | 0.01111515 | −0.0043066 | −0.0103879 | −0.0266405 | 0.063259258 |
| CIL49 | −0.002084 | −0.0060484 | −0.0078571 | 0.03689207 | 0.070671325 |
| CIL50 | −0.0386937 | −0.0211267 | 0.03227487 | 0.03122751 | 0.016756946 |
| CIL51 | 0.04077456 | 0.03262832 | −0.0414541 | −0.0741306 | 0.034681874 |
| CIL52 | 0.03648385 | 0.08326996 | −0.0157785 | 0.0077833 | 0.082646149 |
| CIL55 | 0.01735295 | 0.00355544 | −0.0200804 | 0.08142775 | 0.192397007 |
| CIL56 | 0.03219032 | 0.00499655 | 0.00597842 | 0.1358207 | 0.219400696 |
| CIL58 | 0.00992247 | 0.02130798 | −0.0281144 | −0.0091724 | 0.027134971 |
| CIL60 | 0.02056594 | 0.02704229 | −0.0154202 | 0.04196132 | 0.058879954 |
| CIL62 | −0.0057516 | 0.00294553 | −0.0205525 | 0.01862207 | 0.087356675 |
| CIL63 | 0.00030462 | 0.01459045 | −0.0068124 | 0.01214827 | 0.077758217 |
| CIL64 | 0.00939684 | 0.02721015 | 0.03248984 | 0.0277705 | 0.075703433 |
| CIL66 | −0.0072839 | −0.0038385 | 0.02705047 | −0.0519479 | 0.064436594 |
| CIL67 | −0.0050886 | 0.01429813 | 0.01176843 | −0.0878664 | 0.159935957 |
| CIL69 | 0.02521299 | 0.02982599 | 0.00520114 | 0.17994869 | 0.144850955 |
| CIL70 | 0.02973309 | 0.04884126 | −0.0060271 | 0.20617772 | 0.263347395 |
| CIL71 | 0.03052411 | 0.01393906 | 0.00120448 | −0.0213785 | 0.001502008 |
| CIL72 | −0.0108661 | 0.0301285 | 0.00105307 | 0.00484398 | 0.071016136 |
| CIL74 | −0.0290634 | 0.02962909 | 0.00161925 | 0.00776593 | 0.071540234 |
| CIL75 | −1.616E-05 | 0.04589641 | 0.01183514 | 0.14596013 | 0.229245422 |
| CIL76 | 0.00735075 | 0.01564981 | 0.00434473 | −0.0058295 | −0.026560841 |
| CIL77 | −0.0092733 | −0.0073443 | 0.0334856 | −0.0484787 | 0.049815598 |
| CIL79 | 0.00396667 | 0.00956035 | 0.01543874 | 0.20485377 | 0.213581808 |
| CIL80 | −0.033684 | 0.01802279 | 0.0290131 | 0.01638807 | 0.092706078 |
| CIL87 | −0.0320238 | 0.01489917 | 0.02319253 | 0.00077144 | 0.076394758 |
| CIL88 | −0.0360775 | −0.0365172 | 0.0201045 | −0.0124052 | 0.033993856 |
| CIL89 | −0.0259805 | −0.0703761 | 0.03646289 | 0.03550987 | 0.040691428 |

| | BJ.NAD+ | BJ.NMMA | BJ.Nec-1 | BJ.Pepstatin | BJ.TLCK |
|---|---|---|---|---|---|
| MS275 | 0.12689755 | −0.0037791 | −0.0132868 | −0.01823965 | 0.08473737 |
| Scriptaid | 0.13840299 | 0.02102042 | 0.02803847 | −0.02820409 | 0.07545029 |
| TrichostatinA | 0.05543793 | −0.0186055 | −0.0475068 | −0.01284083 | 0.0287911 |
| Echinomycin | 0.22918456 | 0.01082334 | −0.0190088 | −0.00436871 | −0.001724 |
| Colchicine | 0.11282645 | −0.0052205 | −0.0444276 | 0.00366931 | −0.0133804 |
| NPC25 | 0.07747315 | −0.0077502 | 0.02693649 | 0.00041587 | 0.00565247 |
| NPC4 | 0.00303668 | −0.0106621 | 0.05591668 | −0.00309854 | −0.0010738 |
| NPC7 | 0.03954194 | 0.00518631 | 0.07596296 | 0.0081013 | −0.0072504 |
| Podophyllotoxin | 0.0962667 | −0.0070434 | −0.0416706 | 0.02214061 | −0.0204248 |
| Rotenone | 0.10368941 | 0.00580134 | −0.0288816 | 0.0200717 | −0.0216911 |
| Vinbiastine | 0.13733224 | 0.00810716 | −0.0617589 | 0.00239815 | −0.0036716 |
| Vincristine | 0.12547697 | −0.0033537 | −0.0557183 | −0.00252147 | −0.0125536 |
| DPI3 | 0.02391881 | 0.01402271 | 0.13878977 | 0.0339671 | 0.23010879 |
| DPI4 | 0.03153366 | 0.00496096 | 0.12949554 | 0.03965648 | 0.16121299 |
| DPI6 | 0.01054535 | −0.0078233 | 0.16668804 | 0.01992931 | 0.1418306 |
| RSL3 | 0.04136024 | 0.00780566 | 0.23792845 | −0.00080934 | 0.27316475 |
| Bortezomib | 0.05174981 | −0.0002968 | 0.00229317 | 0.00069802 | 0.07108188 |
| MG132 | 0.04273584 | 0.02073008 | −0.0504018 | −0.02291037 | 0.1241401 |
| MG262 | 0.06083716 | −0.0069261 | −0.0134217 | 0.00662351 | 0.09405199 |
| Erastin | −0.0233386 | −0.0562522 | 0.16649238 | 0.18917929 | 0.01550359 |
| Camptothecin | 0.11203217 | −0.006852 | 0.02477381 | 0.01408015 | 0.02306401 |
| Irinotecan | 0.08680983 | −0.0151973 | 0.05502616 | 0.01485256 | 0.01158128 |
| Daunorubicin | 0.12262643 | −0.0186743 | −0.020549 | 0.02538848 | 0.02855852 |
| Doxorubicin | 0.13394207 | −0.0074862 | −0.0036772 | 0.0177527 | 0.03306748 |
| Etoposide | 0.08358535 | −0.0367759 | −0.0435391 | 0.01632262 | 0.01398922 |
| Mitoxantrone | 0.08732533 | 0.00443081 | −0.0303752 | 0.00326268 | 0.02288009 |
| Cycloheximide | 0.08265474 | 0.00253528 | 0.03326419 | 0.01474665 | 0.03152874 |
| Dinitrophenol | 0.069856 | −0.0273529 | −0.0019545 | 0.05394491 | −0.0425959 |
| NaN3 | 0.06959726 | 0.00587385 | −0.0522878 | 0.01610826 | 0.03199676 |
| Vatinomycin | 0.11006403 | −0.0263396 | 0.01733615 | 0.04946152 | 0.00660171 |
| CIL1 | 0.039405 | −0.0249794 | 0.08160063 | 0.0763918 | 0.01374571 |
| CIL2 | 0.03383486 | −0.0052336 | 0.03180184 | 0.05923483 | 0.06974481 |
| CIL4 | 0.02730981 | −0.0156562 | 0.10151633 | 0.08230554 | 0.06929196 |
| CIL5 | 2.99E-05 | −0.0270966 | 0.03195004 | 0.06042127 | −0.0260298 |
| CIL6 | 0.02657028 | 0.00628736 | 0.01237172 | 0.0371055 | −0.0153571 |
| CIL7 | 0.00904591 | −0.0153267 | 0.02534044 | 0.06230936 | −0.0237259 |
| CIL9 | 0.00071813 | −0.0154109 | 0.02689145 | 0.01819724 | −0.0175244 |
| CIL10 | −0.001182 | 0.00619197 | 0.07272333 | 0.00104409 | −0.0583071 |
| CIL11 | −0.0391938 | −0.0037798 | 0.02973909 | 0.04124625 | −0.0115517 |
| CIL13 | 0.01377788 | −0.0317716 | 0.0473837 | 0.03783902 | 0.3411674 |
| CIL15 | 0.01286697 | −0.0362316 | 0.02390543 | 0.02560014 | −0.0056295 |

TABLE 9-continued

Modulatory profiles of characterized and uncharacterized lethal compounds.

| | | | | | |
|---|---|---|---|---|---|
| CIL16 | −0.0217694 | −0.0193843 | 0.06902775 | 0.02480838 | −0.0251636 |
| CIL17 | −0.0163243 | −0.0168812 | 0.02959089 | 0.03911776 | −0.0786355 |
| CIL18 | 0.00749025 | −0.0237147 | 0.02259594 | 0.04723511 | −0.0382445 |
| CIL20 | 0.0304319 | −0.010461 | 0.01149984 | −0.00251563 | −0.0074299 |
| CIL22 | −0.005902 | −0.007412 | −0.0163259 | 0.02723931 | −0.0132068 |
| CIL23 | 0.00510439 | −0.0124185 | 0.03269009 | −0.00166279 | −0.0078056 |
| CIL25 | 0.061062 | 0.01682877 | 0.03297461 | −0.00414972 | −0.0588887 |
| CIL26 | 0.0056784 | 0.00678111 | −0.0397433 | 0.02267646 | −0.0613286 |
| CIL27 | −0.0135746 | 0.00947413 | −0.0545169 | 0.00650879 | −0.0306493 |
| CIL28 | 0.06230594 | 0.00026396 | 0.00573701 | 0.06165907 | −0.0941654 |
| CIL33 | 0.05051157 | 0.04580018 | −0.0895292 | 0.07671621 | −0.1077058 |
| CIL34 | −0.0043717 | 0.03325703 | −0.0385173 | 0.04418365 | −0.1072627 |
| CIL36 | −0.0182644 | 0.03927146 | −0.1729066 | −0.01890624 | −0.0433688 |
| CIL40 | 0.00558711 | 0.05460608 | 0.02441649 | −0.01642406 | −0.0535803 |
| CIL41 | −0.0197993 | 0.0421872 | 0.09368387 | −0.03127794 | −0.0246306 |
| CIL44 | −0.0416701 | 0.02894312 | −0.0111888 | 0.00245544 | −0.039631 |
| CIL46 | −0.0237067 | 0.03362854 | 0.08455105 | −0.01312611 | −0.097147 |
| CIL47 | −0.0635645 | 0.04023428 | −0.0220279 | 0.0545364 | −0.0376769 |
| CIL48 | −0.0424572 | 0.01412088 | −0.0443391 | −0.01271153 | −0.0133895 |
| CIL49 | 0.02344296 | 0.00689813 | 0.00197172 | 0.02852214 | −0.0354854 |
| CIL50 | −0.0848204 | −0.0045535 | −0.0568274 | 0.00383848 | −0.052247 |
| CIL51 | −0.0173703 | 0.0030163 | 0.03450537 | −0.06742194 | −0.0442069 |
| CIL52 | 0.09321461 | −0.0061184 | 0.03887959 | 0.02195686 | 0.28402574 |
| CIL55 | 0.02771794 | −0.0027585 | 0.09849299 | 0.02873006 | 0.07377767 |
| CIL56 | 0.02644617 | 0.00049055 | 0.23684095 | 0.03544769 | 0.19862485 |
| CIL58 | 0.02238111 | −0.0529865 | 0.09830113 | 0.07532329 | 0.15046424 |
| CIL60 | 0.05735354 | −0.0333761 | 0.08176375 | 0.13594441 | −0.0670478 |
| CIL62 | 0.04148582 | −0.0555592 | 0.19290773 | 0.06831212 | −0.0317476 |
| CIL63 | 0.02351722 | 0.00271866 | 0.02815163 | 0.02881969 | −0.0437018 |
| CIL64 | 0.14219284 | 0.0019661 | 0.05532962 | 0.04261861 | 0.0650817 |
| CIL66 | −0.0264041 | −0.0255773 | 0.0369439 | 0.04468669 | −0.0793466 |
| CIL67 | −0.0727219 | −0.0160091 | −0.0201768 | 0.08702793 | 0.0614094 |
| CIL69 | 0.02202981 | −0.0213286 | 0.17205944 | 0.05309819 | 0.19627093 |
| CIL70 | 0.03107613 | −0.0085471 | 0.12929417 | 0.07714716 | 0.0630101 |
| CIL71 | −0.036561 | −0.000118 | −0.0295579 | −0.01111712 | 0.01513793 |
| CIL72 | −0.0366009 | 0.01422321 | −0.024636 | 0.01988225 | 0.03640616 |
| CIL74 | −0.0590576 | 0.01058899 | −0.024894 | 0.08294342 | −0.0294162 |
| CIL75 | −0.0164272 | −0.0144916 | 0.18828932 | 0.07275235 | 0.23105427 |
| CIL76 | 0.00489521 | −0.0193662 | −0.0283021 | 0.02129585 | −0.0086886 |
| CIL77 | −0.0567652 | −0.0277058 | −0.0654344 | 0.07337511 | −0.0556501 |
| CIL79 | −0.0063695 | −0.0085941 | 0.22575501 | 0.04062847 | 0.19843153 |
| CIL80 | −0.0085154 | −3.885E−05 | −0.0159272 | 0.03142114 | −0.0060943 |
| CIL87 | −0.0329284 | −0.0073839 | −0.0481974 | −0.0328253 | 0.00320572 |
| CIL88 | −0.0355936 | −0.0121722 | −0.0364896 | −0.06126086 | 0.02089869 |
| CIL89 | −0.0393202 | −0.0295688 | −0.0295688 | −0.00629215 | −0.066762 |

| | BJ.atoc | BJ.trolox | BJ.zVAD | HT.3MA | HT.ALLN |
|---|---|---|---|---|---|
| MS275 | −0.0084515 | −0.0011371 | 0.14146731 | −0.0920374 | −0.1325215 |
| Scriptaid | −0.0053962 | −0.0185016 | 0.12050225 | −0.1243573 | −0.1402561 |
| TrichostatinA | −0.0180623 | −0.0267223 | 0.11977296 | −0.1241009 | −0.1481335 |
| Echinomycin | 0.16805955 | −0.043222 | 0.00597268 | 0.30826032 | 0.08399808 |
| Colchicine | −0.02812 | −0.0042293 | 0.0570233 | 0.01860588 | 0.19321494 |
| NPC25 | −0.0050705 | 0.00975904 | 0.07171837 | 0.08924394 | 0.17592665 |
| NPC4 | 0.00195392 | 0.01365968 | 0.04442037 | 0.06849702 | 0.17149162 |
| NPC7 | 0.01389367 | 0.02619418 | 0.05045047 | 0.04871941 | 0.00130774 |
| Podophyllotoxin | 0.00707233 | −0.012817 | 0.04960196 | 0.0013506 | 0.15724862 |
| Rotenone | 0.05115769 | −0.0107482 | 0.04408484 | 0.06288513 | 0.07973252 |
| Vinblastine | 0.14869923 | −0.0114541 | 0.01551736 | 0.05248911 | 0.15265143 |
| Vincristine | 0.04717344 | −0.0330489 | 0.01856344 | 0.02990414 | 0.18689078 |
| DPI3 | 0.43896765 | 0.43427174 | −0.0465249 | −0.007409 | −0.1136639 |
| DPI4 | 0.26106654 | 0.25470923 | −0.0217944 | −0.0014583 | −0.1647522 |
| DPI6 | 0.31847172 | 0.32883594 | −0.0118015 | 0.00819515 | −0.1107117 |
| RSL3 | 0.36011958 | 0.37310011 | 0.00586004 | −0.0747144 | −0.0380195 |
| Bortezomib | 0.01647258 | 0.01237058 | 0.00508615 | −0.0717141 | −0.085871 |
| MG132 | −0.0023264 | −0.0144852 | −0.0845176 | −0.0339243 | −0.21489 |
| MG262 | 0.05198126 | 0.00808713 | −0.0549816 | −0.0656271 | −0.1355736 |
| Erastin | 0.32756245 | 0.24919798 | −0.0053013 | −0.0457811 | −0.068557 |
| Camptothecin | 0.01158062 | 0.04873997 | 0.08240716 | 0.01920351 | 0.03354113 |
| Irinotecan | 0.03987423 | 0.07779279 | 0.07984183 | 0.00553604 | −0.0552172 |
| Daunorubicin | 0.00414462 | −0.0202568 | 0.05593995 | 0.02823215 | 0.00869204 |
| Doxorubicin | 0.01689052 | 0.01163726 | 0.05543158 | 0.03088374 | 0.03102276 |
| Etoposide | −0.0103765 | −0.0180755 | 0.06084183 | 0.00720806 | 0.03276835 |
| Mitoxantrone | 0.02585399 | −0.0186233 | 0.04970382 | 0.02955197 | 0.0735492 |
| Cycloheximide | 0.00016722 | 0.01855954 | 0.02186279 | 0.00551244 | 0.3818123 |
| Dinitrophenol | 0.02317705 | 0.00995695 | −0.0001198 | −0.1332127 | 0.11473914 |
| NaN3 | −0.005135 | −0.0383723 | −0.0010651 | −0.0571935 | 0.06335229 |
| Vatinomycin | 0.28498 | 0.06867276 | 0.03769032 | −0.1652966 | 0.04228034 |

TABLE 9-continued

Modulatory profiles of characterized and uncharacterized lethal compounds.

| | | | | | |
|---|---|---|---|---|---|
| CIL1 | 0.05385054 | 0.08301673 | −0.0470499 | −0.0019681 | 0.10528473 |
| CIL2 | −0.0114945 | 0.00165699 | −0.0039592 | 0.07177774 | 0.0529217 |
| CIL4 | 0.00430676 | 0.0084059 | 0.01241555 | 0.02219194 | 0.02482089 |
| CIL5 | −0.0027101 | 0.01829519 | −0.0205413 | 0.01320494 | 0.07446486 |
| CIL6 | 0.01482359 | −0.0067769 | −0.0031922 | 0.06095929 | 0.04648241 |
| CIL7 | 0.00084946 | 0.04239953 | −0.0583405 | −0.0046258 | 0.11359317 |
| CIL9 | 0.02754398 | 0.05396583 | −0.0270786 | 0.04492152 | −0.0207669 |
| CIL10 | 0.04670042 | 0.05526964 | −0.0073328 | −0.0198166 | 0.10670073 |
| CIL11 | −0.020819 | −0.0178186 | −0.0045166 | 0.00011437 | 0.01794211 |
| CIL13 | −0.0056464 | −0.0066491 | −0.0045682 | 0.02534783 | 0.0164632 |
| CIL15 | −0.0114947 | −0.0102551 | 0.01242501 | 0.02629949 | 0.00012453 |
| CIL16 | −0.0335072 | 0.00368936 | −0.0061661 | 0.02993016 | −0.032855 |
| CIL17 | 0.00645085 | −0.001174 | −0.0231259 | 0.01558063 | 0.03631301 |
| CIL18 | −0.0004228 | 0.03949592 | −0.0054018 | 0.01461487 | 0.07303251 |
| CIL20 | −0.0051132 | 0.02308064 | −0.0403597 | 0.00488149 | 0.09673045 |
| CIL22 | 0.0101546 | 0.0183972 | 0.03093116 | −0.0160623 | 0.02848605 |
| CIL23 | 0.00231459 | −0.0215153 | 0.0469053 | 0.01608989 | 0.00152136 |
| CIL25 | 0.02909253 | −0.0010292 | 0.03879171 | 0.01604736 | −0.0257036 |
| CIL26 | 0.05008099 | 0.0314732 | −0.0032595 | 0.03209618 | 0.00159167 |
| CIL27 | 0.00240378 | 0.00049489 | −0.0035753 | 0.07660012 | 0.16362907 |
| CIL28 | 0.05294996 | 0.06039075 | 0.00623431 | 0.09370094 | 0.04718566 |
| CIL33 | 0.04139859 | −0.0533898 | −0.0267524 | 0.08789041 | 0.04123474 |
| CIL34 | 0.0578079 | 0.00702937 | 0.00599705 | 0.1254804 | 0.15508365 |
| CIL36 | 0.06821973 | −0.0232232 | 0.0096601 | 0.08326909 | 0.14219062 |
| CIL40 | 0.0502196 | 0.03943469 | 0.00797747 | 0.08070401 | 0.17614854 |
| CIL41 | 0.27286743 | 0.18714539 | 0.03607308 | 0.04520507 | 0.09324127 |
| CIL44 | 0.00911865 | −0.0398862 | −0.0168219 | 0.07356209 | 0.13923637 |
| CIL46 | 0.10512996 | 0.04647304 | −0.0515263 | 0.08623972 | 0.03766758 |
| CIL47 | 0.03518558 | −0.028058 | −0.0149664 | 0.07293753 | 0.22270776 |
| CIL48 | 0.01164047 | −0.0340715 | −0.0180689 | 0.08539756 | 0.16107782 |
| CIL49 | −0.0083242 | −0.0233678 | −0.0017621 | 0.0543506 | 0.06619736 |
| CIL50 | 0.00564663 | 0.00486512 | 0.02532048 | −0.0235396 | 0.18885435 |
| CIL51 | 0.02105244 | 0.05843873 | 0.03693029 | −0.1102537 | −0.0787411 |
| CIL52 | 0.08208107 | 0.01188166 | 0.02643387 | −0.0155768 | 0.2564788 |
| CIL55 | 0.18175017 | 0.19779608 | −0.0135613 | 0.00703667 | 0.02517231 |
| CIL56 | 0.29616775 | 0.2616025 | 0.03467497 | −0.033086 | −0.1793586 |
| CIL58 | 0.01276141 | 0.07255912 | 0.00460643 | 0.01140406 | 0.11609447 |
| CIL60 | 0.03955105 | 0.04379633 | −0.0011813 | 0.02575321 | −0.0158789 |
| CIL62 | 0.02712651 | 0.03186254 | 0.03040708 | −0.0090173 | 0.17019511 |
| CIL63 | 0.01699604 | 0.02098909 | 0.04472039 | 0.00891738 | 0.07446255 |
| CIL64 | 0.02331446 | 0.03467968 | 0.00817202 | 0.08632164 | 0.00995343 |
| CIL66 | 0.01039015 | 0.03146974 | 0.00222834 | 0.03556215 | −0.0328894 |
| CIL67 | −0.0150944 | −0.0044336 | 0.01614338 | 0.01770618 | 0.12391603 |
| CIL69 | 0.26783116 | 0.3133252 | 0.04233348 | 0.01872961 | −0.1005245 |
| CIL70 | 0.30465448 | 0.191108 | 0.0332095 | −0.0366043 | −0.1854615 |
| CIL71 | 0.01578726 | 0.00497539 | 0.06648208 | 0.00307792 | −0.0126326 |
| CIL72 | −0.0141221 | 0.00226961 | 0.08776565 | 0.01189674 | 0.0857353 |
| CIL74 | −0.0263164 | −0.0174426 | 0.01184939 | −0.0832325 | 0.12935179 |
| CIL75 | 0.36061903 | 0.37638163 | 0.01441857 | −0.0336856 | −0.0704404 |
| CIL76 | −0.0202205 | −0.0290381 | 0.05031848 | −0.0137338 | 0.08674041 |
| CIL77 | −0.0058929 | −0.0185567 | 0.06873383 | −0.0134697 | 0.111967 |
| CIL79 | 0.47068744 | 0.50412672 | 0.06601613 | −0.0171877 | −0.0838722 |
| CIL80 | −0.0062044 | −0.0006860 | 0.07245022 | 0.03564047 | 0.10205804 |
| CIL87 | 0.00201163 | −0.0357952 | 0.07239753 | −0.0233802 | 0.13886251 |
| CIL88 | 0.02299092 | −0.0325654 | 0.03654718 | −0.0294199 | 0.13385996 |
| CIL89 | 0.02137483 | 0.0079497 | 0.01685657 | −0.054211 | 0.02598681 |

| | HT.ATA | HT.ActD | HT.BHA | HT.BHT | HT.BocD |
|---|---|---|---|---|---|
| MS275 | 0.02120396 | −0.1981516 | −0.048682 | −0.1794314 | 0.02448207 |
| Scriptaid | −0.0387325 | −0.1631887 | −0.0588253 | −0.1030388 | 0.02827963 |
| TrichostatinA | −0.0004817 | −0.1678342 | −0.0695579 | −0.1351852 | 0.04109121 |
| Echinomycin | 0.04087497 | 0.06603729 | 0.02424152 | −0.0407598 | 0.07384558 |
| Colchicine | 0.13248515 | 0.01342724 | 0.01506112 | −0.0067467 | 0.12639405 |
| NPC25 | 0.02995861 | 0.09537898 | 0.03736291 | 0.08587469 | 0.16302178 |
| NPC4 | 0.03000496 | 0.07284775 | 0.04586726 | −0.0223846 | 0.08053185 |
| NPC7 | 0.01607661 | 0.05634308 | 0.0520777 | 0.00336857 | 0.10095325 |
| Podophyllotoxin | 0.12060383 | −0.0009195 | 0.02739229 | 0.00085858 | 0.09840235 |
| Rotenone | 0.05899383 | 0.10621410 | −0.0218389 | 0.02466811 | 0.05103128 |
| Vinbiastine | 0.09963106 | 0.05584248 | −0.0165122 | 0.01379476 | 0.12562051 |
| Vincristine | 0.13037176 | 0.05976018 | −0.0047543 | −0.0156826 | 0.14006758 |
| DPI3 | −0.0428149 | −0.0002473 | 0.40702448 | 0.34683128 | −0.0039141 |
| DPI4 | −0.0362229 | −0.0068307 | 0.28495694 | 0.24859229 | −0.0140724 |
| DPI6 | −0.0419376 | −0.0416732 | 0.35257524 | 0.28208053 | −0.0011769 |
| RSL3 | −0.0453945 | −0.0857906 | 0.37982898 | 0.24437145 | −0.0118449 |
| Bortezomib | 0.05409902 | −0.0722867 | −0.0498515 | −0.1309809 | 0.02873805 |
| MG132 | 0.00576757 | −0.0641667 | −0.1238156 | −0.1271213 | 0.00205102 |
| MG262 | 0.03320394 | −0.0585361 | −0.0764988 | −0.1219041 | 0.00758177 |

TABLE 9-continued

Modulatory profiles of characterized and uncharacterized lethal compounds.

| | | | | | |
|---|---|---|---|---|---|
| Erastin | −0.1314893 | −0.1110882 | 0.17477284 | 0.12434413 | −0.0033408 |
| Camptothecin | −0.00483 | −0.1286722 | 0.04861159 | −0.0841072 | 0.03455369 |
| Irinotecan | 0.00598208 | −0.1215199 | 0.0146573 | −0.0826371 | 0.04301941 |
| Daunorubicin | −0.0018602 | 0.01441852 | 0.01070136 | −0.0560879 | 0.05219776 |
| Doxorubicin | 0.02840528 | 0.00799312 | 0.02167254 | −0.0681508 | 0.05959192 |
| Etoposide | −0.0363022 | −0.0994447 | 0.04757315 | −0.0005481 | 0.05886376 |
| Mitoxantrone | 0.02421666 | −0.0207278 | 0.02090636 | −0.0249046 | 0.06801715 |
| Cycloheximide | −0.0105671 | 0.06056867 | 0.06705416 | −0.0329721 | 0.04129835 |
| Dinitrophenol | −0.0389289 | 0.11863548 | −0.1811047 | −0.1843367 | 0.05040775 |
| NaN3 | 0.03107002 | 0.11974286 | −0.0406068 | −0.1432331 | 0.00899593 |
| Vatinomycin | 0.04038739 | 0.0778977 | −0.0126288 | −0.0523299 | 0.01495644 |
| CIL1 | −0.0478044 | −0.0405747 | 0.02690843 | −0.0849008 | −0.0164407 |
| CIL2 | 0.03084107 | −0.0052281 | −0.0376678 | −0.1327033 | 0.13949477 |
| CIL4 | 0.0280594 | −0.0014633 | −0.0093098 | −0.0221211 | 0.12719391 |
| CIL5 | 0.00058927 | −0.0075302 | −0.0850186 | −0.0991686 | 0.01524426 |
| CIL6 | 0.00765427 | −0.0089279 | −0.0076359 | −0.0611365 | 0.07600404 |
| CIL7 | −0.0167092 | −0.0119692 | −0.0635192 | −0.103029 | 0.07799454 |
| CIL9 | −0.0031435 | −0.0639955 | −0.0447691 | −0.1803047 | −0.0237571 |
| CIL10 | 0.01742637 | −0.0186466 | −0.0286273 | −0.086629 | 0.13845853 |
| CIL11 | 0.01479608 | −0.0342959 | −0.0190179 | −0.0964126 | 0.07910764 |
| CIL13 | 0.04671792 | −0.0432671 | −0.0628773 | −0.1040152 | 0.09941468 |
| CIL15 | −0.0028092 | 0.01241754 | −0.0399345 | −0.1488868 | 0.10209544 |
| CIL16 | 0.00396522 | 0.01875074 | −0.0593716 | −0.1721118 | 0.14140992 |
| CIL17 | −0.0157027 | −0.0398214 | −0.0205226 | −0.1380266 | 0.03130279 |
| CIL18 | 0.00141458 | 0.01840477 | −0.0870338 | −0.1394373 | 0.0660702 |
| CIL20 | −0.0012756 | −0.0066082 | 0.00017152 | −0.080748 | 0.01009418 |
| CIL22 | 0.05907837 | −0.0240194 | 0.00192474 | −0.0523839 | 0.00862815 |
| CIL23 | 0.01792035 | 0.0196907 | 0.00701969 | −0.0276208 | −0.0125905 |
| CIL25 | 0.06488994 | −0.035853 | −0.0154723 | −0.1041257 | 0.05182572 |
| CIL26 | 0.04191602 | −0.0024876 | −0.1441072 | −0.121522 | 0.00899186 |
| CIL27 | 0.04844866 | 0.03171132 | −0.0155971 | −0.0553673 | 0.0032882 |
| CIL28 | 0.06113466 | −0.0135206 | −0.1362427 | −0.1108463 | 0.01461547 |
| CIL33 | 0.04655447 | −0.0326933 | −0.0293756 | −0.1089134 | 0.00630687 |
| CIL34 | 0.05661395 | −0.0322385 | 0.01628473 | −0.1101646 | −0.0074755 |
| CIL36 | 0.05273856 | −0.0440921 | 0.00539978 | −0.1272189 | 0.00216899 |
| CIL40 | 0.06692048 | −0.0654416 | −0.0937176 | −0.150511 | 0.01176086 |
| CIL41 | 0.02642687 | −0.0934252 | 0.13123971 | 0.00933821 | −0.0167806 |
| CIL44 | 0.0592013 | 0.01649407 | −0.0255872 | −0.1006627 | −0.0552012 |
| CIL46 | 0.01619574 | −0.0291586 | −0.1014536 | −0.1471088 | −0.0437101 |
| CIL47 | 0.07043108 | 0.01587837 | −0.0447825 | −0.1469266 | −0.0096169 |
| CIL48 | 0.04683652 | 0.01672523 | −0.0696577 | −0.1546714 | −0.0382283 |
| CIL49 | 0.04767921 | −0.0187376 | −0.0143278 | −0.0829684 | −0.0224007 |
| CIL50 | 0.06517532 | −0.0077502 | 0.00665487 | −0.06029 | 0.00401667 |
| CIL51 | 0.00357883 | 0.02697499 | −0.0796469 | −0.0848758 | −0.0145762 |
| CIL52 | 0.03416515 | 0.07378954 | −0.0130181 | −0.0671898 | 0.00858206 |
| CIL55 | 0.05194555 | −0.0078999 | 0.0959274 | 0.0491901 | 0.0156815 |
| CIL56 | −0.0193853 | −0.1240014 | 0.1773734 | 0.01460369 | −0.0127039 |
| CIL58 | 0.05141171 | 0.02044398 | −0.0398906 | −0.1354996 | −0.020815 |
| CIL60 | 0.07051541 | 0.04832397 | −0.0006407 | −0.1303369 | −0.0405115 |
| CIL62 | 0.0294142 | −0.0114286 | −0.0073935 | −0.1437226 | 0.0024554 |
| CIL63 | 0.07925366 | −0.0032543 | 0.01783848 | −0.1088494 | 0.01854753 |
| CIL64 | 0.1978537 | 0.04801805 | −0.1468952 | −0.3128485 | −0.107814 |
| CIL66 | 0.02652209 | −0.0327722 | −0.0208457 | −0.154242 | −0.0578802 |
| CIL67 | 0.08909056 | 0.06498217 | −0.0355783 | −0.1041323 | −0.0237794 |
| CIL69 | −0.0053581 | −0.0042653 | 0.24891501 | 0.22271496 | −0.0345747 |
| CIL70 | −0.0043783 | −0.0291397 | 0.10618587 | −0.0354134 | −0.030043 |
| CIL71 | 0.0348115 | 0.00070178 | −0.0562239 | −0.0583947 | 0.01088871 |
| CIL72 | 0.0553314 | 0.02923746 | −0.0401283 | −0.1001862 | −0.0241548 |
| CIL74 | 0.01362072 | 0.02636443 | −0.0865918 | −0.0457196 | 0.01242029 |
| CIL75 | −0.0171453 | 0.01891564 | 0.31310244 | 0.28280708 | −0.0121888 |
| CIL76 | 0.04513457 | 0.04285579 | 0.00057803 | −0.0865509 | −0.027674 |
| CIL77 | 0.05491925 | 0.09589947 | −0.0087136 | −0.079983 | −0.0282833 |
| CIL79 | −0.0530223 | −0.0402145 | 0.39088563 | 0.36443077 | −0.0023848 |
| CIL80 | 0.05780885 | 0.08002129 | 0.00945222 | −0.0197054 | −0.0233656 |
| CIL87 | 0.11366272 | −0.0075862 | −0.0033579 | −0.0831667 | −0.0071337 |
| CIL88 | 0.08121765 | −0.0310215 | 0.00710891 | −0.0998787 | 0.02036709 |
| CIL89 | 0.05896078 | 0.03977145 | −0.0061467 | −0.1187912 | −0.0046673 |

| | HT.CHX | HT.Co2+ | HT.CspA | HT.DPQ | HT.EGTA |
|---|---|---|---|---|---|
| MS275 | −0.1188969 | −0.102694 | −0.1885541 | −0.0105775 | −0.0058107 |
| Scriptaid | −0.1048316 | −0.193896 | −0.1413332 | −0.00813 | −0.0176747 |
| TrichostatinA | −0.096958 | −0.0277054 | −0.1436955 | −0.0015533 | −0.0171128 |
| Echinomycin | 0.14361174 | 0.1491729 | −0.084261 | 0.00691846 | 0.00691633 |
| Colchicine | 0.04333171 | 0.10984848 | −0.1208652 | 0.01511414 | −0.000119 |
| NPC25 | 0.1519485 | 0.13013485 | −0.0243371 | 0.01957461 | 0.03077107 |
| NPC4 | 0.12317457 | 0.06041622 | −0.0446754 | −0.0070462 | 0.00516068 |
| NPC7 | 0.13739696 | 0.01909726 | −0.0268684 | 0.01267774 | 0.03356135 |

TABLE 9-continued

Modulatory profiles of characterized and uncharacterized lethal compounds.

| | | | | | |
|---|---|---|---|---|---|
| Podophyllotoxin | 0.07196985 | 0.11023663 | −0.0759222 | 0.00596443 | 0.01145102 |
| Rotenone | 0.07793169 | 0.20027 | −0.1721788 | −0.0054033 | 0.00225841 |
| Vinblastine | 0.06308695 | 0.22685265 | −0.1334704 | 0.00368754 | 0.0105502 |
| Vincristine | 0.08269379 | 0.21695164 | −0.1876483 | 0.01267252 | 0.00923087 |
| DPI3 | 0.03770847 | 0.23127886 | −0.0304777 | 0.04997748 | 0.04922409 |
| DPI4 | −0.0086992 | 0.17414425 | 5.8801E−05 | 0.05528113 | 0.0361033 |
| DPI6 | 0.07054851 | 0.16240191 | −0.0172826 | 0.06163326 | 0.04864836 |
| RSL3 | −0.0509933 | −0.1947562 | −0.1267995 | 0.16532291 | 0.03695606 |
| Bortezomib | 0.02630913 | 0.06444914 | −0.2224122 | 0.01078526 | −0.006629 |
| MG132 | 0.04853848 | −0.0570457 | −0.3220782 | −0.0240645 | 0.00777542 |
| MG262 | −0.0039772 | −0.0442528 | −0.2144673 | 0.00810399 | −0.0011524 |
| Erastin | 0.05504404 | −0.2142077 | 0.02448894 | 0.05672269 | 0.01444339 |
| Camptothecin | 0.05619607 | 0.14156517 | −0.1551597 | 0.00814331 | 0.01652399 |
| Irinotecan | 0.0667595 | 0.02045732 | −0.1317706 | 0.00907953 | 0.01365217 |
| Daunorubicin | 0.05854213 | 0.16142753 | −0.079195 | 0.0088822 | 0.03262034 |
| Doxorubicin | 0.08993251 | 0.26270189 | −0.1098208 | 0.01106636 | 0.03492068 |
| Etoposide | 0.11300892 | 0.39257154 | −0.1769875 | 0.00642178 | 0.02456941 |
| Mitoxantrone | 0.04002351 | 0.38167687 | −0.112673 | 0.00650421 | 0.01801996 |
| Cycloheximide | 0.14620902 | 0.09947986 | 0.04639214 | 0.01424647 | 0.0138591 |
| Dinitrophenol | 0.20975707 | 0.0433563 | −0.1730059 | 0.0815659 | −0.0959985 |
| NaN3 | 0.04722344 | 0.03940525 | −0.0477731 | −0.0079698 | −0.002548 |
| Vatinomycin | 0.10235561 | −0.0618283 | −0.0378938 | 0.17016661 | −0.0448288 |
| CIL1 | 0.09163445 | 0.20478977 | −0.0454163 | 0.04202848 | −0.0066024 |
| CIL2 | 0.1414035 | −0.1320389 | 0.01223619 | −0.0031255 | −0.0056273 |
| CIL4 | 0.10959238 | −0.1439922 | −0.0469582 | 0.00735917 | 0.01533189 |
| CIL5 | 0.0972613 | 0.08697891 | −0.0215948 | 0.00964073 | −0.0092153 |
| CIL6 | 0.16102241 | 0.04207798 | −0.0127452 | 0.04323431 | 0.01026344 |
| CIL7 | 0.05109611 | 0.10624303 | −0.0644051 | 0.00525397 | 0.00645645 |
| CIL9 | 0.07226888 | 0.0175425 | −0.0307928 | −0.0033167 | −0.0068483 |
| CIL10 | 0.05131796 | 0.12255069 | 0.00487182 | 0.0043051 | −0.0077762 |
| CIL11 | 0.00705209 | 0.05357729 | −0.0054982 | 0.00390362 | 0.0040021 |
| CIL13 | 0.03998706 | 0.29237304 | 0.06242739 | −0.0151495 | 0.08353385 |
| CIL15 | 0.06342084 | 0.13972534 | −0.0070316 | −0.0239385 | −0.0006158 |
| CIL16 | 0.08542601 | 0.1550268 | 0.00838857 | −0.022048 | −0.0002723 |
| CIL17 | 0.06579474 | −0.0084365 | −0.0335367 | −0.0230258 | 0.0018567 |
| CIL18 | 0.11789261 | 0.15978519 | −0.0482687 | −0.0127573 | −0.0094606 |
| CIL20 | 0.12124292 | 0.12049185 | −0.0564837 | −0.0377921 | −0.018046 |
| CIL22 | 0.01937859 | −0.0347775 | −0.0361099 | −0.0093401 | −0.0125444 |
| CIL23 | 0.08773004 | 0.0331646 | −0.0232587 | 0.01052194 | −0.0132254 |
| CIL25 | −0.0160441 | −0.0612815 | 0.01072928 | 0.02628733 | 0.01623521 |
| CIL26 | −0.0205236 | −0.0274445 | −0.0422466 | 0.0298704 | 0.00999786 |
| CIL27 | 0.04575936 | 0.046063 | −0.0363878 | 0.02306718 | 0.02603826 |
| CIL28 | 0.03280038 | −0.0329175 | −0.0185839 | 0.04403759 | 0.00586771 |
| CIL33 | 0.06763145 | 0.14175785 | −0.0321298 | 0.02727875 | −0.0074608 |
| CIL34 | 0.04610462 | 0.09925752 | −0.0218141 | 0.03329763 | −0.0020351 |
| CIL36 | −0.0664531 | 0.02820654 | 0.01593074 | 0.05193466 | −0.0131102 |
| CIL40 | −0.0286309 | 0.04910502 | −0.0469721 | 0.04908281 | −0.0264168 |
| CIL41 | −0.0545941 | 0.06388608 | 9.4409E−05 | 0.0428151 | 0.0294626 |
| CIL44 | 0.02873779 | −0.0465752 | −0.0158637 | −0.0166894 | −0.0072668 |
| CIL46 | −0.0190914 | −0.1082153 | 0.00033561 | −0.0016923 | −0.0169929 |
| CIL47 | 0.00787398 | −0.2380995 | 0.01760547 | −0.0203835 | 0.00105146 |
| CIL48 | 0.01479799 | 0.03070109 | 0.00268882 | −0.0003728 | 0.01715062 |
| CIL49 | −0.0094838 | 0.00880832 | 0.04470562 | −0.0241787 | 0.02251689 |
| CIL50 | −0.0482491 | −0.0868821 | −0.0127092 | −0.0158756 | −0.0224416 |
| CIL51 | 0.08663358 | 0.0390822 | 0.00675035 | 0.01090346 | 0.04897337 |
| CIL52 | 0.14735761 | 0.41547366 | 0.05641151 | −0.0133024 | 0.09077934 |
| CIL55 | −0.0103853 | 0.11519832 | −0.0078827 | 0.0140465 | 0.04876502 |
| CIL56 | −0.0723393 | 0.01295837 | 0.01564299 | 0.0624478 | 0.023781 |
| CIL58 | −0.0567432 | 0.09509314 | 0.06761309 | −0.0059223 | 0.05183692 |
| CIL60 | 0.11203194 | −0.0800334 | −0.0048312 | 0.02072829 | 0.05295873 |
| CIL62 | 0.08707299 | 0.03422233 | −0.0013468 | 0.01016954 | 0.04610858 |
| CIL63 | 0.07744277 | 0.02639089 | 0.00306287 | −0.0217193 | 0.06222147 |
| CIL64 | 0.06684839 | 0.41607903 | 0.08661477 | −0.1350243 | 0.18424717 |
| CIL66 | 0.08144049 | −0.0603373 | −0.0546913 | −0.0110529 | 0.03093079 |
| CIL67 | 0.14582237 | 0.03257119 | 0.01638443 | −0.0109218 | 0.12341795 |
| CIL69 | 0.03395238 | 0.07131741 | 0.00984813 | −0.0065882 | 0.06031548 |
| CIL70 | −0.0263072 | 0.019784 | −0.0467956 | 0.0269571 | 0.01851476 |
| CIL71 | 0.07610494 | 0.02342185 | −0.032331 | −0.0035051 | −0.0229848 |
| CIL72 | 0.11473513 | 0.11632921 | −0.0191176 | −0.0315719 | 0.00960798 |
| CIL74 | 0.02524432 | 0.03243519 | −0.0046218 | 0.04846659 | −0.0267434 |
| CIL75 | 0.04020367 | 0.12168756 | −0.0096738 | 0.01971005 | −0.0070184 |
| CIL76 | 0.15052401 | 0.15314755 | −0.0059982 | 0.01553764 | −0.0215115 |
| CIL77 | 0.1436028 | 0.12610682 | −0.0579089 | 0.0034956 | −0.0034501 |
| CIL79 | 0.02793995 | 0.29484557 | −0.0338926 | 0.04763562 | 0.02262115 |
| CIL80 | 0.09740519 | 0.11202522 | 0.01161471 | −0.0171717 | 0.01990089 |
| CIL87 | 0.06730386 | 0.03163242 | −0.0535776 | −0.0256244 | 0.00530494 |
| CIL88 | 0.04477773 | 0.01651643 | −0.0584225 | −0.0143108 | 0.01878024 |
| CIL89 | −0.0086929 | 0.00837676 | −0.0690578 | −0.0052866 | 0.04226482 |

TABLE 9-continued

Modulatory profiles of characterized and uncharacterized lethal compounds.

| | HT.Gd3+ | HT.LNAME | HT.Lmim | HT.NAD+ | HT.NMMA |
|---|---|---|---|---|---|
| MS275 | −0.0102689 | 0.00420427 | −0.0972784 | 0.00087937 | −0.0033302 |
| Scriptaid | −0.0217556 | −0.0026369 | −0.0558337 | 0.01064252 | 0.00886933 |
| TrichostatinA | −0.0033979 | 0.0035016 | −0.0502135 | 0.03432383 | 0.00433465 |
| Echinomycin | 0.01526225 | 0.01177721 | 0.06784009 | 0.17795514 | −0.0009733 |
| Colchicine | 0.01351349 | 0.00823575 | 0.11991903 | 0.1471024 | 0.00858507 |
| NPC25 | 0.00874193 | 0.01017305 | 0.22821299 | 0.16858337 | 0.01131088 |
| NPC4 | 0.01314254 | 0.00258833 | 0.20365836 | 0.11357064 | 0.01570669 |
| NPC7 | 0.02479755 | 0.00219407 | 0.12362177 | 0.09896023 | −0.0072181 |
| Podophyllotoxin | 0.00915994 | −0.0049258 | 0.10975693 | 0.13182264 | 0.00047202 |
| Rotenone | 0.01050591 | −0.0073773 | 0.14131642 | 0.15629326 | 0.00783177 |
| Vinblastine | −0.0025566 | −0.0123136 | 0.12599319 | 0.16821378 | −0.0035162 |
| Vincristine | −0.0009641 | 0.00177863 | 0.11545731 | 0.1698731 | 0.00483074 |
| DPI3 | −0.009591 | −0.0039604 | 0.39279429 | 0.00238937 | −0.0015082 |
| DPI4 | −0.0212108 | 0.01547048 | 0.30856618 | 0.02440851 | −0.0007723 |
| DPI6 | −0.0227614 | −0.0043042 | 0.38620976 | 0.00907448 | −0.0110443 |
| RSL3 | −0.012653 | −0.0108087 | 0.33020083 | 0.00788309 | −0.0055098 |
| Bortezomib | −0.028227 | 0.00992421 | 0.01347348 | 0.13902598 | 0.01353813 |
| MG132 | −0.0110019 | 5.1006E−05 | 0.00133838 | 0.03798455 | 0.01063618 |
| MG262 | −0.0031676 | 0.00700243 | 0.00145721 | 0.07678843 | −0.0042292 |
| Erastin | −0.0132633 | −0.0087309 | 0.21777043 | −0.0299568 | 0.00682629 |
| Camptothecin | 0.02887279 | 0.01135258 | 0.07220067 | 0.060785 | 0.01978231 |
| Irinotecan | 0.01373612 | 0.01215253 | 0.05380647 | 0.03220192 | 0.00973208 |
| Daunorubicin | 0.01529138 | −0.0098523 | 0.06111651 | 0.13051521 | 0.01829966 |
| Doxorubicin | 0.03740828 | 0.00668466 | 0.08822325 | 0.18719506 | 0.02832305 |
| Etoposide | 0.02667925 | 0.00544411 | 0.05001251 | 0.05270336 | 0.01602895 |
| Mitoxantrone | 0.03226623 | 0.01297692 | 0.05677663 | 0.1502147 | 0.02360459 |
| Cycloheximide | 0.00299079 | 0.02188041 | 0.10894658 | 0.07007128 | 0.0198614 |
| Dinitrophenol | −0.0282895 | −0.0088594 | 0.02524142 | 0.11635416 | 0.01660839 |
| NaN3 | −0.0046043 | −0.0135112 | −0.0761287 | 0.06682519 | 0.00282199 |
| Vatinomycin | −0.0045237 | −0.0384324 | 0.1162672 | 0.07832788 | −0.002681 |
| CIL1 | −0.0321493 | 0.03977103 | 0.08631064 | 0.07889481 | −0.0481967 |
| CIL2 | −0.0230384 | 0.02625109 | −0.0301281 | 0.04925344 | −0.0302901 |
| CIL4 | −0.0099527 | 0.01005304 | −0.0192819 | −0.0138124 | −0.007501 |
| CIL5 | −0.0256984 | 0.0226272 | 0.00357399 | 0.03421081 | −0.003405 |
| CIL6 | −0.0289684 | 0.01570488 | −0.0106374 | 0.04899418 | −0.0229193 |
| CIL7 | −0.029815 | 0.01998017 | −0.0026743 | 0.07707444 | −0.024423 |
| CIL9 | −0.0435849 | 0.02123914 | −0.0546891 | 0.02617067 | −0.0373288 |
| CIL10 | −0.0278814 | 0.02616127 | −0.020647 | 0.0408689 | −0.009286 |
| CIL11 | −0.0298047 | 0.02953801 | −0.0340013 | 0.02581914 | −0.0255366 |
| CIL13 | −0.030717 | −0.0796178 | −0.061016 | −0.0446201 | −0.0411831 |
| CIL15 | −0.0388128 | 0.00130904 | −0.0483689 | 0.01762367 | −0.0194345 |
| CIL16 | −0.0407027 | 0.01973692 | −0.0554627 | 0.05126088 | −0.0315355 |
| CIL17 | −0.0431802 | 0.02242474 | −0.0132 | 0.04423236 | −0.0263893 |
| CIL18 | −0.0330227 | 0.0132922 | −0.0049868 | 0.09492877 | −0.0291809 |
| CIL20 | −0.02607 | 0.01702871 | 0.00291412 | 0.05984741 | −0.0208969 |
| CIL22 | −0.0045341 | 0.04607751 | 0.01658507 | 0.01013702 | 0.01444063 |
| CIL23 | −0.000221 | 0.00562841 | 0.01608214 | −0.0002222 | −0.0010838 |
| CIL25 | 0.01712542 | 0.02662905 | 0.01684027 | −0.0305125 | −0.0066394 |
| CIL26 | −0.0053343 | 0.00121517 | −0.0040003 | −0.0140608 | −0.0096924 |
| CIL27 | −0.016795 | 0.00120376 | −0.0010549 | −0.0033996 | −0.0133115 |
| CIL28 | −0.0258257 | −0.0045004 | 0.00131087 | 0.0070887 | −0.0097629 |
| CIL33 | −0.0218244 | 0.00304734 | −0.0070678 | −0.018901 | −0.0022478 |
| CIL34 | −0.0228317 | −0.0051696 | −0.002139 | −0.0055345 | −0.0030313 |
| CIL36 | −0.042672 | −0.0279853 | 0.00421383 | −0.0637848 | −0.0095011 |
| CIL40 | −0.0185952 | −0.0199914 | 0.00048251 | −0.0474936 | −0.0069008 |
| CIL41 | −0.0259176 | −0.0121037 | 0.13770074 | −0.0086566 | −0.0102875 |
| CIL44 | −0.0114691 | −0.0250548 | −0.0076141 | −0.0714428 | −0.0419036 |
| CIL46 | −0.0086171 | −0.0280471 | −0.0316559 | −0.0675446 | 0.0015569 |
| CIL47 | −0.0226292 | −0.0128778 | −0.0417274 | −0.0278389 | −0.0119475 |
| CIL48 | −0.003556 | −0.0408723 | −0.0175732 | −0.0546542 | −0.0190249 |
| CIL49 | 0.00090697 | 0.01289374 | −0.0368471 | −0.0141297 | 0.00042903 |
| CIL50 | −0.0387716 | 0.01805957 | −0.0053598 | 0.00979941 | 0.00419608 |
| CIL51 | 0.00328775 | 0.0109103 | 0.01293031 | 0.0439374 | 0.01561505 |
| CIL52 | −0.006922 | −0.0094118 | 0.02653731 | 0.01944592 | −0.011955 |
| CIL55 | −0.0147883 | 0.00717105 | 0.07004625 | 0.03996362 | 0.00476077 |
| CIL56 | −0.0154241 | 0.05374763 | 0.10168238 | 0.0231475 | −0.0147499 |
| CIL58 | −0.0046743 | −0.0998179 | −0.0725714 | −0.0653865 | −0.0908298 |
| CIL60 | −0.016299 | 0.00439718 | 0.0346384 | 0.01525644 | −0.0109061 |
| CIL62 | −0.0257331 | −0.0035685 | 0.00805599 | −0.016889 | −0.0175391 |
| CIL63 | −0.0316366 | 0.04201046 | 0.03961757 | 0.03315753 | −0.0022977 |
| CIL64 | −0.0263028 | <0.2159453 | −0.2704681 | −0.1970983 | −0.1741564 |
| CIL66 | −0.0175703 | 0.00403506 | 0.01651998 | −0.0110611 | −0.014205 |
| CIL67 | −0.0194487 | −0.0075145 | 0.01911998 | −0.0179485 | −0.0134891 |
| CIL69 | −0.0144554 | −0.045383 | 0.17920333 | 0.03637312 | −0.0404809 |
| CIL70 | −0.0135663 | 0.00599279 | 0.21979664 | 0.04321272 | −0.0058179 |

TABLE 9-continued

Modulatory profiles of characterized and uncharacterized lethal compounds.

| | | | | | |
|---|---|---|---|---|---|
| CIL71 | −0.0155194 | 0.02366266 | −0.0026093 | 0.01545888 | −0.0007859 |
| CIL72 | −9.532E−05 | 0.01225977 | −0.0018208 | 0.00419487 | −0.0044427 |
| CIL74 | −0.008213 | 0.0192517 | 0.02034016 | 0.07663993 | 9.3282E−05 |
| CIL75 | −0.022849 | −0.0173727 | 0.24992353 | −0.0025939 | −0.0279395 |
| CIL76 | −0.0292987 | 0.02220486 | 0.00796408 | 0.00780997 | −0.0079421 |
| CIL77 | −0.0367999 | 0.01693235 | 0.02572953 | 0.00335673 | −0.0150852 |
| CIL79 | −0.0257937 | 0.01224348 | 0.40517143 | −0.0042922 | 0.00319361 |
| CIL80 | −0.0322647 | 0.01972379 | 0.05448637 | 0.01251178 | −0.0125563 |
| CIL87 | −0.0275554 | 0.00525664 | −0.0021155 | −0.0019259 | −0.012374 |
| CIL88 | −0.036514 | 0.02198995 | 0.01907149 | 0.00747768 | −0.000615 |
| CIL89 | −0.0459432 | 0.00306109 | 0.02342444 | 0.02661864 | −0.0090411 |

| | HT.Nec-1 | HT.Pepstatin | HT.SP600125 | HT.TLCK | HT.U0126 |
|---|---|---|---|---|---|
| MS275 | −0.0555719 | −0.0165421 | −0.0990255 | −0.0240373 | −0.0188407 |
| Scriptaid | −0.0561729 | −0.0129585 | −0.0700007 | −0.0557541 | −0.0422842 |
| TrichostatinA | −0.0728913 | −0.0039853 | −0.0686523 | −0.0259878 | −0.0646838 |
| Echinomycin | 0.02092974 | 0.00686125 | 0.08228039 | 0.0064356 | 0.01676216 |
| Colchicine | 0.01660958 | 0.00441257 | −0.0285789 | 0.03060033 | 0.22370553 |
| NPC25 | 0.03331695 | 0.00907117 | 0.04752536 | 0.01191743 | 0.14555698 |
| NPC4 | 0.0515934 | −0.0097394 | 0.0594831 | −0.0170816 | 0.10968643 |
| NPC7 | 0.02936184 | 0.0140623 | 0.05675053 | −0.0171298 | 0.03515321 |
| Podophyllotoxin | −0.0001825 | −0.0005129 | −0.0276787 | 0.06977949 | 0.13541903 |
| Rotenone | 0.00392091 | −0.0225529 | −0.019636 | 0.0438025 | 0.13841211 |
| Vinbiastine | −0.0058737 | −0.0004474 | 0.0028618 | 0.00236221 | 0.13717582 |
| Vincristine | 0.02187585 | 0.00026198 | 0.00089979 | −0.0063942 | 0.19262685 |
| DPI3 | 0.06021328 | 0.02311469 | −0.058705 | 0.30781927 | 0.43976324 |
| DPI4 | 0.05134598 | −0.003295 | −0.0428398 | 0.17609432 | 0.34227684 |
| DPI6 | 0.05782935 | 0.0120804 | −0.0586102 | 0.2543766 | 0.38311656 |
| RSL3 | 0.07095265 | −0.0132658 | −0.1318706 | 0.31517178 | 0.39718399 |
| Bortezomib | −0.0618561 | −8.033E−05 | −0.0302754 | 0.0719481 | −0.0318738 |
| MG132 | −0.0972845 | −0.0273265 | −0.0343148 | 0.01546369 | −0.0709958 |
| MG262 | −0.0681715 | −0.0060693 | −0.0359956 | 0.03565513 | −0.0666432 |
| Erastin | −0.0255149 | −0.0257345 | −0.0368797 | 0.11665403 | 0.15248389 |
| Camptothecin | 0.01101588 | 0.00591775 | 0.02319051 | 0.0438257 | 0.00027174 |
| Irinotecan | 0.0216686 | 0.0147477 | 0.00621888 | 0.02566275 | 0.00698441 |
| Daunorubicin | 0.02173842 | 0.0056488 | −0.0113019 | 0.06428773 | −0.0158987 |
| Doxorubicin | 0.00757748 | 0.00895778 | −0.0214841 | 0.06329923 | −0.0203643 |
| Etoposide | −0.0059495 | −0.001737 | 0.00478042 | 0.1489187 | −0.0262697 |
| Mitoxantrone | 0.01072807 | 0.0206681 | −0.0157506 | 0.06003033 | −0.0320525 |
| Cycloheximide | 0.03735921 | 0.0061635 | −0.0033266 | 0.01836327 | 0.03847567 |
| Dinitrophenol | 0.03763391 | 0.01716386 | −0.1203227 | 0.03576826 | −0.0215633 |
| NaN3 | −0.0296822 | −0.0043368 | −0.0040791 | 0.02260372 | 0.02567325 |
| Vatinomycin | 0.08393792 | 0.01970083 | −0.1610157 | 0.02961013 | 0.00548191 |
| CIL1 | 0.02294445 | 0.00147358 | −0.0491857 | 0.04647174 | 0.14912375 |
| CIL2 | −0.0127254 | 0.00881644 | −0.0036839 | 0.02036906 | 0.02089377 |
| CIL4 | 0.00249863 | 0.00928023 | −0.006297 | 0.01720083 | 0.00056242 |
| CIL5 | 0.00335096 | 0.01964795 | −0.0214887 | −0.0040572 | −0.0294352 |
| CIL6 | 0.01299035 | 0.01879984 | −0.0119461 | −0.0054596 | 0.0484597 |
| CIL7 | 0.00713771 | −0.00124 | −0.0415509 | −0.0111335 | 0.0155565 |
| CIL9 | 0.02132694 | −0.0021878 | 0.01016425 | 0.00551409 | 0.03914784 |
| CIL10 | 0.03697698 | −0.0108718 | −0.0092266 | −0.0016305 | 0.01126286 |
| CIL11 | 0.01983171 | −0.0030957 | −0.028758 | 0.01902218 | 0.06089128 |
| CIL13 | 0.04319318 | −0.0304073 | −0.0797293 | 0.01350303 | 0.0592947 |
| CIL15 | 0.02067279 | −0.0224727 | −0.0239724 | −0.0173117 | 0.08141342 |
| CIL16 | 0.00654015 | −0.0234635 | −0.0219493 | −0.0286311 | 0.05201472 |
| CIL17 | 0.03321398 | −0.0210351 | −0.0131421 | −0.0026391 | 0.04847215 |
| CIL18 | 0.01177279 | −0.032163 | −0.0346469 | −0.030163 | 0.01191696 |
| CIL20 | −0.0008504 | 0.00016309 | −0.025792 | −0.0033667 | 0.02994872 |
| CIL22 | −0.0022834 | 0.00057166 | −0.0017349 | 0.02243652 | 0.06274399 |
| CIL23 | −0.0091711 | −0.0054941 | 0.00961612 | 0.01135686 | 0.02324317 |
| CIL25 | −0.0148096 | 0.0109388 | 0.02383204 | 0.02361905 | −0.0319668 |
| CIL26 | −0.0120433 | 0.00129487 | −0.0105174 | −0.006743 | −0.0264817 |
| CIL27 | −0.0027517 | 0.01174891 | 0.0163087 | −0.006607 | 0.02757687 |
| CIL28 | −0.0302207 | 0.00126773 | 0.01064584 | 0.00513542 | −0.0399002 |
| CIL33 | −0.0021233 | 0.0082125 | 0.00235928 | 0.01726866 | 0.01835922 |
| CIL34 | 0.00686593 | 0.00474178 | −0.0184715 | 0.01693744 | 0.04868298 |
| CIL36 | −0.011675 | 0.00332247 | −0.0200721 | 0.0152678 | 0.05534488 |
| CIL40 | −0.0051299 | −0.00194 | −0.0132347 | 0.00416077 | −0.0001902 |
| CIL41 | 0.03738938 | 0.0042815 | −0.0717017 | 0.02281886 | 0.12025054 |
| CIL44 | −0.0057439 | −0.0039999 | −0.0210979 | 0.02136815 | 0.02689059 |
| CIL46 | −0.0019823 | 0.00167494 | −0.0076843 | 0.01132234 | −0.0067813 |
| CIL47 | −0.0087651 | 0.00218279 | −0.0100931 | 0.04658627 | 0.02649361 |
| CIL48 | 0.00165808 | −0.0099776 | −0.0024138 | 7.0978E−05 | 0.02169423 |
| CIL49 | 0.00344753 | −0.0033156 | 0.02246486 | 0.00922985 | 0.0342359 |
| CIL50 | 0.00128911 | −0.0014853 | −0.0064271 | −0.0179113 | 0.01111688 |
| CIL51 | 0.00509238 | 0.01542012 | −0.0031793 | 0.01271012 | 0.00143333 |
| CIL52 | 0.02401098 | 0.007127 | −0.0081211 | 0.02434163 | −0.0228692 |

TABLE 9-continued

Modulatory profiles of characterized and uncharacterized lethal compounds.

| | | | | | |
|---|---|---|---|---|---|
| CIL55 | 0.04440885 | 0.00539614 | −0.0374682 | 0.01360865 | 0.11427443 |
| CIL56 | 0.0959978 | 0.0126835 | −0.0879927 | 0.13656299 | 0.20114056 |
| CIL58 | 0.00775971 | −0.0126765 | −0.0598748 | −0.0460517 | −0.0318612 |
| CIL60 | −0.0006376 | 0.01083176 | 0.00027971 | −0.0200117 | 0.01614973 |
| CIL62 | 0.10375755 | −0.008295 | −0.011172 | −0.0300719 | −0.0151454 |
| CIL63 | 0.0101043 | 0.01385659 | −0.0072659 | −0.0038932 | 0.03264314 |
| CIL64 | 0.08111458 | −0.0268927 | −0.2293971 | −0.0559641 | −0.0191125 |
| CIL66 | 0.02128777 | 0.00624294 | 0.03361222 | 0.0051314 | 0.01890169 |
| CIL67 | 0.02262162 | 0.01839263 | −0.0186259 | 0.00417225 | 0.00260433 |
| CIL69 | 0.06650416 | 0.01186413 | −0.0908984 | 0.19370261 | 0.32267551 |
| CIL70 | 0.03638609 | 0.01868934 | −0.0889235 | −0.0310472 | 0.09641879 |
| CIL71 | 0.00574381 | −0.0008016 | −0.020035 | −0.0018413 | 0.00294299 |
| CIL72 | 0.0135119 | −0.0136805 | −0.0144137 | 0.02906901 | 0.04439213 |
| CIL74 | 0.00310431 | 0.00621638 | 0.00195294 | 0.00303427 | 0.00203069 |
| CIL75 | 0.07488577 | 0.01122834 | −0.0700855 | 0.26036826 | 0.35244208 |
| CIL76 | 0.01775768 | 0.00123696 | 0.00722099 | 0.01034265 | 0.07720638 |
| CIL77 | 0.00338189 | 0.00162175 | −0.0188939 | 0.00547294 | 0.00650936 |
| CIL79 | 0.07472586 | 0.01455371 | −0.0471988 | 0.3457588 | 0.4407363 |
| CIL80 | 0.00204116 | −0.0123765 | 0.0200436 | 0.0260488 | −0.0104464 |
| CIL87 | −0.0074561 | −0.0048804 | −0.0099304 | −0.0010104 | 0.00227418 |
| CIL88 | 0.00351822 | 0.0070051 | −0.0211583 | 0.00992871 | 0.00960663 |
| CIL89 | 0.00283255 | 0.01266621 | −2.169E−05 | 0.00753856 | 0.01092111 |

| | HT.atoc | HT.bCarotene | HT.deferox | HT.digoxin | HT.trolox |
|---|---|---|---|---|---|
| MS275 | −0.0101635 | −0.030054 | −0.1652583 | −0.1792504 | −0.0259902 |
| Scriptaid | −0.0093307 | −0.0187192 | −0.1469224 | −0.0879295 | −0.0298598 |
| TrichostatinA | −0.0050621 | −0.0347195 | −0.1597123 | −0.1260736 | −0.0338165 |
| Echinomycin | 0.14638974 | −0.0049676 | 0.1664907 | 0.09969184 | −0.0242328 |
| Colchicine | −0.0173042 | 0.01722509 | 0.29837397 | 0.13591788 | 0.01590927 |
| NPC25 | 0.02932732 | −0.0021003 | 0.36869446 | 0.11404384 | 0.00377491 |
| NPC4 | −0.0046734 | −0.0040981 | 0.30213611 | 0.1271105 | −0.0147566 |
| NPC7 | 0.09995549 | −0.0175912 | 0.22103456 | 0.09504661 | 0.00125913 |
| Podophyllotoxin | −0.0202323 | 0.0009225 | 0.31039865 | 0.10979609 | 0.01030472 |
| Rotenone | 0.04769067 | 0.00359379 | 0.34697219 | 0.16171241 | 0.00389493 |
| Vinbiastine | 0.15731554 | 0.00194469 | 0.28465035 | 0.1244578 | −0.0019595 |
| Vincristine | 0.01852742 | 0.01182267 | 0.32174322 | 0.14200631 | −0.0159878 |
| DPI3 | 0.48830882 | −0.0093433 | 0.50494601 | −0.0771195 | 0.43071723 |
| DPI4 | 0.35227875 | −0.0126362 | 0.40953431 | −0.0634303 | 0.31508429 |
| DPI6 | 0.43573174 | −0.0104991 | 0.41669672 | −0.0498795 | 0.36282227 |
| RSL3 | 0.44706907 | −0.0134625 | 0.35079526 | −0.1463351 | 0.42129597 |
| Bortezomib | 0.00702342 | −0.0191437 | −0.0167225 | 0.07916355 | −0.0041833 |
| MG132 | 0.04884257 | 7.0861E−05 | −0.1161718 | 0.08352183 | −0.0161622 |
| MG262 | 0.05222066 | −0.0092548 | −0.0846482 | 0.05596798 | −0.0206824 |
| Erastin | 0.26429415 | −0.0214976 | 0.3025221 | −0.0339298 | 0.20770296 |
| Camptothecin | 0.00400806 | 0.00283709 | 0.12877867 | 0.14416065 | 0.01719276 |
| Irinotecan | 0.01845108 | 0.00045945 | 0.09054955 | 0.08432789 | 0.01452359 |
| Daunorubicin | 0.00989487 | 0.00826483 | 0.15149319 | 0.13983003 | −0.002722 |
| Doxorubicin | 0.00992997 | 0.01512156 | 0.20435466 | 0.19812467 | −0.0141349 |
| Etoposide | −0.0062763 | 0.00392981 | 0.14284045 | 0.13112076 | 0.01328409 |
| Mitoxantrone | 0.04839288 | −0.0039153 | 0.10012715 | 0.13212973 | −0.0138833 |
| Cycloheximide | 0.0166659 | 0.00875763 | 0.20413327 | 0.045701 | 0.02126525 |
| Dinitrophenol | 0.09943976 | −0.0099967 | 0.11141446 | −0.0713337 | 0.03606919 |
| NaN3 | −0.0310041 | 0.00681043 | 0.07881732 | 0.0194835 | −0.0013756 |
| Vatinomycin | 0.22919637 | −0.015257 | 0.00414526 | −0.1615377 | 0.04462648 |
| CIL1 | 0.21597804 | −0.0284574 | 0.0835898 | −0.0038093 | 0.02477115 |
| CIL2 | 0.0475732 | −0.0268688 | 0.02962643 | −0.0122222 | −0.0309394 |
| CIL4 | 0.02362326 | 0.00102644 | −3.785E−05 | −0.0238929 | −0.0201009 |
| CIL5 | 0.03602558 | −0.0140327 | −0.0102471 | 0.00553377 | 0.0124658 |
| CIL6 | 0.12044039 | −0.0173022 | 0.02051429 | 0.00960657 | −0.0169697 |
| CIL7 | 0.02896411 | −0.0174047 | −0.0507117 | 0.00386935 | −0.0063211 |
| CIL9 | 0.05157132 | −0.0065015 | 0.05678115 | −0.0198389 | −0.0359906 |
| CIL10 | 0.10336708 | −0.0120139 | −0.0043187 | 0.01443156 | −0.006674 |
| CIL11 | 0.07926238 | −0.0182738 | 0.02780207 | −0.0137624 | −0.0211487 |
| CIL13 | 0.10290408 | 0.0100602 | 0.05411474 | 0.03512182 | −0.0397506 |
| CIL15 | 0.12236417 | −0.0039057 | 0.04236842 | −0.0123817 | −0.0295595 |
| CIL16 | 0.10252396 | −0.0132248 | 0.05919129 | −0.0188439 | −0.015239 |
| CIL17 | 0.1450374 | −0.005211 | 0.02893647 | −0.0031893 | 0.00459499 |
| CIL18 | 0.12951576 | −0.0001406 | −0.0099506 | −0.0041984 | −0.0120546 |
| CIL20 | 0.02920257 | 0.00861751 | 0.03912145 | 0.01850849 | 0.03002217 |
| CIL22 | 0.04912063 | −0.0117414 | 0.06506518 | 0.05675427 | −0.0049209 |
| CIL23 | 0.03662668 | −0.0011222 | 0.15124603 | 0.03673254 | 0.0044018 |
| CIL25 | 0.04405336 | 0.00908228 | 0.07762606 | −0.0071491 | −0.025622 |
| CIL26 | 0.04649457 | −0.0334855 | −0.1033088 | −0.0364118 | −0.0326987 |
| CIL27 | 0.04361958 | −0.0116561 | 0.14407851 | 0.0012616 | −0.0594296 |
| CIL28 | 0.10678443 | −0.0334142 | −0.0431247 | −0.0071044 | −0.0302473 |
| CIL33 | 0.04094235 | −0.0165102 | 0.10561421 | −0.034127 | −0.0507868 |
| CIL34 | 0.08124871 | 0.00132076 | 0.11145397 | −0.0103167 | −0.0299319 |

TABLE 9-continued

Modulatory profiles of characterized and uncharacterized lethal compounds.

| | | | | | |
|---|---|---|---|---|---|
| CIL36 | 0.08941918 | −0.0052761 | 0.06451547 | −0.0355653 | 0.00242516 |
| CIL40 | 0.12315101 | −0.0178454 | −0.0811097 | −0.0353912 | −0.0276823 |
| CIL41 | 0.31598831 | −0.0218245 | 0.17951591 | −0.0925466 | 0.16096292 |
| CIL44 | 0.04386167 | −0.0201165 | 0.10411951 | 0.01991823 | −0.0210643 |
| CIL46 | 0.04736192 | −0.01026 | 0.03466786 | −0.0467148 | −0.0144967 |
| CIL47 | 0.04666403 | −0.0018324 | 0.01073579 | 0.03488622 | −0.0382838 |
| CIL48 | 0.09021444 | −0.0084499 | 0.12681006 | −0.015135 | −0.0261174 |
| CIL49 | 0.02137465 | −0.0260633 | 0.07453051 | 0.00164748 | −0.0152272 |
| CIL50 | 0.06547382 | 0.01960927 | −0.0408397 | 0.02124336 | −0.0156542 |
| CIL51 | 0.05134539 | 0.03796139 | 0.00406195 | −0.0382123 | −0.012566 |
| CIL52 | 0.07145737 | 0.06783834 | 0.23249093 | −0.005506 | −0.0394203 |
| CIL55 | 0.20744323 | 0.00129686 | 0.11081063 | −0.0490999 | 0.14692164 |
| CIL56 | 0.24364778 | 0.05422681 | 0.12694489 | −0.1401832 | 0.14210439 |
| CIL58 | 0.03304649 | 0.08558235 | 0.08912049 | 0.02289948 | −0.0479106 |
| CIL60 | 0.08708149 | 0.04978843 | 0.07701682 | −0.036018 | −0.0265017 |
| CIL62 | 0.08235099 | 0.02726492 | 0.10607881 | −0.0244838 | −0.0312336 |
| CIL63 | 0.07268938 | 0.06439766 | 0.08988671 | 0.02370705 | 0.03221966 |
| CIL64 | −0.0624863 | 0.16540942 | 0.12701332 | 0.03480285 | −0.0807861 |
| CIL66 | 0.05045432 | 0.03186052 | 0.12989118 | −0.0545586 | −0.0333379 |
| CIL67 | 0.05005779 | 0.04656953 | 0.11763528 | −0.0217528 | −0.0568708 |
| CIL69 | 0.34563046 | −0.0166997 | 0.30053665 | −0.0261029 | 0.26312402 |
| CIL70 | 0.27332319 | −0.0017074 | 0.2561347 | −0.1365882 | 0.12049926 |
| CIL71 | 0.03732862 | −0.0128102 | −0.0036536 | −0.0104564 | −0.013114 |
| CIL72 | −0.0211095 | −0.0123259 | 0.19715488 | −0.0141282 | −0.0359053 |
| CIL74 | 0.07412252 | −0.0203197 | −0.0089452 | −0.0258559 | −0.0236027 |
| CIL75 | 0.3815567 | −0.0187117 | 0.40089859 | −0.0369968 | 0.3451772 |
| CIL76 | 0.00326543 | −0.0071296 | 0.13758731 | 0.01031687 | −0.0270673 |
| CIL77 | 0.02076032 | −0.0050775 | 0.09144811 | −0.0140507 | −0.0106377 |
| CIL79 | 0.44882849 | 0.00567531 | 0.54943789 | −0.0705 | 0.42246924 |
| CIL80 | 0.0048774 | 0.00387361 | 0.16715785 | 0.06492902 | −0.0195351 |
| CIL87 | 0.05929111 | 0.01926934 | 0.07034052 | 0.04582203 | −0.0318765 |
| CIL88 | 0.07161912 | 0.02317928 | 0.06160293 | 0.05526244 | −0.0157674 |
| CIL89 | 0.06709686 | 0.01857298 | 0.04586863 | 0.01145507 | −0.0214735 |

HT.zVAD

| | |
|---|---|
| MS275 | 0.02219614 |
| Scriptaid | 0.02988417 |
| TrichostatinA | 0.0401151 |
| Echinomycin | 0.07367089 |
| Colchicine | 0.13398874 |
| NPC25 | 0.18370661 |
| NPC4 | 0.13439139 |
| NPC7 | 0.09516486 |
| Podophyllotoxin | 0.09401676 |
| Rotenone | 0.01972194 |
| Vinblastine | 0.08923891 |
| Vincristine | 0.11717599 |
| DPI3 | −0.0520186 |
| DPI4 | −0.0445076 |
| DPI6 | −0.0403944 |
| RSL3 | −0.0159859 |
| Bortezomib | 0.01074076 |
| MG132 | −0.0992034 |
| MG262 | −0.0583711 |
| Erastin | −0.0720745 |
| Camptothecin | 0.03249301 |
| Irinotecan | 0.03379276 |
| Daunorubicin | 0.04455104 |
| Doxorubicin | 0.05137839 |
| Etoposide | 0.03817009 |
| Mitoxantrone | 0.03446406 |
| Cycloheximide | 0.03579612 |
| Dinitrophenol | 0.04232695 |
| NaN3 | 0.01031129 |
| Vatinomycin | −0.0575268 |
| CIL1 | −0.0551038 |
| CIL2 | −0.028281 |
| CIL4 | 0.01460239 |
| CIL5 | −0.0137832 |
| CIL6 | −0.0167612 |
| CIL7 | −0.0377272 |
| CIL9 | −0.0016603 |
| CIL10 | −0.0128631 |
| CIL11 | −0.0024945 |
| CIL13 | 0.0116389 |
| CIL15 | −0.0468174 |
| CIL16 | 0.00548187 |

TABLE 9-continued

Modulatory profiles of characterized and uncharacterized lethal compounds.

| | |
|---|---|
| CIL17 | 0.00853559 |
| CIL18 | 0.0100969 |
| CIL20 | −0.0207892 |
| CIL22 | 0.02835078 |
| CIL23 | 0.02042705 |
| CIL25 | 0.03342493 |
| CIL26 | −0.0122635 |
| CIL27 | −0.0150776 |
| CIL28 | −0.0090028 |
| CIL33 | 0.03456928 |
| CIL34 | 0.00714776 |
| CIL36 | −0.0035883 |
| CIL40 | 0.01716741 |
| CIL41 | −0.016697 |
| CIL44 | 0.01751267 |
| CIL46 | 0.0172399 |
| CIL47 | −0.0058941 |
| CIL48 | −0.0050534 |
| CIL49 | 0.00987936 |
| CIL50 | 0.02906893 |
| CIL51 | 0.00779885 |
| CIL52 | 0.02338762 |
| CIL55 | 0.02659525 |
| CIL56 | 0.03666347 |
| CIL58 | 0.0245897 |
| CIL60 | −0.0099218 |
| CIL62 | −0.0179367 |
| CIL63 | 0.0184627 |
| CIL64 | 0.05556764 |
| CIL66 | 0.01628958 |
| CIL67 | 0.00499615 |
| CIL69 | −0.0004734 |
| CIL70 | 0.00227166 |
| CIL71 | 0.01755953 |
| CIL72 | 0.05313729 |
| CIL74 | 0.01022255 |
| CIL75 | 0.00011911 |
| CIL76 | 0.03199583 |
| CIL77 | 0.02553717 |
| CIL79 | 0.00368164 |
| CIL80 | 0.03135047 |
| CIL87 | 0.0225789 |
| CIL88 | 0.04370741 |
| CIL89 | 0.03057583 |

Table 9 provides the raw data used to generate the hierarchical clustering in FIG. 1B. In Table 9, rows are lethal compounds; columns are modulators; values are AUCs.

Example 3

Probe Optimization Led to a Specific Ferroptosis Inducer

Figure 2A:
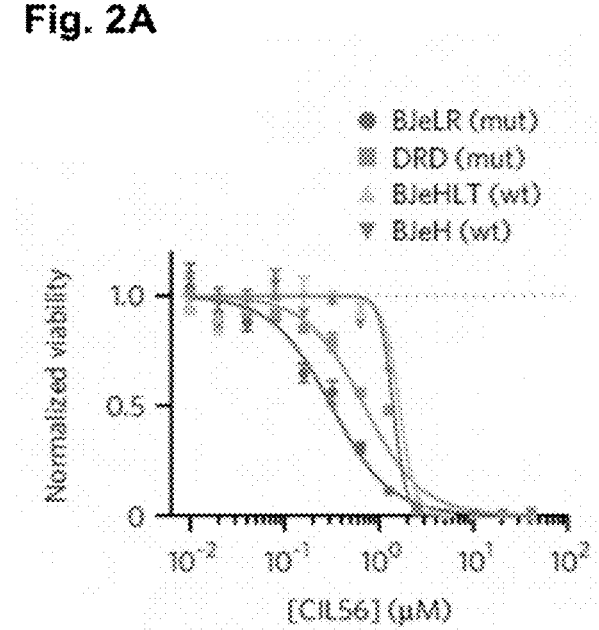
FIGS. 2A-2F show that optimization of CIL56 revealed a potent and selective ferroptosis inducer.
Figure 2B:
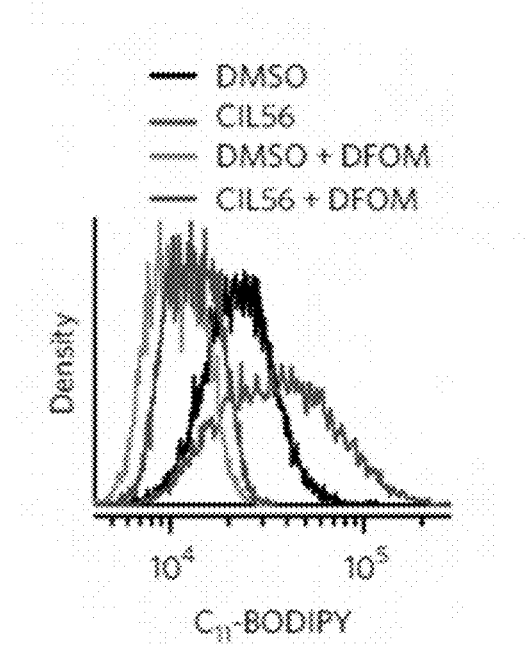
Figure 2C:
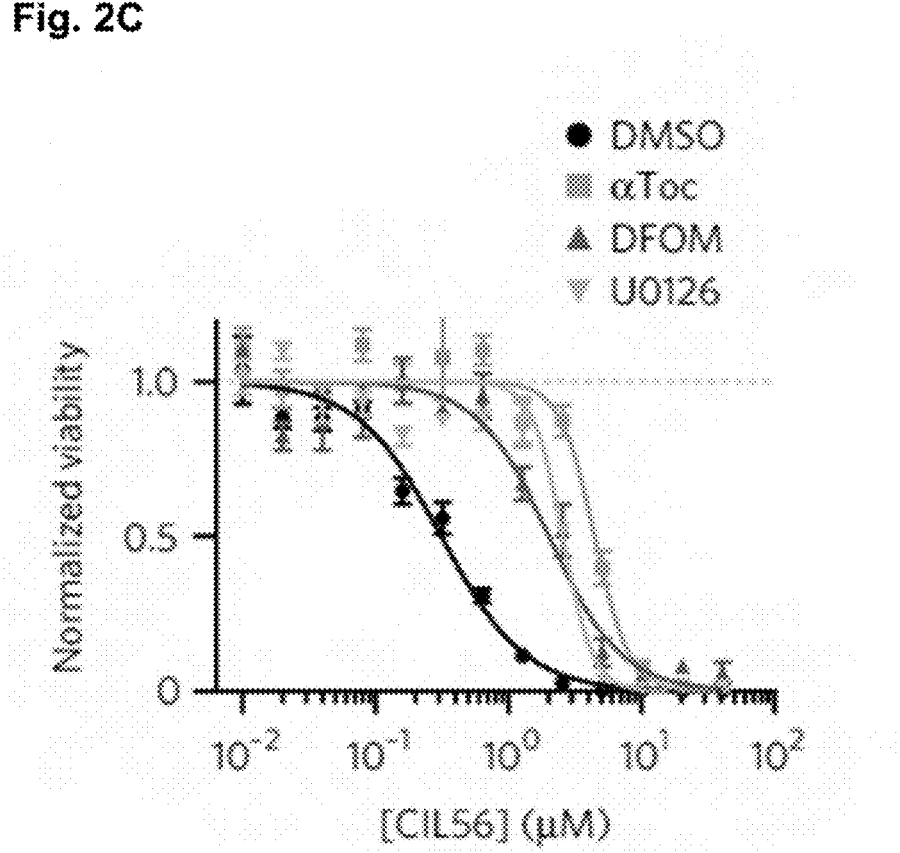
Figure 2D:
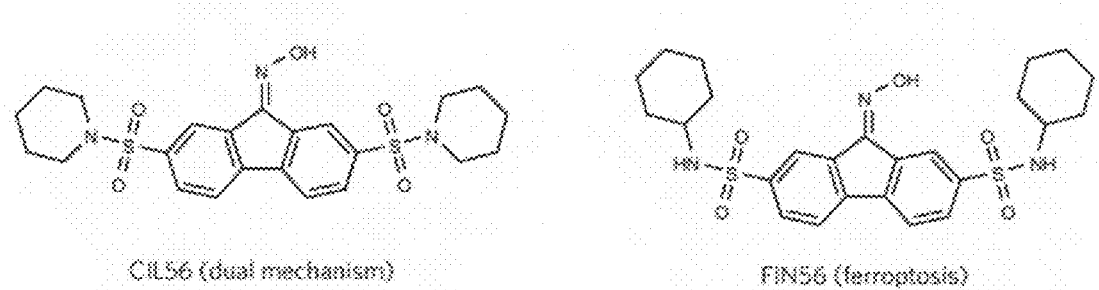
Figure 2E:
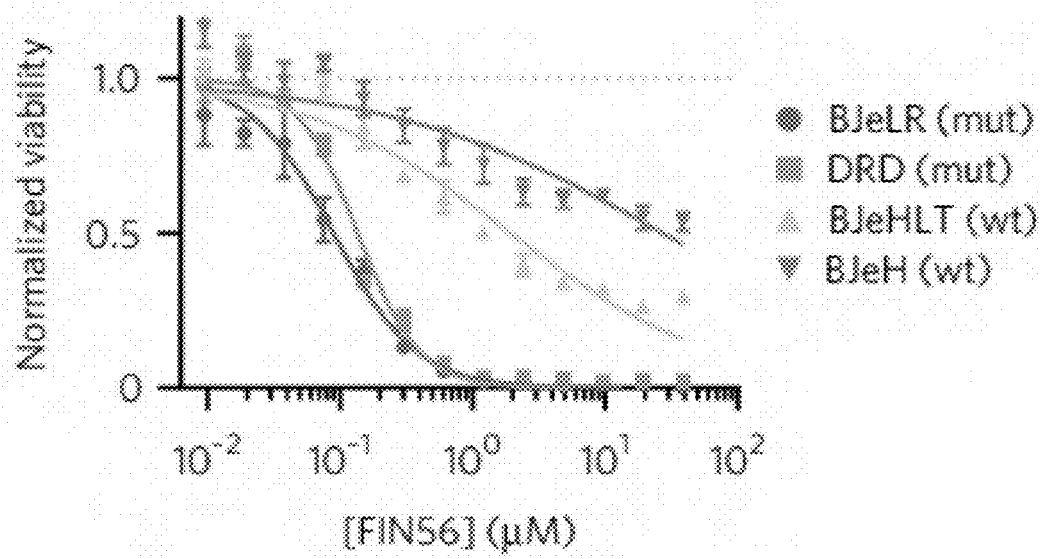
Figure 2F:
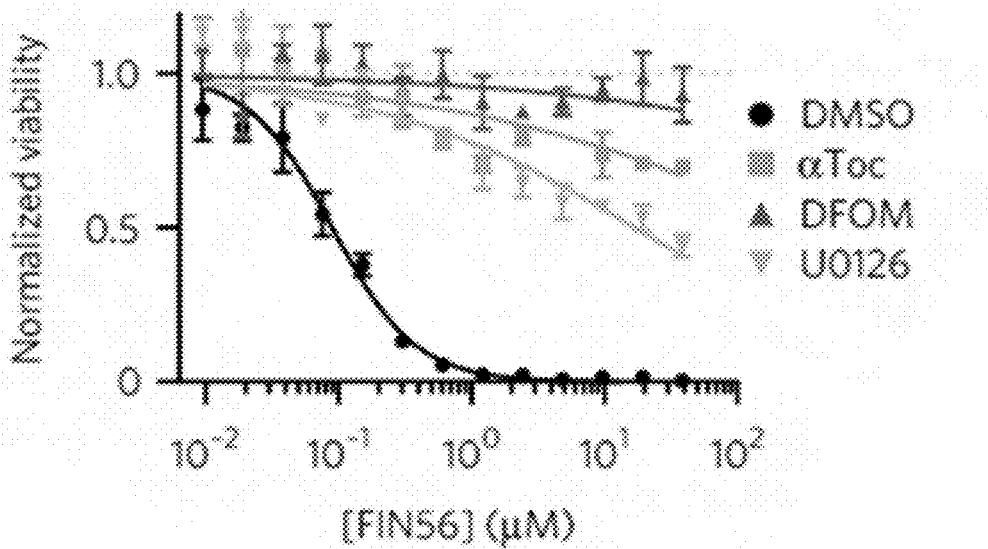

CIL56 induced iron-dependent ROS (FIG. 2B). Antioxidants and iron chelators suppressed the lethality of low concentrations of CIL56 (FIG. 2C). It was hypothesized that CIL56 was capable of engaging two independent death pathways: ferroptosis at low concentrations, and necrotic, non-suppressible cell death at higher concentrations. To identify a more selective analog of CIL56 that retained the ability to induce ferroptosis but lacked the ability to induce the other form of death, structure—activity relationship analysis of the CIL56 scaffold was carried out, which determined that the oxime moiety was crucial for inducing ferroptosis, and that hydrophobicity of the piperidine moieties of CIL56 correlated with potency (FIG. 11). Ultimately, an analog (SRS7-34) that has cyclohexylamine moieties in place of the piperidine moieties of CIL56 was discovered (FIG. 2D). This new compound, termed FIN56 (2) (ferroptosis inducer derived from CIL56), exhibited greater potency as well as greater oncogenic RAS selectivity in the BJ cell line series compared to CIL56 (FIG. 2E); FIN56 was also fully suppressed by the ferroptosis inhibitors deferoxamine and α-tocopherol (FIG. 2F), indicating that it engages only ferroptosis and does not have the ability to engage the second death mechanism activated by CIL56.

Example 4

FIN56-Induced Ferroptosis Involves Decreased GPX4 Abundance

Previously reported ferroptosis inducers either deplete glutathione (by inhibiting cystine uptake) or are covalent GPX4 inhibitors. In the NCI60 cell line panel (Shoemaker et al. 2006), it was found that GPX4 inhibitors were more cell-line selective than compounds inducing glutathione depletion (Shimada et al. 2016) (FIG. 12A). In this regard, FIN56 was more similar to other GPX4 inhibitors than to GSH-depleting compounds. Supporting this, it was found that FIN56 did not deplete glutathione, which suggested that it also did not block cystine import; however, FIN56 did cause the loss of GPX4 activity in cell lysates (FIG. 3A and FIG. 12B). Intriguingly, compared to the covalent GPX4 inhibitor (1S, 3R)-RSL3, FIN56 was slower to induce the accumulation of ROS (FIG. 3B), which suggested that it did not cause a loss of GPX4 activity via direct inhibition of enzymatic activity. Indeed, it was determined that the abundance of GPX4, but not that of the related selenoprotein GPX1, was substantially decreased after FIN56 treatment (5 µM, 10 h) (FIG. 3C and FIGS. 12C-12D). Neither erastin nor (1S, 3R)-RSL3 affected the abundance of GPX4 to the same extent as FIN56, demonstrating that this effect was specific to FIN56. GPX4 knockdown enhanced FIN56 lethality (FIG. 3D), and FIN56-induced cell death was suppressed by GFP-GPX4 fusion-protein overexpression (FIGS. 3E-F and FIGS. 12E-12F), suggesting that the loss of GPX4 was critical for FIN56-induced ferroptosis. It was confirmed that selenite supplementation, which is known to upregulate the expression of selenoproteins, including GPX4 (Romanowska et al. 2007), also suppressed FIN56 lethality (FIGS. 12G-12H). The decrease in GPX4 protein abundance was not inhibited by α-tocopherol, indicating that it was not a downstream consequence of lipid ROS generation. Together, these results suggested that FIN56 triggers ferroptosis through a mechanism involving the downregulation of GPX4 protein abundance.

How FIN56 causes a decrease in the amount of GPX4 protein was further investigated. It was found that the GPX4 transcript level increased, rather than decreased, after FIN56 treatment (FIG. 12, panel (i)), which suggests that FIN56-induced depletion of GPX4 protein is not mediated by transcriptional changes in GPX4 mRNA. Observations that cells treated with cycloheximide, which inhibits ribosome function, did not show substantially decreased amounts of GPX4 protein compared to a housekeeping α-tubulin protein (FIG. 12J) and that knockdown of the gene tRNA isopentenyltransferase 1 (TRIT1) (Fradejas et al. 2013), which has been reported to be required for synthesis of selenoproteins, including of GPX4, did not dramatically affect GPX4 protein abundance (FIGS. 12K-12M) suggested that FIN56 did not inhibit GPX4 protein synthesis but rather induced post-translational GPX4 protein degradation. It is not clear, however, how GPX4 degradation is regulated, because a proteosome inhibitor (MG132) did not inhibit GPX4 degradation significantly or protect cells from FIN56 lethality. It is of note that GPX4 abundance was reported to decrease when the proto-oncogene serine/threonine-protein (Pim) kinases were inhibited (Song et al. 2015); however, this is not relevant to FIN56 lethality because pan-Pim kinase inhibitors did not induce ferroptosis, as these compounds were not suppressed by α-tocopherol (FIG. 12N).

Example 5

SQS Encoded by FDFT1 is a Target Protein of FIN56

To better understand the mechanism of action of FIN56, a search for proteins binding directly to FIN56 was conducted using a chemoproteomic approach. First, structural analogs of FIN56 were explored. This resulted in the creation of SRS11-31, an analog with a polyethylene glycol (PEG) moiety, which induces ferroptosis at tenfold higher $EC_{50}$ than FIN56 (FIG. 4A and FIG. 13). In contrast, substitution of the cyclohexyl moiety in FIN56 with a 4-tetrahydropyran (SRS8-18 (3)) or its PEG conjugate (SRS11-66) (4) resulted in a complete loss of activity. Next, both SRS11-31 (5) (active, or A) and SRS11-66 (inactive, or I) were conjugated to Profinity epoxide resin via an epoxy ring-opening reaction and incubated the resins with HT-1080 whole-cell lysates. Mass spectrometry was used to identify and quantify the pulldown proteins found with each probe. Seventy proteins, excluding universally expressed proteins (actins, tubulins, and ribosome subunits), were found to be more abundant on the resin conjugated with the active probe.

It was then tested that whether these candidate target proteins were inhibited (loss of function) or activated (gain of function) by FIN56 to induce ferroptosis using RNA interference (RNAi). RNAi-mediated knockdown of the relevant target should either enhance or suppress FIN56 sensitivity, depending on FIN56's mechanism of action (FIG. 14A). Expression of many genes is affected by off-target effects of RNAi, and the resulting phenotypes may differ from cell line to cell line; however, on-target effects are more likely to be consistent among different cell lines. Therefore, the effects of up to five short hairpin RNA (shRNA) clones per gene encoding 70 candidate target proteins in four independent ferroptosis-susceptible cell lines: HT-1080, BJeLR, Calu-1 lung adenocarcinoma, and 143B osteosarcoma were examined (FIG. 4B and FIGS. 14B-14C). A search for candidate FIN56 targets responsible for ferroptosis was conducted using two criteria: (i) high selective abundance on the active versus inactive probe resins, and (ii) high proportion of consistently performing shRNAs in all four cell lines subjected to RNAi-mediated silencing of each gene (FIG. 4C and FIG. 14D). Among the 70 tested proteins, it was found that proteins, such as chaperones and nuclear transport proteins, for which knockdown not only enhanced FIN56 lethality but also independently induced toxicity. However, their lethality was not suppressed by α-tocopherol, unlike with GPX4 knockdown, indicating that these cell death phenotypes were distinct from ferroptosis. The potency of FIN56 might be aided by modulation of these essential proteins, but they are not the primary targets of FIN56 (FIG. 4D).

Example 6

Validating the Functional Relevance of the Target

It was found that four of the five shRNAs against FDFT1 mRNA (which encodes SQS protein) suppressed FIN56 consistently in all four cell lines tested, indicating that FIN56 activates, rather than inhibits, SQS (a gain-of-function model). Therefore, how the FIN56-SQS interaction is relevant to FIN56's lethality was investigated. It was confirmed that not only shRNAs targeting FDFT1 but also small-molecule inhibitors of SQS activity (YM-53601 and zaragozic acid A) suppressed FIN56 lethality (FIG. 5A). SQS is an enzyme that acts downstream of 3-hydroxy-3-methylglutaryl-coenzyme A (HMG-CoA) reductase in the mevalonate pathway. SQS couples two farnesyl pyrophosphate (FPP) molecules to form squalene. Inhibition of SQS consequently increases the pool of FPP. FPP is essential for several processes, including protein prenylation and metabolite synthesis (e.g., sterols, coenzyme $Q_{10}$ ($CoQ_{10}$), dolichol, and heme) (Tansey et al. 2000), some subset of which may be relevant to the modulatory effect on ferroptosis sensitivity. Supplementation with FPP indeed suppressed the lethality of FIN56 (FIG. 5B). SQS-FIN56 binding was also examined by confirming that SQS from HT-1080 whole-cell lysate bound selectively to active probes versus to an inactive probe (FIG. 5C). Moreover, bacterially expressed truncated human SQS protein (Liu et al. 2014) (with the lipophilic N and C termini removed) binding to an active affinity probe was efficiently suppressed by pre-incubation of purified SQS protein with FIN56, suggesting that SQS and FIN56 directly interact (FIG. 15).

The role of processes upstream of FPP in the mevalonate pathway was investigated. It was found that statins, chemical inhibitors of HMG-CoA reductase, enhanced FIN56 lethality (FIG. 16A). HMG-CoA reductase synthesizes mevalonic acid (MVA). Supplementation of MVA reversed the effect of cerivastatin, the most potent and selective statin tested (FIGS. 16B-16C), demonstrating that the HMG-CoA-reductase-inhibiting effect of cerivastatin is responsible for its enhancement of FIN56 lethality. However, these effects did not affect GPX4 abundance (FIG. 16D).

More extensive investigation of the mevalonate pathway showed that supplementation of FPP suppressed FIN56 more effectively than treatment with other isoprenoid pyrophosphates did, which suggests that FPP is functionally relevant to the regulation of sensitivity to FIN56 (FIG. 5D). It was found that an inhibitor of squalene monooxygenase, which is involved in a rate-limiting step downstream of SQS in cholesterol synthesis (Chugh et al. 2003), and an SQS inhibitor both suppressed FIN56 lethality, supporting the notion that nonsteroidogenic products of the mevalonate pathway contribute to the suppression of FIN56 (FIG. 5E). It was found that among the metabolites derived from FPP, idebenone, a hydrophilic analog of $CoQ_{10}$, was the only suppressor of FIN56-induced ferroptosis (FIGS. 5F-5G), which suggests that $CoQ_{10}$ mediates the connection between the mevalonate pathway and regulation of sensitivity to FIN56. Note that supplementation of $CoQ_{10}$ itself is known to be ineffective because of its extreme hydrophobicity (Gueven et al. 2015). To further assess the specificity of the three mevalonate-pathway modulators (FPP, YM-53601, and idebenone), and of α-tocopherol, a modulatory profiling scheme was used in HT-1080 cells with lethal compounds, including ones that induce oxidative stress. It was found that both GPX4 inhibitors, FIN56 and (1S, 3R)-RSL3, were potently suppressed by all the compounds (FIG. 5H). Erastin, a GSH depletor, was also suppressed somewhat by the modulators; the rest of the compounds showed more distinct patterns. These results suggest that modulators of the mevalonate pathway are specific inhibitors of ferroptosis, rather than of lethality in general.

$CoQ_{10}$ is an electron carrier in the mitochondrial respiratory chain and an endogenous antioxidant. However, whether it functions in the regulation of ferroptosis via either of these mechanisms remains to be elucidated. 143B cells with or without mitochondrial DNA ($\rho^+$ or $\rho^0$ cells, respectively) were both sensitive to FIN56-induced ferroptosis (FIGS. 17A-17B), which suggests that the respiratory chain is not involved in ferroptosis. The lipophilic antioxidant α-tocopherol suppressed staurosporine-induced cell death, but idebenone enhanced it, suggesting that idebenone has distinct antioxidant properties compared to α-tocopherol. In addition, although both α-tocopherol and idebenone inhibited lipid ROS generation after FIN56 treatment, idebenone treatment did not change the basal lipid ROS level (FIG. 17C). Thus, exactly how $CoQ_{10}$ protects cells from FIN56 remains elusive, but the process may involve reprogramming of lipid metabolism in a way that is not conducive to the execution of ferroptosis, or a specific antioxidant action distinct from that of α-tocopherol.

Example 7

An Acc Inhibitor Prevents GPX4 Protein Degradation

Modulators of the mevalonate pathway, such as idebenone, are potent suppressors of ferroptosis, particularly of direct and indirect GPX4 inhibitors (FIN56 and (1S, 3R)-RSL3) (FIG. 5H); however, these compounds did not block the decrease in GPX4 protein abundance caused by FIN56 treatment or induce overexpression of the protein (FIG. 6A and FIG. 18), indicating that there may be an additional pathway that regulates GPX4 protein level in response to FIN56 treatment. It was discovered that 5-(tetradecyloxy)-2-furoic acid (TOFA), an inhibitor of acetyl-CoA carboxylase (ACC), inhibited the loss of GPX4. TOFA was also found to be a potent suppressor of FIN56 and suppressed lipid ROS generation after FIN56 treatment (FIGS. 6B-6C). ACC is an enzyme involved in fatty acid synthesis. It was previously observed through genetic screening that ACC's activity is involved in the mechanism of non-ferroptotic cell death induced by CIL56 (Dixon et al. 2015). However, ACC itself was not identified as a direct FIN56 target, and the detailed mechanism linking FIN56 to ACC remains to be understood.

In conclusion, characterization of FIN56 revealed that its mechanism involves two distinct pathways (FIG. 6D): degradation of GPX4, which requires the enzymatic activity of ACC; and activation of SQS, which leads to coenzyme $Q_{10}$ depletion. Together these effects result in potent induction of ferroptosis.

Example 8

Total Synthesis and NMR Data of CIL56 and FIN56 and Analogs thereof

Structural analogs of CIL56 and FIN56 were synthesized based on the procedures described in international patent application no. PCT/US2008/006015 by Cholody, W. M. et al. (2008), which is incorporated herein by reference in its entirety. The total synthesis of CIL56 and FIN56 is depicted in Scheme 1.

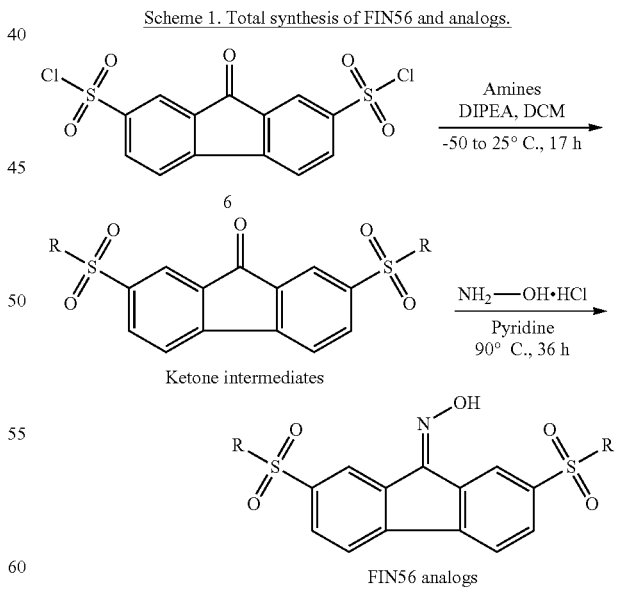

General Procedure A: Preparation of Ketone Compounds 9-oxo-9H-fluorene-2,7-disulfonyl dichloride (6) (1 equiv.) was dissolved in 50 mL of dichloromethane and the mixture was cooled to −50° C. To this mixture was added a primary or secondary amine (e.g. piperidine or cyclohexylamine) (2.6 equiv.) and diisopropylethylamine (2-3 equiv.). The reaction mixture was stirred at room temperature for 17 hrs. The solvent was evaporated and the residue was purified by flash-column chromatography on silica gel to provide the desired ketone compounds. The purity of the ketones were confirmed by different spectroscopic methods such as $^1$H NMR and mass spectrometry.

General Procedure B: Preparation of Oxime Compounds

A mixture of the ketone from the general procedure A (1.0 equiv.) and hydroxylamine hydrochloride (10 equiv.) were dissolved in pyridine (10 mL). The mixture was stirred at 95° C. for 36 hrs. The pyridine was evaporated and the residue was stirred with 1 N hydrogen chloride (HCl) (10 mL) for several mins. White product was collected by filtration, washed with water and dried. The crude material was either crystallized from ethanol or purified by flash-column chromatography on silica gel to provide the desired oxime compounds. The purity of the oximes was confirmed by different spectroscopic methods such as $^1$H NMR and mass spectrometry.

Synthesis of 2,7-bis(piperidin-1-ylsulfonyl)-9H-fluoren-9-one (SRS1-63)

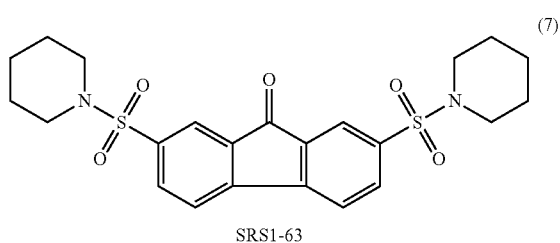 [SMILES: O=C1c2cc(S(=O)(=O)N3CCCCC3)ccc2-c2ccc(S(=O)(=O)N3CCCCC3)cc21]

SRS1-63

(7)

General procedure A was followed, using 9-oxo-9H-fluorene-2,7-disulfonyl dichloride (6) (400 mg, 1.060 mmol), piperidine (273 mL, 2.757 mmol) and diisopropylethylamine (270 mL, 2.120 mmol). The crude reaction mixture was purified by column chromatography (dichloromethane:methanol=40:1) to give the desired 2,7-bis(piperidin-1-ylsulfonyl)-9H-fluoren-9-one (SRS1-63) (7) (420 mg, 0.886 mmol, 84%). $^1$H NMR (400 MHz, CDCl$_3$) δ 8.07 (s, 2H), 7.99 (d, J=7.4 Hz, 2H), 7.79 (d, J=7.8 Hz, 2H), 3.04 (d, J=4.8 Hz, 8H), 1.66 (s, 8H), 1.44 (s, 4H). MS (APCI+, M+1) 475.16.

Synthesis of N2,N7-dicyclohexyl-9-oxo-9H-fluorene-2,7-disulfonamide (SRS7-25)

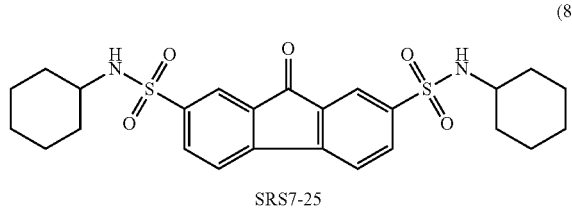

SRS7-25

(8)

General procedure A was followed, with 9-oxo-9H-fluorene-2,7-disulfonyl dichloride (1) (500 mg, 1.326 mmol), cyclohexylamine (394 mL, 3.448 mmol) and diisopropylethylamine (692.9 mL, 3.978 mmol). The crude reaction mixture was purified by column chromatography (dichloromethane:methanol=20:1) to give the desired N2,N7-dicyclohexyl-9-oxo-9H-fluorene-2,7-disulfonamide (SRS7-25) (8) (532 mg, 1.059 mmol, 80%). $^1$H NMR (400 MHz, CDCl$_3$) δ 8.19 (s, 2H), 8.13 (dd, J=7.8, 1.6 Hz, 2H), 7.77 (d, J=7.8 Hz, 2H), 4.57 (d, J=7.7 Hz, 2H), 3.22 (d, J=3.8 Hz, 2H), 1.81 (d, J=9.8 Hz, 4H), 1.65 (s, 4H), 1.32-1.13 (m, 12H); MS (APCI+, M+1) 503.01.

Synthesis of 2,7-bis(piperidin-1-ylsulfonyl)-9H-fluoren-9-one oxime (CIL56)

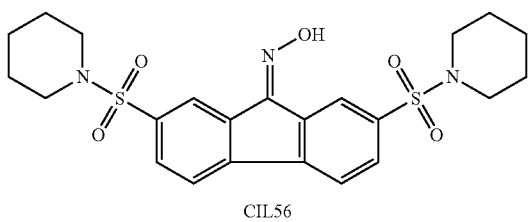

CIL56

(1)

General procedure B was followed, with 2,7-bis(piperidin-1-ylsulfonyl)-9H-fluoren-9-one (SRS1-63) (350 mg, 0.738 mmol), hydroxylamine hydrochloride (509 mg, 7.384 mmol) and pyridine (30 mL). The crude reaction mixture was precipitated as salt after 1 N HCl treatment and washed several times with cold water and ethanol to give the N2,N7-dicyclohexyl-9-oxo-9H-fluorene-2,7-disulfonamide (CIL56) (1) (306 mg, 0.627 mmol, 85%). $^1$H NMR (400 MHz, CDCl$_3$) δ 2.50 (s, 1H), 8.78 (s, 1H), 8.13 (s, 1H), 7.88-7.77 (m, 3H), 7.75 (d, J=1.4 Hz, 1H), 2.96 (d, J=4.8 Hz, 8H), 1.58 (s, 8H), 1.35 (s, 4H); MS (APCI+, M+1) 490.16.

Synthesis of N2,N7-dicyclohexyl-9-(hydroxyimino)-9H-fluorene-2,7-disulfonamide (FIN56)

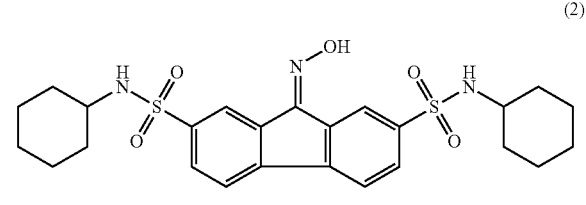

FIN56

(2)

General procedure B was followed, with N2,N7-dicyclohexyl-9-oxo-9H-fluorene-2,7-disulfonamide (SRS7-25) (500 mg, 0.996 mmol), hydroxylamine hydrochloride (687.2 mg, 9.960 mmol) and pyridine (30 mL). The crude reaction mixture was precipitated as a salt after 1 N HCl treatment and washed several times with cold water and ethanol to give the N2,N7-dicyclohexyl-9-oxo-9H-fluorene-2,7-disulfonamide (FIN56) (2) (437 mg, 0.845 mmol, 85%). $^1$H NMR (400 MHz, DMSO) δ 13.28 (s, 1H), 8.82 (s, 1H), 8.25-8.14 (m, 3H), 8.03 (dd, J=8.0, 1.3 Hz, 1H), 7.95 (dd, J=8.0, 1.2 Hz, 1H), 7.85 (d, J=7.4 Hz, 1H), 7.81 (d, J=7.3 Hz, 1H), 3.00 (s, 2H), 1.59 (s, 8H), 1.44 (d, J=11.5 Hz, 2H), 1.22-0.98 (m, 10H); MS (APCI+, M+1) 517.92.

Synthesis 2,7-bis(4,4-difluoropiperidin-1-ylsulfonyl)-9H-fluoren-9-one oxime (SRS5-19)

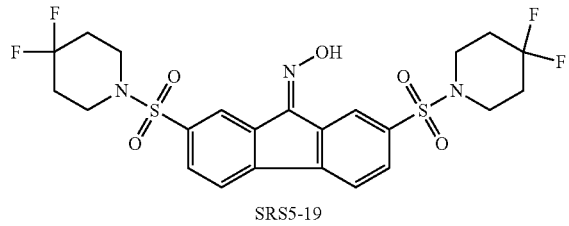 [SMILES: O=S(=O)(c1ccc2c(c1)C(=NO)c1cc(S(=O)(=O)N3CCC(F)(F)CC3)ccc1-2)N1CCC(F)(F)CC1]

SRS5-19

General procedure B was followed, with 2,7-bis(4,4-difluoropiperidin-1-ylsulfonyl)-9H-fluoren-9-one (25 mg, 0.0458 mmol), hydroxylamine hydrochloride (32.0 mg, 0.458 mmol) and pyridine (30 mL). The crude reaction mixture was precipitated as a salt after 1 N HCl treatment and washed several times with cold water and ethanol to give the desired 2,7-bis(4,4-difluoropiperidin-1-ylsulfonyl)-9H-fluoren-9-one oxime (SRS5-19) (10) (15 mg, 0.026 mmol, 58%). $^1$H NMR (400 MHz, DMSO) δ 13.42 (s, 1H), 8.68 (s, 1H), 8.34 (dd, J=17.8, 7.9 Hz, 2H), 8.09-7.87 (m, 13H), 3.15 (s, 8H), 2.08 (s, 8H); MS (APCI+, M+1) 561.95.

Synthesis of 9-(hydroxyimino)-N2,N7-diphenyl-9H-fluorene-2,7-disulfonamide (SRS5-55)

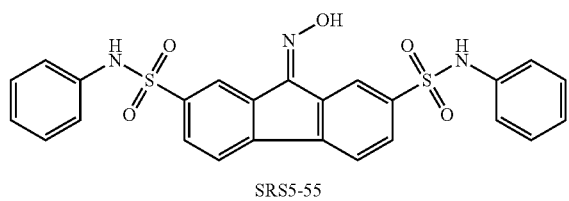

SRS5-55

General procedure B was followed, with 9-oxo-N2,N7-diphenyl-9H-fluorene-2,7-disulfonamide (25 mg, 0.051 mmol), hydroxylamine hydrochloride (35.2 mg, 0.510 mmol) and pyridine (30 mL). The crude reaction mixture was precipitated as a salt after 1 N HCl treatment and washed several times with cold water and ethanol to give the desired 2,7-bis(4,4-difluoropiperidin-1-ylsulfonyl)-9H-fluoren-9-one oxime (SRS5-55) (11) (23 mg, 0.045 mmol, 89%). $^1$H NMR (400 MHz, DMSO) δ 13.32 (s, 1H), 10.36 (d, J=25.6 Hz, 2H), 8.73 (s, 1H), 8.10 (dd, J=14.8, 8.0 Hz, 2H), 8.02 (s, 1H), 7.85 (dd, J=26.4, 8.0 Hz, 2H), 7.29-6.98 (m, 10H); MS (APCI+, M+1) 505.98.

Synthesis of 2,7-bis(4-methylpiperidin-1-ylsulfonyl)-9H-fluoren-9-one oxime (SRS5-57)

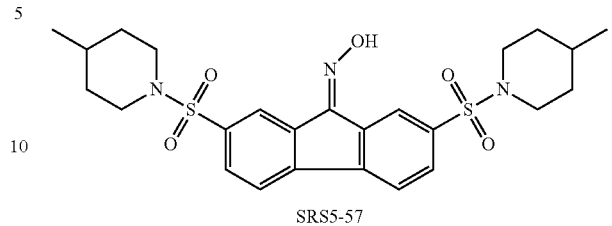

SRS5-57

General procedure B was followed, with 2,7-bis(4-methylpiperidin-1-ylsulfonyl)-9H-fluoren-9-one (25 mg, 0.050 mmol), hydroxylamine hydrochloride (35 mg, 0.5 mmol) and pyridine (30 mL). The crude reaction mixture was precipitated as a salt after 1 N HCl treatment and washed several times with cold water and ethanol to give the desired 2,7-bis(4-methylpiperidin-1-ylsulfonyl)-9H-fluoren-9-one oxime (SRS5-57) (12) (23 mg, 0.044 mmol, 89%). $^1$H NMR (400 MHz, DMSO) δ 13.36 (s, 1H), 8.65 (s, 1H), 8.31 (dd, J=17.4, 7.9 Hz, 2H), 7.92 (dd, J=35.8, 10.2 Hz, 3H), 3.66 (s, 4H), 3.48 (s, 4H), 2.28 (t, J=11.1 Hz, 3H), 1.66 (d, J=11.7 Hz, 3H), 1.23-1.09 (m, 4H), 0.84 (d, J=5.6 Hz, 6H); MS (APCI+, M+1) 518.08.

Synthesis of 2,7-bis(4-methoxypiperidin-1-ylsulfonyl)-9H-fluoren-9-one oxime (SRS6-13)

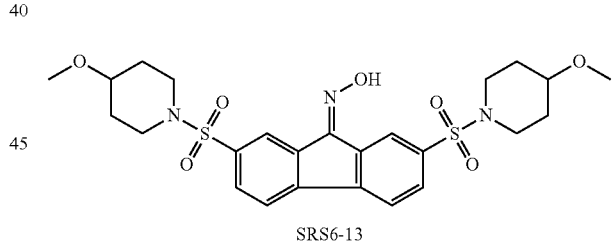

SRS6-13

General procedure B was followed, with 2,7-bis(4-methoxypiperidin-1-ylsulfonyl)-9H-fluoren-9-one (25 mg, 0.047 mmol), hydroxylamine hydrochloride (32 mg, 0.47 mmol) and pyridine (30 mL). The crude reaction mixture was precipitated as a salt after 1 N HCl treatment and washed several times with cold water and ethanol to give the desired 2,7-bis(4-methoxypiperidin-1-ylsulfonyl)-9H-fluoren-9-one oxime (SRS6-13) (13) (19 mg, 0.034 mmol, 74%). $^1$H NMR (400 MHz, DMSO) δ 13.37 (s, 1H), 8.65 (s, 1H), 8.40-8.24 (m, 2H), 7.94 (d, J=34.2 Hz, 3H), 3.23 (s, 2H), 3.12 (s, 10H), 2.88 (s, 4H), 1.83 (s, 4H), 1.54 (s, 4H); MS (APCI+, M+1) 550.01.

Synthesis of 2,7-bis(3,5-dimethylpiperidin-1-ylsulfonyl)-9H-fluoren-9-one oxime (SRS6-15)

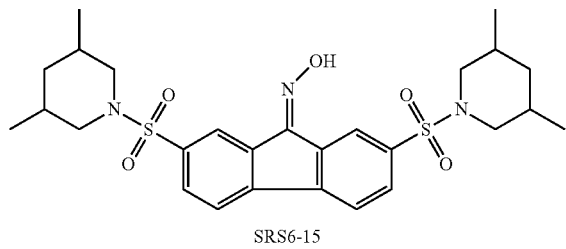

SRS6-15

General procedure B was followed, with 2,7-bis(3,5-dimethylpiperidin-1-ylsulfonyl)-9H-fluoren-9-one (25 mg, 0.047 mmol), hydroxylamine hydrochloride (32.5 mg, 0.47 mmol) and pyridine (30 mL). The crude reaction mixture was precipitated as a salt after 1 N HCl treatment and washed several times with cold water and ethanol to give the desired 2,7-bis(3,5 dimethyl-piperidin-1-ylsulfonyl)-9H-fluoren-9-one oxime (SRS6-15) (14) (21 mg, 0.038 mmol, 82%). $^1$H NMR (400 MHz, DMSO) δ 13.37 (s, 1H), 8.64 (d, J=6.2 Hz, 1H), 8.30 (dd, J=17.5, 8.1 Hz, 2H), 8.01-7.83 (m, 3H), 2.18 (t, J=7.2 Hz, 4H), 1.77 (d, J=5.2 Hz, 4H), 1.66 (d, J=7.4 Hz, 4H), 1.47 (s, 4H), 1.23-1.20 (m, 12H); MS (APCI+, M+1) 546.09.

Synthesis of 2,7-bis(4-hydroxypiperidin-1-ylsulfonyl)-9H-fluoren-9-one oxime (SRS6-23)

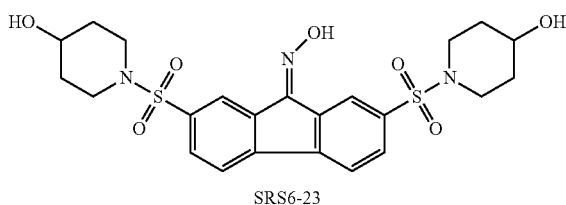 [SMILES: O=S(=O)(c1ccc2c(c1)C(=NO)c1cc(S(=O)(=O)N3CCC(O)CC3)ccc1-2)N1CCC(O)CC1]

SRS6-23

General procedure B was followed with 2,7-bis(4-hydroxypiperidin-1-ylsulfonyl)-9H-fluoren-9-one (25 mg, 0.049 mmol), hydroxylamine hydrochloride (34.1 mg, 0.49 mmol) and pyridine (30 mL). The crude reaction mixture was precipitated as a salt after 1 N HCl treatment and washed several times with cold water and ethanol to give the desired 2,7-bis(4-hydroxypiperidin-1-ylsulfonyl)-9H-fluoren-9-one oxime (SRS6-23) (15) (14 mg, 0.027 mmol, 55%). $^1$H NMR (400 MHz, DMSO) δ 13.36 (s, 1H), 8.65 (s, 1H), 8.31 (dd, J=17.6, 8.1 Hz, 2H), 7.93 (dd, J=34.3, 8.6 Hz, 2H), 3.50 (s, 45H), 3.22 (s, 95H), 2.79 (s, 92H), 1.74 (s, 92H), 1.45 (s, 87H); MS (APCI+, M+1) 522.03.

Synthesis of 2,7-bis(octahydroisoquinolin-2(1H)-ylsulfonyl)-9H-fluoren-9-one oxime (SRS6-25)

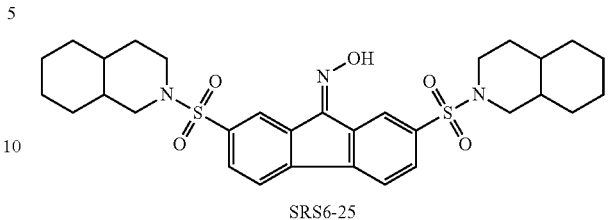

SRS6-25

General procedure B was followed, with 2,7-bis(octahydroisoquinolin-2(1H)-ylsulfonyl)-9H-fluoren-9-one (25 mg, 0.043 mmol), hydroxylamine hydrochloride (29.6 mg, 0.43 mmol) and pyridine (30 mL). The crude reaction mixture was precipitated as a salt after 1 N HCl treatment and washed several times with cold water and ethanol to give the desired 2,7-bis(octahydroisoquinolin-2(1H)-ylsulfonyl)-9H-fluoren-9-one oxime (SRS6-25) (16) (17 mg, 0.028 mmol, 66%). $^1$H NMR (400 MHz, DMSO) δ 13.35 (s, 1H), 8.64 (s, 1H), 8.30 (d, J=9.4 Hz, 2H), 7.92 (d, J=34.3 Hz, 3H), 3.72 (s, 2H), 3.57 (s, 2H), 2.26 (s, 4H), 1.91 (s, 4H), 1.59 (d, J=23.0 Hz, 12H), 1.19 (s, 12H); MS (APCI+, M+1) 598.13.

Synthesis of 2,7-bis(3,3-difluoropiperidin-1-ylsulfonyl)-9H-fluoren-9-one oxime (SRS6-27)

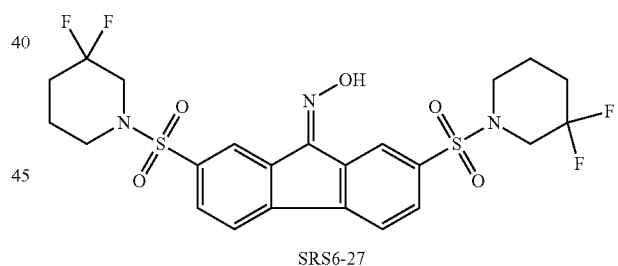

SRS6-27

General procedure B was followed, with 2,7-bis(3,3-difluoropiperidin-1-ylsulfonyl)-9H-fluoren-9-one (25 mg, 0.045 mmol), hydroxylamine hydrochloride (31.5 mg, 0.457 mmol) and pyridine (30 mL). The crude reaction mixture was precipitated as a salt after 1 N HCl treatment and washed several times with cold water and ethanol to give the desired 2,7-bis(3,3-difluoropiperidin-1-ylsulfonyl)-9H-fluoren-9-one oxime (SRS6-27) (17) (14 mg, 0.025 mmol, 55%). $^1$H NMR (400 MHz, DMSO) δ 13.41 (s, 1H), 8.68 (s, 1H), 8.35 (dd, J=18.0, 8.0 Hz, 2H), 8.00 (dd, J=34.5, 8.1 Hz, 3H), 3.32-3.29 (m, 4H), 3.12 (s, 4H), 1.95 (s, 4H), 1.71 (s, 4H); MS (APCI+, M+1) 562.01.

Synthesis of 9-(hydroxyimino)-N2,N7-bis(tetra-hydro-2H-pyran-4-yl)-9H-fluorene-2,7-disulfonamide (SRS8-18)

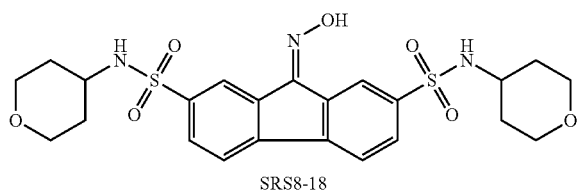

SRS8-18

General procedure B was followed with 9-oxo-N2,N7-bis(tetrahydro-2H-pyran-4-yl)-9H-fluorene-2,7-disulfonamide (9) (25 mg, 0.049 mmol), hydroxylamine hydrochloride (34 mg, 0.494 mmol) and pyridine (30 mL). The crude reaction mixture was precipitated as a salt after 1 N HCl treatment and washed several times with cold water and ethanol to give the desired 9-(hydroxyimino)-N2,N7-bis(tetrahydro-2H-pyran-4-yl)-9H-fluorene-2,7-disulfonamide (SRS8-18) (3) (17 mg, 0.033 mmol, 66%). $^1$H NMR (400 MHz, DMSO) δ 8.77 (s, 1H), 8.22-8.10 (m, 3H), 7.96 (dd, J=33.0, 8.0 Hz, 4H), 3.66 (d, J=11.5 Hz, 4H), 3.17 (dd, J=21.0, 9.6 Hz, 10H), 2.46 (d, J=1.5 Hz, 3H), 1.49 (d, J=11.9 Hz, 5H), 1.41-1.25 (m, 6H); MS (APCI+, M+1) 522.03.

Synthesis of 9-(hydroxyimino)-N2,N7-dimethyl-N2,N7-diphenyl-9H-fluorene-2,7-disulfonamide (SRS6-51)

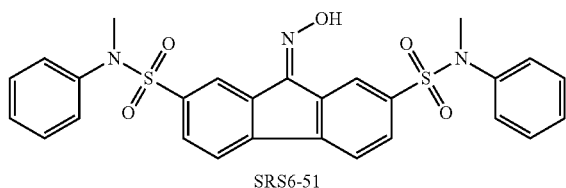

SRS6-51

General procedure B was followed with N2,N7-dimethyl-9-oxo-N2,N7-diphenyl-9H-fluorene-2,7-disulfonamide (25 mg, 0.048 mmol), hydroxylamine hydrochloride (33 mg, 0.48 mmol) and pyridine (30 mL). The crude reaction mixture was precipitated as a salt after 1 N HCl treatment and washed several times with cold water and ethanol to give the desired 9-(hydroxyimino)-N2,N7-dimethyl-N2,N7-diphenyl-9H-fluorene-2,7-disulfonamide (SRS6-51) (18) (21 mg, 0.039 mmol, 82%). 1H NMR (400 MHz, DMSO) δ 13.17 (s, 5H), 8.46 (s, 4H), 8.21 (dd, J=14.4, 8.1 Hz, 10H), 7.73-7.62 (m, 16H), 7.34 (d, J=7.6 Hz, 32H), 7.16 (d, J=7.0 Hz, 23H), 3.19 (s, 40H); MS (APCI+, M+1) 534.01.

Synthesis 2,7-bis(morpholinosulfonyl)-9H-fluoren-9-one oxime (SRS2-95)

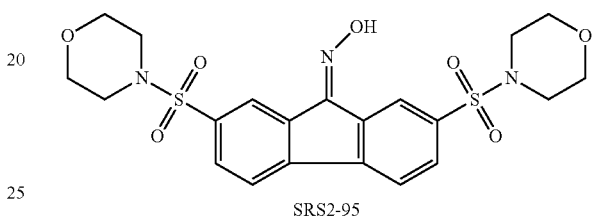

SRS2-95

General procedure B was followed with 2,7-bis(morpholinosulfonyl)-9H-fluoren-9-one (25 mg, 0.052 mmol), hydroxylamine hydrochloride (36 mg, 0.52 mmol) and pyridine (10 mL). The crude reaction mixture was precipitated as a salt after 1 N HCl treatment and washed several times with cold water and ethanol to give the 2,7-bis(morpholinosulfonyl)-9H-fluoren-9-one oxime (SRS2-95) (19) (18 mg, 0.037 mmol, 70%). $^1$H NMR (400 MHz, CDCl$_3$) δ 7.93 (d, J=7.4 Hz, 1H), 7.88-7.77 (m, 2H), 3.12-2.96 (m, 4H), 1.69 (d, J=5.0 Hz, 4H); MS (APCI+, M+1) 494.09.

Synthesis of SRS11-31 and SRS11-66 for Target Identification Study

The total synthesis of SRS11-31 and SRS11-66 is depicted in Scheme 2.

Scheme 2. Total synthesis of SRS11-31 and SRS11-66 for target identification study.

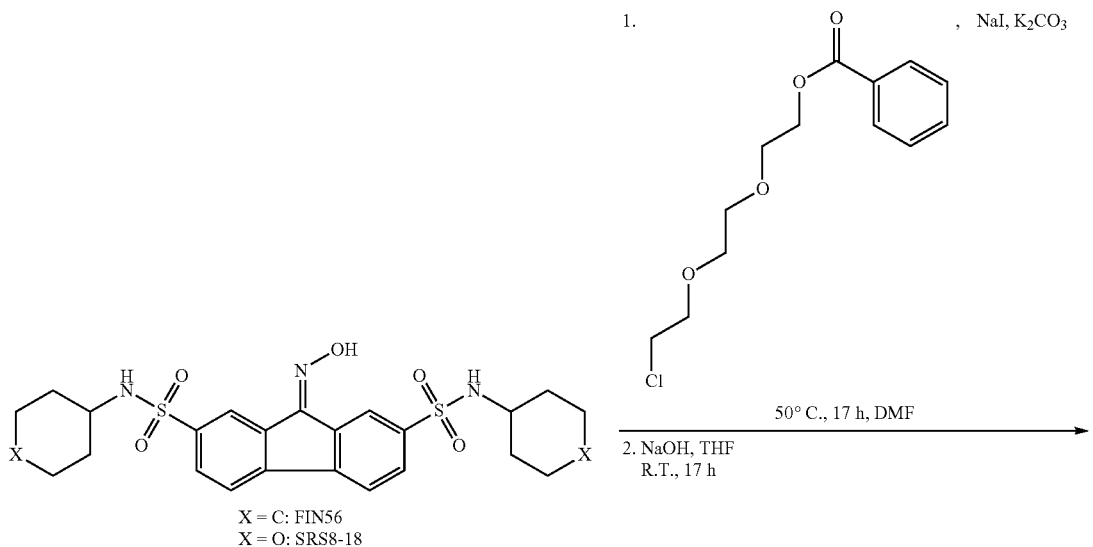

X = C: FIN56
X = O: SRS8-18

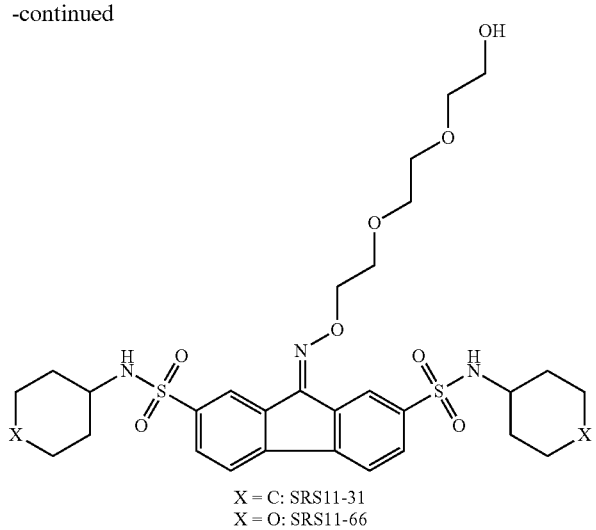

X = C: SRS11-31
X = O: SRS11-66

The N2,N7-dicyclohexyl-9-oxo-9H-fluorene-2,7-disulfonamide (FIN56) or 9-(hydroxyimino)-N2,N7-bis(tetrahydro-2H-pyran-4-yl)-9H-fluorene-2,7-disulfonamide (SRS8-18) were reacted with 2-(2-(2-chloroethoxy)ethoxy) ethyl benzoate (1 equiv) in the presence of sodium iodide (0.5 equiv) and potassium carbonate (3 equiv.) in DMF. The mixture was heated at 50° C. for 17 h then aqueous ammonium chloride was added. The compounds were extracted with ethyl acetate, dried with magnesium sulfate and the organic solvent was evaporated under vacuum. The mass of the desired ester intermediates were confirmed by LC/MS and used without further purification. To the ester intermediates were added sodium hydroxide (NaOH; 5 equiv.) in THF (2 ml). The mixture were stirred for 17 h at room temperature then acidified to pH=5. The compounds were extracted with ethyl acetate, dried with magnesium sulfate and the solvent was evaporated. The crud material was either crystallized from ethanol or purified by flash-column chromatography on silica gel to provide the desired oxime compounds. The purity of the oxime alcohol linkers SRS11-31 (4) and SRS11-66 (5) were confirmed by $^1$H NMR and Mass.

N2,N7-dicyclohexyl-9-(2-(2-(2-hydroxyethoxy)ethoxy) ethoxyimino)-9H-fluorene-2,7-disulfonamide (SRS11-31) (5)

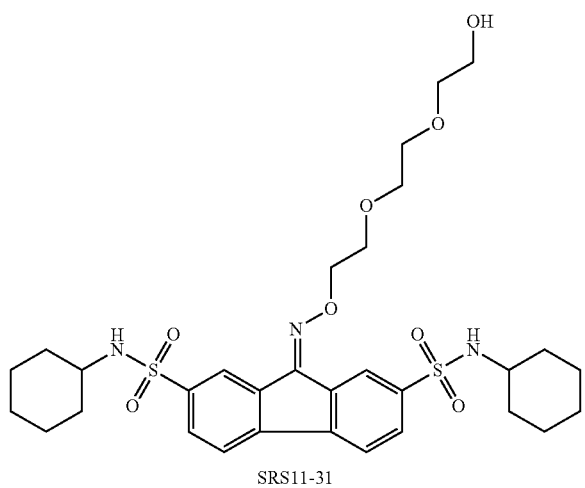 [SMILES: O=S(=O)(NC1CCCCC1)c1ccc2c(c1)C(=NOCCOCCOCCO)c1cc(S(=O)(=O)NC3CCCCC3)ccc1-2]

SRS11-31

$^1$H NMR (400 MHz, CDCl$_3$) δ 8.79 (d, J=12.2 Hz, 1H), 8.29 (d, J=7.8 Hz, 1H), 8.07-8.00 (m, 1H), 8.00-7.92 (m, 1H), 7.80 (dd, J=12.1, 5.8 Hz, 2H), 5.90 (t, J=11.3 Hz, 1H), 5.10 (dd, J=13.9, 9.9 Hz, 1H), 4.63 (s, 2H), 3.74 (d, J=3.9 Hz, 8H), 3.65 (d, J=3.9 Hz, 2H), 3.16 (s, 2H), 1.82 (s, 8H), 1.62 (s, 4H), 1.51 (d, J=10.4 Hz, 2H), 1.21 (s, 6H). MS (APCI+, M+1) 650.19.

9-(2-(2-(2-hydroxyethoxy)ethoxy)ethoxyimino)-N2,N7-bis(tetrahydro-2H-pyran-4-yl)-9H-fluorene-2,7-disulfonamide (SRS11-66) (4)

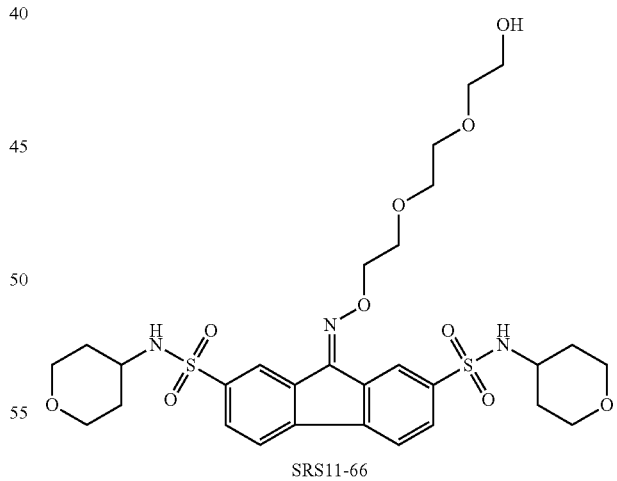

SRS11-66

$^1$H NMR (400 MHz, CDCl$_3$) δ 8.83 (s, 1H), 8.31 (s, 1H), 8.06 (d, J=7.3 Hz, 1H), 7.97 (d, J=7.7 Hz, 1H), 7.82 (t, J=7.6 Hz, 2H), 6.22 (d, J=7.2 Hz, 1H), 4.92 (d, J=7.3 Hz, 1H), 4.66 (s, 2H), 3.96 (s, 4H), 3.76 (d, J=9.2 Hz, 2H), 3.70 (s, 2H), 3.34-3.30 (m, 4H), 1.69 (s, 4H), 1.53 (d, J=6.2 Hz, 2H), 1.25 (dd, J=35.5, 16.2 Hz, 10H); MS (APCI+, M+1) 654.01.

Example 9

Enforcing Cell-Based Phenotypic Screening with Polypharmacology to Interpret Compound Mechanisms of Action Cell-based phenotypic high-throughput screening using chemical libraries has been a successful approach for modern drug discovery for decades. Many small molecules with novel biological activities have been discovered in this manner. However, characterizing the mechanism of action of hit compounds discovered through this approach is often a challenging problem. We proposed a novel computational framework to approach this problem using ligand-based pharmacophore target prediction program, known as Similarity Ensemble Approach (SEA). Integrating phenotypic screening with prediction of target proteins, we sought to understand the multi-modal mechanisms of cell death induced by a lethal compound, CIL56. Since it is computationally inexpensive, this polypharmacology approach will serve as a compensatory approach to interpret the phenotypic screening results.

High-throughput screening of small molecules has been essential tool not only in drug discovery but also in basic chemical biology problems for decades. Two major screening strategies are target-based and phenotype-based: target-based screening seeks compounds that bind to and perturb proteins of interest in vitro and is used when a particular target is already implicated in disease. However, in many more cases, disease-modifying targets are unknown. In these cases, phenotypic screening of small molecules for activity in cellular models of disease is powerful both to investigate disease mechanisms and to discover potential drugs.

However, even after compounds yielding desired effects (e.g., synthetic lethality in specific cancer genetic backgrounds) are discovered through the phenotypic screening, it is non-trivial to identify the mechanism of action of compounds. Most small molecules, particularly those with higher lipophilicity and lower molecular weight, bind to more than one protein, and yet targets and downstream mechanisms of most compounds remain largely elusive (Hu et al. 2015).

Ideally, one would like to systematically define in a screening experiment which cellular mechanisms are responsible for the effect. However, this requires that relevant targets and mechanisms be defined for all screening compounds, which is not practical currently. However, to compensate for this limitation, chemoinformatic efforts to predict binding targets of small molecules have been made. Similarity Ensemble Approach (SEA) is one such algorithm that compares the structure of a query compound with diverse collection of small molecule agonists and antagonists of each protein in a database, assembled from previous assays n (Keiser et al. 2007). The analysis computes a likelihood of the query molecule targeting each protein. While it is still at its earlier stage and there is a room for improvement, SEA has been utilized to investigate clinically available drugs, and multiple functionally relevant targets of them were successfully identified previously (Keiser et al. 2007; Keiser et al. 2009; Gregori-Puigjané et al. 2012).

In this study, we aimed to test whether high-throughput screening of a compound library could be used to define the molecular mechanism of a probe compound; we propose an analytic framework termed 'target enrichment analysis (TEA). TEA integrates phenotypic screening of a chemical library with ligand-based target predictions using SEA (FIG. 21). The goal of TEA is to improve the predictions of SEA based on experimental data. TEA attempts to find the common target(s) of compounds that are discovered to be effective in chemical library screening. TEA prioritizes ligand-target relationships initially given by SEA to suggest which ligand-target predictions are more likely to be true-positives that explain the signaling event inside the phenomenon of interest. Therefore, predictions given by TEA are more likely to be functionally meaningful than those given by SEA.

The TEA workflow consists of four steps: (i) performing cell-based high-throughput screening using a chemical library, (ii) predicting target proteins using SEA for each of the screening compounds, and (iii) integrating data acquired in the previous steps, and identifying protein targets over-represented among hit compounds from the first step that induce the desired phenotype using one sample Kolmogorov-Smirnov (KS) test. This is analogous to assess whether a predefined set of genes are over-/under-expressed among a data set in Gene Set Enrichment Analysis (GSEA) (Subramanian et al. 2005); the algorithm used here assesses whether a predefined set of compounds assigned to a target are overrepresented among hit compounds of a phenotypic assay. However, this does not immediately give us proteins targeted by the hit compounds because similar sets of compounds often bind to multiple proteins, e.g., ones in the same family. The algorithm cannot distinguish proteins that are more likely to be responsible for the phenomena without further experimental perturbation. However, at least to highlight such redundancy, (iv) the algorithm tests for significant overlap of between compound sets targeting each proteins. The third and fourth steps of TEA algorithm should pick ligand-target predictions more reliable and functionally relevant to the phenotype of interest, among ones predicted by SEA that are generally highly false positive.

As a proof of principle, we applied TEA to seek for the mechanism of action of CIL56, a multimodal lethal compound, inducing both ferroptosis and non-apoptotic non-ferroptotic cell death (Shimada et al. 2016). Ferroptosis occurs in cells when glutathione peroxidase 4 (GPX4) is inhibited and lipid peroxides accumulate to lethal levels in cells. Lipophilic antioxidants and iron chelators suppress ferroptotic cell death (Shimada et al. 2016). CIL56 was initially identified as a ferroptosis inducer, because antioxidants and iron chelators suppress its lethality up to 10-fold in ferroptosis-sensitive HT-1080 cells. However, the same ferroptosis suppressors inhibit other ferroptosis inducers completely, suggesting that CIL56 induces ferroptosis as well as a mechanistically distinct cell death at higher concentrations. We termed this secondary cell death necrosis for the sake of convenience, because CIL56 was found not to induce apoptosis but completely uncharacterized otherwise (Shimada et al. 2016). We later created a structurally similar molecule FIN56 that induces only ferroptosis, but not necrosis, supporting the notion that CIL56 induces both ferroptosis and necrosis (Shimada et al. 2016) (FIG. 22).

A molecule inducing more than one phenotype is generally challenging to study, because it is potentially confusing as to which phenotype is relevant to detected molecular changes. While our exploration of structural analogs of CIL56 eventually discovered a selective ferroptosis inducer FIN56, this selective molecule was not available at the time the screening for this study was performed. Therefore, we studied CIL56-induced cell death (Dixon et al. 2015; Viswanathan et al. 2017) using TEA.

To distinguish ferroptosis from necrosis induced by CIL56, we treated HT-1080 cells under two different conditions: "CIL56 only (C)" or "concomitant treatment of CIL56 and α-tocopherol (C+A)". The former induces both ferroptosis at lower concentrations and necrosis at higher concentrations while the latter induces only necrosis because a lipophilic antioxidant α-tocopherol completely suppresses ferroptosis, according to the previous study of FIN56 (Shimada et al. 2016).

In the first step of TEA, we screened for enhancers and suppressors of CIL56-induced cell death. We seeded 1,000 HT-1080 cells in 384 well plates, and immediately treated them with a lethal stimulus (either C or C+A) and one of 2,000 death modulators from the MicroSource bioactive compound library. Cells were incubated for 48 h before adding AlamarBlue (Invitrogen) and fluorescence (488/535) was measured on a Victor3 plate reader (PerkinElmer).

Next, we computationally predicted target proteins of each of 2,000 death modulators using SEA. Reference compound sets were extracted from chemical library screening experiments deposited in ChEMBL (Gaulton et al. 2012). First, all compounds with binding activity data for any better than or smaller to 10 µM were extracted and a compound set was associated with each target. Second, starting with the same compound sets, all ligands from orthologous eukaryotic targets were merged and clustered using Ward's clustering method (Ward 1963) implementation by ChemAxon. SEA was used as a ligand-based method to calculate the similarity between the query compounds and the different reference sets of ligands (Keiser et al. 2007). This method uses SciTegic's topological extended connectivity fingerprints (ECFP_4) (Rogers and Hahn 2010) to mathematically describe each molecule. To compare two sets of compounds, all pairwise Tanimoto similarities were calculated for the molecules in each set and those above a predetermined similarity threshold are summed in a raw score. This raw score was transformed into a Z-score based on the standard deviation calculated on a randomized background distribution. An expectation value (E-value) is calculated for this Z-score using a statistical technique analogous to the one used by the basic local alignment search tool (BLAST) (Altschul et al. 1990), calculating the probability of observing a given score by random chance alone. Predictions whose E-values were less than 1 were used for predicted ligand-target relationships in TEA. Of 2,000 death modulators, 1,482 were predicted to target 512 proteins (data not shown).

Third, we sorted the 1,482 death modulator treatments based on their effects on each lethal stimulus (i.e., suppressing most to enhancing most), and performed a one-sample KS test to assess overrepresentation of each compound set among enhancers or suppressors per protein target. We identified proteins that may (a) enhance ferroptosis, (b) suppress ferroptosis, (c) enhance necrosis, or (d) suppress necrosis (FIG. 22).

Lastly, we computed overlaps of compounds among the predicted protein targets. This revealed sets of proteins, such that the same compounds were predicted to perturb each set of proteins. Through TEA, we predicted that three non-overlapping compound sets targets nine potential target proteins to perturb CIL56-induced ferroptosis or necrosis (Table 10).

TABLE 10

Three distinct sets of CIL56 enhancer/suppressors and their predicted targets.

| Compound set | Predicted target | Protein name | Ferroptosis | Necrosis | OI within the set | Expected effect on ferroptosis |
|---|---|---|---|---|---|---|
| 1 | MMP1 | Matrix Metalloproteinase 1 | Not available.[*1] | Enhancer | 0.9-1 | Not available.[*1] |
|   | NR3C1 | Glucocorticoid Receptor |   |   |   |   |
|   | NR3C2 | Mineralocorticoid Receptor |   |   |   |   |
|   | PGR | Progesterone Receptor |   |   |   |   |
| 2 | ADRA1B | Adrenoreceptor a1B | Suppressor | Suppressor | 1 | Modulation of $Ca^{2+}$ signaling |
|   | ADRA1D | Adrenoreceptor a1D |   |   |   |   |
|   | CALM3 | Calmodulin 3 |   |   |   |   |
| 3 | ALOX12 | Arachidonate Lipoxygenase 12 | Suppressor | No effect | 0.6 | ALOXs produce lipid ROS |
|   | ALOX15 | Arachidonate Lipoxygenase 15 |   |   |   |   |

[*1]Necrotic cell death was enhaced by cmpd set #1, and became more potent than ferroptotic cell death.

The first compound set we examined was enhancers of necrosis. Because necrosis was more potentiated than ferroptosis, we could not tell if ferroptosis was affected from this analysis. These compounds were predicted to bind to matrix metalloprotease 1 (MMP1) and/or nuclear receptors (NR3C1, MR3C2, PGR).

The second compound set examined was suppressors of ferroptosis that have no effect on necrosis; these were predicted to target two proteins: arachidonate lipoxygenases (ALOX), ALOX12 and ALOX15. ALOXs peroxidize polyunsaturated fatty acids such as arachidonic acids, whose products are lipid signaling molecules mediating inflammatory signaling. While there are five ALOXs in humans (ALOX5, ALOX12, ALOX12B, ALOX15 and ALOX15B), only three were used in SEA's ligand-target predictions (ALOX5, ALOX12, and ALOX15). Whichever ALOX species may be genuinely relevant to CIL56-induced ferroptosis, ALOX proteins are suggested to be involved in some form of ferroptosis (Yang et al. 2016; Shintoku et al. 2017).

The third compound set examined was suppressors of both ferroptosis and necrosis. These were predicted to target three proteins: alpha-1 ($\alpha_1$) adrenergic receptors 1B and 1D and calmodulin 3. Activation of $\alpha_1$ activates phospholipase C and increases Ca(II). Calmoduline 3 is a calcium-binding protein. Since all three proteins are relevant to calcium signaling, we hypothesized that calcium mediates FIN56-induced ferroptosis. Flow cytometry with a Fluo-4 Ca(II) indicator showed that 2 µM FIN56 treatment increased intracellular Ca(II) levels in HT-1080 cells over the course of 9 h. Moreover, intracellular calcium induction with treatment with two ionophores (1 μM ionomycin, 0.25 μM A23187) or a sodium-potassium pump inhibitor (0.5 μM digoxin) enhanced FIN56 lethality, while Ca(II) chelators (2 μM EGTA or 10 μM BAPTA) suppressed it. These data indicated that Ca(II) plays a critical role in FIN56-induced ferroptosis (FIGS. 23A-23B).

Involvement of Ca(II) and ALOX in cell death mechanism points to glutamate-induced toxicity in neuronal cells, known as oxytosis (Tobaben et al. 2011; Henke et al. 2013), High concentrations of glutamate inhibit the function of the cystine-glutamate antiporter (system $x_c^-$), reduces the enzymatic activity of GPX4 and consequently induces massive lipophilic reactive oxygen species generation. FIN56 does not inhibit system $x_c^-$ (Shimada et al. 2016).

In summary, TEA predicted some aspects of ferroptosis, that is the involvement of ALOX and Ca(II) for progression of ferroptotic cell death. Whether the predicted individual genes are truly involved in the mechanism of action further require single or combination of functional gene deletion. On the other hand, CIL56-induced necrosis is still much elusive. While a few enhancer molecules and predicted targets against the necrosis were discovered, it was not so beneficial towards understanding the mechanism as suppressor molecules, since synergism of lethality can occur more unexpectedly. There were only a few studies that explored the mechanism of action of CIL56-induced necrosis phenotype (Dixon et al. 2015), however, one of them performed a haploid cell screening system may be relevant; they discovered several genes whose deletion rescued cells from CIL56-induced lethality (ZDHHCS, TECR, ACACA, NADK) (Dixon et al. 2015). Because deletion of the genes made cells resistant to the concentration that induces both necrosis and ferroptosis in multiple cell lines (5.5 μM), these genes' functions may be involved in progression of both cell death phenotypes.

TEA can serve as a compensatory approach to other technologies. In most phenotypic screening experiments, only a handful of hit compounds were further studied but the rest of the information is discarded. By integrating with ligand-target prediction such as SEA, we could identify the mechanisms of action of the hit molecules simultaneously. However, one needs to be cautious using such predictions; no ligand-based target prediction algorithms including SEA is a self-contained technology yet, and experimental validation needs to follow. But by collecting reference datasets (ChEMBL) and improvement prediction algorithms (SEA), phentotypic screening of compound library should better serve as a routine to understand the molecular mechanisms.

The embodiments described in this disclosure can be combined in various ways. Any aspect or feature that is described for one embodiment can be incorporated into any other embodiment mentioned in this disclosure. While various novel features of the inventive principles have been shown, described and pointed out as applied to particular embodiments thereof, it should be understood that various omissions and substitutions and changes may be made by those skilled in the art without departing from the spirit of this disclosure. Those skilled in the art will appreciate that the inventive principles can be practiced in other than the described embodiments, which are presented for purposes of illustration and not limitation.

DOCUMENTS CITED

Alegre-Aguarón, E. et al. Growth factor priming differentially modulates components of the extracellular matrix proteome in chondrocytes and synovium-derived stem cells. PLoS One 9, e88053 (2014).

Altschul, S. F.; Gish, W.; Miller, W.; Myers, E. W.; Lipman, D. J. Basic Local Alignment Search Tool. *J. Mol. Biol.* 1990, 215 (3), 403-410.http://doi.org/10.1016/S0022-2836(05)80360-2.

Aravind, L., Dixit, V. M. & Koonin, E. V. The domains of death: evolution of the apoptosis machinery. Trends Biochem. Sci. 24, 47-53 (1999).

Backman, T. W. H., Cao, Y. & Girke, T. ChemMine tools: an online service for analyzing and clustering small molecules. Nucleic Acids Res. 39, W486-W491 (2011).

Berghe T V, Linkermann A, Jouan-Lanhouet S, Walczak H, Vandenabeele P. Regulated necrosis: the expanding network of non-apoptotic cell death pathways. Nat. Rev. Mol. Cell Biol. 2014; 15:135-147.

Cholody, W. M. et al. Derivatives of fluorene, anthracene, xanthene, dibenzosuberone and acridine and uses thereof. US patent application PCT/US2008/006015 (2008).

Chugh, A., Ray, A. & Gupta, J. B. Squalene epoxidase as hypocholesterolemic drug target revisited. Prog. Lipid Res. 42, 37-50 (2003).

Degterev, A. et al. Chemical inhibitor of nonapoptotic cell death with therapeutic potential for ischemic brain injury. Nat. Chem. Biol. 1, 112-119 (2005).

Degterev, A. et al. Identification of RIP1 kinase as a specific cellular target of necrostatins. Nat. Chem. Biol. 4, 313-321 (2008).

Dixon S J, et al. Ferroptosis: An Iron-Dependent Form of Nonapoptotic Cell Death. Cell. 2012; 149:1060-1072.

Dixon S J, et al. Pharmacological inhibition of cystine-glutamate exchange induces endoplasmic reticulum stress and ferroptosis. eLife. 2014; 3:e02523.

Dixon, S. J. et al. Human haploid cell genetics reveals roles for lipid metabolism genes in nonapoptotic cell death. ACS Chem. Biol. 10, 1604-1609 (2015).

Fradejas, N. et al. Mammalian Trit1 is a tRNA([Ser]Sec)-isopentenyl transferase required for full selenoprotein expression. Biochem. J. 450, 427-432 (2013).

Fuchs, Y. & Steller, H. Programmed cell death in animal development and disease. Cell 147, 742-758 (2011).

Gaulton, A.; Bellis, L. J.; Bento, A. P.; Chambers, J.; Davies, M.; Hersey, A.; Light, Y.; McGlinchey, S.; Michalovich, D.; Al-Lazikani, B.; et al. ChEMBL: A Large-Scale Bioactivity Database for Drug Discovery. *Nucleic Acids Res.* 2012, 40 (D1), D1100-D1107. http://doi.org/10.1093/nar/gkr777.

Gregori-Puigjané, E.; Setola, V.; Hert, J.; Crews, B. A.; Irwin, J. J.; Lounkine, E.; Marnett, L.; Roth, B. L.; Shoichet, B. K. Identifying Mechanism-of-Action Targets for Drugs and Probes. Proc. Natl. Acad. Sci. 2012, 109 (28), 11178-11183. https://doi.org/10.1073/pnas.1204524109.

Gueven, N., Woolley, K. & Smith, J. Border between natural product and drug: comparison of the related benzoquinones idebenone and coenzyme Q10. Redox Biol. 4, 289-295 (2015).

Hahn, W. C. et al. Creation of human tumour cells with defined genetic elements. Nature 400, 464-468 (1999).

Hayano, M., Yang, W. S., Corn, C. K., Pagano, N. C. & Stockwell, B. R. Loss of cysteinyl-tRNA synthetase (CARS) induces the transsulfuration pathway and inhibits ferroptosis induced by cystine deprivation. Cell Death Differ. 23, 270-278 (2016).

Henke, N.; Albrecht, P.; Bouchachia, I.; Ryzantseva, M.; Knoll, K.; Lewerenz, J.; Kaznacheyeva, E.; Maher, P.; Methner, A. The Plasma Membrane Channel ORAI1

Mediates Detrimental Calcium Influx Caused by Endogenous Oxidative Stress. *Cell Death Dis.* 2013, 4 (1), e470. https://doi.org/10.1038/cddis.2012.216.

Hirsch, H. A. et al. A transcriptional signature and common gene networks link cancer with lipid metabolism and diverse human diseases. Cancer Cell 17, 348-361 (2010).

Hitomi, J. et al. Identification of a molecular signaling network that regulates a cellular necrotic cell death pathway. Cell 135, 1311-1323 (2008).

Hu, Y.; Jasial, S.; Bajorath, J. Promiscuity Progression of Bioactive Compounds over Time. *F1000Research* 2015. https://doi.org/10.12688/f1000research.6473.2.

Imai, H. & Nakagawa, Y. Biological significance of phospholipid hydroperoxide glutathione peroxidase (PHGPx, GPx4) in mammalian cells. Free Radic. Biol. Med. 34, 145-169 (2003).

Kaczmarek, A., Vandenabeele, P. & Krysko, D. V. Necroptosis: the release of damage-associated molecular patterns and its physiological relevance. Immunity 38, 209-223 (2013).

Kamphorst, J. J., Fan, J., Lu, W., White, E. & Rabinowitz, J. D. Liquid chromatography-high resolution mass spectrometry analysis of fatty acid metabolism. Anal. Chem. 83, 9114-9122 (2011).

Keiser, M. J.; Roth, B. L.; Armbruster, B. N.; Ernsberger, P.; Irwin, J. J.; Shoichet, B. K. Relating Protein Pharmacology by Ligand Chemistry. *Nat. Biotechnol.* 2007, 25 (2), 197-206. https://doi.org/10.1038/nbt1284.

Keiser, M. J.; Setola, V.; Irwin, J. J.; Laggner, C.; Abbas, A. I.; Hufeisen, S. J.; Jensen, N. H.; Kuijer, M. B.; Matos, R. C.; Tran, T. B.; et al. Predicting New Molecular Targets for Known Drugs. *Nature* 2009, 462 (7270), 175-181. https://doi.org/10.1038/nature08506.

Kono, H. & Rock, K. L. How dying cells alert the immune system to danger. Nat. Rev. Immunol. 8, 279-289 (2008).

Linkermann, A. et al. Synchronized renal tubular cell death involves ferroptosis. Proc. Natl. Acad. Sci. USA 111, 16836-16841 (2014).

Linkermann, A., Stockwell, B. R., Krautwald, S. & Anders, H.-J. Regulated cell death and inflammation: an auto-amplification loop causes organ failure. Nat. Rev. Immunol. 14, 759-767 (2014).

Liu, C.-I. et al. Structural insights into the catalytic mechanism of human squalene synthase. Acta Crystallogr. D Biol. Crystallogr. 70, 231-241 (2014).

Rogers, D.; Hahn, M. Extended-Connectivity Fingerprints. *J. Chem. Inf. Model.* 2010, 50 (5), 742-754. http://doi.org/10.1021/ci100050t.

Romanowska, M. et al. Effects of selenium supplementation on expression of glutathione peroxidase isoforms in cultured human lung adenocarcinoma cell lines. Lung Cancer 55, 35-42 (2007).

Santos, C. R. & Schulze, A. Lipid metabolism in cancer. FEBS J. 279, 2610-2623 (2012).

Shimada, K. et al. Global survey of cell death mechanisms reveals metabolic regulation of ferroptosis. Nat. Chem. Biol. 2016 July; 12(7):497-503.

Shimada, K., Hayano, M., Pagano, N. C. & Stockwell, B. R. Cell-line selectivity improves the predictive power of pharmacogenomic analyses and helps identify NADPH as biomarker for ferroptosis sensitivity. Cell Chem. Biol. 23, 225-235 (2016).

Shintoku, R.; Takigawa, Y.; Yamada, K.; Kubota, C.; Yoshimoto, Y.; Takeuchi, T.; Koshiishi, I.; Torii, S. Lipoxygenase-mediated Generation of Lipid Peroxides Enhances Ferroptosis Induced by Erastin and RSL3. *Cancer Sci.* 2017, 108 (11), 2187-2194. https://doi.org/10.1111/cas.13380.

Shoemaker, R. H. The NCI60 human tumour cell line anticancer drug screen. Nat. Rev. Cancer 6, 813-823 (2006).

Skouta, R. et al. Ferrostatins inhibit oxidative lipid damage and cell death in diverse disease models. J. Am. Chem. Soc. 136, 4551-4556 (2014).

Song, J. H. et al. Deletion of Pim kinases elevates the cellular levels of reactive oxygen species and sensitizes to K-Ras-induced cell killing. Oncogene 34, 3728-3736 (2015).

Subramanian, A.; Tamayo, P.; Mootha, V. K.; Mukherjee, S.; Ebert, B. L.; Gillette, M. A.; Paulovich, A.; Pomeroy, S. L.; Golub, T. R.; Lander, E. S.; et al. Gene Set Enrichment Analysis: A Knowledge-Based Approach for Interpreting Genome-Wide Expression Profiles. *Proc. Natl. Acad. Sci. U.S.A.* 2005, 102 (43), 15545-15550.

Takahashi, N. et al. Necrostatin-1 analogues: critical issues on the specificity, activity and in vivo use in experimental disease models. Cell Death Dis. 3, e437 (2012).

Tansey, T. R. & Shechter, I. Structure and regulation of mammalian squalene synthase. Biochim. Biophys. Acta 1529, 49-62 (2000).

Tobaben, S.; Grohm, J.; Seiler, A.; Conrad, M.; Plesnila, N.; Culmsee, C. Bid-Mediated Mitochondrial Damage Is a Key Mechanism in Glutamate-Induced Oxidative Stress and AIF-Dependent Cell Death in Immortalized HT-22 Hippocampal Neurons. *Cell Death Differ.* 2011, 18 (2), 282-292. httos://doi.org/10.1038/cdd.2010.92.

Vanden Berghe, T., Linkermann, A., Jouan-Lanhouet, S., Walczak, H. & Vandenabeele, P. Regulated necrosis: the expanding network of non-apoptotic cell death pathways. Nat. Rev. Mol. Cell Biol. 15, 135-147 (2014).

Viswanathan, V. S.; Ryan, M. J.; Dhruv, H. D.; Gill, S.; Eichhoff, O. M.; Seashore-Ludlow, B.; Kaffenberger, S. D.; Eaton, J. K.; Shimada, K.; Aguirre, A. J.; et al. Dependency of a Therapy-Resistant State of Cancer Cells on a Lipid Peroxidase Pathway. *Nature* 2017, 547 (7664), 453. https://doi.org/10.1038/nature23007.

Ward, J. H. Hierarchical Grouping to Optimize an Objective Function. *J. Am. Stat. Assoc.* 1963, 58 (301), 236-244. https://doi.org/10.1080/01621459.1963.10500845.

Wolpaw, A. J. et al. Modulatory profiling identifies mechanisms of small molecule-induced cell death. Proc. Natl. Acad. Sci. USA 108, E771-E780 (2011).

Yagoda, N. et al. RAS-RAF-MEK-dependent oxidative cell death involving voltage-dependent anion channels. Nature 447, 864-868 (2007).

Yang, W. S.; Kim, K. J.; Gaschler, M. M.; Patel, M.; Shchepinov, M. S.; Stockwell, B. R. Peroxidation of Polyunsaturated Fatty Acids by Lipoxygenases Drives Ferroptosis. *Proc. Natl. Acad. Sci.* 2016, 113 (34), E4966-E4975. https://doi.org/10.1073/pnas.1603244113.

Yang, W. S. & Stockwell, B. R. Synthetic lethal screening identifies compounds activating iron-dependent, nonapoptotic cell death in oncogenic-RASharboring cancer cells. Chem. Biol. 15, 234-245 (2008).

Yang, W. S. et al. Regulation of ferroptotic cancer cell death by GPX4. Cell 156, 317-331 (2014).

What is claimed is:

1. A compound having the structure of formula (I):

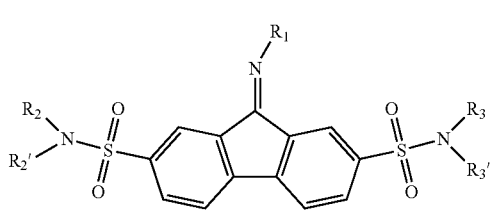

wherein:
- $R_1$ is selected from the group consisting of H, and $-(OCH_2CH_2)_xOH$;
- X is an integer from 1 to 6; and
- $R_2$, $R_2'$, $R_3$, and $R_3'$ independently are selected from the group consisting of H, $C_{3-8}$cycloalkyl, and combinations thereof, or $R_2$ and $R_2'$ may be joined together to form a pyridinyl or pyranyl and $R_3$ and $R_3'$ may be joined together to form a pyridinyl or pyranyl;

or an N-oxide, or pharmaceutically acceptable salt thereof;

with the proviso that the compound is not

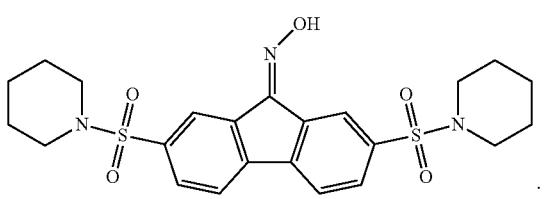 [SMILES: O=S(=O)(c1ccc2c(c1)C(=NO)c1cc(S(=O)(=O)N3CCCCC3)ccc1-2)N1CCCCC1]

2. A compound having the structure of formula (II):

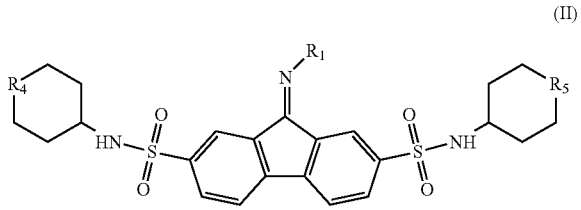

wherein:
- $R_1$ is $-(OCH_2CH_2)_xOH$;
- X is an integer from 1 to 6; and
- $R_4$ and $R_5$ are independently selected from the group consisting of $CH_2$ and O;

or an N-oxide, or pharmaceutically acceptable salt thereof, or wherein:

$R_1$ is OH and (1) $R_4$ and $R_5$ are both O; or (2) $R_4$ is $CH_2$ and $R_5$ is O; or (3) $R_4$ is O and $R_5$ is $CH_2$;

or an N-oxide, or pharmaceutically acceptable salt thereof.

3. A compound according to claim 2, which is selected from the group consisting of:

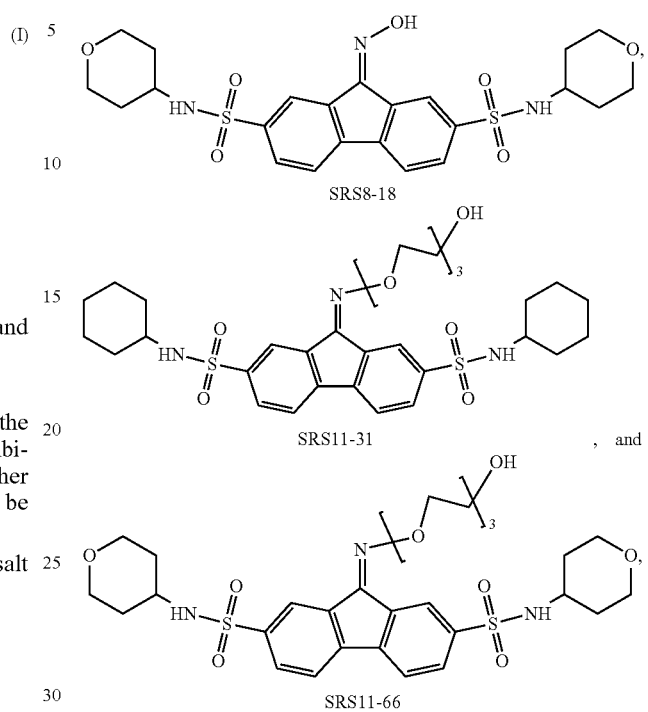

and combinations thereof, or an N-oxide, or pharmaceutically acceptable salt thereof.

4. A composition comprising a compound according to any one of claims 1-3, and a pharmaceutically acceptable carrier, adjuvant, or vehicle.

5. A pharmaceutically acceptable salt of a compound according to any one of claims 1-3.

6. A composition comprising a pharmaceutically acceptable salt of a compound according to any one of claims 1-3 and a pharmaceutically acceptable carrier, adjuvant, or vehicle.

7. A method for inducing ferroptosis in a cell comprising contacting the cell with an effective amount of a compound having the structure of formula (I):

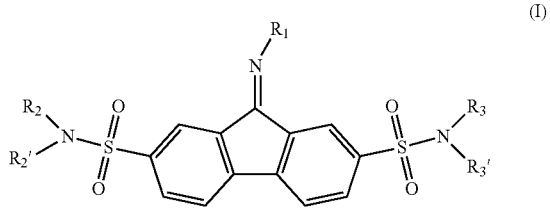

wherein:
- $R_1$ is selected from the group consisting of H, OH, and $(OCH_2CH_2)_xOH$;
- X is an integer from 1 to 6; and
- $R_2$, $R_2'$, $R_3$, and $R_3'$ independently are selected from the group consisting of H, $C_{3-8}$cycloalkyl, and combinations thereof, or $R_2$ and $R_2'$ may be joined together to form a pyridinyl or pyranyl and $R_3$ and $R_3'$ may be joined together to form a pyridinyl or pyranyl;

or an N-oxide, or pharmaceutically acceptable salt thereof.

8. A method for inducing ferroptosis in a cell comprising contacting the cell with an effective amount of a compound having the structure of formula (II):

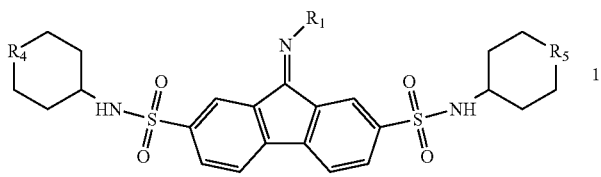

(II)

wherein:

$R_1$ is selected from the group consisting of OH and —$(OCH_2CH_2)_xOH$;

X is an integer from 1 to 6; and $R_4$ and $R_5$ are independently selected from the group consisting of $CH_2$ and O;

or an N-oxide, or pharmaceutically acceptable salt thereof.

9. A method for inducing ferroptosis in a cell comprising contacting the cell with an effective amount of a compound selected from the group consisting of:

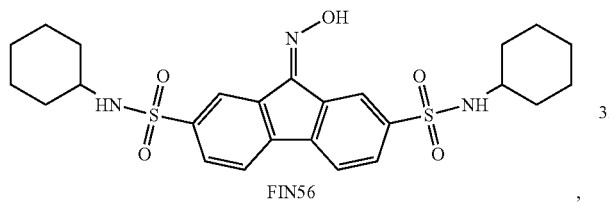

FIN56

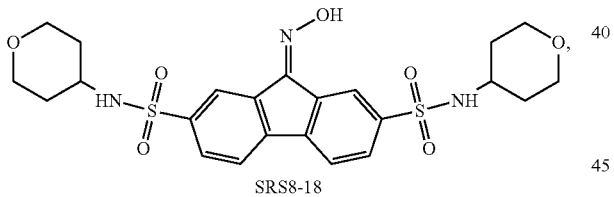

SRS8-18

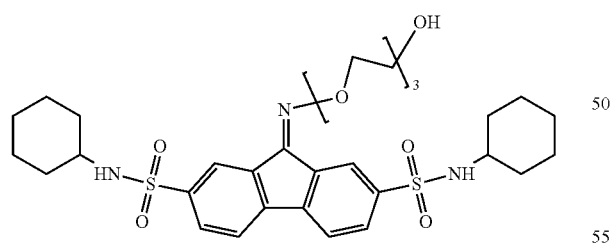

SRS11-31

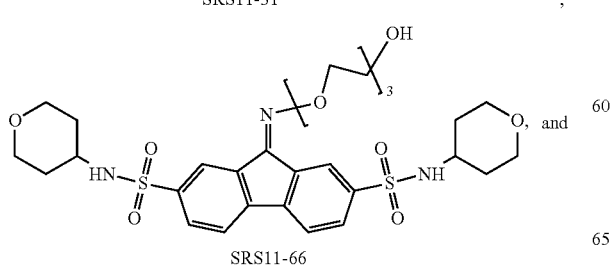

SRS11-66 and

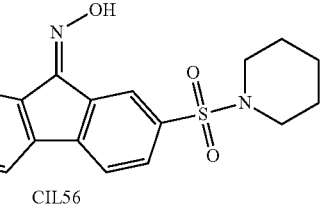

CIL56 and combinations thereof, or an N-oxide, or pharmaceutically acceptable salt thereof.

10. The method according to claim 7, wherein the compound is FIN56:

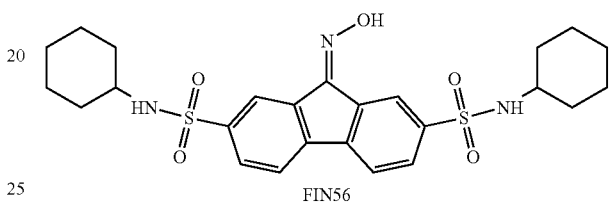

FIN56 or an N-oxide, or pharmaceutically acceptable salt thereof.

11. The method according to any one of claims 7-10, wherein the cell is a mammalian cell.

12. The method according to claim 11, wherein the cell is a human cell.

13. The method according to any one of claims 7-10, wherein the cell is from a laboratory animal.

14. The method according to any one of claims 7-10, which is carried out in vitro, or ex vivo.

15. A method for decreasing GPX4 in a cell, comprising contacting the cell with an effective amount of a compound having the structure of formula (I):

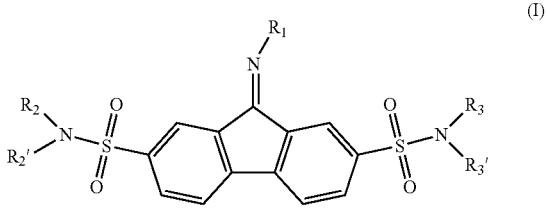

(I)

wherein:

$R_1$ is selected from the group consisting of H, OH, and —$(OCH_2CH_2)_xOH$;

X is an integer from 1 to 6; and $R_2$, $R_2'$, $R_3$, and $R_3'$ independently are selected from the group consisting of H, $C_{3-8}$cycloalkyl, and combinations thereof, or $R_2$ and $R_2'$ may be joined together to form a pyridinyl or pyranyl and $R_3$ and $R_3'$ may be joined together to form a pyridinyl or pyranyl;

or an N-oxide, or pharmaceutically acceptable salt thereof.

16. A method for decreasing GPX4 in a cell, comprising contacting the cell with an effective amount of a compound having the structure of formula (II):

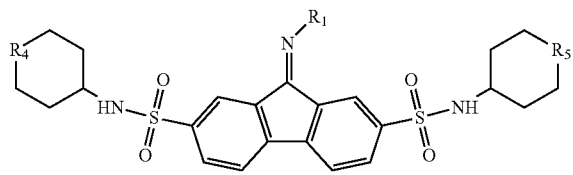

(II)

wherein:

R₁ is selected from the group consisting of OH and —(OCH₂CH₂)ₓOH;

X is an integer from 1 to 6; and

R₄ and R₅ are independently selected from the group consisting of CH₂ and O;

or an N-oxide, or pharmaceutically acceptable salt thereof.

17. A method for decreasing GPX4 in a cell, comprising contacting the cell with an effective amount of a compound selected from the group consisting of:

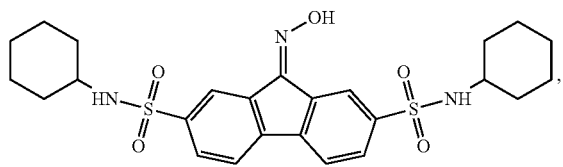

FIN56

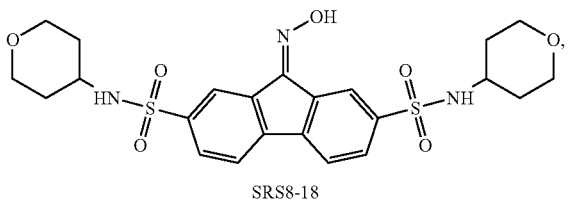

SRS8-18

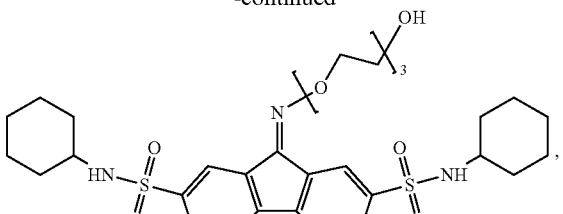

SRS11-31

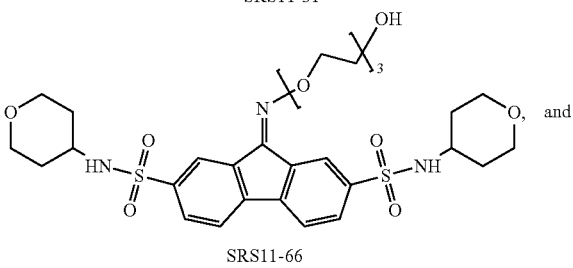

SRS11-66

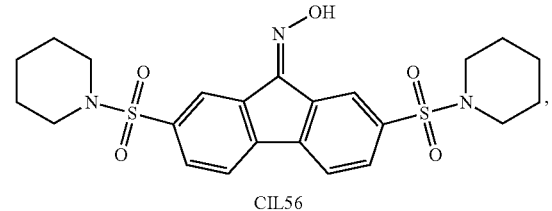

CIL56 and combinations thereof, or an N-oxide, or pharmaceutically acceptable salt thereof.

18. The method according to claim 15, wherein the compound is FIN56:

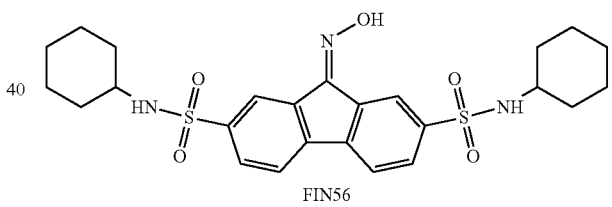

FIN56 or an N-oxide, or pharmaceutically acceptable salt thereof.

19. The method according to any one of claims 15-18, wherein the cell is a mammalian cell.

* * * * *